(12) United States Patent
Ebner et al.

(10) Patent No.: US 6,635,743 B1
(45) Date of Patent: Oct. 21, 2003

(54) APOPTOSIS INDUCING MOLECULE II AND METHODS OF USE

(75) Inventors: Reinhard Ebner, Gaithersburg, MD (US); Guo-Liang Yu, Berkeley, CA (US); Steven M. Ruben, Olney, MD (US); Stephen Ullrich, Rockville, MD (US); Yifan Zhai, Guilford, CT (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/523,323

(22) Filed: Mar. 10, 2000

Related U.S. Application Data

(63) Continuation-in-part of application No. 09/252,656, filed on Feb. 19, 1999, now Pat. No. 6,495,520, which is a continuation-in-part of application No. 09/027,287, filed on Feb. 20, 1998, now Pat. No. 6,479,254, which is a continuation-in-part of application No. 09/003,886, filed on Jan. 7, 1998, now abandoned, which is a continuation-in-part of application No. 08/822,953, filed on Mar. 21, 1997, now abandoned.

(60) Provisional application No. 60/168,380, filed on Dec. 2, 1999, provisional application No. 60/148,326, filed on Aug. 11, 1999, provisional application No. 60/142,657, filed on Jul. 6, 1999, provisional application No. 60/137,457, filed on Jun. 4, 1999, provisional application No. 60/124,041, filed on Mar. 11, 1999, provisional application No. 60/075,409, filed on Feb. 20, 1998, provisional application No. 60/030,157, filed on Oct. 31, 1996, and provisional application No. 60/013,923, filed on Mar. 22, 1996.

(51) Int. Cl.[7] .................. C07K 16/00; C07K 16/24; C07K 14/525; G01N 33/53

(52) U.S. Cl. .................. 530/388.23; 530/387.3; 530/388.1; 530/389.1; 530/389.2; 530/387.1; 435/7.1; 930/144

(58) Field of Search .................. 530/387.1, 387.3, 530/388.1, 388.23, 389.1, 389.2; 435/7.1; 930/144

(56) References Cited

U.S. PATENT DOCUMENTS

| | | |
|---|---|---|
| 4,002,531 A | 1/1977 | Royer .................. 195/68 |
| 4,444,887 A | 4/1984 | Hoffmann .................. 435/140 |
| 4,474,893 A | 10/1984 | Reading .................. 436/547 |
| 4,714,681 A | 12/1987 | Reading .................. 435/240 |
| 4,716,111 A | 12/1987 | Osband et al. .................. 435/68 |
| 4,816,397 A | 3/1989 | Boss et al. .................. 435/68 |
| 4,816,567 A | 3/1989 | Cabilly et al. .................. 530/387 |
| 4,925,648 A | 5/1990 | Hansen et al. .................. 424/1.1 |
| 4,946,778 A | 8/1990 | Ladner et al. .................. 435/69.9 |
| 4,946,788 A | 8/1990 | Delespesse .................. 435/240.27 |
| 5,225,539 A | 7/1993 | Winter .................. 530/387.3 |
| 5,258,498 A | 11/1993 | Huston et al. .................. 530/350 |
| 5,349,052 A | 9/1994 | Delgado et al. .................. 530/351 |
| 5,474,981 A | 12/1995 | Leder et al. .................. 514/12 |
| 5,530,101 A | 6/1996 | Queen et al. .................. 530/387.3 |
| 5,565,332 A | 10/1996 | Hoogenboom et al. .... 435/69.1 |
| 5,573,920 A | 11/1996 | Randle et al. .................. 435/7.9 |
| 5,585,089 A | 12/1996 | Queen et al. .................. 424/133.1 |
| 5,601,819 A | 2/1997 | Wong et al. .................. 424/136.1 |
| 5,643,575 A | 7/1997 | Martinez et al. .................. 424/194.1 |
| 5,807,715 A | 9/1998 | Morrison et al. .................. 435/69.6 |
| 5,811,097 A | 9/1998 | Allison et al. .................. 424/144.1 |

FOREIGN PATENT DOCUMENTS

| | | |
|---|---|---|
| CA | 2045869 | 12/1991 |
| EP | 0 239 400 B1 | 9/1987 |
| EP | 0 282 317 A2 | 9/1988 |
| EP | 0 399 816 B1 | 11/1990 |
| EP | 0 401 384 B1 | 12/1990 |
| EP | 0 439 095 B1 | 7/1991 |
| EP | 0 506 477 B1 | 9/1992 |
| EP | 0 519 596 A1 | 12/1992 |
| EP | 0 592 106 A1 | 4/1994 |
| EP | 0 682 110 A1 | 11/1995 |
| EP | 0 897 114 A2 | 2/1999 |
| EP | 0 897 114 | 2/1999 |
| JP | 8-191204 | 7/1996 |
| JP | 8-211695 | 8/1996 |
| JP | 9-019330 | 1/1997 |
| WO | WO 90/13649 | 11/1990 |
| WO | WO 91/00360 | 1/1991 |
| WO | WO 91/09967 | 7/1991 |
| WO | WO 91/10741 | 7/1991 |
| WO | WO 92/05793 | 4/1992 |
| WO | WO 92/06194 | 4/1992 |
| WO | WO 92/08802 | 5/1992 |
| WO | WO 92/22324 | 12/1992 |
| WO | WO 93/17715 | 9/1993 |
| WO | WO 93/21232 | 10/1993 |
| WO | WO 95/06058 | 3/1995 |
| WO | WO 96/14328 | 5/1996 |
| WO | WO 96/26736 | 9/1996 |
| WO | WO 96/33735 | 10/1996 |
| WO | WO 96/34095 | 10/1996 |

(List continued on next page.)

OTHER PUBLICATIONS

Harrop, J., et al., "HVEM–L, A Novel Ligand for HVEM/TR2, Stimulates NF–κB Dependent Transcription and T Cell Proliferation," *J. Int. Cytokine Res.* 18:A–39 (1998).

(List continued on next page.)

*Primary Examiner*—David S. Romeo
(74) *Attorney, Agent, or Firm*—Sterne, Kessler, Goldstein & Fox P.L.L.C.

(57) ABSTRACT

The present invention relates to a novel member of the TNF-Ligand superfamily. More specifically, isolated nucleic acid molecules are provided encoding a human Apoptosis Inducing Molecule II (AIM II). AIM II polypeptides are also provided, as are vectors, host cells and recombinant methods for producing the same. The invention further relates to screening methods for identifying agonists and antagonists of AIM II activity. Also provided are therapeutic methods for treating lymphadenopathy, aberrant bone development, autoimmune and other immune system diseases, graft versus host disease, rheumatoid arthritis, osteoarthritis and to inhibit neoplasia, such as tumor cell growth.

39 Claims, 48 Drawing Sheets

FOREIGN PATENT DOCUMENTS

| WO | WO 96/34096 | 10/1996 |
|---|---|---|
| WO | WO 96/36720 | 11/1996 |
| WO | WO 96/39515 | 12/1996 |
| WO | WO 97/33899 | 9/1997 |
| WO | WO 97/33904 | 9/1997 |
| WO | WO 97/34911 | 9/1997 |
| WO | WO 97/41831 | 11/1997 |
| WO | WO 98/02543 | 1/1998 |
| WO | WO 98/03648 | 1/1998 |
| WO | WO 98/06842 | 2/1998 |
| WO | WO 98/07832 | 2/1998 |
| WO | WO 98/07880 | 2/1998 |
| WO | WO 98/16654 | 4/1998 |
| WO | WO 98/18921 | 5/1998 |
| WO | WO 98/24893 | 6/1998 |
| WO | WO 98/25967 | 6/1998 |
| WO | WO 98/28424 | 7/1998 |
| WO | WO 98/28426 | 7/1998 |
| WO | WO 98/30693 | 7/1998 |
| WO | WO 98/30694 | 7/1998 |
| WO | WO 98/32466 | 7/1998 |
| WO | WO 98/32856 | 7/1998 |
| WO | WO 98/41629 | 9/1998 |
| WO | WO 98/46645 | 10/1998 |
| WO | WO 98/50433 | 11/1998 |
| WO | WO 98/54202 | 12/1998 |
| WO | WO 98/54323 | 12/1998 |
| WO | WO 98/56892 | 12/1998 |
| WO | WO 99/02563 | 1/1999 |
| WO | WO 99/11662 | 3/1999 |
| WO | WO 99/35262 | 7/1999 |
| WO | WO 99/42584 | 8/1999 |

OTHER PUBLICATIONS

Aggarwal, B.B, and Natarajan, K., "Tumor necrosis factors: Developments during the last decade," *Eur. Cytokine Netw.* 7:93–124 (Apr.–Jun. 1996).

Anderson, D. et al, "A homologue of the TNF receptor and its ligand enhance T–cell growth and dendritic–cell function," *Nature* 390:175–179 (Nov. 1997).

Barton, G.J., *Protein Structure Prediction, A Practical Approach*, IRL Press, Oxford, UK (1996), pp. 31–63.

Brunner, T. et al.,"Cell–autonomous Fas (CD95)/Fas–ligand interaction mediates activation–induced apoptosis in T–cell hybridomas," *Nature* 373:441–444 (Feb. 1995).

Chen, C.–M. et al., "Direct Interaction of Hepatitis C Virus Core Protein with the Cellular Lymphotoxin–β Receptor Modulates the Signal Pathway of the Lymphotoxin–β Receptor," *J. Virol.* 71:9417–9426 (Dec. 1997).

Font, J. et al., "Elevated Soluble CD27 Levels in Serum of Patients with Systemic Lupus Erythematosus," *Clin. Immunol. Immunopathol.* 81:239–243 (Dec. 1996).

George, D.G. et al., "Current Methods in Sequence Comparison and Analysis," *Macromolecular Sequencing and Synthesis, Selected Methods and Applications*, Sclesinger, D.H., ed., Liss Inc. Pbl., New York, NY (1988), pp 127–149.

Gruss, H.–J., "Molecular, structural, and biological characteristics of the tumor necrosis factor ligand superfamily," *Int. J. Clin. Lab. Res.* 26:143–159 (Jan. 1996).

Gruss, H.J. and Dower, S.K., "The TNF ligand superfamily and its relevance for human diseases," *Cytokines and Molecular Therapy* 1:75–105 (Jun. 1995).

Gruss, H.J. and Dower, S.K., "Tumor Necrosis Factor Ligand Superfamily: Involvement in the Pathology of Malignant Lymphomas," *Blood* 85:3378–3404 (Jun. 1995).

Gruss, H.J. and Herman, F., "CD30 Ligand, a Member of the TNF Ligand Superfamily, with Growth and Activation Control for CD30+ Lymphoid and Lymphoma Cells," *Leukemia and Lymphoma* 20:397–409 (Feb. 1996).

Gruss, H.J., et al., "Structural and biological features of the TNF receptor and TNF ligand superfamilies: Interactive signals in the pathobiology of Hodgkins disease," *Annals of Oncology* 7(Suppl. 4):s19–s26 (1996).

Harrop, J.A., "Herpesvirus Entry Mediator Ligand (HVEM–L), a Novel Ligand for HVEM/TR2, Stimulates Proliferation of T Cells and Inhibits HT29 Cell Growth," *J. Biol. Chem.* 273:27548–27556 (Oct. 1998).

Ju, S.–T. et al., "Fas(CD95)/FasL interactions required for programmed cell death after T–cell activation," *Nature* 373:444 (Feb. 1995).

Kallio, P. et al., "Soluble CD27 in thyroid disorders," *J. Lab Clin. Med.* 132:478–482 (Dec. 1998).

Kersten. M.J. et al., "Elevation of Cerebrospinal Fluid Soluble CD27 Levels in Patients With Meningeal Localization of Lymphoid Malignancies," *Blood* 87:1985–1989 (Mar. 1996).

Kwon, B.S. et al., "A Newly Identified Member of the Tumor Necrosis Factor Receptor Superfamily with a Wide Tissue Distribution and Involvement in Lymphocyte Activation," *J. Biol. Chem.* 272:14272–14276 (May 1997).

Lundwall, A., "Characterization of the gene for prostate–specific anitgen, a human glandular kallikrein," *Biochem. Biophys. Res. Commun.,* 161:1151–1159 (Jun. 1989).

Mauri, D.N. et al., "Light, a New Member of the TNF Superfamily, and Lymphotoxin α Are Ligands for Herpesvirus Entry Mediator," *Immunity* 8:21–30 (Jan. 1998).

Nagumo, H. et al., "CD27/CD70 Interaction Augments IgE Secretion by Promoting the Differentiation of Memory B Cells into Plasma Cells," *J. Immun.* 161:6492–6502 (Dec. 1998).

Pandanilam, B. et al., "Expression of CD27 and ischemia/reperfusion–induced expression of its ligand Siva in rat kidneys," *Kidney Int.* 54:1967–1975 (Dec. 1998).

Ranheim, E.A. et al.,"Expression of CD27 and its Ligand, CD70, on Chronic Lymphocytic Leukemia B Cells," *Blood* 85:3556–3565 (Jun. 1995).

Rennert, P.D. et al., "Selective disruption of lymphotoxin ligands reveals a novel set of mucosal lymph nodes and unique effects on lymph node cellular organization," *Int. Immunol.* 9:1627–1639 (Nov. 1997).

Sigurdsson, T. et al., "Peridontal Regenerative Potential of Space–Providing Expanded Polytetrafluoroethylene Membranes and Recombinant Human Bone Morphogenetic Proteins," *J. Periodontol.* 66:511–521 (Jun. 1995).

Suda, T. et al., "Molecular Cloning and Expression of the Fas Ligand, a Novel Member of the Tumor Necrosis Factor Family," *Cell* 75:1169–1178 (1993).

Swaak, A.J.G. et al., "Serum Levels of Soluble Forms of T–Cell Activation Antigens CD27 and CD25 in Systemic Lupus Erythematosus in Relation with Lymphocytes Count and Disease Course," *Clin. Rheumatol.* 14:293–300 (May 1995).

Takahashi, T., et al. "Generalized Lymphoproliferative Disease in Mice, Caused by a Point Mutation in the Fas Ligand," *Cell* 76:969–976 (1994).

Takahashi, T., et al., "Human Fas ligand: gene structure, chromosomal location and species specificity," *International Immunology* 6:1567–1574 (1994).

Takeda, Y. et al., Rapid acceleration of neutrophil apoptosis by tumor necrosis factor α, *International Immunology* 5:691–694 (1993).

Tan, K.B., "Characterization of a novel TNF–like ligand and recently described TNF ligand and TNF receptor superfamily genes and their constitutive and inducible expression in hematopoietic and non–hematopoietic cells," *Gene* 204:35–46 (Dec. 1997).

Tanaka, M. et al., "Expression of the functional soluble form of human Fas ligand in activated lymphocytes," *EMBO J.* 14:1129–1135 (Mar. 1995).

NCBI Entrez, GenBank Report, Accession No. M27274, submitted by Lundwall, A., (Nov. 1989).

NCBI Entrez. GenBank Report, Accession No. T74524, submitted by Hillier et al. (Mar. 1995).

NCBI Entrez, GenBank Report, Accession No. H73550, submitted by Hillier et al. (Oct. 1995).

NCBI Entrez, GenBank Report, Accession No. N77915, submitted by Hillier et al. (Mar. 1996).

NCBI Entrez, GenBank Report, Accession No. AA491814, from NCI–CGAP (Aug. 1997).

NCBI Entrez, GenBank Report, Accession No. AA570740, from NCI–CGAP (Sep. 1997).

NCBI Entrez, GenBank Report, Accession No. AA747757, from NCI–CGAP (Feb. 1998).

NCBI Entrez, GenBank Report, Accession No. AA568204, from NCI–CGAP (Mar. 1999).

English translation of Japanese Patent Application No. 8–191204 (Document AI1).

English Translation of Japanese Patent Application No. 8–211695 (Document AJ1).

English translation of Japanese Patent Application No. 9–019330 (Document AI2).

Armitage, R.J., "Tumor necrosis factor receptor superfamily members and their ligands," *Curr. Opin. Immunol.* 6:407–413 (1994).

Baens, M., et al., "Construction and Evaluation of an hncDNA Library of Human 12p Transcribed Sequences Derived from a Somatic Cell Hybrid," *Genomics* 16:214–218 (1993).

Bartuněk, P., et al., "Avian Stem Cell Factor (SCF): Production and Characterization of the Recombinant HIS–tagged SCF of Chicken and its Neutralizing Antibody," *Cytokine* 8:14–20 (Jan. 1996).

Better, M., et al., "*Escherichia coli* Secretion of an Active Chimeric Antibody Fragment," *Science* 240:1041–1043 (1988).

Beutler, B., and Cerami, A., "Tumor Necrosis, Cachexia, Shock, and Inflammation: A Common Mediator," *Ann. Rev. Biochem.* 57:505–518 (1988).

Bird, R.E., et al., "Single–Chain Antigen–Binding Proteins," *Science* 242:423–426 (1988).

Blazar, B.R., et al., "In Vivo Blockade of CD28/CTLA4: B7/BB1 Interaction With CTLA4–Ig Reduces Lethal Murine Graft–Versus–Host Disease Across the Major Histocompatibility Complex Barrier in Mice," *Blood* 83:3815–3825 (1994).

Browning, J.L., et al., "Signaling through the Lymphotoxin β Receptor Induces the Death of Some Adenocarcinoma Tumor Lines," *J. Exp. Med.* 183:867–878 (Mar. 1996).

Caliceti, P., et al., "Biopharmaceutical Properties of Uricase Conjugated to Neutral and Amphiphilic Polymers," *Bioconjugate Chem.* 10:638–646 (Aug. 1999).

Carlson, N.G., et al., "Identification of Amino Acids in the Glutamate Receptor, GluR3, Important for Antibody–binding and Receptor–specific Activation," *J. Biol. Chem.* 272:11295–11301 (Apr. 1997).

Chaplin, D.D., and Fu, Y.–x., "Cytokine regulation of secondary lymphoid organ development," *Curr. Opin. Immunol.* 10:289–297 (Jun. 1998).

Chen, L., et al., "Costimulation of Antitumor Immunity by the B7 Counterreceptor for the T Lymphocyte Molecules CD28 and CTLA–4," *Cell* 71:1093–1102 (1992).

Chen, Z., et al., "Effects of Interleukin–1α, Interleukin–1 Receptor Antagonist, and Neutralizing Antibody on Proinflammatory Cytokine Expression by Human Squamous Cell Carcinoma Lines," *Cancer Res.* 58:3668–3676 (Aug. 1998).

Chinnaiyan, A.M., et al., "Signal Transduction by DR3, a Death Domain–Containing Receptor Related to TNFR–1 and CD95," *Science* 274:990–992 (Nov. 1996).

Cross, A.H., et al., "Long–Term Inhibition of Murine Experimental Autoimmune Encephalomyelitis Using CTLA–4–Fc Supports a Key Role for CD28 Costimulation," *J. Clin. Invest.* 95:2783–2789 (Jun. 1995).

Degli–Esposti, M.A., et al., "Cloning and Characterization of TRAIL–R3, a Novel Member of the Emerging TRAIL Receptor Family," *J. Exp. Med.* 186:1165–1170 (Oct. 1997).

Degli–Esposti, M.A., et al., "Activation of the Lymphotoxin β Receptor by Cross–Linking Induces Chemokine Production and Growth Arrest in A375 Melanoma Cells," *J. Immunol.* 158:1756–1762 (Feb. 1997).

Delgado, C., et al., "The Uses and Properties of PEGLinked Proteins," *Clin. Rev. Ther. Drug Carrier Systems* 9:249–304 (1992).

Deng, B., et al., "An Agonist Murine Monoclonal Antibody to the Human c–Mpl Receptor Stimulates Megakaryocytopoiesis," *Blood* 92:1981–1988 (Sep. 1998).

Desbarats, J., et al., "Newly discovered role for Fas ligand in the cell–cycle arrest of $CD4^+T$ cells," *Nature Med.* 4:1377–1382 (Dec. 1998).

Durie, F.H., et al., "Antibody to the Ligand of CD40, gp39, Blocks the Occurrence of the Acute and Chronic Forms of Graft–vs–Host Disease," *J. Clin. Invest.* 94:1333–1338 (1994).

Dürkop, H., et al., "Molecular Cloning and Expression of a New Member of the Nerve Growth Factor Receptor Family That Is Characteristic for Hodgkin's Disease," *Cell* 68:421–427 (1992).

Fell, H.P., et al., "Genetic Construction and Characterization of a Fusion Protein Consisting of a Chimeric F(ab') with Specificity for Carcinomas and Human Il–2," *J. Immunol.* 146:2446–2452 (1991).

Fiers, W., "Tumor necrosis factor," *FEBS Lett.* 285:199–212 (1991).

Folkman, J., "Clinical Applications of Research on Angiogenesis," *New Englamd J. Med.* 333:1757–1763 (Dec. 1995).

Francis, G.E. et al., "PEGylation of cytokines and other therapeutic proteins and peptides: the importance of biological optimisation of coupling techniquers," *Intl. J. Hematol.* 68:1–18 (Jul. 1998).

Gillies, S.D., et al., "High–level expression of chimeric antibodies using adapted cDNA variable region cassettes," *J. Immunol. Meth.* 125:191–202 (1989).

Gillies, S.D., et al., "Antibody–targeted interleukin 2 stimulates T–cell killing of autologous tumor cells," *Proc. Natl. Acad. Sci. USA* 89:1428–1432 (1992).

Goeddel, D.V., et al., "Tumor Necrosis Factors: Gene Structure and Biological Activities," in *Cold Spring Harbor Symposia on Quantitative Biology, vol. LI: Molecular Biology of* Homo sapiens, Cold Spring Harbor, NY (1986), pp. 597–609.

Hahne, M., et al., "April, a New Ligand of the Tumor Necrosis Factor Family, Stimulates Tumor Cell Growth," *J. Exp. Med.* 188:1185–1190 (Sep. 1998).

Harrop, J.A., et al., "Antibodies to TR2 (Herpesvirus Entry Mediator), a New Member of the TNF Receptor Superfamily, Block T Cell Proliferation, Expression of Activation Markers, and Production of Cytokines," *J. Immunol.* 161:1786–1794 (Aug. 1998).

Hauser, S. and Weich, H.A., "A Heparin–Binding Form of Placenta Growth Factor (P1GF–2) is Expressed in Human Umbilical Vein Endothelial Cells and in Placenta," *Growth Factors* 9:259–268 (1993).

Howard, S.T., et al., "Vaccinia Virus Homologues of the Shope Fibroma Virus Inverted Terminal Repeat Proteins and a Discontinuous ORF Related to the Tumor Necrosis Factor Receptor Family," *Virol.* 180:633–647 (1991).

Hsu, H., et al., "ATAR, a Novel Tumor Necrosis Factor Receptor Family Member, Signals through TRAF2 and TRAF5," *J. Biol. Chem.* 272:13471–13474 (May 1997).

Hu, F.Q., et al., "Cowpox Virus Contains Two Copies of an Early Gene Encoding a Soluble Secreted Form of the Type II TNF Receptor," *Virol.* 204:343–356 (1994).

Hu, S., et al., "Characterization of TNFRSF19, a Novel Member of the Tumor Necrosis Factor Receptor Superfamily," *Genomics* 62:103–107 (Nov. 1999).

Huston, J.S., et al., "Protein engineering of antibody binding sites: Recovery of specific activity in an anti–dioxin single–chain Fv analogue produced in *Escherichia coli*," *Proc. Natl. Acad. Sci. USA* 85:5879–5883 (1988).

Huston, J.S., et al., "Protein Engineering of Single–Chain Fv Analogs and Fusion Proteins," *Methods Enzymol.*, 203:46–88 (1991).

Itoh, N., et al., "The Polypeptide Encoded by the cDNA for Human Cell Surface Antigen Fas Can Mediate Apoptosis," *Cell.* 66:233–243 (1991).

Johnson, D., et al., "Expression and Structure of the Human NGF Receptor," *Cell.* 47:545–554 (1986).

Kostelny, S.A., et al., "Formation of a Bispecific Antibody by the Use of Leucine Zippers," *J. Immunol.* 148:1547–1553 (1992).

Kwon, B.S., and Weissman, S.M., "cDNA sequences of two inducible T–cell genes," *Proc. Natl. Acad. Sci. USA* 86:1963–1967 (1989).

Lenschow, D.J., et al., "Long–Term Survival of Xenogeneic Pancreatic Islet Grafts Induced by CTLA4Ig," *Science* 257:789–792 (1992).

Liautard, J., et al., "Specific Inhibition of Il–6 Signalling with Monoclonal Antibodies Against the gp130 Receptor," *Cytokine* 9:233–241 (Apr. 1997).

Loetscher, H., et al., "Molecular Cloning and Expression of the Human 55 kd Tumor Necrosis Factor Recptor," *Cell* 61:351–359 (1990).

Mackay, F., and Browning, J.L., "Turning off follicular dendritic cells," *Nature* 395:26–27 (Sep. 1998).

Malik, F., et al., "Polyethylene Glycol (PEG)–modified Granulocyte–Macrophage Colony–stimulating Factor (GM–CSF) with Conserved Biological Activity," *Exp. Hematol.* 20:1028–1035 (1992).

Mallett, S., et al., "Characterization of the MRC OX40 antigen of activated CD4 positive T lymphocytes—a molecule related to nerve growth factor receptor," *EMBO J.* 9:1063–1068 (1990).

Matsumoto, M., et al., "Role of Lymphotoxin and the Type I TNF Receptor in the Formation of Germinal Centers," *Science* 271:1289–1291 (Mar. 1996).

Melero, I., et al., "Monoclonal antibodies against the 4–1BB T–cell activation molecule eradicate established tumors," *Nature Med.* 3:682–685 (Jun. 1997).

Montgomery, R.I., et al., "Herpes Simplex Virus–1 Entry into Cells Mediated by a Novel Member of the TNF/NGF Receptor Family," *Cell* 87:427–436 (Nov. 1996).

Morpurgo, M., et al., "Covalent Modification of Mushroom Tyrosinase with Different Amphiphic Polymers for Pharmaceutical and Biocatalysis Applications," *App. Biochem. Biotech.* 56:59–72 (Jan. 1996).

Morrison, S.L., "Transfectomas Provide Novel Chimeric Antibodies," *Science* 229:1202–1207 (1985).

Moses, M.A., and Langer, R., "Inhibitors of Angiogenesis," *Biotechnol.* 9:630–634 (1991).

Muller, Y.A., et al., "VEGF and the Fab fragment of a humanized neutralizing antibody: crystal structure of the complex at 2.4 Å resolution and mutational analysis of the interface," *Structure* 6:1153–1167 (Sep. 1998).

Mullinax, R.L., et al., "Expression of a Heterodimeric Fab Antibody Protein in One Cloning Step," *BioTechniques* 12:864–869 (1992).

Nagata, S., "Apoptosis by Death Factor," *Cell* 88:355–365 (Feb. 1997).

Naramura, M. et al., "Mechanisms of cellular cytotoxicity mediated by a recombinant antibody–1L2 fusion protein against human melanoma cells," *Immunol. Lett.* 39:91–99 (1993).

Oi, V.T., and Morrison, S.L., "Chimeric Antibodies," *BioTechniques* 4:214–221 (1986).

Padlan, E.A., "A possible procedure for reducing the immunogenicity of antibody variable domains while preserving their ligand–binding properties," *Mol. Immunol.* 28:489–498 (1991).

Pan, G., et al., "An Antagonist Decoy Receptor and a Death Domain–Containing Receptor for TRAIL," *Science* 277:815–818 (Aug. 1997).

Pitard, V., et al., "Production and characterization of monoclonal antibodies against the leukemia inhibitory factor low affinity receptor, gp190," *J. Immunol. Meth.* 205:177–190 (Jul. 1997).

Pitti, R.M., et al., "Genomic amplification of a decoy receptor for Fas ligand in lung and colon cancer," *Nature* 396:699–703 (Dec. 1998).

Prat, M., et al., "Agonistic monoclonal antibodies against the Met receptor dissect the biological responses to HGF," *J. Cell Sci.* 111:237–247 (Jan. 1998).

Riechmann, L., et al., "Reshaping human antibodies for therapy," *Nature* 332:323–327 (1988).

Roguska, M.A., et al., "Humanization of murine monoclonal antibodies through variable domain resurfacing," *Proc. Natl. Acad. Sci. USA* 91:969–973 (1994).

Sawai, H., "Direct Production of the Fab Fragment Derived From the Sperm Immobilizing Antibody Using Polymerase Chain Reaction and cDNA Expression Vectors," *Am. J. Reprod. Immunol.* 34:26–34 (Jul. 1995).

Schall, T.J., et al., "Molecular Cloning and Expression of a Receptor for Human Tumor Necrosis Factor," *Cell* 61:361–370 (1990).

Schneider, P., et al., "Conversion of Membrane–bound Fas(CD95) Ligand to Its Soluble Form Is Associated with Downregulation of Its Proapoptotic Activity and Loss of Liver Toxicity," *J. Exp. Med* 187:1205–1213 (Apr. 1998).

Schwartz, R.H., "Costimulation of T Lymphocytes: The Role of CD28, CTLA–4, and B7/BB1 in Interleukin–2 Production and Immunotherapy," *Cell.* 71:1065–1068 (1992).

Sheridan, J.P., et al., "Control of TRAIL–Induced Apoptosis by a Family of Signaling and Decoy Receptors," *Science* 277:818–821 (Aug. 1997).

Shu, L., et al., "Secretion of a single–gene–encoded immunoglobulin from myeloma cells," *Proc. Natl. Acad. Sci. USA* 90:7995–7999 (1993).

Simonet, W.S. et al., "Osteoprotegerin: A Novel Secreted Protein Involved in the Regulation of Bone Density," *Cell* 89:309–319 (Apr. 1997).

Skerra, A., and Plückthun, A., "Assembly of a Functional Immunoglobulin $F_v$ Fragment in *Escherichia coli*," *Science* 240:1038–1041 (1988).

Smith, C.A., "A Receptor for Tumor Necrosis Factor Defines an Unusual Family of Cellular and Viral Proteins," *Science* 248:1019–1023 (1990).

Speiser, D.E., "TNF Receptor p55 Controls Early Acute Graft–Versus–Host Disease," *J. Immunol.* 158:5185–5190 (Jun. 1997).

Studnicka, G.M., et al., "Human–engineered monoclonal antibodies retain full specific binding activity by preserving non–CDR complementarity–modulating residues," *Protein Engineering* 7:805–814 (1994).

Suzuki, I., and Fink, P.J., "Maximal Proliferation of Cytotoxic T Lymphocytes Requires Reverse Signaling through Fas Ligand," *J. Exp. Med.* 187:123–128 (Jan. 1998).

Tamada, K., et al., "Light, a TNF–Like Molecule, Costimulates T Cell Proliferation and Is Required for Dendritic Cell–Mediated Allogeniec T Cell Response," *J. Immunol.* 164:4105–4110 (Apr. 2000).

Tamada, K., et al., "Modulation of T–Cell–mediated immunity in tumor and graft–versus–host disease models through the LIGHT co–stimulatory pathway," *Nature Med.* 6:283–289 (Mar. 2000).

Tewari, M., and Tixit, V.M., "Recent advances in tumor necrosis factor and CD40 signaling," *Gen. Dev.* 6:39–44 (Feb. 1996).

Tutt, A., et al., "Trispecific F(ab')$_3$ Derivatives That Use Cooperative Signaling via the TCR/CD3 Complex and CD2 to Activate and Redirect Resting Cytotoxic T Cells," *J. Immunol.* 147:60–69 (1991).

Twyman, R.E., et al., "Glutamate Receptor Antibodies Activate a Subset of Receptors and Reveal an Agonist Binding Site," *Neuron* 14:755–762 (Apr. 1995).

Van Lier, R.A.W., et al., "Tissue Distribution and Biochemical and Functional Properties of Tp55 (CD27), a Novel T Cell Differentiation Antigen," *J. Immunol.* 139:1589–1596 (1987).

Via, C.S., and Shearer, G.M., "T–cell interactions in autoimmunity: insights from a murine model of graft–versus–host disease," *Immunol. Today* 9:207–213 (1988).

Vorobjev, P.E., et al., "Oligonucleotide Conjugated to Linear and Branched High Molecular Weight Polyethylene Glycol as Substrates for RNase H," *Nucleosides & Nucleotides* 18:2745–2750 (Nov.–Dec. 1999).

Ward, E.S., et al., "Binding activities of a repertoire of single immunoglobulin variable domains secreted from *Escherichia coli*," *Nature* 341:544–546 (1989).

Ware, C.F., et al., "The Ligands and Receptors of the Lymphotoxin System," in *Pathways for Cytolysis*, Griffiths, G.M., and Tschopp, J., eds., Springer–Verlag, Berlin (1995), pp. 175–218.

Yoon, D.–Y., and Dinarello, C.A., "Antibodies to Domains II and III of the IL–1 Receptor Accessory Protein Inhibit IL–1β Activity But Not Binding: Regulation of IL–1 Responses Is Via Type I Receptor, Not the Accessory Protein," *J. Immunol.* 160:3170–3179 (Apr. 1998).

Yu, K.–Y., et al., "A Newly Identified Member of Tumor Necrosis Factor Receptor Superfamily (TR6) Suppresses LIGHT–mediated Apoptosis," *J. Biol. Chem.* 274:13733–13736 (May 1999).

Zhai, Y., et al., "LIGHT, A Novel Ligand for Lymphotoxin β Receptor and TR2/HVEM Induces Apoptosis and Suppresses In Vivo Tumor Formation Via Gene Transfer," *J. Clin. Invest.* 102:1142–1151 (Sep. 1998).

Zhu, Z., et al., "Inhibition of Vascular Endothelial Growth Factor–induced Receptor Activation with Anti–Kinase Insert Domain–containing Receptor Single–Chain Antibodies from a Phage Display Library," *Cancer Res.* 58:3209–3214 (Aug. 1998).

```
            10                      30                      50
GAGGTTGAAGGACCCAGGCGTGTCAGCCCTGCTCCAGAGACCTTGGGCATGGAGGAGAGT
---------+---------+---------+---------+---------+---------+
                                                  M  E  E  S
            70                      90                     110
GTCGTACGGCCCTCAGTGTTTGTGGTGGATGGACAGACCGACATCCCATTCACGAGGCTG
---------+---------+---------+---------+---------+---------+
 V  V  R  P  S  V  F  V  V  D  G  Q  T  D  I  P  F  T  R  L
         130                     150                     170
GGACGAAGCCACCGGAGACAGTCGTGCAGTGTGGCCCGGGTGGGTCTGGGTCTCTTGCTG
---------+---------+---------+---------+---------+---------+
 G  R  S  H  R  R  Q  S  C  S  V  A  R  V  G  L  G  L  L  L
         190                     210                     230
TTGCTGATGGGGGCTGGGCTGGCCGTCCAAGGCTGGTTCCTCCTGCAGCTGCACTGGCGT
---------+---------+---------+---------+---------+---------+
 L  L  M  G  A  G  L  A  V  Q  G  W  F  L  L  Q  L  H  W  R
         250                     270                     290
CTAGGAGAGATGGTCACCCGCCTGCCTGACGGACCTGCAGGCTCCTGGGAGCAGCTGATA
---------+---------+---------+---------+---------+---------+
 L  G  E  M  V  T  R  L  P  D  G  P  A  G  S  W  E  Q  L  I
         310                     330                     350
CAAGAGCGAAGGTCTCACGAGGTCAACCCAGCAGCGCATCTCACAGGGGCCAACTCCAGC
---------+---------+---------+---------+---------+---------+
 Q  E  R  R  S  H  E  V  N  P  A  A  H  L  T  G  A  N  S  S
         370                     390                     410
TTGACCGGCAGCGGGGGGCCGCTGTTATGGGAGACTCAGCTGGGCCTGGCCTTCCTGAGG
---------+---------+---------+---------+---------+---------+
 L  T  G  S  G  G  P  L  L  W  E  T  Q  L  G  L  A  F  L  R
         430                     450                     470
GGCCTCAGCTACCACGATGGGGCCCTTGTGGTCACCAAAGCTGGCTACTACTACATCTAC
---------+---------+---------+---------+---------+---------+
 G  L  S  Y  H  D  G  A  L  V  V  T  K  A  G  Y  Y  Y  I  Y
         490                     510                     530
TCCAAGGTGCAGCTGGGCGGTGTGGGCTGCCCGCTGGGCCTGGCCAGCACCATCACCCAC
---------+---------+---------+---------+---------+---------+
 S  K  V  Q  L  G  G  V  G  C  P  L  G  L  A  S  T  I  T  H
         550                     570                     590
GGCCTCTACAAGCGCACACCCCGCTACCCCGAGGAGCTGGAGCTGTTGGTCAGCCAGCAG
---------+---------+---------+---------+---------+---------+
 G  L  Y  K  R  T  P  R  Y  P  E  E  L  E  L  L  V  S  Q  Q
         610                     630                     650
TCACCCTGCGGACGGGCCACCAGCAGCTCCCGGGTCTGGTGGGACAGCAGCTTCCTGGGT
```

GGTGTGGTACACCTGGAGGCTGGGGAGGAGGTGGTCGTCCGTGTGCTGGATGAACGCCTG
  ---------+---------+---------+---------+---------+---------+
   G  V  V  H  L  E  A  G  E  E  V  V  V  R  V  L  D  E  R  L
         730                 750                 770

GTTCGACTGCGTGATGGTACCCGGTCTTACTTCGGGGCTTTCATGGTGTGAAGGAAGGAG
  ---------+---------+---------+---------+---------+---------+
   V  R  L  R  D  G  T  R  S  Y  F  G  A  F  M  V  *
         790                 810                 830

CGTGGTGCATTGGACATGGGTCTGACACGTGGAGAACTCAGAGGGTGCCTCAGGGGAAAG
  ---------+---------+---------+---------+---------+---------+
         850                 870                 890

AAAACTCACGAAGCAGAGGCTGGGCGTGGTGGCTCTCGCCTGTAATCCCAGCACTTTGGG
  ---------+---------+---------+---------+---------+---------+
         910                 930                 950

AGGCCAAGGCAGGCGGATCACCTGAGGTCAGGAGTTCGAGACCAGCCTGGCTAACATGGC
  ---------+---------+---------+---------+---------+---------+
         970                 990                 1010

AAAACCCCATCTCTACTAAAAATACAAAAATTAGCCGGACGTGGTGGTGCCTGCCTGTAA
  ---------+---------+---------+---------+---------+---------+
         1030                1050                1070

TCCAGCTACTCAGGAGGCTGAGGCAGGATAATTTTGCTTAAACCCGGGAGGCGGAGGTTG
  ---------+---------+---------+---------+---------+---------+
         1090                1110                1130

CAGTGAGCCGAGATCACACCACTGCACTCCAACCTGGGAAACGCAGTGAGACTGTGCCTC
  ---------+---------+---------+---------+---------+---------+
         1150

AAAAAAAAAAAAAAAAAAAAAAAAAAAAA
  ---------+---------+---------
```

FIG.1B

```
                 10                  30
ATTCCCCGGGCCCGGGTGGGTCTGGGTCTCTTGCTGTTGCTGATG
---------+---------+---------+---------+-----
 I  P  R  A  R  V  G  L  G  L  L  L  L  L  M
    50               70                  90

GGGGCCGGGCTGGCCGTCCAAGGCTGGTTCCTCCTGCAGCTGCAC
----+---------+---------+---------+---------+
 G  A  G  L  A  V  Q  G  W  F  L  L  Q  L  H
                  110                130

TGGCGTCTAGGAGAGATGGTCACCCGCCTGCCTGACGGACCTGCA
---------+---------+---------+---------+-----
 W  R  L  G  E  M  V  T  R  L  P  D  G  P  A
          150                  170

GGCTCCTGGGAGCAGCTGATACAAGAGCGAAGGTCTCACGAGGTC
----+---------+---------+---------+---------+
 G  S  W  E  Q  L  I  Q  E  R  R  S  H  E  V
        190                 210

AACCCAGCAGCGCATCTCACAGGGGCCAACTCCAGCTTGACCGGC
---------+---------+---------+---------+-----
 N  P  A  A  H  L  T  G  A  N  S  S  L  T  G
    230                 250               270

AGCGGGGGGCCGCTGTTATGGGAGACTCAGCTGGGCCTGGCCTTC
----+---------+---------+---------+---------+
 S  G  G  P  L  L  W  E  T  Q  L  G  L  A  F
                 290                  310

CTGAGGGGCCTCAGCTACCACGATGGGGCCCTTGTGGTCACCAAA
---------+---------+---------+---------+-----
 L  R  G  L  S  Y  H  D  G  A  L  V  V  T  K
              330                 350

GCTGGCTACTACTACATCTACTCCAAGGTGCAGCTGGGCGGTGTG
----+---------+---------+---------+---------+
 A  G  Y  Y  Y  I  Y  S  K  V  Q  L  G  G  V
           370                 390

GGCTGCCCGCTGGGCCTGGCCAGCACCATCACCCACGGCCTCTAC
---------+---------+---------+---------+-----
 G  C  P  L  G  L  A  S  T  I  T  H  G  L  Y
    410                 430                450

AAGCGCACACCCCGCTACCCCGAGGAGCTGGAGCTGTTGGTCAGC
----+---------+---------+---------+---------+
 K  R  T  P  R  Y  P  E  E  L  E  L  L  V  S
                 470                  490
```

FIG. 1C

```
CAGCAGTCACCCTGCGGACGGGCCACCAGCAGCTCCCGGGTCTGG
--------+---------+---------+---------+-----
 Q  Q  S  P  C  G  R  A  T  S  S  S  R  V  W
           510                530

TGGGACAGCAGCTTCCTGGGTGGTGTGGTACACCTGGAGGCTGGG
----+---------+---------+---------+---------+
 W  D  S  S  F  L  G  G  V  V  H  L  E  A  G
        550                570

GAGGAGGTGGTCGTCCGTGTGCTGGATGAACGCCTGGTTCGACTG
---------+---------+---------+---------+-----
 E  E  V  V  V  R  V  L  D  E  R  L  V  R  L
   590            610               630

CGTGATGGTACCCGGTCTTACTTCGGGGCTTTCATGGTGTGAAGG
----+---------+---------+---------+---------+
 R  D  G  T  R  S  Y  F  G  A  F  M  V  *
                 650              670

AAGGAGCGTGGTGCATTGGACATGGGTCTGACACGTGGAGAACTC
---------+---------+---------+---------+-----
          690              710

AGAGGGTGCCTCAGGGGAAAGAAAACTCACGAAGCAGAGGCTGGG
----+---------+---------+---------+---------+
          730              750

CGTGGTGGCTCTCGCCTGTAATCCCAGCACTTTGGGAGGCCAAGG
---------+---------+---------+---------+-----
          770              790             810

CAGGCGGATCACCTGAGGTCAGGAGTTCGAGACCAGCCTGGCTAA
----+---------+---------+---------+---------+
          830              850

CATGGCAAAACCCCATCTCTACTAAAAATACAAAAATTAGCCGGA
---------+---------+---------+---------+-----
           870             890

CGTGGTGGTGCCTGCCTGTAATCCAGCTACTCAGGAGGCTGAGGC
----+---------+---------+---------+---------+
          910              930

AGGATAATTTTGCTTAAACCCGGGAGGCGGAGGTTGCAGTGAGCC
---------+---------+---------+---------+-----
          950              970             990

GAGATCACACCACTGCACTCCAACCTGGGAAACGCAGTGAGACTG
----+---------+---------+---------+---------+
               1010

TGCCTCAAAAAAAACAAAAAAAAAAAAA
---------+---------+--------
```

```
    QTARQHPSMELAKSTLKPAAHLIGDPSS-- Majority
             190              200              210
 77 AGSWEQLIQERRSHEVNPAAHLTGANSSLT   Aim-2.aa
181 SCSNCKKSLECTKLCLPQIENVKGTEDSGT   huTNFalpha.prot
 46 QTARQHPKMHLAHSTLKPAAHLIGDPSK--   huTNFbeta.prot
 46 QTARQHPKMHLAHSTLKPAAHLIGDPSK--   huLymphotoxin.prot
128 EKQIGHPSPPPEKKELRKVAHLTGKSNS--   huFasLigand.prot -QN-PLL---------------------WE  Majority
             220              230              240
107 GSGGPLL---------------------WE  Aim-2.aa
211 TVLLPLVIFFGLCLLSLLFIGLMYRYQRWK  huTNFalpha.prot
 74 -QN-SLL---------------------WR  huTNFbeta.prot
 74 -QN-SLL---------------------WR  huLymphotoxin.prot
156 -RSMPLE---------------------WE  huFasLigand.prot ANLGRAF---------------------LQDG Majority
             250              260              270
116 TQLGLAF---------------------LR-G  Aim-2.aa
241 SKLYSIVCGKSTPEKEGELEGTTTKPLAPN   huTNFalpha.prot
 81 ANTDRAF---------------------LQDG huTNFbeta.prot
 81 ANTDRAF---------------------LQDG huLymphotoxin.prot
164 DTYGIVL---------------------L-SG huFasLigand.prot
```

FIG. 2D

```
        F S L S N G S L V V P T S G I Y F V Y S Q V V F S G K A Y S   Majority
                            280                 290                 300
126     L S Y H D G A L V V T K A G Y Y Y I Y S K V Q L G G V G C P   Aim-2.aa
271     P S F S P T P G F T P T L G F S P V P S S T F T S S S T Y T   huTNFalph.prot
 92     F S L S N N S L L V P T S G I Y F V Y S Q V V F S G K A Y S   huTNFbeta.prot
 92     F S L S N N S L L V P T S G I Y F V Y S Q V V F S G K A Y S   huLymphotoxin.prot
174     V K Y K K G G L V I N E T G L Y F V Y S K V Y F R G Q S C N   huFasLigand.prot P G A X S S P L Y L A H E V Q L R S S Q Y P F H V P L L S S   Majority
                            310                 320                 330
156     L G L A S T - - I T H G L Y K R T P R Y P E E L E L L V S     Aim-2.aa
301     P G D C P N F A A P R R E V - - A P P Y Q G A D P I L A T     huTNFalph.prot
122     P K A P S S P L Y L A H E V Q L F S S Q Y P F H V P L L S S   huTNFbeta.prot
122     P K A T S S P L Y L A H E V Q L F S S Q Y P F H V P L L S S   huLymphotoxin.prot
204     - - - N L P L S H K V Y M R N S K Y P Q D L V M M E G         huFasLigand.prot Q K M V Y - - - P G L Q E P W L D S S Y L G A A F Q L T Q G   Majority
                            340                 350                 360
183     Q Q S P C G R A T S S S R V W W D S S F L G G V V H L E A G   Aim-2.aa
328     A - L A S D P I P N P L Q K W E D S A H K P Q S L D T D D P   huTNFalph.prot
152     Q K M V Y - - - P G L Q E P W L H S M Y H G A A F Q L T Q G   huTNFbeta.prot
152     Q K M V Y - - - P G L Q E P W L H S M Y H G A A F Q L T Q G   huLymphotoxin.prot
228     K M M S Y - - - C T T G Q M W A R S S Y L G A V F N L T S A   huFasLigand.prot
```

```
                    DQLSVHVDGIPLLVLSEST-VFF-------  Majority

|------|------|------|
                    370    380    390

213  EEVVVRVLDERLVRLRDGTRSYF-------  Aim-2.aa
357  ATLYAVVENVPPLRWKEFVRRLGLSDHEID  huTNFalpha.prot
179  DQLSTHTDGIPHLVLSPST-VFF-------  huTNFbeta.prot
179  DQLSTHTDGIPHLVLSPST-VFF-------  huLymphotoxin.prot
255  DHLYVNSELSLVNFEESQ-TFF--------  huFasLigand.prot -------GAFA-L----------------  Majority

|------|------|
                    400    410    420

236  -------GAFMV-----------------  Aim-2.aa
387  RLELQNGRCLREAQYSMLATWRRRTPRREA  huTNFalpha.prot
201  -------GAFA-L----------------  huTNFbeta.prot
201  -------GAFA-L----------------  huLymphotoxin.prot
277  -------GLYK-L----------------  huFasLigand.prot
```

```
                430              440              450
       | - - - - | - - - - - - - - | - - - - - - - - | - - -    Majority 241                                                              Aim-2.aa
417    T L E L L G R V L R D M D L L G C L E D I E E A L C G P A A  huTNFalpha.prot
205                                                              huTNFbeta.prot
205                                                              huLymphotoxin.prot
281                                                              huFasLigand.prot

| - - - - | - - - - - - - - | - - - - - - - - | - - -    Majority

241                                                              Aim-2.aa
447    L P P A P S L L R                                         huTNFalpha.prot
205                                                              huTNFbeta.prot
205                                                              huLymphotoxin.prot
281                                                              huFasLigand.prot
```

DECORATION 'DECORATION #1': SHADE (WITH SOLID BRIGHT COLBALT) RESIDUES THAT MATCH Aim-2.aa EXACTLY.

| CELL LINES | LTγ EXPRESSION[1] | LTβR EXPRESSION[1] | TR2 EXPRESSION[1] | GROWTH INHIBITION BY LTγ[2] |
|---|---|---|---|---|
| MDA-MB-231 | − | ++ | ++ | ++ |
| MCF-7 | − | ++ | ++ | ++ |
| HT-29 | − | +++ | ++ | ++++ |
| MC-3 | − | ++ | − | − |
| U93T | − | − | + | − |
| MCF-10A | ++ | + | ± | − |
| PBMC[3] | + | − | + | − |
| T-CELLS | + | − | ++ | − |
| TIL 1200 | + | − | + | − |
| Jurkat | − | − | + | − |

1. EXPRESSION OF LTγ WAS DETERMINED BY RT-PCR ASSAY; EXPRESSION OF LTβR AND TR2 WAS DETERMINED BY FACS ANALYSIS;
2. CYTOTOXICITY WAS CARRIED OUT WITH 50ng/ml OF LTγ IN THE PRESENCE OF 10 μ/ml OF IFNγ. +: 30% INHIBITION, ++:50% INHIBITION, +++;80% INHIBITION, −: LESS THAN 10% INHIBITION.
3. LTγ WAS FOUND ONLY IN ACTIVATED PBMC NOT IN RESTING PBMC.

FIG.8L

```
                                         -35      OPERATOR 1
1   AAGCTTAAAAAACTGCAAAAAATAGT TTGACT TGTGAGCGGATAACAAT

-10                  OPERATOR 2
50  TAAGAT GTACCCA ATTGTGAGCGGATAACAAT TTCACACATTAA

S/D
94  AGAGGAG AAATTA CATATG
```

FIG.11

MRALEGPGLSLLCLVLALPALLPVPAVRGVAETPTYPWRDAETGERLVCAQCPPGTFVQRPCRRDSPTTC
GPCPPRHYTQFWNYLERCRYCNVLCGEREEEARACHATHNRACRCRTGFFAHAGFCLEHASCPPGAGVIA
PGTPSQNTQCQPCPPGTFSASSSSSEQCQPHRNCTALGLALNVPGSSSHDTLCTSCTGFPLSTRVPGAEE
CERAVIDFVAFQDISIKRLQRLLQALEAPEGWGPTPRAGRAALQLKLRRRLTELLGAQDGALLVRLLQAL
RVARMPGLERSVRERFLPVH

| | | | | | | |
|---|---|---|---|---|---|---|
| TNFR-I | V C PQCKYIHPQNNSI | | C TK | C HKGTYLYND | C PGPGQDTD | C R |
| TNFR-II | T C RLREYDQTAQM | | C SK | C SPGQHAKVF | C TKTSDTV | C D |
| 4-1BB | — | | — | C PAGTF | C DNNRNQI | C S |
| TR2(HVEM) | S C KEDEYPVGSE | C | C PK | C SPGYRVKEA | C GELGTV | C E |
| LTβR | T C RDQEKEYYEPQHRI | C | C SR | C PPGTYVSAK | C SRIRDTV | C A |
| TR1(OPG) | — | | C DK | C PPGTYLKQH | C TAKWKTV | C A |
| TRG | — | | C AQ | C PPGTFVQRP | C RRDSPTT | C G |
| | | | | | | |
| TNFR-I | E C ESGSFTASENHLRH | C LS | C SK | C RKEMGQVELSS | C TVDRDTV | C G |
| TNFR-II | S C EDSTYTQLWNWVPE | C LS | C GSR | C SSDQVETQA | C TREQNRI | C T |
| 4-1BB | P C PPNSFSSAGGQRT | C DI | C RQ | C KGVFRTRKE | C SSTSNAE | C D |
| TR2(HVEM) | P C PPGTYTAHLNCLSK | C LQ | C QM | C DPAMGLRASRN | C SRTENAV | C G |
| LTβR | T C AENSYNEHMNYLII | C QL | C RP | C DPVMGLEETAP | C TSKRKTQ | C R |
| TR1(OPG) | — | C LY | C SPV | C KELQYVKQE | C NRTHNRV | C E |
| TRG | P C PPRHYTQFWNYLER | C RY | C NVL | C GEREEEARA | C HATHNRA | C R |
| | | | | | | |
| TNFR-I | C RKNQYRHYWSENLFQ | C FN | C SL | C LNGTVHLS | C QEKQNTV | C T |
| TNFR-II | C RPGWY C ALSKQEG | C RL | C APLRK | C RPGFGVARP | G TETSDVV | C K |
| 4-1BB | C TPGFH C LGAG | C SM | C EQD | C KQGQELTKKG | C KD | C — |
| TR2(HVEM) | C SPGHF C IVQDGDH | C A | C RAYAT | S SPGQRVQKG | G TEAQDTL | C Q |
| LTβR | C QPGMF C AAWALE | C TH | C ELLSD | C PPGTEAELKDEV | G KGNNH | C V |
| TR1(OPG) | C KEGRYLEIE F | C LK | C RS | C PPGFGVVQA | G TPERNTV | C K |
| TRG | C RTGFFAHAGF | C LE | C HAS | C PPGAGVIAP | G TPSQNTQ | C Q |
| | | | | | | |
| TNFR-I | — C HAGFFLRENE | C VS | C SN | C KKSLE | C TKL | C L |
| TNFR-II | P C APGTFSNTTSSTDI | C RP | C HQI | C NVVAIP | G NASMDAV | C T |
| 4-1BB | — C F-GTFNKQKRGI | C RP | C H WTN | C SLDGKSVLVN | G TKERDVV | C G |
| TR2(HVEM) | N C PPGTFSPNGTLEE | C QH | C QTK | C SWLVTKA | G AGTSSSH | W V |
| LTβR | P C KAGHFQNTSSPSAR | C QP | C H TR | C ENQGLVEAAP | G TAQSDTT | C K |
| TR1(OPG) | R C PDGFFSNETSSKAP | C RK | C H TN | C SVFGLLLTQK | G NATHDNI | C S |
| TRG | P C PPGTFSASSSSSEQ | C QP | C H RN | C TALGLALNVP | G SSSHDTL | C T |

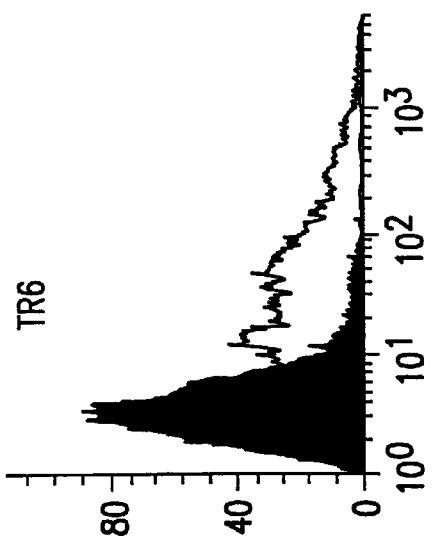
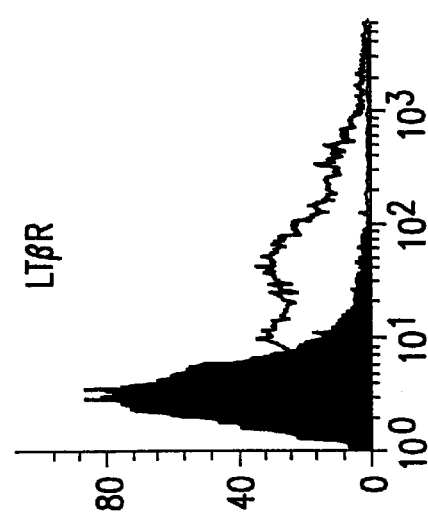
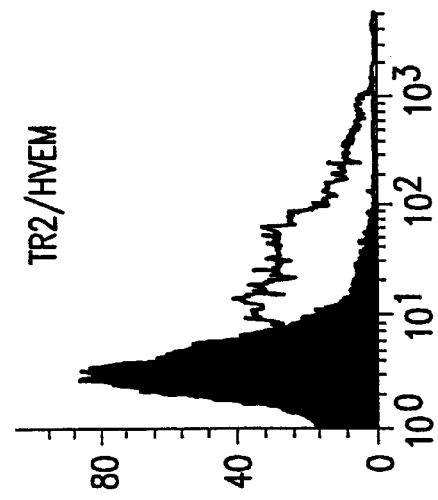

FIG. 17A

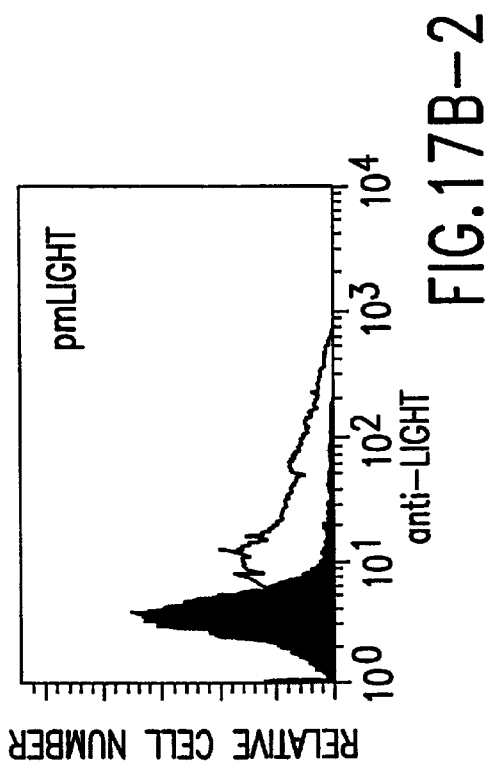
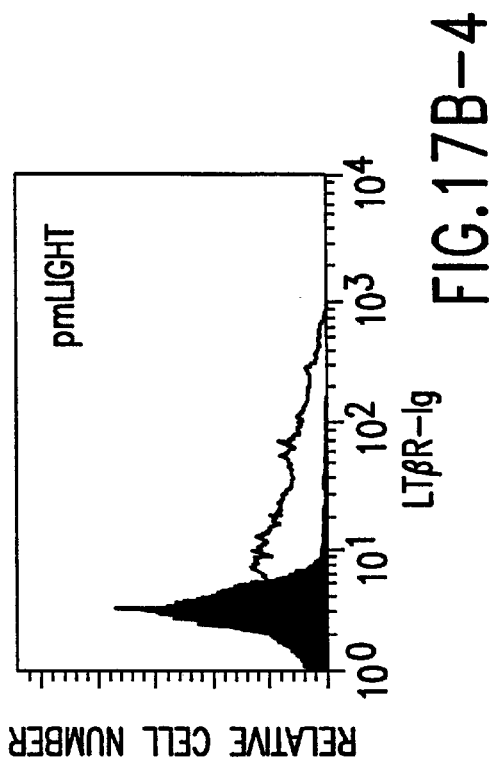
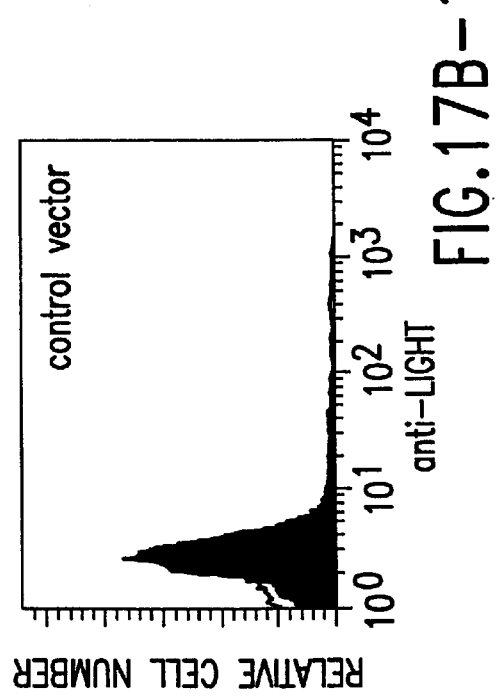
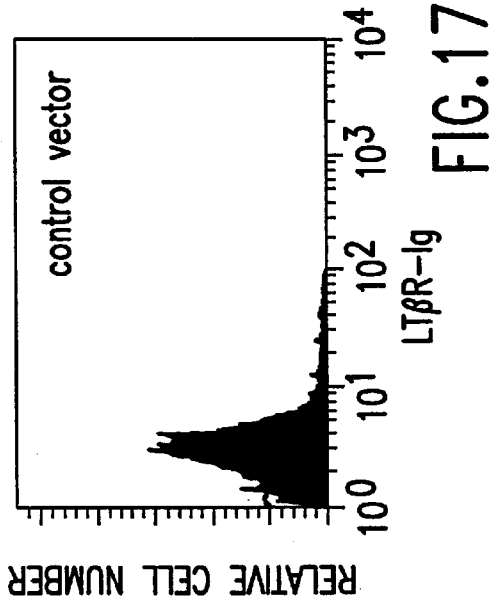

APOPTOSIS INDUCING MOLECULE II AND METHODS OF USE

CROSS-REFERENCE TO RELATED APPLICATIONS

The present application claims benefit to the filing dates of U.S. Provisional Application No. 60/168,380, filed Dec. 2, 1999; U.S. Provisional Application No. 60/148,326, filed Aug. 11, 1999; U.S. Provisional Application No. 60/142,657, filed Jul. 6, 1999; U.S. Provisional Application No. 60/137,457, filed Jun. 4, 1999; and U.S. Provisional Application No. 60/124,041, filed Mar. 11, 1999, and is a continuation-in-part of U.S. application Ser. No. 09/252,656, filed Feb. 19, 1999 now U.S. Pat. No. 6,495,520, each of which is incorporated herein by reference; said Ser. No. 09/252,656 claims benefit to the filing date of U.S. Provisional Application No. 60/075,409, filed Feb. 20, 1998, and is a continuation-in-part of U.S. application Ser. No. 09/027,287, filed on Feb. 20, 1998 now U.S. Pat. No. 6,479,254, each of which is herein incorporated by reference; said Ser. No. 09/027,287 is a continuation-in-part of U.S. application Ser. No. 09/003,886, filed Jan. 7, 1998 now abandoned, which is herein incorporated by reference; said Ser. No. 09/003,886 is a continuation-in-part of U.S. application Ser. No. 08/822,953, filed Mar. 21, 1997 now abandoned, which is herein incorporated by reference; said Ser. No. 08/822,953 claims benefit to the filing dates of U.S. Provisional Application No. 60/013,923, filed Mar. 22, 1996 and U.S. Provisional Application No. 60/030,157, filed Oct. 31, 1996, each of which is incorporated herein by reference.

FIELD OF THE INVENTION

The present invention relates to a novel member of the TNF-Ligand superfamily. More specifically, isolated nucleic acid molecules are provided encoding a human Apoptosis Inducing Molecule II (AIM II). AIM II polypeptides are also provided, as are vectors, host cells and recombinant methods for producing the same. The invention further relates to screening methods for identifying agonists and antagonists of AIM II activity. Also provided are therapeutic methods for treating lymphadenopathy, aberrant bone development, autoimmune and other immune system diseases, graft versus host disease, rheumatoid arthritis, osteoarthritis and to inhibit neoplasia, such as tumor cell growth.

RELATED ART

Human tumor necrosis factors a (TNF-α) and β (TNF-β, or lymphotoxin) are related members of a broad class of polypeptide mediators, which includes the interferons, interleukins and growth factors, collectively called cytokines (Beutler, B. and Cerami, A., *Annu. Ret. Immunol.* 7:625–655 (1989)).

Tumor necrosis factor (TNF-α and TNF-β) was originally discovered as a result of its anti-tumor activity, however, now it is recognized as a pleiotropic cytokine capable of numerous biological activities including apoptosis of some transformed cell lines, mediation of cell activation and proliferation and also as playing important roles in immune regulation and inflammation.

To date, known members of the TNF-ligand superfamily include TNF-α, TNF-β (lymphotoxin-α), LT-β, OX40L, Fas ligand, CD30L, CD27L, CD40L and 4-IBBL. The ligands of the TNF ligand superfamily are acidic, TNF-like molecules with approximately 20% sequence homology in the extracellular domains (range, 12%–36%) and exist mainly as membrane-bound forms with the biologically active form being a trimeric/multimeric complex. Soluble forms of the TNF ligand superfamily have only been identified so far for TNF, LTα, and Fas ligand (for a general review, see Gruss, H. and Dower, S. K., *Blood*, 85(12):3378–3404 (1995)), which is hereby incorporated by reference in its entirety.

These proteins are involved in regulation of cell proliferation, activation, and differentiation, including control of cell survival or death by apoptosis or cytotoxicity (Armitage, R. J., *Curr. Opin. Immunol.* 6:407 (1994) and Smith, C. A., *Cell* 75:959 (1994)).

Mammalian development is dependent on both the proliferation and differentiation of cells as well as programmed cell death which occurs through apoptosis (Walker et al., *Methods Achiev. Exp. Pathol.* 13:18 (1988). Apoptosis plays a critical role in the destruction of immune thymocytes that recognize self antigens. Failure of this normal elimination process may play a role in autoimmune diseases (Gammon et al., *Immunology Today* 12:193 (1991)).

Itoh et al. (*Cell* 66:233(1991)) described a cell surface antigen, Fas/CD95 that mediates apoptosis and is involved in clonal deletion of T-cells. Fas is expressed in activated T-cells, B-cells, neutrophils and in thymus, liver, heart and lung and ovary in adult mice (Watanabe-Fukunaga et al., *J. Immunology.* 148: 1274 (1992)). In experiments where a monoclonal Ab to Fas is cross-linked to Fas, apoptosis is induced (Yonehara et al., *J. Exp. Med.* 169:1747 (1989); Trauth et al., *Science* 245:301 (1989)). In addition, there is an example where binding of a monoclonal Ab to Fas may stimulate T-cells under certain conditions (Alderson et al., *J. Exp. Med.* 178:2231 (1993)).

Fas antigen is a cell surface protein of relative MW of 45 Kd. Both human and murine genes for Fas have been cloned by Watanabe-Fukunaga et al., (*J. Immunol.* 148:1274 (1992)) and Itoh et al. (*Cell* 66:233 (1991)). The proteins encoded by these genes are both transmembrane proteins with structural homology to the Nerve Growth Factor/Tumor Necrosis Factor receptor superfamily, which includes two TNF receptors, the low affinity Nerve Growth Factor receptor and the $LT_\beta$ receptor CD40, CD27, CD30, and OX40.

Recently the Fas ligand has been described (Suda et al., *Cell* 75:1169 (1993)). The amino acid sequence indicates that Fas ligand is a type II transmembrane protein belonging to the TNF family. Fas ligand is expressed in splenocytes and thymocytes. The purified Fas ligand has a MW of 40 kd.

Recently, it has been demonstrated that Fas/Fas ligand interactions are required for apoptosis following the activation of T-cells (Ju et al., *Nature* 373:444 (1995); Brunner et al., *Nature* 373:441 (1995)). Activation of T-cells induces both proteins on the cell surface. Subsequent interaction between the ligand and receptor results in apoptosis of the cells. This supports the possible regulatory role for apoptosis induced by Fas/Fas ligand interaction during normal immune responses.

The polypeptide of the present invention has been identified as a novel member of the TNF ligand super-family based on structural and biological similarities.

Clearly, there is a need for factors that regulate activation, and differentiation of normal and abnormal cells. There is a need, therefore, for identification and characterization of such factors that modulate activation and differentiation of cells, both normally and in disease states. In particular, there is a need to isolate and characterize additional Fas ligands that control apoptosis for the treatment of autoimmune disease, graft versus host disease, rheumatoid arthritis and lymphadenopathy.

SUMMARY OF THE INVENTION

The present invention provides isolated nucleic acid molecules comprising, or alternatively consisting of, a polynucleotide encoding the AIM II polypeptide having the amino acid sequence shown in FIGS. 1A and 1B (SEQ ID NO:2) or the amino acid sequence encoded by the cDNA deposited as ATCC Deposit Number 97689 on Aug. 22, 1996. The present invention also provides isolated nucleic acid molecules comprising, or alternatively consisting of, a polynucleotide encoding the AIM II polypeptide having the amino acid sequence shown in FIGS. 1C and 1D (SEQ ID NO:39) or the amino acid sequence encoded by the cDNA deposited as ATCC Deposit Number 97483 on Mar. 15, 1996.

The present invention also relates to recombinant vectors, which include the isolated nucleic acid molecules of the present invention, and to host cells containing the recombinant vectors, as well as to methods of making such vectors and host cells and for using them for production of AIM II polypeptides or peptides by recombinant techniques.

The invention further provides an isolated AIM II polypeptide having an amino acid sequence encoded by a polynucleotide described herein.

As used herein the term "AIM II" polypeptide includes membrane-bound proteins (comprising, or alternatively consisting of, a cytoplasmic domain, a transmembrane domain, and an extracellular domain) as well as truncated proteins that retain the AIM II polypeptide activity. In one embodiment, soluble AIM II polypeptides comprise, or alternatively consist of, all or part of the extracellular domain of an AIM II protein, but lack the transmembrane region that would cause retention of the polypeptide on a cell membrane. Soluble AIM II may also include part of the transmembrane region or part of the cytoplasmic domain or other sequences, provided that the soluble AIM II protein is capable of being secreted. A heterologous signal peptide can be fused to the N-terminus of the soluble AIM II polypeptide such that the soluble AIM II polypeptide is secreted upon expression.

The invention also provides for AIM II polypeptides, particularly human AIM II polypeptides, which may be employed to treat afflictions such as lymphadenopathy, rheumatoid arthritis, autoimmune disease (e.g., inflammatory autoimmune diseases, myasthenia gravis), graft versus host disease, IgE-mediated allergic reactions, anaphylaxis, adult respiratory distress syndrome, Crohn's disease, allergic asthma, acute lymphoblastic leukemia (ALL), non-Hodgkin's lymphoma (NHL), and Graves' disease. These polypeptides of the invention may also be used to stimulate peripheral tolerance, destroy some transformed cell lines, mediate cell activation and proliferation and are functionally linked as primary mediators of immune regulation and inflammatory response.

The invention further provides compositions comprising, or alternatively consisting of, an AIM II polynucleotide or an AIM II polypeptide for administration to cells in vitro, to cells ex vivo and to cells in vivo, or to a multicellular organism. In certain particularly preferred embodiments of this aspect of the invention, the compositions comprise, or alternatively consist of, an AIM II polynucleotide for expression of an AIM II polypeptide in a host organism for treatment of disease. Particularly preferred in this regard is expression in a human patient for treatment of a dysfunction associated with aberrant endogenous activity of an AIM II.

The present invention also provides a screening method for identifying compounds capable of enhancing or inhibiting a cellular response induced by AIM II, which involves contacting cells which express AIM II with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for AIM II agonists and antagonists is provided. The antagonists may be employed to treat, prevent, diagnose, and/or prognose septic shock, inflammation, cerebral malaria, activation of the HIV virus, graft-host rejection, immunodeficiency, bone resorption, and cachexia (wasting or malnutrition). In a preferred embodiment, the AIM II antagonists of the invention (e.g., anti-AIM II antibodies) are used to treat, prevent, diagnose, and/or prognose graft versus host disease.

In a further aspect of the invention, AIM II may be used to treat rheumatoid arthritis (RA) by inhibiting the increase in angiogenesis or increase in endothelial cell proliferation required to sustain an invading pannus in bone and cartilage as is often observed in RA.

In an additional aspect of the invention, AIM II may be used to inhibit or activate a cellular response mediated by a cellular receptor (e.g., LT-β-R, TR2, CD27, and TRANK) by either inhibiting the binding of a ligand to the receptor or by binding to the receptor and activating a receptor mediated cellular response.

An additional aspect of the invention is related to a method for treating an individual in need of an increased level of AIM II activity in the body comprising administering to such an individual a composition comprising, or alternatively consisting of, a therapeutically effective amount of an isolated AIM II polypeptide of the invention or an agonist thereof.

A still further aspect of the invention is related to a method for treating an individual in need of a decreased level of AIM II activity in the body comprising, administering to such an individual a composition comprising, or alternatively consisting of, a therapeutically effective amount of an AIM II antagonist.

BRIEF DESCRIPTION OF THE FIGURES

FIG. 4B shows colony formation of MDA-MB-231/WT, MDA-MB-231/Neo and MDA-MB-231/AIM II cells in 0.33% agarose.

FIGS. 8A–8M. Cell surface expression of the LTβR or TR2 by the FACS analyses using LTβR (FIGS. 8A–8D) or TR2 (FIGS. 8E–8H) mAb. MDA-MB-231 (FIGS. 8A and 8E), HT-29 (FIGS. 8B and 8F), MC-3 (FIGS. 8C and 8G), U93T (FIGS. 8D and 8H). FACS binding analyses of soluble AIM II protein alone (FIG. 8I) and blocking of a soluble AIM II protein binding by preincubation with the LTβR-Fc fusion protein (FIG. 8J) or TR2-Fc fusion protein (FIG. 8K) in MDA-MB-231 cells. FIG. 8L summarizes the surface expression of LTβR and TR2 in various cell lines. Effects of LTβR-Fc or TR2-Fc fusion protein to block the sAIM II-mediated cytotoxicity in HT-29 cells (FIG. 8M). Cells were plated into 96-well plates and sAIM II (10 ng/ml) was added in the presence of 5 U/ml of IFNγ with various amounts of sLTβR-Fc (open circle with LTβR-Fc alone, filled circle LTβR-Fc, and IFNγ) or TR2-Fc fusion protein (open triangle with TR-2Fc alone, filled triangle TR2-Fc with sLTγ and IFNγ). Cells were incubated for five days and the viability of cells was determined by XTT assays.

FIG. 11 shows the nucleotide sequence of the regulatory elements of the pHE promoter (SEQ ID NO:51). The two lac operator sequences, the Shine-Delgarno sequence (S/D), and the terminal HindIII and NdeI restriction sites (italicized) are indicated.

FIGS. 14A–14B show the sequence of TR6 and aligned amino acid sequence of cysteine-rich motif (A) Shows a deduced amino acid sequence of TR6 (SEQ ID NO:52). The signal sequence is underlined. The potential N-glycosylation site (NCT, amino acid residues 173–175) is boxed. The N-terminal amino acid sequence of recombinant TR6-(His) reads as VAETPT - - - , which indicates that the first 29 amino acids constitute a signal sequence. (B) Shows an aligned amino acid sequence of cysteine-rich motif of TR6 with other TNF receptor family members (SEQ ID NO:53–58). The amino acid sequence of TR6 (SEQ ID NOs:52 and 59) was aligned with those of TNFR-I, TNFR-II, 4-1BB, TR2 (HVEM), LTβR and TR1 (OPG) on the basis of sequence homology and conserved cysteines.

FIGS. 15A–15C show the identification of the membrane-bound TR6 ligand. HEK293 EBNA cells were transfected with pCEP4 control vector (shaded area) or with pCEP4/ encoding full-length AIM II (LIGHT) cDNA (solid line). Cells were incubated with (A) HVEM/TR2-Fc (0.34 (g), (B) LTβR-Fc (0.34 (g), (C) TR6-(His) (0.34 (g) or buffer control (same as vector). Cells were stained with anti-hIgG-FITC for detecting HVEM/TR2 and LTβR binding. For detecting TR6 binding, cells were stained with anti-poly(His) and anti-mIgG-FITC. They were analyzed for binding by FACS.

FIG. 17 shows the amino acid sequence and expression of mouse AIM II (LIGHT). The putative amino acid sequence of mouse AIM II deduced from the cDNA sequence was aligned with that of human AIM II (FIG. 17A). To obtain the optimal alignment, several gaps (−) were introduced with the ClustalW program using Macvector software (version 6.5). Homology regions are boxed and identical residues shaded. The transmembrane region (TM) is underlined. The asterisk (*) indicates the position of the predicted N-glycosylation site. The amino acid numbers are shown on the sides of the alignment. The data shown in FIG. 17B was generated using human 293 cells transfected with the pmAIM II ("pmLIGHT," FIGS. 17B-2 and 17B-4) or pcDNA3 ("control," FIGS. 17B-1 and 17B-3) and stained with LTβR-Ig (FIGS. 17B-3 and 17B-4) or the anti-AIM II antibody ("anti-LIGHT," FIGS. 17B-1 and 17B-2)), followed by FITC-conjugated goat anti-human IgG or anti-rabbit IgG, respectively (solid line). Staining with human IgGI or rabbit IgG were used as controls (shaded area).

Figures 1, 19A:
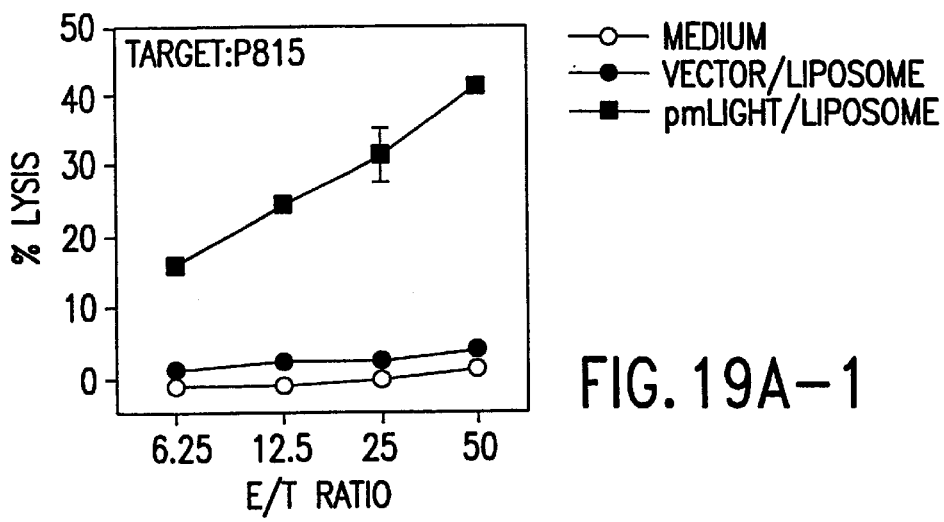
FIGS. 1A and 1B show the nucleotide (SEQ ID NO:1) and deduced amino acid (SEQ ID NO:2) sequences of AIM II. The protein has a deduced molecular weight of about 26.4 kDa. The predicted Transmembrane Domain of the AIM II protein is underlined.
FIGS. 1C and 1D show the nucleotide (SEQ ID NO:38) and deduced amino acid (SEQ ID NO:39) sequences of a partial AIM II cDNA that was also obtained.
FIG. 19 shows that AIM II DNA injection induces enhanced cytolytic T cell (CTL) responses and regression of established P815 tumor with memory tumor immunity. To generate the data shown in FIG. 19A, DBA/2 mice were inoculated with 2×10$^5$ cells of P815 cells at day 0 and then intratumorally injected with medium, pcDNA3 or pmAIM II mixed with liposome at day 7, 9 and 11. Seven days after last injection, spleen cells were harvested and re-stimulated with irradiated P815 cells for 4 days. The CTL activity was assessed by a standard 4 hr $^{51}$Cr release assay against P815 (FIG. 19A-1) and L1210 (FIG. 19A-2) cells in indicated effector:target (E/T) ratios. The results are expressed as the means±SD of triplicate wells. Similar results were obtained in three independent experiments.
Figures 2, 19A:
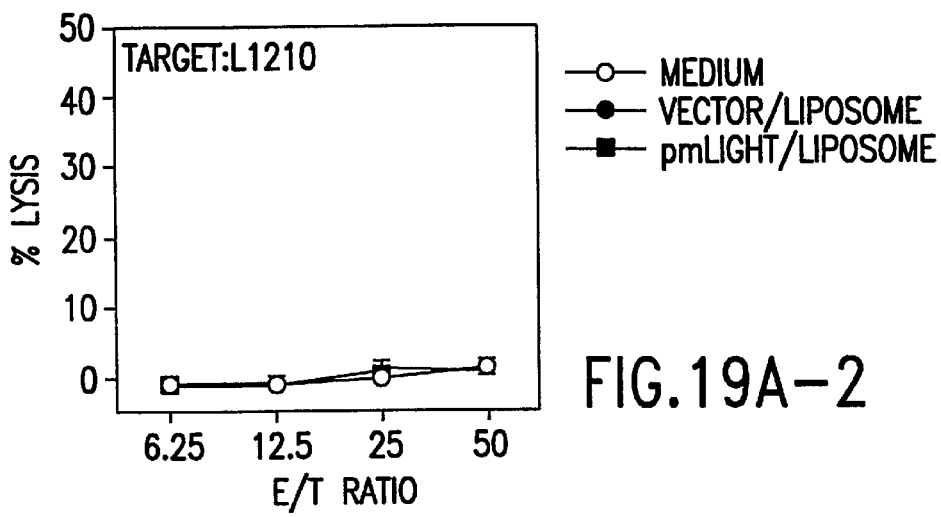
FIGS. 2A–2F show the regions of similarity between the amino acid sequences of the AIM II protein and human TNF-α (SEQ ID NO: 3), human TNF-β (SEQ ID NO:4), human lymphotoxin (SEQ ID NO:5) and human Fas Ligand (SEQ ID NO:6).
Figure 19B:
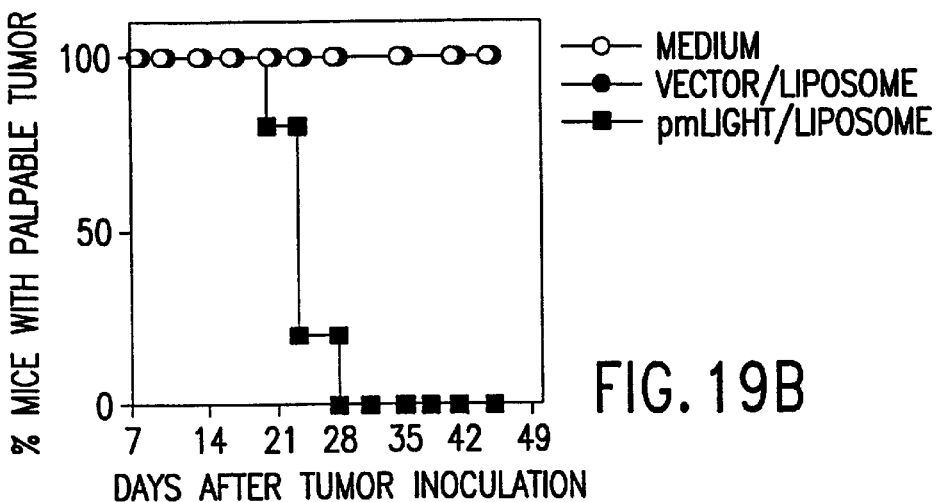

To generate the data shown in FIG. 19B, DBA/2 mice were inoculated s.c. with 2×10$^5$ cells of P815 cells at day 0. Seven days later the mice with palpable tumor nodules were intratumorally injected with either medium, pcDNA3 or pmAIM II mixed with liposome. The injections were repeated on day 10, 14 and 17. Tumor sizes were assessed by measuring diameters, and the tumor with more than 2 mm in the longest diameter was considered as a palpable tumor. The results are expressed as percentage of mice with palpable tumor. Similar results were obtained in three independent experiments.

Figures 1, 19C:
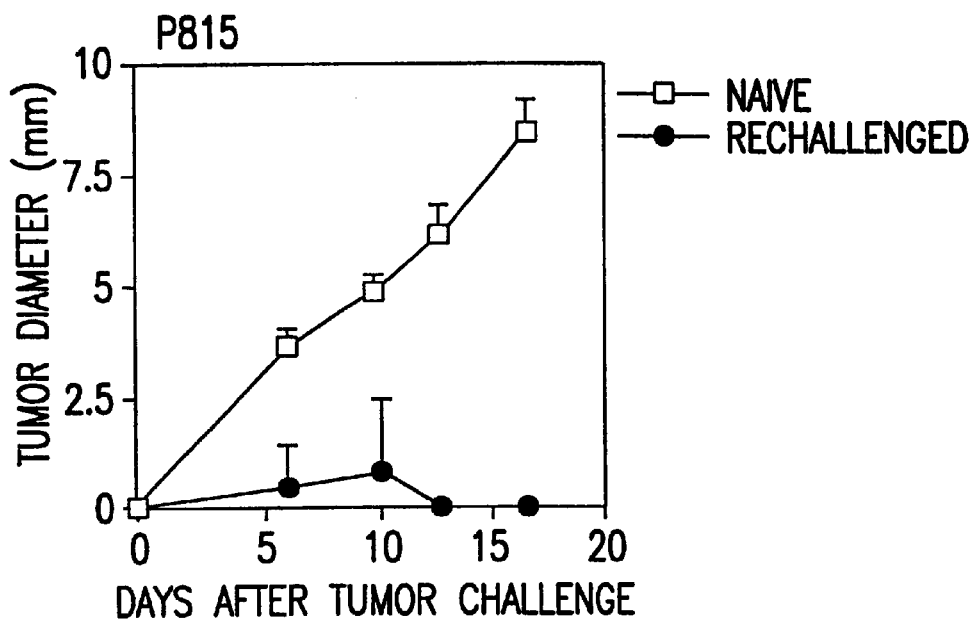
Figures 2, 19C:
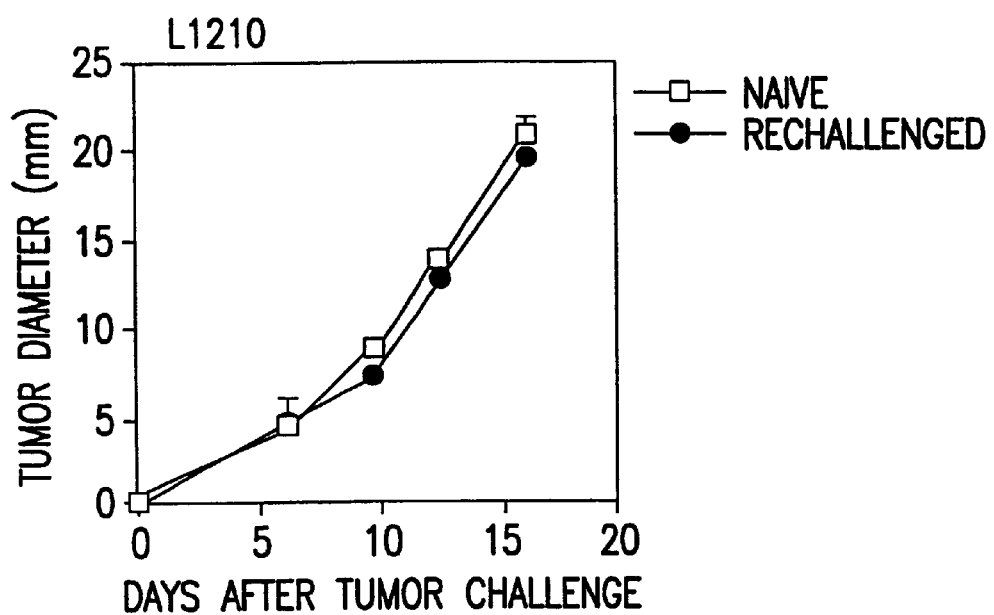

To generate the data shown in FIG. 19C, the mice which had regressed P815 tumor after pmAIM II treatment were s.c. challenged with 2×10$^5$ P815 cells at the right back (FIG. 19C-1) and the same number of L1210 cells at the left back (FIG. 19C-2) 40 days after primary tumor inoculation. Naive DBA/2 mice receiving both P815 and L1210 challenges were used as controls. Tumor sizes were assessed by measuring perpendicular diameters. The results are expressed as average±SD of 5 mice in each group.

FIG. 20 shows the inhibition of GVHD by blockage of AIM II. (FIGS. 20A and 20B) Sub-lethally (4 Gy) irradiated BDF1 mice were injected i.v. with 7×10$^7$ cells of B6 splenocytes on day 0. The recipient mice were administered i.v. with either LTβR-Ig or control human IgG1 at 100 μg per mouse on day—1, 2, 5, 8, 11, 14 and 17 (control Ig were administered until day 11 because all mice died in day 12). The survival (FIG. 20A) and body weight (FIG. 20B) of the recipients were monitored daily. The results in FIG. 20B are expressed as average grams±SEM of five mice in each group.

Non-irradiated BDF1 mice were injected i.v. with 7×10$^7$ cells of either B6 (B6-F1) or BDF1 (F1-F1) splenocytes on day 0. The recipient mice were administered i.v. with either LTβR-Ig or control human IgG1 at 100 μg/mouse on day—1, 1, 3, 5, 7, 9. At day 11, the splenocytes were prepared from the recipient mice and assayed for their CTL activity against P815 (H-2$^d$) (FIG. 20C-2) and EL-4 (H-2$^b$) (FIG. 20C-2) in a standard $^{51}$Cr release assay without further stimulation in vitro.

Figure 20A:
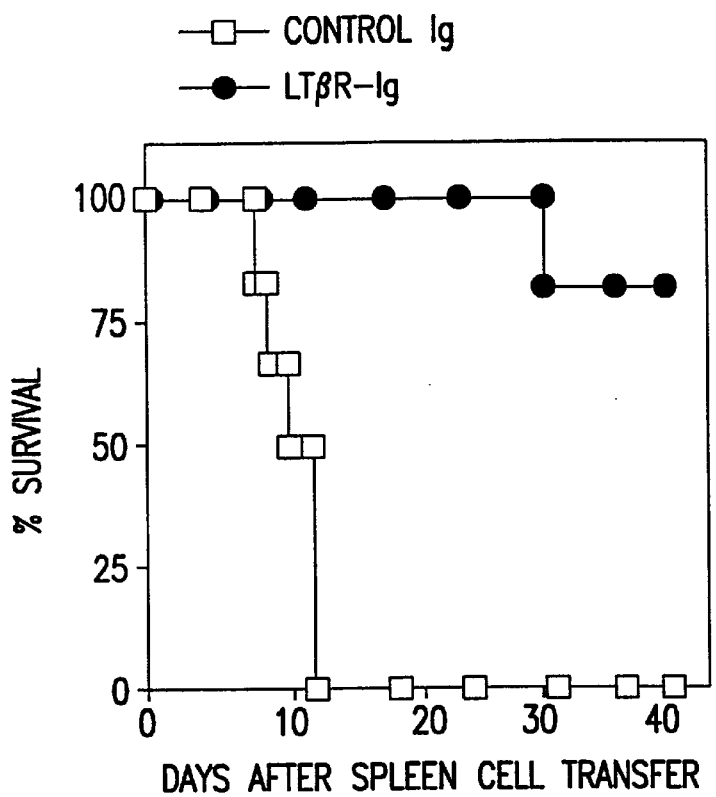
Figure 20B:
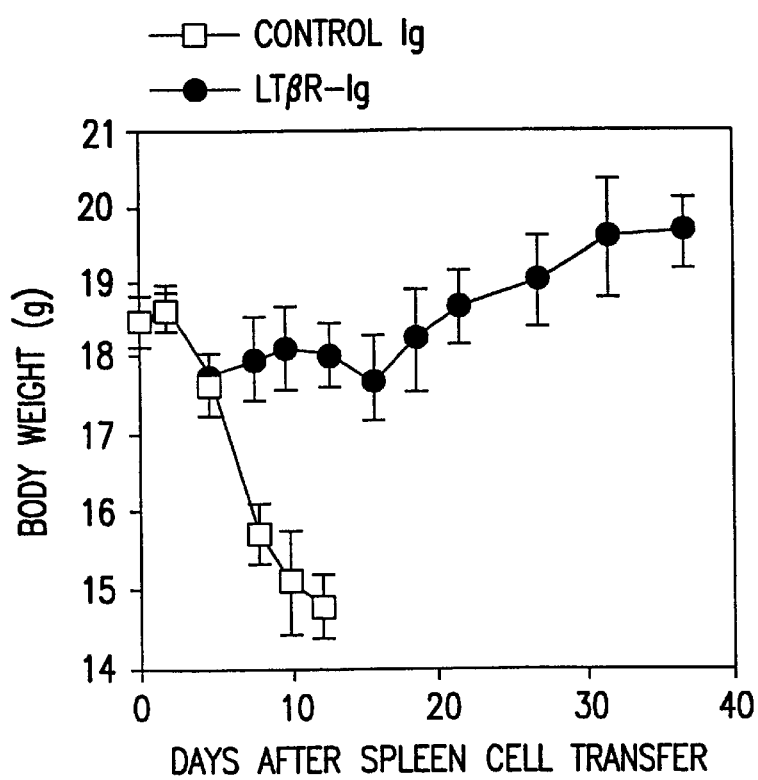
Figures 1, 20C:
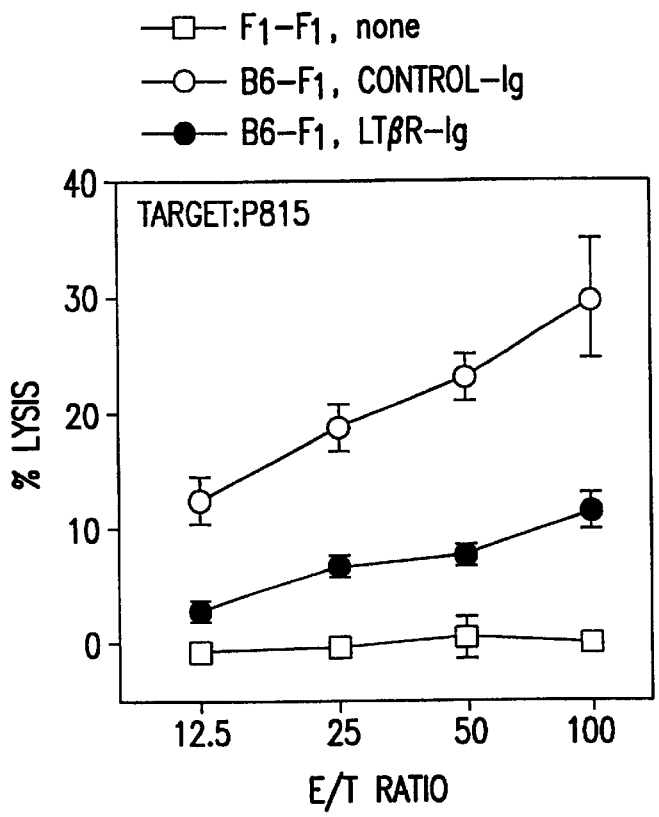
Figures 2, 20C:
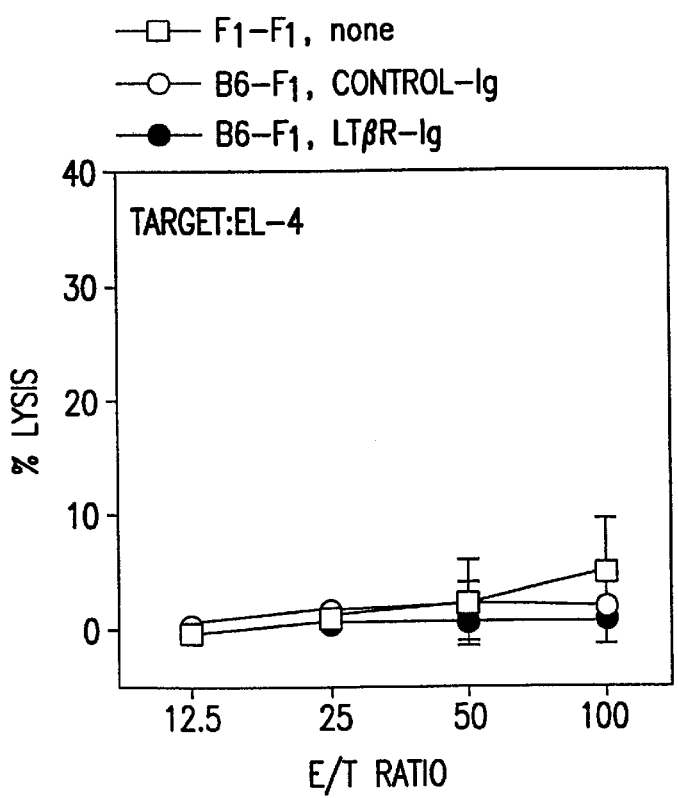
Figures 1, 20D:
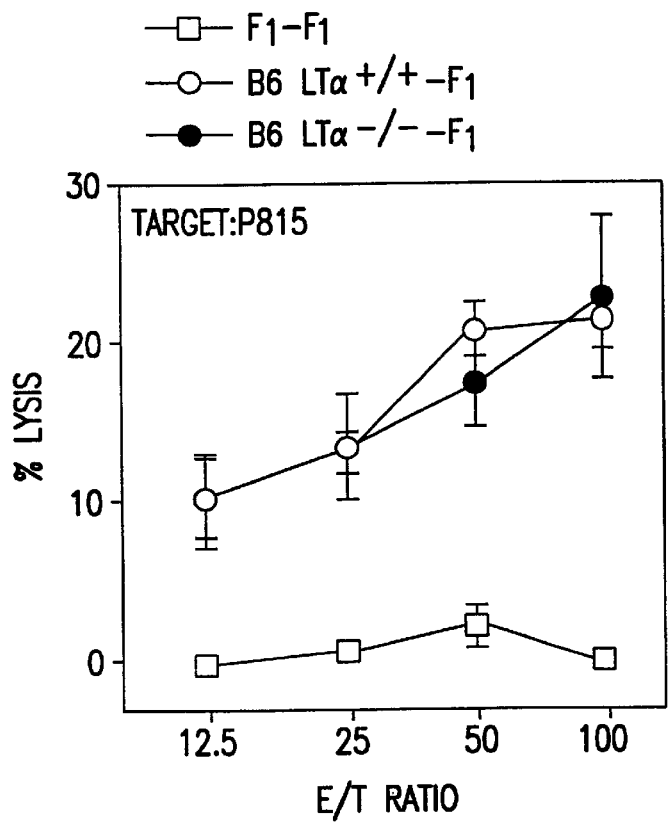
Figures 2, 20D:
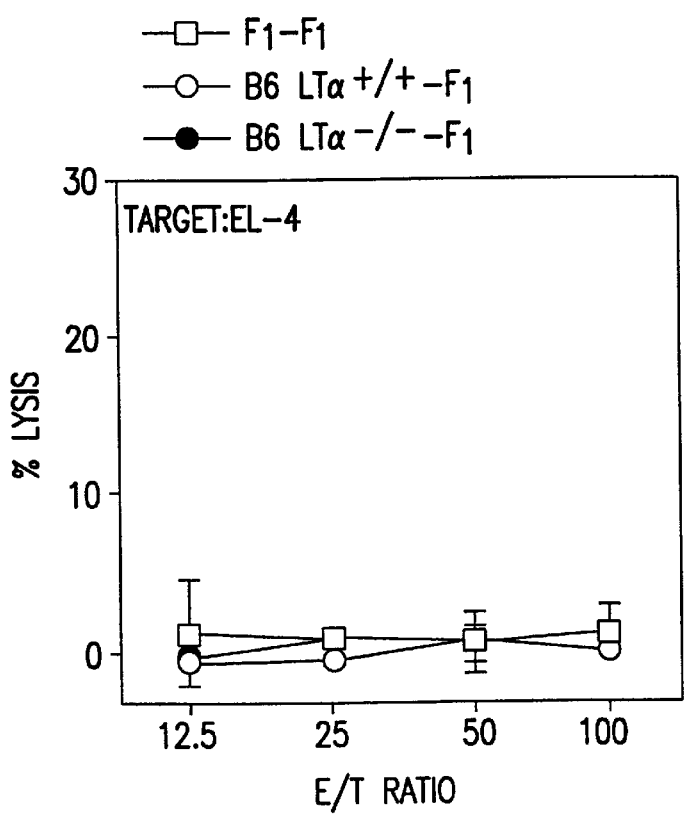

Non-irradiated BDF1 mice were injected i.v. with 7×10$^7$ cells of B6 LTα$^{-/-}$ or LTα$^{+/+}$ splenocytes on day 0. BDF1 mice injected with BDF1 splenocytes (7×10$^7$ cells) were used as controls (F1-F1). On day 11, CTL activity of recipient splenocytes were assessed as described above. (FIGS. 20D-1 and 20D2).

Purified T cells (1×10$^6$ cells/ml) of B6 LTα$^{-/-}$ splenocytes were cultured with irradiated BALB/c splenocytes (1×10$^6$ cells/ml) in the presence of 25 μg of LTβR-Ig or control human IgG1. After 5 days, the CTL activity against C26 (H-2$^d$) (FIG. 20E-1) and EL-4 (H-2$^b$) (FIG. 20E-2) was examined in a standard $^{51}$Cr release assay. The results are expressed as the means±SD of triplicate wells (FIGS. 20C1-2, 20D1-2, and 20E1-2).

FIG. 21 shows cytokine production by modulation of AIM II costimulatory pathway. Purified T cells (1×10$^6$ cells/ml) were stimulated with immobilized AIM II.flag fusion protein (3.2 μg/ml) in 96-well flat-bottomed microplates in the presence or absence of immobilized anti-CD3 (0.5 μg/ml). After 48 hours, the culture supernatants were collected and the cytokine production was assessed by sandwich ELISA. The cytokines measured were interferon-γ (FIG. 21A-1), GM-CSF (FIG. 21A-2), interleukin-4 (FIG. 21A-3), and interleukin-10 (FIG. 21A-4). The data shown in FIG. 21B was generated using T cells (1×10$^6$ cells/ml) purified from LTα$^{-/-}$ splenocytes cultured with irradiated BALB/c splenocytes (1×10$^6$ cells/ml) in the presence of 25 μg/ml of LTβR-Ig fusion protein or control human IgG1. After 72 hours, the culture supernatants were harvested and the cytokine production was assessed by sandwich ELISA. The cytokines measured were interferon-γ (FIG. 21B-1), GM-CSF (FIG. 21B-2), interleukin-4 (FIG. 21B-3), and interleukin-10 (FIG. 21B-4). IL-10 was not detectable (n.d.) (<0.3 ng/ml) in all wells.

DETAILED DESCRIPTION

The present invention provides isolated nucleic acid molecules comprising, or alternatively consisting of, a polynucleotide encoding an AIM II polypeptide having the amino acid sequence shown in FIGS. 1A and 1B (SEQ ID NO:2), which was determined by sequencing a cDNA. The AIM II protein of the present invention shares sequence homology with human TNF-α (SEQ ID NO:3), human TNF-β (SEQ ID NO:4), human lymphotoxin (SEQ ID NO:5) and human Fas Ligand (SEQ ID NO:6) (FIGS. 2A–2F). The nucleotide sequence shown in FIGS. 1A and 1B (SEQ ID NO:1) were obtained by sequencing the cDNA, which was deposited on Aug. 22, 1996, at the American Type Culture Collection, 10801 University Blvd., Manassas, Va. 20110-2209, USA, and given accession number 97689. The deposited cDNA is contained in the pBluescript SK(−) plasmid (Stratagene, La Jolla, Calif.). The nucleotide sequence shown in FIGS. 1C and 1D was obtained by sequencing the cDNA, which was deposited on Mar. 15, 1996, at the American Type Culture Collection, 10801 University Blvd., Manassas, Va. 20110-2209, USA, and given accession number 97483.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A and 1B, a nucleic acid molecule of the present invention encoding an AIM II polypeptide may be obtained using standard cloning and screening procedures, such as those for cloning cDNAs using mRNA as starting material. Illustrative of the invention, the nucleic acid molecule described in FIGS. 1A and 1B (SEQ ID NO:1) was discovered in a cDNA library derived from human macrophage ox LDL (HMCCB64). The gene was also identified in cDNA libraries from activated T-cells (HT4CC72). The determined nucleotide sequence of the AIM II cDNA of FIGS. 1A and 1B (SEQ ID NO:1) contains an open reading frame encoding a protein of 240 amino acid residues, with an initiation codon at positions 49–51 of the nucleotide sequence in FIGS. 1A and 1B (SEQ ID NO:1), an extracellular domain comprising, or alternatively consisting of, amino acid residues from about 60 to about 240 in FIGS. 1A and 1B (SEQ ID NO:2), a transmembrane domain comprising, or alternatively consisting of, amino acid residues from about 37 to about 59 in FIGS. 1A and 1B (SEQ ID NO:2), a intracellular domain comprising, or alternatively consisting of, amino acid residues from about 1 to about 36 in FIGS. 1A and 1B (SEQ ID NO:2) and a deduced molecular weight of about 26.4 kDa. The AIM II protein shown in FIGS. 1A and 1B (SEQ ID NO:2) is about 27% identical and about 51% similar to the amino acid sequence of human Fas Ligand (FIGS. 2A–2F) and is about 26% identical and about 47% similar to the amino acid sequence of human TNF-α (FIGS. 2A–2F). TNF-ligand like molecules function as dimers, given that AIM II is homologous to TNF-ligand like molecules, it is likely that it also functions as a homodimer.

As one of ordinary skill would appreciate, due to the possibilities of sequencing errors discussed above, the predicted AIM II polypeptide encoded by the deposited cDNA comprises about 240 amino acids, but may be anywhere in the range of 230–250 amino acids. It will further be appreciated that, depending on the criteria used, concerning the exact "address" of, the extracelluar, intracellular and transmembrane domains of the AIM II polypeptide differ slightly. For example, the exact location of the AIM II extracellular domain in FIGS. 1A and 1B (SEQ ID NO:2) may vary slightly (e.g., the address may "shift" by about 1 to 5 residues) depending on the criteria used to define the domain.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

However, a nucleic acid contained in a clone that is a member of a library (e.g., a genomic or cDNA library) that has not been isolated from other members of the library (e.g., in the form of a homogeneous solution containing the clone and other members of the library) or a chromosome isolated or removed from a cell or a cell lysate (e.g., a "chromosome spread," as in a karyotype), is not "isolated" for the purposes of the invention. As discussed further herein, isolated nucleic acid molecules according to the present invention may be produced naturally, recombinantly, or synthetically.

Isolated nucleic acid molecules of the present invention include DNA molecules comprising, or alternatively consisting of, an open reading frame (ORF) shown in FIGS. 1A and 1B (SEQ ID NO:1) or FIGS. 1C and 1D (SEQ ID NO:38); DNA molecules comprising, or alternatively consisting of, the coding sequence for the AIM II protein shown in FIGS. 1A and 1B (SEQ ID NO:2) or FIGS. 1C and 1D (SEQ ID NO:39); and DNA molecules which comprise, or alternatively consist of, a sequence substantially different from those described above but which, due to the degeneracy of the genetic code, still encode the AIM II protein. Of course, the genetic code is well known in the art. Thus, it would be routine for one skilled in the art to generate such degenerate variants.

Nucleic acid molecules according to the present invention further include those encoding the full-length AIM II polypeptide lacking the N-terminal methionine.

In addition, the invention provides a nucleic acid molecule having a nucleotide sequence related to a portion of SEQ ID NO:1 which has been determined from the following related cDNA: HT4CC72R (SEQ ID NO:20).

In another aspect, the invention provides isolated nucleic acid molecules encoding the AIM II polypeptide having an amino acid sequence encoded by the cDNA contained in the plasmid deposited as ATCC Deposit No. 97689 on Aug. 22, 1996, or by the cDNA contained in the plasmid deposited as ATCC Deposit No. 97483 on Mar. 15, 1996. Preferably, this nucleic acid molecule will encode the polypeptide encoded by one of the above-described deposited cDNAs. The invention further provides an isolated nucleic acid molecule having the nucleotide sequence shown in FIGS. 1A and 1B (SEQ ID NO:1) or FIGS. 1C and 1D (SEQ ID NO:38) or the nucleotide sequence of one of the AIM II cDNAs contained in the above-described deposited plasmids, or a nucleic acid molecule having a sequence complementary to one of the above sequences. Such isolated molecules, particularly DNA molecules, are useful, for example, as probes for gene mapping, by in situ hybridization with chromosomes, and for detecting expression of the AIM II gene in human tissue, for instance, by Northern blot analysis.

Further embodiments of the invention include isolated nucleic acid molecules comprising, or alternatively consisting of, a polynucleotide having a nucleotide sequence at least 80% identical, and more preferably at least 85%, 90%, 92%, 95%, 96%, 97%, 98% or 99% identical to (a) a nucleotide sequence encoding the AIM II polypeptide having the complete amino acid sequence in FIGS. 1A and 1B (SEQ ID NO:2) or FIGS. 1C and 1D (SEQ ID NO:39); (b) a nucleotide sequence encoding the AIM II polypeptide having the amino acid sequence in FIGS. 1A and 1B (SEQ ID NO:2), but lacking the N-terminal methionine; (c) a nucleotide sequence encoding the AIM II polypeptide having the complete amino acid sequence encoded by the cDNA contained in ATCC Deposit No. 97689 or ATCC Deposit 97483; (d) a nucleotide sequence encoding the AIM II polypeptide extracellular domain; (e) a nucleotide sequence encoding the AIM II polypeptide transmembrane domain; (f) a nucleotide sequence encoding the AIM II polypeptide intracellular domain; (g) a nucleotide sequence encoding a soluble AIM II polypeptide having the extracellular and intracellular domains but lacking the transmembrane domain; and (h) a nucleotide sequence complementary to any of the nucleotide sequences in (a), (b), (c), (d), (e), (f) or (g) above.

Additional embodiments of the invention include isolated nucleic acid molecules comprising, or alternatively consisting of, a polynucleotide having a nucleotide sequence at least 80% identical, and more preferably at least 85%, 90%, 92%, 95%, 96%, 97%, 98% or 99% identical to (a) a nucleotide sequence encoding the AIM II polypeptide having the sequence of amino acids about 1 to about 208 in FIGS. 1C and 1D (SEQ ID NO:39); (b) a nucleotide sequence encoding the AIM II polypeptide having the sequence of amino acids about 7 to about 208 in FIGS. 1C and 1D (SEQ ID NO:39); (c) a nucleotide sequence encoding the AIM II polypeptide having the sequence of amino acids about 34 to about 208 in FIGS. 1C and 1D (SEQ ID NO:39); and (d) a nucleotide sequence complementary to any of the nucleotide sequences in (a), (b), or (c) above.

As a practical matter, whether any particular nucleic acid molecule is at least 80%, 85%, 90%, 92%, 95%, 96%, 97%, 98% or 99% identical to, for instance, the nucleotide sequence shown in FIGS. 1A and 1B (SEQ ID NO: 1) or FIGS. 1C and 1D (SEQ ID NO:38) or to the nucleotide sequence of the deposited cDNA can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

By a polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence encoding the AIM II polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. The query sequence may be an entire sequence shown in FIGS. 1A and 1B or FIGS. 1C and 1D, the ORF (open reading frame), or any fragment specified as described herein.

As a practical matter, whether any particular nucleic acid molecule or polypeptide is at least 80%, 85%, 90%, 92%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237–245 (1990)). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a match/alignment of the first 10 bases at the 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

The present application is directed to nucleic acid molecules at least 80%, 85%, 90%, 92%, 95%, 96%, 97%, 98% or 99% identical to the nucleic acid sequence shown in FIGS. 1A and 1B (SEQ ID NO:1) or FIGS. 1C and 1D (SEQ ID NO:38) or to the nucleic acid sequence of the deposited cDNAs, irrespective of whether they encode a polypeptide having AIM II activity. This is because even where a particular nucleic acid molecule does not encode a polypeptide having AIM II activity, one of skill in the art would still know how to use the nucleic acid molecule, for instance, as a hybridization probe or a polymerase chain reaction (PCR) primer. Uses of the nucleic acid molecules of the present invention that do not encode a polypeptide having AIM II activity include, inter alia, (1) isolating the AIM II gene or allelic variants thereof in a cDNA library; (2) in situ hybridization (e.g. "FISH") to metaphase chromosomal spreads to provide precise chromosomal location of the AIM II gene, as described in Verma et al., *Human Chromosomes: A Manual of Basic Techniques*, Pergamon Press, New York (1988); and (3) Northern Blot analysis for detecting AIM II mRNA expression in specific tissues.

Preferred, however, are nucleic acid molecules having sequences at least 80%, 85%, 90%, 92%, 95%, 96%, 97%, 98% or 99% identical to the nucleic acid sequence shown in FIGS. 1A and 1B (SEQ ID NO:1) or FIGS. 1C and 1D (SEQ ID NO:38) or to the nucleic acid sequence of one of the deposited cDNAs which do, in fact, encode a polypeptide having AIM II protein activity. By "a polypeptide having AIM II activity" is intended polypeptides exhibiting activity similar, but not necessarily identical, to an activity of the AIM II protein of the invention, as measured in a particular biological assay. For example, AIM II protein cytotoxic activity can be measured using propidium iodide staining to demonstrate apoptosis as described by Zarres et al., *Cell* 70: 31–46 (1992). Alternatively, AIM II induced apoptosis can also be measured using TUNEL staining as described by Gavierli et al., *J. Cell. Biol.* 119: 493–501 (1992). Further included within the scope of the invention are polypeptides encoded by these polynucleotides.

Briefly, the propidium iodide staining is performed as follows. Cells either from tissue or culture are fixed in formaldehyde, cut into frozen sections and stained with propidium iodide. The cell nuclei are visualized by propidium iodide using confocal fluorescent microscopy. Cell death is indicated by pyknotic nuclei (chromosome clumping, shrinking and/or fragmentation of nuclei).

Of course, due to the degeneracy of the genetic code, one of ordinary skill in the art will immediately recognize that a large number of the nucleic acid molecules having a sequence at least 80%, 85%, 90%, 92%, 95%, 96%, 97%, 98% or 99% identical to the nucleic acid sequence of one of the deposited cDNAs or the nucleic acid sequence shown in FIGS. 1A and 1B (SEQ ID NO:1) or FIGS. 1C and 1D (SEQ ID NO:38) will encode a polypeptide "having AIM II protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having AIM II protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Preferably, the polynucleotides and polynucleotide fragments of the invention encode a polypeptide which demonstrates an AIM II functional activity. By a polypeptide demonstrating an AIM II "functional activity" is meant, a polypeptide capable of displaying one or more known functional activities associated with a full-length and/or secreted AIM II polypeptide. Such functional activities include, but are not limited to, biological activity, antigenicity, ability to bind (or compete with a polypeptide for binding) to an anti-AIM II antibody, immunogenicity (ability to generate antibody which binds to a polypeptide), ability to form multimers with polypeptides of the invention, and ability to bind to a receptor or ligand for a polypeptide (e.g., TR2 (International Publication No. WO 96/34095), LT-β receptor, TR6 (International Publication No. WO 98/30694), and CD27)).

The functional activity of AIM II polypeptides, and fragments, variants derivatives, and analogs thereof, can be assayed by various methods.

For example, in one embodiment where one is assaying for the ability to bind or compete with full-length polypeptide for binding to anti-AIM II antibody, various immunoassays known in the art can be used, including but not limited to, competitive and non-competitive assay systems using techniques such as radioimmunoassays, ELISA (enzyme linked immunosorbent assay), "sandwich"immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a ligand is identified (e.g., DR5 (See, International Publication No. WO 98/41629), TR10 (See, International Publication No. WO 98/54202), 312C2 (See, International Publication No. WO 98/06842), and TR11, TR11SV1, and TR11SV2 (See, U.S. application Ser. No. 09/176,200)), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, E. et al., 1995, Microbiol. Rev. 59:94–123. In another embodiment, physiological correlates of binding to its substrates (signal transduction) can be assayed.

Other methods will be known to the skilled artisan and are within the scope of the invention.

The present invention is further directed to polynucleotides comprising, or alternatively consisting of, fragments of the isolated nucleic acid molecules described herein. By a fragment of an isolated nucleic acid molecule having the nucleotide sequence of one of the deposited cDNAs or the nucleotide sequence shown in FIGS. 1A and 1B (SEQ ID NO:1) or FIGS. 1C and 1D (SEQ ID NO:38) is intended fragments at least about 15 nt, and more preferably at least about 20 nt, still more preferably at least about 30 nt, and even more preferably, at least about 40 nt in length which are useful as diagnostic probes and primers as discussed herein. In this context "about" includes the particularly recited value and values larger or smaller by several (5, 4, 3, 2, or 1) nucleotides. Of course, larger fragments 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125 or 1150 nt in length are also useful according to the present invention as are fragments corresponding to most, if not all, of the nucleotide sequence of one of the deposited cDNAs or as shown in FIGS. 1A and 1B (SEQ ID NO:1) or FIGS. 1C and 1D (SEQ ID NO:38). By a fragment at least 20 nt in length, for example, is intended fragments which include 20 or more contiguous bases from the nucleotide sequence of one of the deposited cDNAs or the nucleotide sequence as shown in FIGS. 1A and 1B (SEQ ID NO:1) or FIGS. 1C and 1D (SEQ ID NO:38).

The present invention is further directed to polynucleotides comprising, or alternatively consisting of, fragments of isolated nucleic acid molecules which encode subportions of AIM II domains. In particular, the invention provides polynucleotides comprising, or alternatively consisting of, the nucleotide sequences of a member selected from the group consisting of nucleotides 49–108, 59–118, 69–128, 79–138, 89–148, 99–156, 109–156, 109–168, 119–178, 129–188, 139–198, 149–208, 157–216, 157–225, 168–227, 178–237, 188–247, 198–257, 208–267, 218–277, 226–285, 236–295, 246–305, 256–315, 266–325, 276–335, 286–345, 296–355, 306–365, 316–375, 326–385, 336–395, 346–405, 356–415, 366–425, 376–435, 386–445, 396–455, 409–469, 456–515, 476–536, 496–556, 516–575, 536–595, 576–635, 596–655, 636–695, 656–715, 696–755, 706–765, and 716–768 of SEQ ID NO:1.

The present invention is further directed to polynucleotides comprising, or alternatively consisting of, isolated nucleic acid molecules which encode domains of AIM II. In one aspect, the invention provides polynucleotides comprising, or alternatively consisting of, nucleic acid molecules which encode beta-sheet regions of AIM II set out in Table 2. Representative examples of such polynucleotides comprise, or alternatively consist of, nucleic acid molecules which encode a polypeptide having an amino acid sequence selected from the group consisting of amino acid residues from about 7 to about 14, amino acid residues from about 18 to about 23, amino acid residues from about 17 to about 25, amino acid residues from about 33 to about 46, amino acid residues from about 35 to about 39, amino acid residues from about 57 to about 60, amino acid residues from about 67 to about 72, amino acid residues from about 102 to about 107, amino acid residues from about 121 to about 126, amino acid residues from about 131 to about 166, amino acid residues from about 141 to about 152, amino acid residues from about 158 to about 169, amino acid residues from about 213 to about 221, and amino acid residues from about 232 to about 240 of SEQ ID NO:2. The invention is further directed to isolated polypeptides comprising, or alternatively consisting of, an amino acid sequence selected from the group consisting of amino acid residues from about 7 to about 14, amino acid residues from about 18 to about 23, amino acid residues from about 17 to about 25, amino acid residues from about 33 to about 46, amino acid residues from about 35 to about 39, amino acid residues from about 57 to about 60, amino acid residues from about 67 to about 72, amino acid residues from about 102 to about 107, amino acid residues from about 121 to about 126, amino acid residues from about 131 to about 166, amino acid residues from about 141 to about 152, amino acid residues from about 158 to about 169, amino acid residues from about 213 to about 221, and amino acid residues from about 232 to about 240 of SEQ ID NO:2. In this context "about" includes the particularly recited value and values larger or smaller by several (5, 4, 3, 2, or 1) amino acids.

Nucleic acid fragments of the present invention include nucleic acid molecules encoding beta-sheet regions of the AIM II protein, as well as isolated nucleic acid molecules comprising, or alternatively consisting of, a polynucleotide having a nucleotide sequence at least 80% identical, and more preferably at least 85%, 90%, 92%, 95%, 96%, 97%, 98% or 99% identical to nucleic acid molecules encoding beta-sheet regions of the AIM II protein. Polynucleotides encoding polypeptides at least 80%, 85%, 90%, 92%, 95%, 96%, 97%, 98%, or 99% identical to beta-sheet regions are also with the scope of the invention, as are the polypeptides encoded by these polynucleotides.

The present invention is also directed to polynucleotides comprising, or alternatively consisting of, isolated nucleic acid molecules which encode a polypeptide having an amino acid sequence selected from the group consisting of amino acid residues from about 94 to about 100, amino acid residues from about 121 to about 124, amino acid residues from about 127 to about 135, amino acid residues from about 139 to about 149, amino acid residues from about 160 to about 168, amino acid residues from about 175 to about 185, amino acid residues from about 197 to about 209, amino acid residues from about 213 to about 220, and amino acid residues from about 232 to about 240 of SEQ ID NO:2. The invention is further directed to isolated polypeptides comprising, or alternatively consisting of, an amino acid sequence selected from the group consisting of amino acid residues from about 94 to about 100, amino acid residues from about 121 to about 124, amino acid residues from about 127 to about 135, amino acid residues from about 139 to about 149, amino acid residues from about 160 to about 168, amino acid residues from about 175 to about 185, amino acid residues from about 197 to about 209, amino acid residues from about 213 to about 220, and amino acid residues from about 232 to about 240 of SEQ ID NO:2. In this context "about" includes the particularly recited value and values larger or smaller by several (5, 4, 3, 2, or 1) amino acids.

Preferred nucleic acid fragments of the present invention include nucleic acid molecules encoding epitope-bearing portions of the AIM II protein. In particular, such nucleic acid fragments of the present invention include nucleic acid molecules encoding: a polypeptide comprising, or alternatively consisting of, one, two, three, four, five, or more amino acid sequences selected from amino acid residues from about 13 to about 20 in FIGS. 1A and 1B (SEQ ID NO:2); a polypeptide comprising, or alternatively consisting of, amino acid residues from about 23 to about 36 in FIG. 1 (SEQ ID NO:2); a polypeptide comprising, or alternatively consisting of, amino acid residues from about 69 to about 79 in FIGS. 1A and 1B (SEQ ID NO:2); a polypeptide comprising, or alternatively consisting of, amino acid residues from about 85 to about 94 in FIGS. 1A and 1B (SEQ ID NO:2), a polypeptide comprising, or alternatively consisting of, amino acid residues from about 167 to about 178 in FIGS. 1A and 1B (SEQ ID NO:2); a polypeptide comprising, or alternatively consisting of, amino acid residues from about 184 to about 196 in FIGS. 1A and 1B (SEQ ID NO:2); and a polypeptide comprising, or alternatively consisting of, amino acid residues from about 221 to about 233 in FIGS. 1A and 1B (SEQ ID NO:2). In this context "about" includes the particularly recited value and values larger or smaller by several (5, 4, 3, 2, or 1) amino acids. The inventors have determined that the above polypeptide fragments are antigenic regions of the AIM II protein. Methods for determining other such epitope-bearing portions of the AIM II protein are described in detail below. Polypeptides encoded by these polynucleotides are also encompassed by the invention.

As is discussed be low in more detail, AIM II polynucleotides may be used in accordance with the present invention for a variety of applications, particularly those that make use of the chemical and biological properties of the AIM II. Among these applications is autoimmune disease, immunodeficiency and aberrant cellular proliferation. Additional applications relate to diagnosis and to treatment of disorders of cells, tissues and organisms.

In another aspect, the invention provides an isolated nucleic acid molecule comprising, or alternatively consisting of, a polynucleotide which hybridizes under stringent hybridization conditions to a portion of the polynucleotide in a nucleic acid molecule of the invention described above, for instance, the complement of a polynucleotide fragment described herein, or the cDNA plasmid contained in ATCC Deposit 97689 or ATCC Deposit 97483. By "stringent hybridization conditions" is intended overnight incubation at 42° C. in a solution comprising, or alternatively consisting of: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. In this context "about" includes the particularly recited value and values larger or smaller by several (5, 4, 3, 2, or 1) nucleotides. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., one of the deposited cDNAs or the nucleotide sequence as shown in FIGS. 1A and 1B (SEQ ID NO:1) or FIGS. 1C and 1D (SEQ ID NO:38)).

Of course, a polynucleotide which hybridizes only to a poly A sequence (such as the 3' terminal poly(A) tract of the AIM II cDNA shown in FIGS. 1A and 1B (SEQ ID NO:1) or FIGS. 1C and 1D (SEQ ID NO:38)), or to a complementary stretch of T (or U) resides, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA generated from an oligo-dT primed cDNA library).

As indicated, nucleic acid molecules of the present invention which encode an AIM II polypeptide may include, but are not limited to those encoding the amino acid sequence of the polypeptide, by itself; the coding sequence for the polypeptide and additional sequences, such as those encoding a leader or secretory sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767 (1984). As discussed below, other such fusion proteins include the AIM II fused to Fc at the N- or C-terminus.

The present invention further relates to variants of the nucleic acid molecules of the present invention, which encode portions, analogs or derivatives of the AIM II protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985).

Non-naturally occurring variants may be produced using art-known mutagenesis techniques, which include, but are not limited to: oligonucleotide mediated mutagenesis, alanine scanning, PCR mutagenesis, site-directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London Ser.A* 317:415 (1986)).

Such variants include those produced by nucleotide substitutions, deletions or additions which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the AIM II protein or portions thereof Also especially preferred in this regard are conservative substitutions.

Vectors and Host Cells

The present invention also relates to vectors which include the isolated DNA molecules of the present invention, host cells which are genetically engineered with the recombinant vectors, and the production of AIM II polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

In addition to the use of expression vectors in the practice of the present invention, the present invention further includes novel expression vectors comprising operator and promoter elements operatively linked to nucleotide sequences encoding a protein of interest. One example of such a vector is pHE4-5 which is described in detail below.

Figure 10:
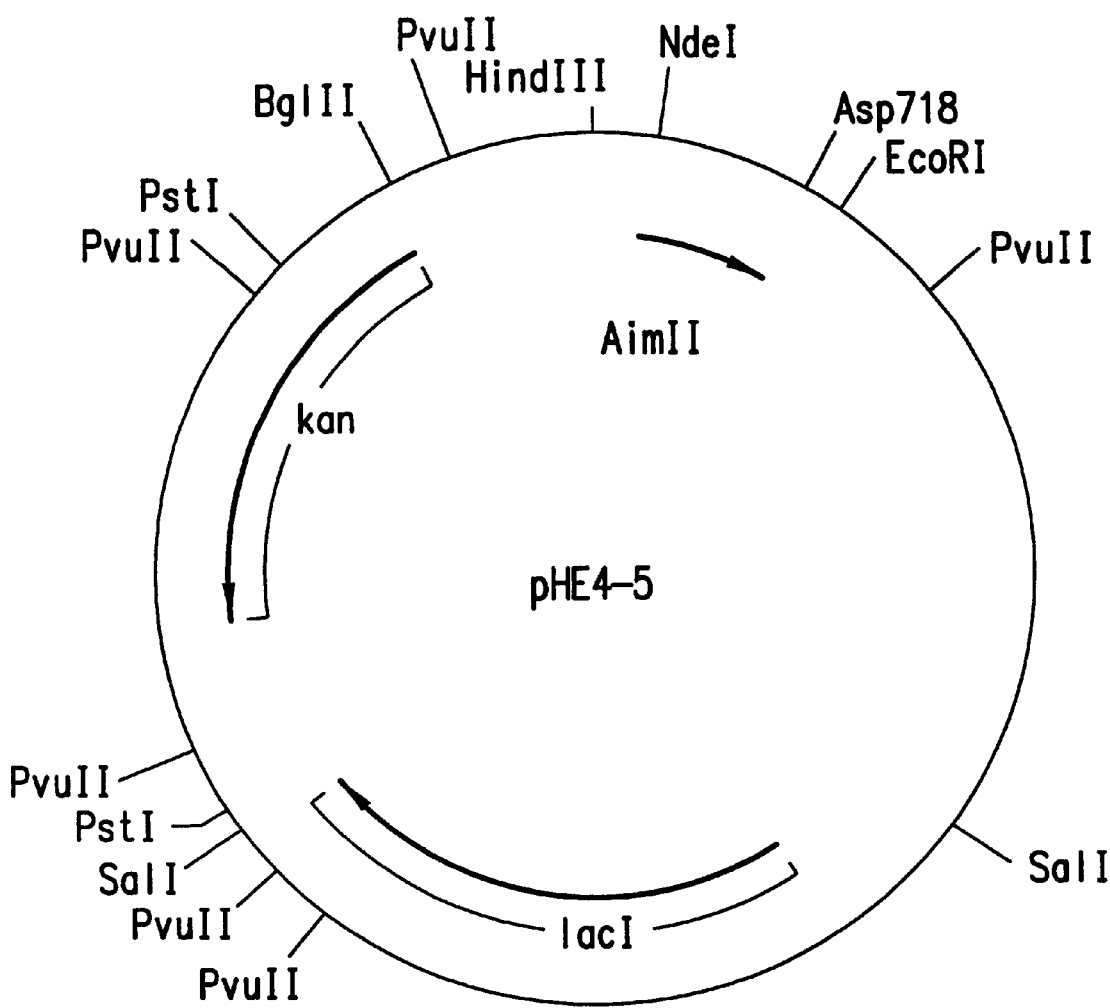
FIG. 10 shows a schematic representation of the pHE4-5 expression vector (SEQ ID NO:50) and the subcloned AIM II cDNA coding sequence. The locations of the kanamycin resistance marker gene, the AIM II coding sequence, the oriC sequence, and the lacIq coding sequence are indicated.

As summarized in FIGS. 10 and 11, components of the pHE4-5 vector (SEQ ID NO:50) include: 1) a neomycin-phosphotransferase gene as a selection marker, 2) an *E. coli* origin of replication, 3) a T5 phage promoter sequence, 4) two lac operator sequences, 5) a Shine-Delgarno sequence, 6) the lactose operon repressor gene (lacIq). The origin of replication (oriC) is derived from pUC19 (LTI, Gaithersburg, Md.). The promoter sequence and operator sequences were made synthetically. Synthetic production of nucleic acid sequences is well known in the art. *Clontech 95/96 Catalog*, pages 215–216, CLONTECH, 1020 East Meadow Circle, Palo Alto, Calif. 94303. A nucleotide sequence encoding AIM II (SEQ ID NO:1), is operatively linked to the promoter and operator by inserting the nucleotide sequence between the NdeI and Asp718 sites of the pHE4-5 vector.

As noted above, the pHE4-5 vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of downstream (i.e., 3') sequences. However, the lacIq gene product dissociates from the lac operator in the presence of either lactose or certain lactose analogs, e.g. isopropyl B-D-thiogalactopyranoside (IPTG). AIM II thus is not produced in appreciable quantities in uninduced host cells containing the pHE4-5 vector. Induction of these host cells by the addition of an agent such as IPTG, however, results in the expression of the AIM II coding sequence.

The promoter/operator sequences of the pHE4-5 vector (SEQ ID NO :51) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., *Textbook of Biochemistry with Clinical Correlations*, 4th Edition (1997), pages 802–807.

The pHE4 series of vectors contain all of the components of the pHE4-5 vector except for the AIM II coding sequence. Features of the pHE4 vectors include optimized synthetic T5 phage promoter, lac operator, and Shine-Delgarno sequences. Further, these sequences are also optimally spaced so that expression of an inserted gene may be tightly regulated and high level of expression occurs upon induction.

Among known bacterial promoters suitable for use in the production of proteins of the present invention include the *E.*

*coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the *Rous Sarcoma* Virus (RSV), and metallothionein promoters, such as the mouse metallothionein-I promoter.

The pHE4-5 vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4-5 vector (SEQ ID NO:50).

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL-5-receptor has been fused with Fc portions for the purpose of high-throughput screening assays to identify antagonists of hIL-5. See, D. Bennett et al., *Journal of Molecular Recognition*, Vol. 8:52–58 (1995) and K. Johanson et al., *The Journal of Biological Chemistry*, Vol. 270, No. 16:9459–9471 (1995).

The AIM II protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., AIM II coding sequence), and/or to include genetic material (e.g., heterologous polynucleotide sequences) that is operably associated with AIM II polynucleotides of the invention, and which activates, alters, and/or amplifies endogenous AIM II polynucleotides. For example, techniques known in the art may be used to operably associate heterologous control regions (e.g., promoter and/or enhancer) and endogenous AIM II polynucleotide sequences via homologous recombination (see, e.g., U.S. Pat. No. 5,641,670, issued Jun. 24, 1997; WO 96/29411, published Sep. 26, 1996; WO 94/12650, published Aug. 4, 1994; Koller et al., *Proc. Natl. Acad. Sci. USA* 86:8932–8935 (1989); and Zijlstra et al., *Nature* 342:435–438 (1989), the disclosures of each of which are incorporated by reference in their entireties).

AIM II Polypeptides and Fragments

The invention further provides an isolated AIM II polypeptide having the amino acid sequence encoded by one of the deposited cDNAs, or the amino acid sequence in FIGS. 1A and 1B (SEQ ID NO:2) or FIGS. 1C and 1D (SEQ ID NO:39), or a peptide or polypeptide comprising, or alternatively consisting of, a portion of the above polypeptides.

The polypeptides of the present invention include the polypeptide encoded by one of the deposited cDNAs, the polypeptide of FIGS. 1A and 1B (SEQ ID NO:2) or FIGS. 1C and 1D (SEQ ID NO:39), the polypeptide of FIGS. 1A and 1B (SEQ ID NO:2) lacking the N-terminal methionine, the extracellular domain, the transmembrane domain, the intracellular domain, soluble polypeptides comprising, or alternatively consisting of, all or part of the extracellular and intracellular domains but lacking the transmembrane domain, as well as polypeptides which are at least 80% identical, more preferably at least 85%, 90%, 92% or 95% identical, still more preferably at least 96%, 97%, 98% or 99% identical to the polypeptide encoded by one of the deposited cDNAs, to the polypeptide of FIGS. 1A and 1B (SEQ ID NO:2) or FIGS. 1C and 1D (SEQ ID NO:39), and also include portions of such polypeptides with at least 30 amino acids and more preferably at least 50 amino acids.

The polypeptides of the present invention further include (a) the AIM II polypeptide having the sequence of amino acids about 1 to about 208 in FIGS. 1C and 1D (SEQ ID NO:39); (b) the AIM II polypeptide having the sequence of amino acids about 7 to about 208 in FIGS. 1C and 1D (SEQ ID NO:39); and (c) the AIM II polypeptide having the sequence of amino acids about 34 to about 208 in FIGS. 1C and 1D (SEQ ID NO:39), as well as polypeptides which are at least 80% identical, more preferably at least 85%, 90%, 92% or 95% identical, still more preferably at least 96%, 97%, 98% or 99% identical to the polypeptide encoded by one of the deposited cDNAs, to the polypeptide of FIGS. 1A and 1B (SEQ ID NO:2) or FIGS. 1C and 1D (SEQ ID NO:39), and also include portions of such polypeptides with at least 30 amino acids and more preferably at least 50 amino acids.

By a polypeptide having an amino acid sequence at least, for example, 95% "identical" to a reference amino acid sequence of an AIM II polypeptide is intended that the amino acid sequence of the polypeptide is identical to the reference sequence except that the polypeptide sequence may include up to five amino acid alterations per each 100 amino acids of the reference amino acid of the AIM II polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance the amino acid sequence shown in FIGS. 1A and 1B (SEQ ID NO:2) or FIGS. 1C and 1D (SEQ ID NO:39) or to the amino acid sequence encoded by one of the deposited cDNAs can be determined conventionally using known computer programs such the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 92%, 95%, 96%, 97%, 98% or 99% identical to, for instance, the amino acid sequences shown in Table 1 or to the amino acid sequence encoded by the deposited DNA can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237–245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix= PAM 0, k-tuple=2, Mismatch Penalty=1, Joining Penalty= 20, Randomization Group Length=0, CutoffScore=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues of the query (reference) sequence that extend past the N- or C-termini of the subject sequence are considered for the purposes of manually adjusting the percent identity score. That is, only residues which are not matched/aligned with the N- or C-termini of the query sequence are counted when manually adjusting the percent identity score.

For example, a 90 amino acid residue subject sequence is aligned with a 100 residue query sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The natural processed form of AIM II that was affinity purified on an LT-β receptor column from conditioned media of MCA-38 cells transformed with full length AIM II cDNA is Leu-83 to Val-240 in SEQ ID NO:2. (See Example 10). However, it appears that AIM II is processed differently in COS cells, producing an AIM II that is cleaved between Glu-67 and Met-68 to yield a polypeptide having amino acids 68–240 in SEQ ID NO:2. In addition, COS cells also cleave the AIM II between Met-68 and Val-69, resulting a polypeptide having amino acids 69–240 in SEQ ID NO:2.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host. For example, a recombinantly produced version of the AIM II polypeptide can be substantially purified by the one-step method described in Smith and Johnson, Gene 67:31–40 (1988).

The AIM II polypeptides of the invention may be in monomers or multimers (i.e., dimers, trimers, tetramers and higher multimers). Accordingly, the present invention relates to monomers and multimers of the AIM II polypeptides of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only AIM II polypeptides of the invention (including AIM II fragments, variants, splice variants, and fusion proteins, as described herein). These homomers may contain AIM II polypeptides having identical or different amino acid sequences. In a specific embodiment, a homomer of the invention is a multimer containing only AIM II polypeptides having an identical amino acid sequence. In another specific embodiment, a homomer of the invention is a multimer containing AIM II polypeptides having different amino acid sequences. In specific embodiments, the multimer of the invention is a homodimer (e.g., containing AIM II polypeptides having identical or different amino acid sequences) or a homotrimer (e.g., containing AIM II polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the AIM II and AIM II polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the AIM II polypeptides of the invention. Such covalent associations may involve one or more amino acid residues contained in the polypeptide sequence (e.g., that recited in SEQ ID NO:2 or SEQ ID NO:39, or contained in the polypeptide encoded by a cDNA of the deposits designated as ATCC Accession 97689 or 97483). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in an AIM II fusion protein. In one example, covalent associations are between the heterologous sequence contained in a fusion protein of the invention (see, e.g., U.S. Pat. No. 5,478,925). In a specific example, the covalent associations are between the heterologous sequence contained in an AIM II-Fc fusion protein of the invention (as described herein). In another specific example, covalent associations of fusion proteins of the invention are between heterologous polypeptide sequence from another TNF family ligand/receptor member that is capable of forming covalently associated multimers, such as for example, oseteoprotegerin (see, e.g., WO 98/49305, the contents of which are herein incorporated by reference in its entirety).

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion used to a polypeptide of the present invention may comprise the hinge region, CH1 domain, CH2 domain, and CH3 domain or any combination of whole domains or portions thereof The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336, 603, 5,622,929, 5,359,046, 5,349,053, 5,447,851, 5,112,946; EP 0 307 434, EP 0 367 166; WO 96/04388, WO 91/06570; Ashkenazi, A. et al. *PNAS* 88:10535–10539 (1991); Zheng, X. X. et al. *J. Immunol.* 154:5590–5600 (1995); and Vil, H. et al. *PNAS* 89:11337–11341 (1992) (said references incorporated by reference in their entireties).

As used herein the term "AIM II" polypeptide includes membrane-bound proteins (comprising, or alternatively consisting of, a cytoplasmic domain, a transmembrane domain, and an extracellular domain) as well as truncated proteins that retain the AIM II functional activity. In one embodiment, soluble AIM II polypeptides comprise, or alternatively consisting of, all or part of the extracellular domain of an AIM II protein, but lack the transmembrane region that would cause retention of the polypeptide on a cell membrane. Soluble AIM II may also include part of the transmembrane region or part of the cytoplasmic domain or other sequences, provided that the soluble AIM II protein is capable of being secreted. A heterologous signal peptide can be fused to the N-terminus of the soluble AIM II polypeptide such that the soluble AIM II polypeptide is secreted upon expression.

The polypeptide of the present invention have uses that include, but are not limited to, functioning as a molecular weight marker on SDS-PAGE gels or on molecular sieve gel filtration columns using methods well known to those of skill in the art.

It will be recognized in the art that some amino acid sequences of the AIM II polypeptide can be varied without significant effect of the structure or function of the protein. If such differences in sequence are contemplated, it should be remembered that there will be critical areas on the protein which determine activity.

Thus, the invention further includes variations of the AIM II polypeptide which show substantial AIM II polypeptide activity or which include regions of AIM II protein such as the protein portions discussed below. Such mutants include deletions, insertions, inversions, repeats, and type substitutions. As indicated above, guidance concerning which amino acid changes are likely to be phenotypically silent can be found in Bowie, J. U., et al., "Deciphering the Message in Protein Sequences: Tolerance to Amino Acid Substitutions," *Science* 247: 1306–1310(1990). Polynucleotides encoding these fragments, derivatives or analogs are also encompassed by the invention.

Thus, the fragment, derivative or analog of the polypeptide of FIGS. 1A and 1B (SEQ ID NO:2) or FIGS. 1C and 1D (SEQ ID NO :39), or that encoded by one of the deposited cDNAs, may be (i) one in which one or more of the amino acid residues (e.g., 3, 5, 8, 10, 15 or 20) are substituted with a conserved or non-conserved amino acid residue (preferably a conserved amino acid residue) and such substituted amino acid residue may or may not be one encoded by the genetic code, or (ii) one in which one or more of the amino acid residues includes a substituent group (e.g., 3, 5, 8, 10, 15 or 20), or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein. Polynucleotides encoding these fragments, derivatives or analogs are also encompassed by the invention.

Of particular interest are substitutions of charged amino acids with another charged amino acid and with neutral or negatively charged amino acids. The latter results in proteins with reduced positive charge to improve the characteristics of the AIM II protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

The replacement of amino acids can also change the selectivity of binding to cell surface receptors. Ostade et al., *Nature* 361:266–268 (1993) describes certain mutations resulting in selective binding of TNF-α to only one of the two known types of TNF receptors. Thus, the AIM II receptor of the present invention may include one or more (e.g., 3, 5, 8, 10, 15 or 20) amino acid substitutions, deletions or additions, either from natural mutations or human manipulation.

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given AIM II polypeptide will not be more than 50, 40, 30, 25, 20, 15, 10, 5 or 3.

Amino acids in the AIM II protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro, or in vitro proliferative activity. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

Also included in the present invention are amino terminal deletion mutants. Such mutants include those comprising the amino acid sequence shown in SEQ ID NO:2 having a deletion of at least first N-terminal amino acid but not more than the first 114 N-terminal amino acid residues of SEQ ID NO:2. Alternatively, the deletion will include at least the first 35 N-terminal amino acid residues but not more than the first 114 N-terminal amino acid residues of SEQ ID NO:2. Alternatively, the deletion will include at least the first 59 N-terminal amino acid residues but not more than the first 114 N-terminal amino acid residues of SEQ ID NO:2. Alternatively, the deletion will include at least the first 67 N-terminal amino acid residues but not more than the first 114 N-terminal amino acid residues of SEQ ID NO:2. Alternatively, the deletion will include at least the first 68 N-terminal amino acid residues but not more than the first 114 N-terminal amino acid residues of SEQ ID NO:2. Alternatively, the deletion will include at least the first 73 N-terminal amino acid residues but not more than the first 114 N-terminal amino acid residues of SEQ ID NO:2. Alternatively, the deletion will include at least the first 82 N-terminal amino acid residues but not more than the first 114 N-terminal amino acid residues of SEQ ID NO:2. Alternatively, the deletion will include at least the first 100 N-terminal amino acid residues but not more than the first 114 N-terminal amino acid residues of SEQ ID NO:2. Polynucleotides encoding these deletion mutants are also encompassed by the invention, as are polynucleotides at least 80%, 85%, 90%, 92%, 95%, 96%, 97%, 98%, or 99% identical to polynucleotides encoding the deletion mutants described above and polynucleotides encoding polypeptides at least 80%, 85%, 90%, 92%, 95%, 96%, 97%, 98%, or 99% identical to these deletion mutants. The present invention also encompasses the above polynucleotides fused to a heterologous polynucleotides and polypeptide expression products of these polynucleotides.

In addition to the ranges of N-terminal deletion mutants described above, the present invention is also directed to all combinations of the above described ranges. For example, the deletions of at least the first 59 N-terminal amino acid residues but not more than the first 67 N-terminal amino acid residues of SEQ ID NO:2; deletions of at least the first 59 N-terminal amino acid residues but not more than the first 68 N-terminal amino acid residues of SEQ ID NO:2; deletions of at least the first 59 N-terminal amino acid residues but not more than the first 73 N-terminal amino acid residues of SEQ ID NO:2; deletions of at least the first 59 N-terminal amino acid residues but not more than the first 82 N-terminal amino acid residues of SEQ ID NO:2; deletions of at least the first 59 N-terminal amino acid residues but not more than the first 100 N-terminal amino acid residues of SEQ ID NO:2; deletions of at least the first 67 N-terminal amino acid residues but not more than the first 73 N-terminal amino acid residues of SEQ ID NO:2; deletions of at least the first 67 N-terminal amino acid residues but not more than the first 82 N-terminal amino acid residues of SEQ ID NO:2; deletions of at least the first 67 N-terminal amino acid residues but not more than the first 100 N-terminal amino acid residues of SEQ ID NO:2; deletions of at least the first 68 N-terminal amino acid residues but not more than the first 73 N-terminal amino acid residues of SEQ ID NO:2; deletions of at least the first 68 N-terminal amino acid residues but not more than the first 82 N-terminal amino acid residues of SEQ ID NO: 2; deletions of at least the first 68 N-terminal amino acid residues but not more than the first 100 N-terminal amino acid residues of SEQ ID NO:2; deletions of at least the first 73 N-terminal amino acid residues but not more than the first 82 N-terminal amino acid residues of SEQ ID NO:2; deletions of at least the first 73 N-terminal amino acid residues but not more than the first 100 N-terminal amino acid residues of SEQ ID NO:2; deletions of at least the first 82 N-terminal amino acid residues but not more than the first 100 N-terminal amino acid residues of SEQ ID NO:2; etc. etc. . . . Polynucleotides encoding these deletion mutants are also encompassed by the invention, as are polynucleotides at least 80%, 85%, 90%, 92%, 95%, 96%, 97%, 98%, or 99% identical to polynucleotides encoding the deletion mutants described above and polynucleotides encoding polypeptides at least 80%, 85%, 90%, 92%, 95%, 96%, 97%, 98%, or 99% identical to these deletion mutants. The present invention also encompasses the above polynucleotides fused to a heterologous polynucleotides and polypeptide expression products of these polynucleotides.

Preferred AIM II polypeptides are those having one or more of the sequences shown below (numbering starts with the first amino acid in the protein (Met):

| | |
|---|---|
| Gln(residue 60) to Val(residue 240) | Ser(79) to Val(240) |
| Leu(61) to Val(240) | Trp(80) to Val(240) |
| His(62) to Val(240) | Glu(81) to Val(240) |
| Trp(63) to Val(240) | Gln(82) to Val(240) |
| Arg(64) to Val(240) | Leu(83) to Val(240) |
| Leu(65) to Val(240) | Ile(84) to Val(240) |
| Gly(66) to Val(240) | Gln(85) to Val(240) |
| Glu(67) to Val(240) | Glu(86) to Val(240) |
| Met(68) to Val(240) | Arg(87) to Val(240) |
| Val(69) to Val(240) | Arg(88) to Val(240) |
| Thr(70) to Val(240) | Ser(89) to Val(240) |
| Arg(71) to Val(240) | His(90) to Val(240) |
| Leu(72) to Val(240) | Glu(91) to Val(240) |
| Pro(73) to Val(240) | Val(92) to Val(240) |
| Asp(74) to Val(240) | Asn(93) to Val(240) |
| Gly(75) to Val(240) | Pro(94) to Val(240) |
| Pro(76) to Val(240) | Ala(95) to Val(240) |
| Ala(77) to Val(240) | Ala(96) to Val(240) |
| Gly(78) to Val(240) | His(97) to Val(240) |

Leu(98) to Val(240)
Thr(99) to Val(240)
Gly(100) to Val(240)
Ala(101) to Val(240)
Asn(102) to Val(240)
Ser(103) to Val(240)
Ser(104) to Val(240)
Leu(105) to Val(240)
Thr(106) to Val(240)
Gly(107) to Val(240)
Ser(108) to Val(240)
Gly(109) to Val(240)
Gly(110) to Val(240)
Pro(111) to Val(240)
Leu(112) to Val(240)
Leu(113) to Val(240)
Trp(114) to Val(240)

Particularly preferred embodiments include polypeptides comprising, or alternatively consisting of, one or more of the AIM II N-terminal deletions Gln-60 to Val-240 (AIM II (aa 60-240)), Met-68 to Val-240 (AIM II (aa 68-240)), Val-69 to Val-240 (AIM II (aa 69-240)), Asp-74 to Val-240 (AIM II (aa 74-240)), Leu-83 to Val-240 (AIM II (aa 83-240)), and Ala-101 to Val-240 (AIM II (aa 101-240)). Polynucleotides encoding these polypeptides are also encompassed by the invention, as are polynucleotides at least 80%, 85%, 90%, 92%, 95%, 96%, 97%, 98%, or 99% identical to polynucleotides encoding the polypeptides described above and polynucleotides encoding polypeptides at least 80%, 85%, 90%, 92%, 95%, 96%, 97%, 98%, or 99% identical to these polypeptides. The present invention also encompasses the above polynucleotides fused to a heterologous polynucleotides and polypeptide expression products of these polynucleotides.

Even if deletion of one or more amino acids from the N-terminus of a protein results in modification or loss of one or more biological functions of the protein, other biological activities may still be retained. Thus, the ability of shortened AIM II muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an AIM II mutein with a large number of deleted N-terminal amino acid residues may retain some biological or immunogenic activities. In fact, peptides composed of as few as six AIM II amino acid residues may often evoke an immune response.

Accordingly, the present invention further provides polypeptides having one or more residues deleted from the amino terminus of the AIM II amino acid sequence shown in FIGS. 1A and 1B (SEQ ID NO:2 up to the phenylalanine residue at position number 235, and polynucleotides encoding such polypeptides. In particular, the present invention provides polypeptides comprising, or alternatively consisting of, the amino acid sequence of residues n-314 of FIGS. 1A and 1B (SEQ ID NO:2), where n is an integer in the range of 2 to 235, and 236 is the position of the first residue from the N-terminus of the complete AIM II polypeptide believed to be required for at least immunogenic activity of the AIM II polypeptide. Polynucleotides encoding these polypeptides are also encompassed by the invention.

More in particular, the invention provides polynucleotides encoding polypeptides comprising, or alternatively consisting of, the amino acid sequence of a member selected from the group consisting of residues of E-2 to V-240; E-3 to V-240; S-4 to V-240; V-5 to V-240; V-6 to V-240; R-7 to V-240; P-8 to V-240; S-9 to V-240; V-10 to V-240; F-11 to V-240; V-12 to V-240; V-13 to V-240; D-14 to V-240; G-15 to V-240; Q-16 to V-240; T-17 to V-240; D-18 to V-240; I-19 to V-240; P-20 to V-240; F-21 to V-240; T-22 to V-240; R-23 to V-240; L-24 to V-240; G-25 to V-240; R-26 to V-240; S-27 to V-240; H-28 to V-240; R-29 to V-240; R-30 to V-240; Q-31 to V-240; S-32 to V-240; C-33 to V-240; S-34 to V-240; V-35 to V-240; A-36 to V-240; R-37 to V-240; V-38 to V-240; G-39 to V-240; L-40 to V-240; G-41 to V-240; L-42 to V-240; L-43 to V-240; L-44 to V-240; L-45 to V-240; L-46 to V-240; M-47 to V-240; G-48 to V-240; A-49 to V-240; G-50 to V-240; L-51 to V-240; A-52 to V-240; V-53 to V-240; Q-54 to V-240; G-55 to V-240; W-56 to V-240; F-57 to V-240; L-58 to V-240; L-59 to V-240; Q-60 to V-240; L-61 to V-240; H-62 to V-240; W-63 to V-240; R-64 to V-240; L-65 to V-240; G-66 to V-240; E-67 to V-240; M-68 to V-240; V-69 to V-240; T-70 to V-240; R-71 to V-240; L-72 to V-240; P-73 to V-240; D-74 to V-240; G-75 to V-240; P-76 to V-240; A-77 to V-240; G-78 to V-240; S-79 to V-240; W-80 to V-240; E-81 to V-240; Q-82 to V-240; L-83 to V-240; I-84 to V-240; Q-85 to V-240; E-86 to V-240; R-87 to V-240; R-88 to V-240; S-89 to V-240; H-90 to V-240; E-91 to V-240; V-92 to V-240; N-93 to V-240; P-94 to V-240; A-95 to V-240; A-96 to V-240; H-97 to V-240; L-98 to V-240; T-99 to V-240; G-100 to V-240; A-101 to V-240; N-102 to V-240; S-103 to V-240; S-104 to V-240; L-105 to V-240; T-106 to V-240; G-107 to V-240; S-108 to V-240; G-109 to V-240; G-110 to V-240; P-111 to V-240; L-112 to V-240; L-113 to V-240; W-114 to V-240; E-115 to V-240; T-116 to V-240; Q-117 to V-240; L-118 to V-240; G-119 to V-240; L-120 to V-240; A-121 to V-240; F-122 to V-240; L-123 to V-240; R-124 to V-240; G-125 to V-240; L-126 to V-240; S-127 to V-240; Y-128 to V-240; H-129 to V-240; D-130 to V-240; G-131 to V-240; A-132 to V-240; L-133 to V-240; V-134 to V-240; V-135 to V-240; T-136 to V-240; K-137 to V-240; A-138 to V-240; G-139 to V-240; Y-140 to V-240; Y-141 to V-240; Y-142 to V-240; I-143 to V-240; Y-144 to V-240; S-145 to V-240; K-146 to V-240; V-147 to V-240; Q-148 to V-240; L-149 to V-240; G-150 to V-240; G-151 to V-240; V-152 to V-240; G-153 to V-240; C-154 to V-240; P-155 to V-240; L-156 to V-240; G-157 to V-240; L-158 to V-240; A-159 to V-240; S-160 to V-240; T-161 to V-240; I-162 to V-240; T-163 to V-240; H-164 to V-240; G-165 to V-240; L-166 to V-240; Y-167 to V-240; K-168 to V-240; R-169 to V-240; T-170 to V-240; P-171 to V-240; R-172 to V-240; Y-173 to V-240; P-174 to V-240; E-175 to V-240; E-176 to V-240; L-177 to V-240; E-178 to V-240; L-179 to V-240; L-180 to V-240; V-181 to V-240; S-182 to V-240; Q-183 to V-240; Q-184 to V-240; S-185 to V-240; P-186 to V-240; C-187 to V-240; G-188 to V-240; R-189 to V-240; A-190 to V-240; T-191 to V-240; S-192 to V-240; S-193 to V-240; S-194 to V-240; R-195 to V-240; V-196 to V-240; W-197 to V-240; W-198 to V-240; D-199 to V-240; S-200 to V-240; S-201 to V-240; F-202 to V-240; L-203 to V-240; G-204 to V-240; G-205 to V-240; V-206 to V-240; V-207 to V-240; H-208 to V-240; L-209 to V-240; E-210 to V-240; A-211 to V-240; G-212 to V-240; E-213 to V-240; E-214 to V-240; V-215 to V-240; V-216 to V-240; V-217 to V-240; R-218 to V-240; V-219 to V-240; L-220 to V-240; D-221 to V-240; E-222 to V-240; R-223 to V-240; L-224 to V-240; V-225 to V-240; R-226 to V-240; L-227 to V-240; R-228 to V-240; D-229 to V-240; G-230 to V-240; T-231 to V-240; R-232 to V-240; S-233 to V-240; Y-234 to V-240; and F-235 to V-240 of the AIM II sequence shown in SEQ ID NO:2 (which is identical to the sequence shown as FIGS. 1A and 1B, with the exception that the amino acid residues in SEQ ID NO:2 are numbered consecutively from 1 through 240 from the N-terminus to the C-terminus). The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

As mentioned above, even if deletion of one or more amino acids from the C-terminus of a protein results in modification or loss of one or more biological functions of the protein, other biological activities may still be retained. Thus, the ability of the shortened AIM II mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an AIM II mutein with a large number of deleted C-terminal amino acid residues may retain some biological or immunogenic activities. In fact, peptides composed of as few as six AIM I amino acid residues may often evoke an immune response.

Accordingly, the present invention further provides polypeptides having one or more residues deleted from the carboxy terminus of the amino acid sequence of the AIM II polypeptide shown in FIGS. 1A and 1B (SEQ ID NO:2), up to the valine residue at position number 6, and polynucleotides encoding such polypeptides. In particular, the present invention provides polypeptides comprising, or alternatively consisting of, the amino acid sequence of residues 1-m of FIGS. 1A and 1B (i.e., SEQ ID NO:2), where m is an integer in the range of 6 to 239, and 6 is the position of the first residue from the C-terminus of the complete AIM II polypeptide believed to be required for at least immunogenic activity of the AIM II polypeptide. Polynucleotides encoding these polypeptides are also encompassed by the invention.

More in particular, the invention provides polynucleotides encoding polypeptides comprising, or alternatively consisting of, the amino acid sequence of a member selected from the group consisting of residues M-1 to M-239; M-1 to F-238; M-1 to A-237, M-1 to G-236; M-1 to F-235; M-1 to Y-234; M-1 to S-233; M-1 to R-232; M-1 to T-231; M-1 to G-230; M-1 to D-229; M-1 to R-228; M-1 to L-227; M-1 to R-226; M-1 to V-225; M-1 to L-224; M-1 to R-223; M-1 to E-222; M-1 to D-221; M-1 to L-220; M-1 to V-219; M-1 to R-218; M-1 to V-217; M-1 to V-216; M-1 to V-215; M-1 to E-214; M-1 to E-213; M-1 to G-212; M-1 to A-211; M-1 to E-210; M-1 to L-209; M-1 to H-208; M-1 to V-207; M-1 to V-206; M-1 to G-205; M-1 to G-204; M-1 to L-203; M-1 to F-202; M-1 to S-201; M-1 to S-200; M-1 to D-199; M-1 to W-198; M-1 to W-197; M-1 to V-196; M-1 to R-195; M-1 to S-194; M-1 to S-193; M-1 to S-192; M-1 to T-191; M-1 to A-190; M-1 to R-189; M-1 to G-188; M-1 to C-187; M-1 to P-186; M-1 to S-185; M-1 to Q-184; M-1 to Q-183; M-1 to S-182; M-1 to V-181; M-1 to L-180; M-1 to L-179; M-1 to E-178; M-1 to L-177; M-1 to E-176; M-1 to E-175; M-1 to P-174; M-1 to Y-173; M-1 to R-172; M-1 to P-171; M-1 to T-170; M-1 to R-169; M-1 to K-168; M-1 to Y-167; M-1 to L-166; M-1 to G-165; M-1 to H-164; M-1 to T-163; M-1 to I-162; M-1 to T-161; M-1 to S-160; M-1 to A-159; M-1 to L-158; M-1 to G-157; M-1 to L-156; M-1 to P-155; M-1 to C-154; M-1 to G-153; M-1 to V-152; M-1 to G-151; M-1 to G-150; M-1 to L-149; M-1 to Q-148; M-1 to V-147; M-1 to K-146; M-1 to S-145; M-1 to Y-144; M-1 to I-143; M-1 to Y-142; M-1 to Y-141; M-1 to Y-140; M-1 to G-139; M-1 to A-138; M-1 to K-137; M-1 to T-136; M-1 to V-135; M-1 to V-134; M-1 to L-133; M-1 to A-132; M-1 to G-131; M-1 to D-130; M-1 to H-129; M-1 to Y-128; M-1 to S-127; M-1 to L-126; M-1 to G-125; M-1 to R-124; M-1 to L-123; M-1 to F-122; M-1 to A-121; M-1 to L-120; M-1 to G-119; M-1 to L-118; M-1 to Q-117; M-1 to T-116; M-1 to E-115; M-1 to W-114; M-1 to L-113; M-1 to L-112; M-1 to P-111; M-1 to G-110; M-1 to G-109; M-1 to S-108; M-1 to G-107; M-1 to T-106; M-1 to L-105; M-1 to S-104; M-1 to S-103; M-1 to N-102; M-1 to A-101; M-1 to G-100; M-1 to T-99; M-1 to L-98; M-1 to H-97; M-1 to A-96; M-1 to A-95; M-1 to P-94; M-1 to N-93; M-1 to V-92; M-1 to E-91; M-1 to H-90; M-1 to S-89; M-1 to R-88; M-1 to R-87; M-1 to E-86; M-1 to Q-85; M-1 to I-84; M-1 to L-83; M-1 to Q-82; M-1 to E-81; M-1 to W-80; M-1 to S-79; M-1 to G-78; M-1 to A-77; M-1 to P-76; M-1 to G-75; M-1 to D-74; M-1 to P-73; M-1 to L-72; M-1 to R-71; M-1 to T-70; M-1 to V-69; M-1 to M-68; M-1 to E-67; M-1 to G-66; M-1 to L-65; M-1 to R-64; M-1 to W-63; M-1 to H-62; M-1 to L-61; M-1 to Q-60; M-1 to L-59; M-1 to L-58; M-1 to F-57; M-1 to W-56; M-1 to G-55; M-1 to Q-54; M-1 to V-53; M-1 to A-52; M-1 to L-51; M-1 to G-50; M-1 to A-49; M-1 to G-48; M-1 to M-47; M-1 to L-46; M-1 to L-45; M-1 to L-44; M-1 to L-43; M-1 to L-42; M-1 to G-41; M-1 to L-40; M-1 to G-39; M-1 to V-38; M-1 to R-37; M-1 to A-36; M-1 to V-35; M-1 to S-34; M-1 to C-33; M-1 to S-32; M-1 to Q-31; M-1 to R-30; M-1 to R-29; M-1 to H-28; M-1 to S-27; M-1 to R-26; M-1 to G-25; M-1 to L-24; M-1 to R-23; M-1 to T-22; M-1 to F-21; M-1 to P-20; M-1 to I-19; M-1 to D-18; M-1 to T-17; M-1 to Q-16; M-1 to G-15; M-1 to D-14; M-1 to V-13; M-1 to V-12; M-1 to F-11; M-1 to V-10; M-1 to S-9; M-1 to P-8; M-1 to R-7; M-1 to V-6 of the sequence of the AIM II sequence shown in FIGS. 1A and 1B (which is identical to the sequence shown as SEQ ID NO:2, with the exception that the amino acid residues in SEQ ID NO:2 are numbered consecutively from 1 through 240 from the N-terminus to the C-terminus). The present invention is also directed to nucleic acid molecules comprising, or alternatively consisting of, a polynucleotide sequence at least 80%, 85%, 90%, 92%, 95%, 96%, 97%, 98%, or 99% identical to the polynucleotide sequences encoding the polypeptides described above. The present invention also encompasses the above polynucleotide sequences fused to a heterologous polynucleotide sequence. Polypeptides encoded by these polynucleotide sequences are also encompassed by the invention.

The invention also provides polypeptides having one or more amino acids deleted from both the amino and the carboxyl termini of an AIM II polypeptide, which may be described generally as having residues n-m of FIGS. 1A and 1B (i.e., SEQ ID NO:2), where n and m are integers as described above.

In additional embodiments, the present invention provides polynucleotides encoding polypeptides comprising, or alternatively consisting of, the amino acid sequence of residues 83-$m^1$ of FIGS. 1A and 1B (i.e., SEQ ID NO:2), where $m^1$ is an integer from 89 to 239, corresponding to the position of the amino acid residue in FIGS. 1A and 1B (SEQ ID NO:2). For example, the invention provides polynucleotides encoding polypeptides comprising, or alternatively consisting of, the amino acid sequence of a member selected from the group consisting of residues L-83 to M-239; L-83 to F-238; L-83 to A-237; L-83 to G-236; L-83 to F-235; L-83 to Y-234; L-83 to S-233; L-83 to R-232; L-83 to T-231; L-83 to G-230; L-83 to D-229; L-83 to R-228; L-83 to L-227; L-83 to R-226; L-83 to V-225; L-83 to L-224; L-83 to R-223; L-83 to E-222; L-83 to D-221; L-83 to L-220; L-83 to V-219; L-83 to R-218; L-83 to V-217; L-83 to V-216; L-83 to V-215; L-83 to E-214; L-83 to E-213; L-83 to G-212; L-83 to A-211; L-83 to E-210; L-83 to L-209; L-83 to H-208; L-83 to V-207; L-83 to V-206; L-83 to G-205; L-83 to G-204; L-83 to L-203; L-83 to F-202; L-83 to S-201; L-83 to S-200; L-83 to D-199; L-83 to W-198; L-83 to W-197; L-83 to V-196; L-83 to R-195; L-83 to S-194; L-83 to S-193; L-83 to S-192; L-83 to T-191; L-83 to A-190; L-83 to R-189; L-83 to G-188; L-83 to C-187; L-83 to P-186; L-83 to S-185; L-83 to Q-184; L-83 to Q-183; L-83 to S-182; L-83 to V-181; L-83 to L-180; L-83 to L-179; L-83 to E-178; L-83 to L-177; L-83 to E-176; L-83 to E-175; L-83 to P-174; L-83 to Y-173; L-83 to R-172; L-83 to P-171; L-83 to T-170; L-83 to R-169; L-83 to K-168; L-83 to Y-167; L-83 to L-166; L-83 to G-165; L-83 to H-164; L-83 to T-163; L-83 to Y-162; L-83 to T-161; L-83 to S-160; L-83 to A-159; L-83 to L-158; L-83 to G-157; L-83 to L-156; L-83 to P-155; L-83 to C-154; L-83 to T-153; L-83 to V-152; L-83 to G-151; L-83 to S-150; L-83 to L-149; L-83 to Q-148; L-83 to V-147; L-83 to K-146; L-83 to S-145; L-83 to Y-144; L-83 to I-143; L-83 to Y-142; L-83 to Y-141; L-83 to Y-140; L-83 to G-139; L-83 to A-138; L-83 to K-137; L-83 to T-136; L-83 to V-135; L-83 to V-134; L-83 to L-143; L-83 to A-132; L-83 to G-131; L-83 to D-130; L-83 to H-129; L-83 to Y-128; L-83 to S-127; L-83 to L-126; L-83 to G-125; L-83 to R-124; L-83 to L-123; L-83 to F-122; L-83 to A-121; L-83 to L-120; L-83 to G-119; L-83 to L-118; L-83 to Q-117; L-83 to T-116; L-83 to E-115; L-83 to W-114; L-83 to L-113; L-83 to L-112; L-83 to P-111; L-83 to G-110; L-83 to G-109; L-83 to S-108; L-83 to G-107; L-83 to T-106; L-83 to L-105; L-83 to S-104; L-83 to S-103; L-83 to N-102; L-83 to A-101; L-83 to G-100; L-83 to T-99; L-83 to L-98; L-83 to H-97; L-83 to A-96; L-83 to A-95; L-83 to P-94; L-83 to N-93; L-83 to V-92; L-83 to E-91; L-83 to H-90; and L-83 to S-89; of the sequence of the AIM II sequence shown in FIGS. 1A and 1B (SEQ ID NO:2). The present application is also directed to nucleic acid molecules comprising, or alternatively consisting of, a polynucleotide sequence at least 80%, 85%, 90%, 92%, 95%, 96%, 97%, 98% or 99% identical to the polynucleotide sequence encoding the AIM II polypeptides described above. The present invention also encompasses the above polynucleotide sequences fused to a heterologous polynucleotide sequence. Polypeptides encoded by these polynucleotide sequences are also encompassed by the invention.

In additional embodiments, the polynucleotides of the invention encode functional attributes of AIM II. Preferred embodiments of the invention in this regard include fragments that comprise, or alternatively consist of, one, two, three, four or more of one or more of the following functional domains: alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of AIM II.

The data representing the structural or functional attributes of AIM II set forth in FIGS. 3A–3F and/or Table 2 was generated using the various identified modules and algorithms of the DNA*STAR set on default parameters. In a preferred embodiment, the data presented in columns VIII, IX, XIII, and XIV of Table 2 can be used to determine regions of AIM II which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Certain preferred regions in these regards are set out in FIGS. 3A–3F, but may, as shown in Table 2, be represented or identified in tabular form. The DNA*STAR computer algorithm used to generate FIGS. 3A–3F (set on the original default parameters) was used to present the data in FIGS. 3A–3F in a tabular format (See Table 2). The tabular format of the data in FIG. 3A–3F may be used to easily determine specific boundaries of a preferred region.

The above-mentioned preferred regions set out in FIGS. 3A–3F and in Table 2 include, but are not limited to, regions of the aforementioned types identified by analysis of the amino acid sequence set out in FIGS. 1A and 1B. As set out in FIGS. 3A–3F and in Table 2, such preferred regions include Garnier-Robson alpha-regions, beta-regions, turn-regions, and coil-regions (columns I, III, V, and VII in Table 2), Chou-Fasman alpha-regions, beta-regions, and turn-regions (columns II, IV, and VI in Table 2), Kyte-Doolittle hydrophilic regions (column VIII in Table 2), Hopp-Woods hydrophobic regions (column IX in Table 2), Eisenberg alpha- and beta-amphipathic regions (columns X and XI in Table 2), Karplus-Schulz flexible regions (column XII in Table 2), Jameson-Wolf regions of high antigenic index (column XIII in Table 2), and Emini surface-forming regions (column XIV in Table 2).

TABLE 2

| Res | Position | I | II | III | IV | V | VI | VII | VIII | IX | X | XI | XII | XIII | XIV |
|---|---|---|---|---|---|---|---|---|---|---|---|---|---|---|---|
| Met | 1 | A | — | — | — | — | — | — | 0.19 | −0.71 | — | — | — | 0.95 | 1.49 |
| Glu | 2 | A | — | — | — | — | — | — | −0.28 | −0.50 | * | — | — | 0.50 | 0.87 |
| Glu | 3 | A | — | — | B | — | — | — | 0.22 | −0.29 | * | — | — | 0.30 | 0.50 |
| Ser | 4 | A | — | — | B | — | — | — | 0.40 | −0.71 | * | * | — | 0.60 | 0.99 |
| Val | 5 | A | — | — | B | — | — | — | 0.49 | −0.90 | * | * | — | 0.60 | 0.89 |
| Val | 6 | A | — | — | B | — | — | — | 0.23 | −0.51 | — | — | — | 0.60 | 0.69 |
| Arg | 7 | — | — | B | — | — | T | — | −0.47 | 0.13 | * | * | — | 0.10 | 0.38 |
| Pro | 8 | — | — | B | — | — | T | — | −1.32 | 0.53 | * | * | — | −0.20 | 0.44 |
| Ser | 9 | — | — | B | — | — | T | — | −1.88 | 0.53 | * | — | — | −0.20 | 0.44 |
| Val | 10 | — | — | B | — | — | T | — | −1.02 | 0.53 | * | * | — | −0.20 | 0.17 |
| Phe | 11 | — | — | B | — | — | — | — | −0.51 | 0.53 | — | * | — | −0.40 | 0.18 |
| Val | 12 | — | — | B | — | — | — | — | −0.62 | 0.53 | — | * | — | −0.12 | 0.13 |
| Val | 13 | — | — | B | — | — | T | — | −0.72 | 0.54 | — | * | — | 0.36 | 0.31 |
| Asp | 14 | — | — | B | — | — | T | — | −0.42 | 0.39 | — | * | F | 1.09 | 0.52 |
| Gly | 15 | — | — | — | — | T | T | — | −0.46 | −0.40 | — | * | F | 2.52 | 1.17 |
| Gln | 16 | — | — | — | — | T | T | — | 0.03 | −0.36 | — | * | F | 2.80 | 1.11 |
| Thr | 17 | — | — | — | B | — | — | C | 0.19 | −0.57 | — | * | F | 2.22 | 1.03 |
| Asp | 18 | — | — | B | B | — | — | — | 0.73 | 0.21 | — | * | F | 0.69 | 0.90 |
| Ile | 19 | — | — | B | B | — | — | — | 0.84 | 0.27 | — | * | F | 0.41 | 0.75 |
| Pro | 20 | — | — | B | B | — | — | — | 0.38 | −0.13 | * | * | — | 0.73 | 1.02 |
| Phe | 21 | — | — | B | B | — | — | — | 0.03 | 0.07 | * | — | — | −0.30 | 0.50 |
| Thr | 22 | — | — | B | B | — | — | — | 0.46 | 0.50 | * | — | — | −0.26 | 0.71 |
| Arg | 23 | — | — | B | B | — | — | — | 0.16 | −0.19 | * | — | F | 1.13 | 0.90 |
| Leu | 24 | — | — | — | B | T | — | — | 1.01 | −0.23 | * | — | F | 2.02 | 1.39 |
| Gly | 25 | — | — | — | B | T | — | — | 1.33 | −0.51 | * | — | F | 2.66 | 1.31 |
| Arg | 26 | — | — | — | — | T | T | — | 2.14 | −1.00 | * | — | F | 3.40 | 1.31 |
| Ser | 27 | — | — | — | — | T | T | — | 2.46 | −1.00 | * | — | F | 3.06 | 3.11 |
| His | 28 | — | — | — | — | T | T | — | 2.04 | −1.29 | * | — | F | 3.03 | 5.44 |
| Arg | 29 | — | — | — | — | T | T | — | 2.19 | −1.33 | * | — | F | 3.00 | 3.72 |
| Arg | 30 | — | — | — | — | T | — | — | 2.23 | −0.76 | * | * | F | 2.77 | 1.49 |
| Gln | 31 | — | — | — | — | T | T | — | 1.27 | −0.76 | * | — | F | 2.94 | 1.47 |
| Ser | 32 | — | — | — | — | T | T | — | 0.98 | −0.61 | * | — | F | 3.10 | 0.56 |
| Cys | 33 | — | — | B | — | — | T | — | 1.12 | −0.11 | * | — | — | 1.94 | 0.29 |
| Ser | 34 | — | — | B | — | — | T | — | 0.16 | −0.11 | * | — | — | 1.63 | 0.32 |
| Val | 35 | — | — | B | B | — | — | — | −0.30 | 0.13 | * | * | — | 0.32 | 0.18 |
| Ala | 36 | — | — | B | B | — | — | — | −1.11 | 0.17 | — | * | — | 0.01 | 0.33 |
| Arg | 37 | — | — | B | B | — | — | — | −1.16 | 0.29 | * | * | — | −0.30 | 0.20 |
| Val | 38 | — | — | B | B | — | — | — | −1.30 | 0.33 | * | * | — | −0.30 | 0.27 |
| Gly | 39 | — | — | B | B | — | — | — | −1.81 | 0.37 | * | * | — | −0.30 | 0.22 |
| Leu | 40 | — | A | B | — | — | — | — | −1.77 | 0.56 | * | * | — | −0.60 | 0.09 |
| Gly | 41 | — | A | B | — | — | — | — | −1.99 | 1.24 | * | * | — | −0.60 | 0.10 |
| Leu | 42 | — | A | B | — | — | — | — | −2.91 | 1.29 | * | * | — | −0.60 | 0.09 |
| Leu | 43 | — | A | B | — | — | — | — | −2.66 | 1.54 | — | — | — | −0.60 | 0.09 |
| Leu | 44 | — | A | B | — | — | — | — | −2.66 | 1.47 | — | — | — | −0.60 | 0.09 |
| Leu | 45 | — | A | B | — | — | — | — | −2.43 | 1.47 | — | — | — | −0.60 | 0.10 |
| Leu | 46 | — | A | B | — | — | — | — | −2.43 | 1.29 | — | — | — | −0.60 | 0.13 |
| Met | 47 | A | A | — | — | — | — | — | −2.43 | 1.03 | — | — | — | −0.60 | 0.15 |
| Gly | 48 | A | — | — | — | — | T | — | −2.21 | 1.03 | — | — | — | −0.20 | 0.15 |
| Ala | 49 | A | — | — | — | — | T | — | −2.26 | 0.84 | — | — | — | −0.20 | 0.19 |
| Gly | 50 | A | — | — | — | — | T | — | −1.44 | 0.80 | — | — | — | −0.20 | 0.14 |
| Leu | 51 | A | — | — | — | — | T | — | −0.98 | 0.59 | — | — | — | −0.20 | 0.25 |
| Ala | 52 | — | A | B | — | — | — | — | −0.67 | 0.59 | — | * | — | −0.60 | 0.24 |
| Val | 53 | A | A | — | — | — | — | — | −1.02 | 1.00 | — | — | — | −0.60 | 0.26 |
| Gln | 54 | — | A | B | — | — | — | — | −1.24 | 1.36 | — | * | — | −0.60 | 0.27 |
| Gly | 55 | — | A | B | — | — | — | — | −1.71 | 1.36 | — | * | — | −0.60 | 0.22 |
| Trp | 56 | A | A | — | — | — | — | — | −0.90 | 1.54 | — | * | — | −0.60 | 0.24 |
| Phe | 57 | — | A | B | — | — | — | — | 1.12 | 1.30 | — | * | — | −0.60 | 0.24 |
| Leu | 58 | — | A | B | — | — | — | — | −0.30 | 1.59 | — | * | — | −0.60 | 0.20 |
| Leu | 59 | — | A | B | — | — | — | — | −0.59 | 1.66 | * | * | — | −0.60 | 0.26 |
| Gln | 60 | — | A | B | — | — | — | — | −0.13 | 1.66 | * | * | — | −0.60 | 0.32 |
| Leu | 61 | — | A | — | — | — | — | C | −0.66 | 0.87 | * | * | — | −0.40 | 0.76 |
| His | 62 | — | A | — | — | — | — | C | −0.30 | 0.87 | * | * | — | −0.40 | 0.76 |
| Trp | 63 | — | A | — | — | — | — | C | 0.51 | 0.61 | * | * | — | −0.40 | 0.43 |
| Arg | 64 | A | A | — | — | — | — | — | 0.72 | 0.21 | * | * | — | −0.30 | 0.91 |
| Leu | 65 | A | A | — | — | — | — | — | −0.13 | 0.14 | * | * | — | −0.30 | 0.66 |
| Gly | 66 | — | A | — | — | T | — | — | 0.37 | 0.29 | * | * | — | 0.10 | 0.47 |
| Glu | 67 | — | A | B | — | — | — | — | 0.51 | −0.14 | * | * | — | 0.30 | 0.34 |
| Met | 68 | — | A | B | — | — | — | — | −0.01 | −0.14 | * | * | — | 0.30 | 0.82 |
| Val | 69 | — | A | B | — | — | — | — | −0.33 | −0.14 | * | — | — | 0.64 | 0.68 |
| Thr | 70 | — | A | B | — | — | — | — | 0.48 | −0.11 | * | — | — | 0.98 | 0.61 |
| Arg | 71 | — | A | B | — | — | — | — | 0.48 | −0.14 | * | * | F | 1.62 | 1.02 |
| Leu | 72 | — | — | B | — | — | T | — | 0.27 | −0.33 | * | — | F | 2.36 | 1.37 |
| Pro | 73 | — | — | — | — | T | T | — | 0.28 | −0.54 | * | — | F | 3.40 | 1.16 |
| Asp | 74 | — | — | — | — | T | T | — | 0.79 | −0.53 | * | — | F | 2.91 | 0.75 |
| Gly | 75 | — | — | — | — | T | — | C | 0.80 | −0.10 | * | — | F | 2.07 | 0.91 |
| Pro | 76 | — | — | — | — | T | — | C | 0.40 | 0.40 | * | — | F | 1.73 | 0.78 |
| Ala | 77 | — | — | — | — | T | — | C | 1.21 | 0.09 | — | — | F | 0.79 | 0.49 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 78 | — | — | — | — | — | T | C | 1.42 | 0.09 | — | — | F | 0.45 | 0.86 |
| Ser | 79 | — | — | — | — | — | T | C | 0.61 | 0.06 | * | — | F | 0.45 | 0.97 |
| Trp | 80 | A | A | — | — | — | — | — | 0.07 | 0.31 | * | — | F | -0.15 | 0.79 |
| Glu | 81 | A | A | — | — | — | — | — | 0.28 | 0.50 | * | — | — | -0.60 | 0.56 |
| Gln | 82 | A | A | — | — | — | — | — | 0.87 | 0.47 | — | * | — | -0.60 | 0.72 |
| Leu | 83 | A | A | — | — | — | — | — | 1.32 | 0.09 | — | — | — | -0.15 | 1.19 |
| Ile | 84 | A | A | — | — | — | — | — | 1.73 | -0.83 | — | — | — | 0.75 | 1.35 |
| Gln | 85 | A | A | — | — | — | — | — | 1.72 | -0.83 | — | — | F | 0.90 | 1.52 |
| Glu | 86 | A | A | — | — | — | — | — | 1.69 | -0.84 | — | — | F | 0.90 | 2.48 |
| Arg | 87 | A | A | — | — | — | — | — | 1.69 | -1.03 | — | — | F | 0.90 | 4.81 |
| Arg | 88 | — | A | — | — | T | — | — | 1.64 | -1.71 | — | — | F | 1.30 | 4.81 |
| Ser | 59 | — | A | — | — | T | — | — | 2.53 | -1.47 | — | — | F | 1.30 | 2.06 |
| His | 90 | — | A | — | — | — | — | C | 2.32 | -1.07 | — | — | — | 0.95 | 1.69 |
| Glu | 91 | — | A | — | — | — | — | C | 1.73 | -0.64 | * | — | — | 0.95 | 1.34 |
| Val | 92 | — | A | — | — | — | — | C | 1.03 | -0.14 | * | — | — | 0.65 | 1.01 |
| Asn | 93 | — | — | — | — | — | T | C | 0.89 | -0.03 | — | * | — | 0.90 | 0.75 |
| Pro | 94 | A | — | — | — | — | T | — | 0.38 | -0.03 | — | * | — | 0.70 | 0.59 |
| Ala | 95 | A | — | — | — | — | T | — | 0.10 | 0.66 | — | * | — | -0.20 | 0.65 |
| Ala | 96 | A | — | — | — | — | T | — | -0.24 | 0.50 | — | * | — | -0.20 | 0.59 |
| His | 97 | A | — | — | — | — | — | — | 0.02 | 0.53 | — | * | — | -0.10 | 0.37 |
| Leu | 98 | A | — | — | — | — | — | — | 0.02 | 0.60 | — | — | — | -0.40 | 0.37 |
| Thr | 99 | — | — | B | — | — | — | — | -0.07 | 0.50 | — | — | — | -0.40 | 0.60 |
| Gly | 100 | — | — | — | — | — | — | C | 0.22 | 0.39 | — | — | F | 0.25 | 0.59 |
| Ala | 101 | — | — | — | — | — | — | C | 0.00 | 0.27 | — | — | F | 0.25 | 0.96 |
| Asn | 102 | — | — | B | — | — | T | — | -0.28 | 0.27 | — | — | F | 0.25 | 0.55 |
| Ser | 103 | — | — | B | — | — | T | — | 0.19 | 0.27 | — | — | F | 0.25 | 0.80 |
| Ser | 104 | — | — | B | — | — | T | — | 0.20 | 0.27 | — | * | F | 0.25 | 0.78 |
| Leu | 105 | — | — | B | — | — | T | — | 0.20 | 0.16 | — | — | F | 0.25 | 0.65 |
| Thr | 106 | — | — | B | — | — | — | — | 0.44 | 0.19 | — | * | F | 0.05 | 0.18 |
| Gly | 107 | — | — | — | — | T | T | — | 0.23 | 0.23 | — | — | F | 0.65 | 0.35 |
| Ser | 108 | — | — | — | — | T | T | — | -0.28 | 0.27 | — | — | F | 0.65 | 0.66 |
| Gly | 109 | — | — | — | — | — | T | C | -0.79 | 0.27 | — | — | F | 0.45 | 0.38 |
| Gly | 110 | — | — | — | — | — | T | C | -0.27 | 0.47 | — | — | F | 0.15 | 0.32 |
| Pro | 111 | — | A | — | — | — | — | C | 0.04 | 0.96 | — | — | F | -0.25 | 0.25 |
| Leu | 112 | — | A | — | — | — | — | C | 0.08 | 0.57 | — | — | F | -0.25 | 0.43 |
| Leu | 113 | — | A | B | — | — | — | — | 0.38 | 0.63 | — | * | — | -0.60 | 0.63 |
| Trp | 114 | — | A | B | — | — | — | — | -0.09 | 0.60 | — | — | — | -0.60 | 0.71 |
| Glu | 115 | — | A | B | — | — | — | — | -0.09 | 0.86 | — | * | — | -0.60 | 0.71 |
| Thr | 116 | A | A | — | — | — | — | — | -0.69 | 0.60 | — | * | F | -0.45 | 0.85 |
| Gln | 117 | A | A | — | — | — | — | — | -0.17 | 0.60 | — | * | F | -0.45 | 0.67 |
| Leu | 118 | A | A | — | — | — | — | — | -0.36 | 0.19 | — | — | — | -0.30 | 0.39 |
| Gly | 119 | A | A | — | — | — | — | — | -0.88 | 0.97 | * | * | — | -0.60 | 0.23 |
| Leu | 120 | A | A | — | — | — | — | — | -0.77 | 1.17 | * | * | — | -0.60 | 0.11 |
| Ala | 121 | — | A | B | — | — | — | — | -0.80 | 0.77 | * | — | — | -0.60 | 0.26 |
| Phe | 122 | — | A | B | — | — | — | — | -1.61 | 0.51 | * | — | — | -0.60 | 0.26 |
| Leu | 123 | — | A | B | — | — | — | — | -1.10 | 0.77 | * | — | — | -0.60 | 0.26 |
| Arg | 124 | — | A | B | — | — | — | — | -1.00 | 0.47 | * | — | — | -0.60 | 0.35 |
| Gly | 125 | — | A | B | — | — | — | — | -0.22 | 0.73 | — | — | — | -0.60 | 0.63 |
| Leu | 126 | — | — | B | — | — | — | — | 0.37 | 0.44 | * | — | — | -0.25 | 1.05 |
| Ser | 127 | — | — | — | — | — | — | C | 0.72 | -0.24 | * | — | — | 0.70 | 0.89 |
| Tyr | 128 | — | — | — | — | — | — | C | 0.94 | 0.19 | * | * | — | 0.10 | 0.89 |
| His | 129 | — | — | — | — | T | T | — | 0.02 | 0.26 | * | — | — | 0.65 | 1.09 |
| Asp | 130 | — | — | — | — | T | T | — | -0.49 | 0.26 | — | — | — | 0.50 | 0.67 |
| Gly | 131 | — | — | B | — | — | T | — | -0.53 | 0.51 | — | — | — | -0.20 | 0.32 |
| Ala | 132 | — | — | B | — | — | T | — | -0.54 | 0.40 | * | — | — | -0.20 | 0.17 |
| Leu | 133 | — | — | B | B | — | — | — | -0.26 | 0.39 | * | — | — | -0.30 | 0.15 |
| Val | 134 | — | — | B | B | — | — | — | -0.81 | 0.39 | * | — | — | -0.30 | 0.30 |
| Val | 135 | — | — | B | B | — | — | — | -1.16 | 0.46 | * | — | — | -0.60 | 0.30 |
| Thr | 136 | — | — | B | B | — | — | — | -1.06 | 0.39 | — | — | — | -0.30 | 0.36 |
| Lys | 137 | — | — | B | — | — | T | — | -0.71 | 0.46 | — | — | F | -0.05 | 0.77 |
| Ala | 138 | — | — | B | — | — | T | — | -0.14 | 0.17 | — | — | — | -0.05 | 1.62 |
| Gly | 139 | — | — | B | — | — | T | — | -0.18 | 0.69 | — | — | — | -0.05 | 1.76 |
| Tyr | 140 | — | — | B | — | — | T | — | 0.43 | 0.89 | * | — | — | -0.20 | 0.62 |
| Tyr | 141 | — | — | B | B | — | — | — | 0.44 | 1.64 | — | — | — | -0.60 | 0.96 |
| Tyr | 142 | — | — | B | B | — | — | — | 0.44 | 1.53 | — | * | — | -0.45 | 1.30 |
| Ile | 143 | — | — | B | B | — | — | — | 0.18 | 1.10 | — | * | — | -0.45 | 1.66 |
| Tyr | 144 | — | — | B | B | — | — | — | 0.52 | 0.99 | — | * | — | -0.60 | 0.78 |
| Ser | 145 | — | — | B | B | — | — | — | -0.04 | 0.63 | — | * | - | -0.60 | 0.87 |
| Lys | 146 | — | — | B | B | — | — | — | -0.14 | 0.56 | - | * | — | -0.45 | 1.02 |
| Val | 147 | — | — | B | B | — | — | — | -0.24 | 0.30 | — | * | — | -0.30 | 0.64 |
| Gln | 148 | — | — | B | B | — | — | — | -0.21 | -0.03 | — | * | — | 0.30 | 0.48 |
| Leu | 149 | — | — | B | B | — | — | — | -0.31 | 0.23 | — | * | — | -0.30 | 0.18 |
| Gly | 150 | — | — | B | B | — | — | — | -0.68 | 0.66 | — | * | — | -0.60 | 0.24 |
| Gly | 151 | — | — | B | B | — | — | — | -0.93 | 0.59 | — | * | — | -0.60 | 0.07 |
| Val | 152 | — | — | B | B | — | — | — | -0.89 | 0.61 | — | — | — | -0.60 | 0.14 |
| Gly | 153 | — | — | B | — | — | — | — | -1.23 | 0.61 | — | — | — | 0.40 | 0.11 |
| Cys | 154 | — | — | B | — | — | T | — | -1.23 | 0.61 | — | — | — | -0.20 | 0.11 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Pro | 155 | — | — | B | — | — | T | — | −1.48 | 0.87 | — | — | — | −0.20 | 0.13 |
| Leu | 156 | — | — | B | — | — | T | — | −1.43 | 0.73 | — | — | — | −0.20 | 0.13 |
| Gly | 157 | — | — | B | — | — | T | — | −0.89 | 0.69 | — | — | — | −0.20 | 0.32 |
| Leu | 158 | — | — | B | B | — | — | — | −1.43 | 0.60 | — | — | — | −0.60 | 0.30 |
| Ala | 159 | — | — | B | B | — | — | — | −1.08 | 0.86 | — | — | — | −0.60 | 0.26 |
| Ser | 160 | — | — | B | B | — | — | — | −0.90 | 0.66 | — | — | — | −0.60 | 0.37 |
| Thr | 161 | — | — | B | B | — | — | — | −0.43 | 0.73 | * | — | F | −0.45 | 0.62 |
| Ile | 162 | — | — | B | B | — | — | — | −0.90 | 0.47 | * | — | — | −0.60 | 0.60 |
| Thr | 163 | — | — | B | B | — | — | — | −0.33 | 0.66 | * | — | — | −0.60 | 0.37 |
| His | 164 | — | — | B | B | — | — | — | 0.30 | 1.03 | * | — | — | −0.60 | 0.40 |
| Gly | 165 | — | — | B | B | — | — | — | 0.71 | 0.54 | — | — | — | −0.45 | 1.15 |
| Leu | 166 | — | — | B | B | — | — | — | 0.71 | −0.14 | — | — | — | 0.75 | 1.56 |
| Tyr | 167 | — | — | — | B | T | — | — | 1.39 | −0.14 | * | — | — | 1.45 | 1.66 |
| Lys | 168 | — | — | — | B | T | — | — | 1.81 | −0.21 | * | — | F | 1.90 | 2.59 |
| Arg | 169 | — | — | B | — | — | — | — | 1.60 | −0.64 | * | — | F | 2.30 | 6.15 |
| Thr | 170 | — | — | — | — | — | T | C | 1.73 | −0.57 | * | — | F | 3.00 | 6.15 |
| Pro | 171 | — | — | — | — | — | T | C | 2.54 | −0.90 | * | — | F | 2.70 | 4.75 |
| Arg | 172 | — | — | — | — | — | T | C | 2.79 | −0.90 | * | — | F | 2.40 | 4.20 |
| Tyr | 173 | — | — | — | — | — | T | C | 1.93 | −0.90 | * | * | F | 2.10 | 5.05 |
| Pro | 174 | — | A | — | — | — | — | C | 1.82 | −0.70 | * | * | F | 1.40 | 2.69 |
| Glu | 175 | A | A | — | — | — | — | — | 1.32 | −1.13 | * | * | F | 0.90 | 2.38 |
| Glu | 176 | A | A | — | — | — | — | — | 0.72 | −0.44 | * | * | F | 0.60 | 1.25 |
| Leu | 177 | A | A | — | — | — | — | — | −0.24 | −0.51 | * | * | — | 0.60 | 0.67 |
| Glu | 178 | A | A | — | — | — | — | — | −0.30 | −0.30 | * | — | — | 0.30 | 0.29 |
| Leu | 179 | A | A | — | — | — | — | — | −0.09 | 0.09 | — | — | — | −0.30 | 0.22 |
| Leu | 180 | A | A | — | — | — | — | — | −0.09 | 0.49 | — | — | — | −0.60 | 0.47 |
| Val | 181 | A | A | — | — | — | — | — | −0.39 | 0.20 | — | * | — | −0.30 | 0.47 |
| Ser | 182 | A | A | — | — | — | — | — | 0.21 | 0.59 | — | — | F | −0.45 | 0.76 |
| Gln | 183 | — | — | — | — | T | — | — | −0.46 | 0.33 | — | — | F | 0.60 | 1.42 |
| Gln | 184 | — | — | B | — | — | — | — | 0.01 | 0.21 | — | * | F | 0.20 | 1.02 |
| Ser | 185 | — | — | — | — | — | T | C | 0.93 | 0.00 | * | * | F | 0.45 | 0.76 |
| Pro | 186 | — | — | — | — | T | T | — | 1.20 | −0.39 | — | * | F | 1.25 | 0.85 |
| Cys | 187 | — | — | — | — | T | T | — | 1.19 | −0.29 | — | * | F | 1.25 | 0.50 |
| Gly | 188 | — | — | B | — | — | T | — | 0.89 | −0.20 | — | * | F | 1.15 | 0.54 |
| Arg | 189 | — | — | B | B | — | — | — | 0.59 | −0.20 | — | * | F | 1.05 | 0.47 |
| Ala | 190 | — | — | B | B | — | — | — | 0.59 | −0.24 | * | * | F | 1.50 | 1.16 |
| Thr | 191 | — | — | — | B | — | — | C | 0.91 | −0.43 | — | * | F | 2.00 | 1.58 |
| Ser | 192 | — | — | — | — | — | T | C | 0.72 | −0.86 | — | * | F | 3.00 | 1.58 |
| Ser | 193 | — | — | B | — | — | T | — | 0.78 | −0.21 | — | * | F | 2.20 | 1.16 |
| Ser | 194 | — | — | B | — | — | T | — | 0.38 | 0.20 | * | * | F | 1.15 | 0.84 |
| Arg | 195 | — | — | B | — | — | T | — | 0.97 | 0.63 | * | * | F | 0.55 | 0.66 |
| Val | 196 | — | — | B | B | — | — | — | 0.98 | 0.24 | * | * | — | 0.00 | 0.82 |
| Trp | 197 | — | — | — | B | T | — | — | 0.98 | 0.24 | * | * | — | 0.10 | 0.82 |
| Trp | 198 | — | — | B | B | — | — | — | 0.58 | 0.24 | — | * | — | −0.30 | 0.56 |
| Asp | 199 | — | — | B | — | — | T | — | 0.07 | 1.03 | — | * | F | −0.05 | 0.66 |
| Ser | 200 | — | — | — | — | — | T | C | −0.39 | 1.07 | — | * | F | 0.15 | 0.52 |
| Ser | 201 | — | — | — | — | — | T | C | 0.12 | 0.59 | — | — | F | 0.15 | 0.49 |
| Phe | 202 | — | — | — | — | T | T | — | −0.44 | 0.10 | — | — | F | 0.65 | 0.29 |
| Leu | 203 | — | — | — | B | — | — | C | −1.01 | 0.74 | — | — | — | −0.40 | 0.16 |
| Gly | 204 | — | — | — | B | — | — | C | −1.04 | 1.00 | — | — | — | −0.40 | 0.09 |
| Gly | 205 | — | — | — | B | — | — | C | −1.56 | 1.11 | — | — | — | −0.40 | 0.14 |
| Val | 206 | — | A | B | — | — | — | — | −1.26 | 1.01 | — | * | — | −0.60 | 0.14 |
| Val | 207 | — | A | B | — | — | — | — | −1.14 | 0.33 | — | — | — | −0.30 | 0.24 |
| His | 208 | A | A | — | — | — | — | — | −0.68 | 0.40 | — | — | — | −0.60 | 0.25 |
| Leu | 209 | A | A | — | — | — | T | — | −0.33 | 0.40 | — | — | — | −0.60 | 0.33 |
| Glu | 210 | A | A | — | — | — | — | — | 0.01 | −0.24 | — | * | — | 0.30 | 0.77 |
| Ala | 211 | A | A | — | — | — | — | — | 0.01 | −0.89 | — | — | F | 0.75 | 0.98 |
| Gly | 212 | A | A | — | — | — | — | — | 0.01 | −0.74 | — | * | F | 0.75 | 0.88 |
| Glu | 213 | A | A | — | B | — | — | — | −0.81 | −0.79 | * | * | F | 0.75 | 0.38 |
| Glu | 214 | A | A | — | B | — | — | — | 0.11 | −0.14 | * | * | F | 0.45 | 0.28 |
| Val | 215 | A | A | — | B | — | — | — | −0.74 | −0.64 | * | * | — | 0.60 | 0.55 |
| Val | 216 | A | A | — | B | — | — | — | −0.97 | −0.43 | * | * | — | 0.30 | 0.24 |
| Val | 217 | A | A | — | B | — | — | — | −0.62 | 0.26 | * | * | — | −0.30 | 0.11 |
| Arg | 218 | A | A | — | B | — | — | — | −0.62 | 0.26 | * | * | — | −0.30 | 0.25 |
| Val | 219 | A | A | — | B | — | — | — | −0.51 | −0.39 | * | * | — | 0.30 | 0.59 |
| Leu | 220 | A | A | — | B | — | — | — | −0.47 | −1.03 | * | — | — | 0.75 | 1.56 |
| Asp | 221 | A | A | — | B | — | — | — | −0.17 | −0.99 | * | — | F | 0.75 | 0.66 |
| Glu | 222 | A | A | — | — | — | — | — | 0.50 | −0.34 | — | — | F | 0.45 | 0.66 |
| Arg | 223 | A | A | — | — | — | — | — | −0.42 | −0.99 | * | * | F | 0.90 | 1.56 |
| Leu | 224 | A | A | — | — | — | — | — | 0.54 | −0.99 | * | * | — | 0.60 | 0.77 |
| Val | 225 | — | A | B | — | — | — | — | 1.36 | −0.99 | * | * | — | 0.94 | 0.87 |
| Arg | 226 | — | A | B | — | — | — | — | 1.01 | −0.99 | — | * | — | 1.28 | 0.74 |
| Leu | 227 | — | — | B | — | — | T | — | 0.70 | −0.56 | * | * | — | 2.02 | 0.89 |
| Arg | 228 | — | — | B | — | — | T | — | 0.70 | −0.76 | — | * | F | 2.66 | 1.73 |
| Asp | 229 | — | — | — | — | T | T | — | 1.21 | −1.40 | * | * | F | 3.40 | 1.73 |
| Gly | 230 | — | — | — | — | T | T | — | 1.82 | −1.01 | * | * | F | 3.06 | 2.81 |
| Thr | 231 | — | — | — | — | T | — | — | 1.01 | −0.94 | * | * | F | 2.52 | 2.25 |

TABLE 2-continued

| Res | Position | I | II | III | IV | V | VI | VII | VIII | IX | X | XI | XII | XIII | XIV |
|---|---|---|---|---|---|---|---|---|---|---|---|---|---|---|---|
| Arg | 232 | — | — | B | — | — | — | — | 1.48 | −0.16 | * | * | F | 1.48 | 1.17 |
| Ser | 233 | — | — | B | — | — | T | — | 0.78 | 0.27 | * | * | F | 0.74 | 1.17 |
| Tyr | 234 | — | — | B | — | — | T | — | 0.08 | 0.34 | * | — | — | 0.10 | 0.82 |
| Phe | 235 | — | — | B | — | — | T | — | −0.18 | 0.64 | — | — | — | −0.20 | 0.36 |
| Gly | 236 | — | — | B | — | — | T | — | −0.72 | 1.26 | — | — | — | −0.20 | 0.27 |
| Ala | 237 | — | A | B | — | — | — | — | −1.22 | 1.51 | — | — | — | −0.60 | 0.13 |
| Phe | 238 | — | A | B | — | — | — | — | −1.31 | 1.19 | — | — | — | −0.60 | 0.19 |
| Met | 239 | — | A | B | — | — | — | — | −1.46 | 0.83 | — | — | — | −0.60 | 0.24 |
| Val | 240 | — | A | B | — | — | — | — | −1.14 | 0.83 | — | — | — | −0.60 | 0.30 |

Among highly preferred fragments in this regard are those that comprise regions of AIM II that combine several structural features, such as several of the features set out above in Table 2.

The present invention is further directed to isolated polypeptides comprising, or alternatively consisting of, fragments of AIM II. In particular, the invention provides isolated polypeptides comprising, or alternatively consisting of, the amino acid sequences of a member selected from the group consisting of amino acids 1–60, 11–70, 21–80, 31–90, 41–100, 51–110, 61–120, 71–130, 81–140, 91–150, 101–160, 111–170, 121–180, 131–190, 141–200, 151–210, 161–220, 171–230, and 181–240 of SEQ ID NO:2, as well as isolated polynucleotides which encode these polypeptides.

The present invention is also directed to isolated polypeptides comprising, or alternatively consisting of, domains of AIM II. In particular, the invention provides polypeptides comprising, or alternatively consisting of, beta-sheet regions of AIM II set out in Table 2. These polypeptides include polypeptides comprising, or alternatively consisting of, amino acid sequences of a member selected from the group consisting of amino acid residues from about 7 to about 14, amino acid residues from about 18 to about 23, amino acid residues from about 17 to about 25, amino acid residues from about 33 to about 46, amino acid residues from about 35 to about 39, amino acid residues from about 57 to about 60, amino acid residues from about 67 to about 72, amino acid residues from about 102 to about 107, amino acid residues from about 121 to about 126, amino acid residues from about 131 to about 166, amino acid residues from about 141 to about 152, amino acid residues from about 158 to about 169, amino acid residues from about 213 to about 221, and amino acid residues from about 232 to about 240 of SEQ ID NO:2. The invention is further directed to isolated polynucleotides comprising, or alternatively consisting of, nucleic acid molecules which encode the beta-sheet regions set out in Table 2, and isolated polypeptides comprising, or alternatively consisting of, amino acid sequences at least 80% identical, and more preferably at least 85%, 90%, 92%, 95%, 96%, 97%, 98% or 99% identical to nucleic acid molecules encoding beta-sheet regions of the AIM II protein.

The invention is also directed to isolated polypeptides comprising, or alternatively consisting of, fragments of AIM II which have one or more functional activity associated with AIM II polypeptides having the amino acid sequence of SEQ ID NO:2 or SEQ ID NO:39, as well as isolated polynucleotides encoding these polypeptides.

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al. *Cell* 37:767–778 (1984) at 777.

The present invention encompasses polypeptides comprising, or alternatively consisting of, an epitope of the polypeptide having an amino acid sequence of SEQ ID NO:2 or SEQ ID NO:39, or an epitope of the polypeptide sequence encoded by a polynucleotide sequence contained in deposited clone identified as ATCC Accession No. 97689 or 97483 or encoded by a polynucleotide that hybridizes to the complement of the sequence of SEQ ID NO:1 or SEQ ID NO:38 or contained in deposited clone identified as ATCC Accession No. 97689 or 97483 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1 or SEQ ID NO:38), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., *Proc. Natl. Acad. Sci. USA* 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments that function as epitopes may be produced by any conventional means. (See, e.g., Houghten, *Proc. Natl. Acad. Sci. USA* 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 15, at least 20, at least 25, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. Antigenic epitopes can be used as the target molecules in immunoassays. (See, for instance, Wilson et al., *Cell* 37:767–778 (1984); Sutcliffe et al., *Science* 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). A preferred immunogenic epitope includes the secreted protein. The polypeptides comprising one or more immunogenic epitopes may be presented for eliciting an antibody response together with a carrier protein, such as an albumin, to an animal system (such as, for example, rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Non-limiting examples of antigenic polypeptides or peptides that can be used to generate AIM II-specific antibodies include: a polypeptide comprising, or alternatively consisting of, amino acid residues from about 13 to about 20 in FIGS. 1A and 1B (SEQ ID NO:2); a polypeptide comprising, or alternatively consisting of, amino acid residues from about 23 to about 36 in FIGS. 1A and 1B (SEQ ID NO:2); a polypeptide comprising, or alternatively consisting of, amino acid residues from about 69 to about 79 in FIGS. 1A and 1B (SEQ ID NO:2); a polypeptide comprising, or alternatively consisting of, amino acid residues from about 85 to about 94 in FIGS. 1A and 1B (SEQ ID NO:2); a polypeptide comprising, or alternatively consisting of, amino acid residues from about 167 to about 178 in FIGS. 1A and 1B (SEQ ID NO:2); a polypeptide comprising, or alternatively consisting of, amino acid residues from about 184 to about 196 in FIGS. 1A and 1B (SEQ ID NO:2); and a polypeptide comprising, or alternatively consisting of, amino acid residues from about 221 to about 233 in FIGS. 1A and 1B (SEQ ID NO: 2). In this context, the term "about" includes the particular recited ranges and ranges larger or smaller by several (5, 4, 3, 2, or 1) amino acids at either terminus or at both termini. As indicated above, the inventors have determined that the above polypeptide fragments are antigenic regions of the AIM II protein. Polynucleotides encoding these polypeptides are also encompassed by the invention.

The epitope-bearing peptides and polypeptides of the invention may be produced by any conventional means. Houghten, R. A. General method for the rapid solid-phase synthesis of large numbers of peptides: specificity of antigen-antibody interaction at the level of individual amino acids. *Proc. Natl Acad. Sci. USA* 82:5131–5135 (1985). This "Simultaneous Multiple Peptide Synthesis (SMPS)" process is further described in U.S. Pat. No. 4,631,211 to Houghten et al. (1986).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.*, 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as, for example, rabbits, rats, and mice are immunized with either free or carrier-coupled peptides, for instance, by intraperitoneal and/or intradermal injection of emulsions containing about 100 micrograms of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., *Nature*, 331:84–86 (1988). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., *J. Biochem.*, 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto Ni$^{2+}$ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2) :76–82 (1998); Hansson et al., J. Mol. Biol. 287:265–76 (1999); and Lorenzo and Blasco, Biotechniques 24(2) :308–313 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide coding a polypeptide of the invention may be recombined with one or more components, motifs, sections, parts, domains, fragments, etc. of one or more heterologous molecules.

A list of exemplified amino acid sequences comprising immunogenic epitopes are shown in Table 2. It is pointed out that Table 2 only lists amino acid residues comprising epitopes predicted to have the highest degree of antigenicity using the algorithm of Jameson and Wolf, Comp. Appl. Biosci. 4:181–186 (1988) (said references incorporated by reference in their entireties). The Jameson-Wolf antigenic analysis was performed using the computer program PROTEAN, using default parameters (Version 3.11 for the Power MacIntosh, DNASTAR, Inc., 1228 South Park Street Madison, Wis.). Table 2 and portions of polypeptides not listed in Table 2 are not considered non-immunogenic. The immunogenic epitopes of Table 2 is an exemplified list, not an exhaustive list, because other immunogenic epitopes are merely not recognized as such by the particular algorithm used. Amino acid residues comprising other immunogenic epitopes may be routinely determined using algorithms similar to the Jameson-Wolf analysis or by in vivo testing for an antigenic response using methods known in the art. See, e.g., Geysen et al., supra; U.S. Pat. Nos. 4,708,781; 5,194, 392; 4,433,092; and 5,480,971 (said references incorporated by reference in their entireties).

It is particularly pointed out that the amino acid sequences of Table 2 comprise immunogenic epitopes. Table 2 lists only the critical residues of immunogenic epitopes determined by the Jameson-Wolf analysis. Thus, additional flanking residues on either the N-terminal, C-terminal, or both N- and C-terminal ends may be added to the sequences of Table 2 to generate an epitope-bearing polypeptide of the present invention. Therefore, the immunogenic epitopes of Table 2 may include additional N-terminal or C-terminal amino acid residues. The additional flanking amino acid residues may be contiguous flanking N-terminal and/or C-terminal sequences from the polypeptides of the present invention, heterologous polypeptide sequences, or may include both contiguous flanking sequences from the polypeptides of the present invention and heterologous polypeptide sequences.

The immunogenic and antigenic epitope-bearing fragments may be specified by either the number of contiguous amino acid residues, as described above, or further specified by N-terminal and C-terminal positions of these fragments on the amino acid sequence of SEQ ID NO:2. Every combination of a N-terminal and C-terminal position that a fragment of, for example, at least 7 or at least 15 contiguous amino acid residues in length could occupy on the amino acid sequence of SEQ ID NO:2 is included in the invention. Again, "at least 7 contiguous amino acid residues in length" means 7 amino acid residues in length or any integer between 7 amino acids and the number of amino acid residues of the full length polypeptide of the present invention. Specifically, each and every integer between 7 and the number of amino acid residues of the full length polypeptide are included in the present invention.

Immunogenic and antigenic epitope-bearing polypeptides of the invention are useful, for example, to make antibodies which specifically bind the polypeptides of the invention, and in immunoassays to detect the polypeptides of the present invention. The antibodies are useful, for example, in affinity purification of the polypeptides of the present invention. The antibodies may also routinely be used in a variety of qualitative or quantitative immunoassays, specifically for the polypeptides of the present invention using methods known in the art. See, e.g., Harlow et al., *Antibodies: A Laboratory Manual.*, (Cold Spring Harbor Laboratory Press; 2nd Ed. 1988).

The epitope-bearing polypeptides of the present invention may be produced by any conventional means for making polypeptides including synthetic and recombinant methods known in the art. For instance, epitope-bearing peptides may be synthesized using known methods of chemical synthesis. For instance, Houghten has described a simple method for the synthesis of large numbers of peptides, such as 10–20 mgs of 248 individual and distinct 13 residue peptides representing single amino acid variants of a segment of the HA1 polypeptide, all of which were prepared and characterized (by ELISA-type binding studies) in less than four weeks (Houghten et al., *Proc. Natl. Acad. Sci. U.S.A.* 82:5131–5135 (1985)). This "Simultaneous Multiple Peptide Synthesis (SMPS)"process is further described in U.S. Pat. No. 4,631,211 to Houghten and coworkers (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously (Houghten et al., *Proc. Natl. Acad. Sci. U.S.A.* 82:5131–5135 (1985) at 5134).

Epitope-bearing polypeptides of the present invention are used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.* 66:2347–2354(1985). If in vivo immunization is used, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as N-maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. This has been shown, e.g., for chimeric proteins consisting of the first two domains of the human CD4-polypeptide and various domains of the constant regions of the heavy or light chains of mammalian immunoglobulins. See, e.g., EPA 0,394,827; Traunecker et al., *Nature* 331:84–86 (1988). Fusion proteins that have a disulfide-linked dimeric structure due to the IgG portion can also be more efficient in binding and neutralizing other molecules than monomeric polypeptides or fragments thereof alone. See, e.g., Fountoulakis et al., *J. Biochem.* 270:3958–3964 (1995). Nucleic acids encoding the above epitopes can also be recombined with a gene of interest as an epitope tag to aid in detection and purification of the expressed polypeptide.

In addition, proteins of the invention can be chemically synthesized using techniques known in the art (e.g., see Creighton, 1983, Proteins: Structures and Molecular Principles, W.H. Freeman & Co., N.Y., and Hunkapiller, M. et al., *Nature* 310:105–111 (1984)). For example, a peptide corresponding to a fragment of the AIM II polypeptides of the invention can be synthesized by use of a peptide synthesizer. Furthermore, if desired, nonclassical amino acids or chemical amino acid analogs can be introduced as a substitution or addition into the AIM II polypeptide sequence. Non-classical amino acids include, but are not limited to, to the D-isomers of the common amino acids, 2,4-diaminobutyric acid, alpha-amino isobutyric acid, 4-aminobutyric acid, Abu, 2-amino butyric acid, alpha-Abu, alpha-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, alpha-alanine, fluoro-amino acids, designer amino acids such as alpha-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487(1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention additionally, encompasses AIM II polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of AIM II which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59–72 (1996); Vorobjev et al., *Nucleosides Nucleotides* 18:2745–2750 (1999); and Caliceti et al., *Bioconjug. Chem.* 10:638–646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., *Exp. Hematol.* 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues, glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249–304 (1992); Francis et al., *Intern. J. of Hematol.* 68:1–18 (1998); U.S. Pat. No. 4,002,531; U.S. Pat. No. 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monmethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoreothane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1–3, 2–4, 3–5, 4–6, 5–7, 6–8, 7–9, 8–10, 9–11, 10–12, 11–13, 12–14, 13–15, 14–16, 15–17, 16–18, 17–19, or 18–20 polyethylene glycol moieties per protein molecule. Methods for determining the degree of substitution are discussed, for example, in Delgado et al., *Crit. Rev. Thera. Drug Carrier Sys.* 9:249–304 (1992).

Antibodies

The present invention further relates to antibodies and T-cell antigen receptors (TCR) which immunospecifically bind a polypeptide, preferably an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following:

hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine, donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention that they recognize or specifically bind. The epitope(s) or polypeptide portion(s) may be specified as described herein, e.g., by N-terminal and C-terminal positions, by size in contiguous amino acid residues, or listed in the Tables and Figures. Antibodies that specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies that bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$M, $10^{-2}$M, $5 \times 10^{-3}$M, $10^{-3}$M, $5 \times 10^{-4}$M, $10^{-4}$M, $5 \times 10^{-5}$M, $10^{-5}$M, $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 90%, at least 80%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand or receptor activity by at least 90%, at least 80%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation. The antibodies may be specified as agonists, antagonists or inverse agonists for biological activities comprising the specific biological activities of the peptides of the invention disclosed herein. Thus, the invention further relates to antibodies which act as agonists or antagonists of the polypeptides of the present invention. The above antibody agonists can be made using methods known in the art. See, e.g., PCT publication WO 96/40281; U.S. Pat. No. 5,811,097; Deng et al., *Blood* 92(6):1981–1988 (1998); Chen et al., *Cancer Res.* 58(16):3668–3678 (1998); Harrop et al., *J. Immunol.* 161(4): 1786–1794 (1998); Zhu et al., *Cancer Res.* 58(15):3209–3214 (1998); Yoon et al., *J. Immunol.* 160(7):3170–3179 (1998); Prat et al., *J. Cell. Sci.* 111(Pt2):237–247 (1998); Pitard et al., *J. Immunol. Methods* 205(2): 177–190(1997); Liautard et al., *Cytokine* 9(4):233–241 (1997); Carlson et al., *J. Biol. Chem.* 272(17): 11295–11301 (1997); Taryman et al., *Neuron* 14(4):755–762 (1995); Muller et al., *Structure* 6(9):1153–1167 (1998); Bartunek et al., *Cytokine* 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., PCT publications WO 92/08495; WO 91/14438; WO 89/12624; U.S. Pat. No. 5,314,995; and EP 396,387.

The antibodies of the invention include derivatives that are modified, i.e, by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen of interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced. Thus, the term "monoclonal antibody" is not limited to antibodies produced through hybridoma technology. Monoclonal antibodies can be prepared using a wide variety of techniques known in the art including the use of hybridoma and recombinant and phage display technology.

Methods for producing and screening for specific antibodies using hybridoma technology are routine and well-known in the art and are discussed in detail in Example 23. Briefly, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41–50 (1995); Ames et al., *J. Immunol. Methods* 184:177–186 (1995); Kettleborough et al., *Eur. J. Immunol.* 24:952–958 (1994); Persic et al., *Gene* 187:9–18 (1997); Burton et al., *Advances in Immunology* 57:191–280(1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864–869 (1992); and Sawai et al., *AJRI* 34:26–34 (1995); and Better et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, *Science* 229:1202 (1985); Oi et al., *BioTechniques* 4:214 (1986); Gillies et al., (1989) *J. Immunol. Methods* 125:191–202; U.S. Pat. Nos. 5,807,715; 4,816,567; and 4,816397, which are incorporated herein by reference in their entireties. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530, 101; and 5,585,089), veneering or resurfacing (EP 592,106; EP 519,596; Padlan, Molecular Immunology 28(4/5) :489–498 (1991); Studnicka et al., Protein Engineering 7(6):805–814 (1994); Roguska. et al., PNAS 91:969–973 (1994)), and chain shuffling (U.S. Pat. No. 5,565,332).

Completely human antibodies are particularly desirable for therapeutic. treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring that express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65–93). For a detailed discussion of this technology for producing human antibodies and human monoclonal antibodies and protocols for producing such antibodies, see, e.g., PCT publications WO 98/24893; WO 96/34096; WO 96/33735; U.S. Pat. Nos. 5,413,923; 5,625,126; 5,633,425; 5,569,825; 5,661,016; 5,545,806; 5,814,318; and 5,939,598, which are incorporated by reference herein in their entirety. In addition, companies such as Abgenix, Inc. (Freemont, Calif.) and GenPharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB. J.* 7(5):437–444 (1989) and Nissinoff, *J. Immunol.* 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

A. Polynucleotides Encoding Antibodies.

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., *BioTechniques* 17:242 (1994)), which, briefly, involves the synthesis of overlapping oligonucleotides containing portions of the sequence encoding the antibody, annealing and ligation of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., *J. Mol. Biol.* 278:457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., 1984, Proc. Natl. Acad. Sci. 81:851–855; Neuberger et al., 1984, Nature 312:604–608; Takeda et al., 1985, Nature 314:452–454) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,694,778; Bird, 1988, Science 242:423–42; Huston et al., 1988, Proc. Natl. Acad. Sci. USA 85:5879–5883; and Ward et al., 1989, Nature 334:544–54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., 1988, Science 242:1038–1041).

B. Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, e.g., a heavy or light chain of an antibody of the invention, requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; Cockett et al., 1990, Bio/Technology 8:2).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., 1983, EMBO J. 2:1791), in which the antibody coding sequence may be ligated individually into the vector in frame with the lac Z coding region so that a fusion protein is produced; pIN vectors (Inouye & Inouye, 1985, Nucleic Acids Res. 13:3101–3109; Van Heeke & Schuster, 1989, J. Biol. Chem. 24:5503–5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, 1984, Proc. Natl. Acad. Sci. USA 81:355–359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIB TECH 11(5): 155–215); and hygro, which confers resistance to hygromycin (Santerre et al., 1984, Gene 30:147). Methods commonly known in the art of recombinant DNA technology which can be used are described in Ausubel et al. (eds.), 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY.; Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, Nature 322:52; Kohler, 1980, Proc. Natl. Acad. Sci. USA 77:2197). The coding sequences for the heavy and light chains may comprise cDNA or genomic DNA.

Once an antibody molecule of the invention has been recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins.

C. Antibody Conjugates

The present invention encompasses antibodies recombinantly fused or chemically conjugated (including both covalently and non-covalently conjugations) to a polypeptide (or portion thereof, preferably at least 10, 20 or 50 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20 or 50 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides of the present invention may be fused or conjugated to the above antibody portions to increase the in vivo half life of the polypeptides or for use in immunoassays using methods known in the art. Further, the polypeptides of the present invention may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5 receptor, have been fused with Fc portions for the purpose of high-throughput screening assays to identify antagonists of hIL-5. (See, D. Bennett et al., *J. Molecular Recognition* 8:52–58 (1995); K. Johanson et al., *J. Biol. Chem.* 270:9459–9471 (1995).

Moreover, the antibodies or fragments thereof of the present invention can be fused to marker sequences, such as a peptide to facilitates their purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag"tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

Further, an antibody or fragment thereof may be conjugated to a therapeutic moiety such as a cytotoxin, e.g., a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

D. Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

Such assays are routine and well known in the art (see, e.g., Ausubel et al., eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al., eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al., eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest is conjugated to a labeled compound (e.g., $^{3}H$ or $^{125}I$) in the presence of increasing amounts of an unlabeled second antibody.

E. Antibody Based Therapies

The present invention is further directed to antibody-based therapies which involve administering antibodies of the invention to an animal, preferably a mammal, and most preferably a human, patient for treating one or more of the disorders or conditions described herein. Therapeutic compounds of the invention include, but are not limited to, antibodies of the invention (including fragments, analogs and derivatives thereof as described herein) and nucleic acids encoding antibodies of the invention (including fragments, analogs and derivatives thereof as described herein. The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein such as, for example, graft versus host disease and autoimmune diseases, disorders, or conditions associated with such diseases or disorders (including, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, systemic lupus erhythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid; Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders), and immunodeficiencies or conditions associated with such diseases or disorders (including, but not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome), severe combined immunodeficiency, DiGeorge anomaly, thymichypoplasia, chronic mucocutaneous candidiasis, natural killer cell deficiency, idiopathic CD4+ T-lymphocytopenia, and immunodeficiency with predominant T-cell defect.

In a specific embodiment, antibodies of the invention are be used to treat, inhibit, prognose, diagnose or prevent graft versus host disease and autoimmune disease.

In a specific embodiment, antibodies of the invention are be used to treat, inhibit, prognose, diagnose or prevent rheumatoid arthritis.

In another specific embodiment, antibodies of the invention are used to treat, inhibit, prognose, diagnose or prevent systemic lupus erythematosis. The treatment and/or prevention of diseases and disorders associated with aberrant expression and/or activity of a polypeptide of the invention includes, but is not limited to, alleviating symptoms associated with those diseases and disorders. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g., as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Identification of AIM II Agonists and Antagonists

The invention also provides a method of screening compounds to identify those which enhance or block the action of AIM II on cells, such as its interaction with AIM II-binding molecules such as receptor molecules. An agonist is a compound which increases the natural biological functions of AIM II or which functions in a manner similar to AIM II, while antagonists decrease or eliminate such functions.

For example, a cellular compartment, such as a membrane preparation, may be prepared from a cell that expresses a molecule that binds AIM II, such as a molecule of a signaling or regulatory pathway modulated by AIM II. The preparation is incubated with labeled AIM II in the absence or the presence of a candidate molecule which may be an AIM II agonist or antagonist. The ability of the candidate molecule to bind the binding molecule or AIM II itself is reflected in decreased binding of the labeled ligand. Molecules which bind gratuitously, i.e., without inducing the effects of AIM II when bound to the AIM II binding molecule, are most likely to be good antagonists. Molecules that bind well and elicit effects that are the same as or closely related to AIM II, are good agonists.

AIM II-like effects of potential agonists and antagonists may by measured, for instance, by determining activity of a second messenger system following interaction of the candidate molecule with a cell or appropriate cell preparation, and comparing the effect with that of AIM II or molecules that elicit the same effects as AIM II. Second messenger systems that may be useful in this regard include but are not limited to AMP guanylate cyclase, ion channel or phosphoinositide hydrolysis second messenger systems.

Another example of an assay for AIM II antagonists is a competitive assay that combines AIM II and a potential antagonist with membrane-bound AIM II receptor molecules or recombinant AIM II receptor molecules under appropriate conditions for a competitive inhibition assay. AIM II can be labeled, such as by radioactivity, such that the number of AIM II molecules bound to a receptor molecule can be determined accurately to assess the effectiveness of the potential antagonist.

Potential antagonists include small organic molecules, peptides, polypeptides and antibodies that bind to a polypeptide of the invention, and thereby inhibit or extinguish its activity. Potential antagonists also may be small organic molecules, a peptide, a polypeptide such as a closely related protein or antibody that binds the same sites on a binding molecule, such as a receptor molecule, without inducing AIM II-induced activities, thereby preventing the action of AIM II by excluding AIM II from binding. Antagonists of the invention include fragments of the AIM II polypeptide having the amino acid sequence shown in SEQ ID NO:2.

Other potential antagonists include antisense molecules. Antisense technology can be used to control gene expression through antisense DNA or RNA or through triple-helix formation. Antisense techniques are discussed, for example, in Okano, J. Neurochem. 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research 6:3073 (1979); Cooney et al., Science 241:456 (1988); and Dervan et al., Science 251:1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of AIM II. The antisense RNA oligonucleotide hybridizes to the mRNA in vivo and blocks translation of the mRNA molecule into AIM II polypeptide. The oligonucleotides described above can also be delivered to cells such that the antisense RNA or DNA may be expressed in vivo to inhibit production of AIM II.

Therapeutic Uses of AIM II, AIM II Agonists and AIM II Antagonists

The Tumor Necrosis Factor (TNF) family ligands are known to be among the most pleiotropic cytokines, inducing a large number of cellular responses, including cytotoxicity, anti-viral activity, immunoregulatory activities, and the transcriptional regulation of several genes (Goeddel, D. V. et al., "Tumor Necrosis Factors: Gene Structure and Biological Activities," Symp. Quant. Biol. 51:597–609 (1986), Cold Spring Harbor; Beutler, B., and Cerami, A., Annu. Rev. Biochem. 57:505–518 (1988); Old, L. J., Sci. Am. 258:59–75 (1988); Fiers, W., FEBS Lett. 285:199–224 (1991)). The TNF-family ligands induce such various cellular responses by binding to TNF-family receptors.

AIM II polynucleotides, polypeptides, agonists or antagonists of the invention may be used in developing treatments for any disorder mediated (directly or indirectly) by defective, or insufficient amounts of AIM II. AIM II polypeptides, agonists or antagonists may be administered to a patient (e.g., mammal, preferably human) afflicted with such a disorder. Alternatively, a gene therapy approach may be applied to treat such disorders. Disclosure herein of AIM II nucleotide sequences permits the detection of defective AIM II genes, and the replacement thereof with normal AIM II-encoding genes. Defective genes may be detected in in vitro diagnostic assays, and by comparison of the AIM II nucleotide sequence disclosed herein with that of a AIM II gene derived from a patient suspected of harboring a defect in this gene.

The AIM II polypeptide of the present invention may be employed to treat lymphoproliferative disease which results in lymphadenopathy, the AIM II mediates apoptosis by stimulating clonal deletion of T-cells and may therefore, be employed to treat autoimmune disease, to stimulate peripheral tolerance and cytotoxic T-cell mediated apoptosis. The AIM II may also be employed as a research tool in elucidating the biology of autoimmune disorders including systemic lupus erythematosus (SLE), Graves' disease, immunoproliferative disease lymphadenopathy (IPL), angioimmunoproliferative lymphadenopathy (AIL), immunoblastive lymphadenopathy (IBL), rheumatoid arthritis, diabetes, and multiple sclerosis, allergies and to treat graft versus host disease.

The AIM II polynucleotides, polypeptides and/or agonists or antagonists of the invention may also be used to treat, prevent, diagnose and/or prognose diseases which include, but are not limited to, autoimmune disorders, immunodeficiency disorders, and graft versus host disease.

The AIM II polypeptide of the present invention may also be employed to inhibit neoplasia, such as tumor cell growth. The AIM II polypeptide may be responsible for tumor destruction through apoptosis and cytotoxicity to certain cells. AIM II may also be employed to treat diseases which require growth promotion activity, for example, restenosis, since AIM II has proliferation effects on cells of endothelial origin. AIM II may, therefore, also be employed to regulate hematopoiesis in endothelial cell development.

Diseases associated with increased cell survival, or the inhibition of apoptosis, that may be treated, prevented, diagnosed and/or prognosed with the AIM II polynucleotides, polypeptides and/or agonists or antagonists of the invention include, but are not limited to, cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune disorders (such as, multiple sclerosis, Sjogren's syndrome, Grave's disease, Hashimoto's thyroiditis, autoimmune diabetes, biliary cirrhosis, Behcet's disease, Crohn's disease, polymyositis, systemic lupus erythematosus and immune-related glomerulonephritis, autoimmune gastritis, autoimmune thrombocytopenic purpura, and rheumatoid arthritis) and viral infections (such as herpes viruses, pox viruses and adenoviruses), inflammation, graft vs. host disease (acute and/or chronic), acute graft rejection, and chronic graft rejection. In preferred embodiments, AIM II polynucleotides, polypeptides, agonists, or antagonists of the invention are used to inhibit growth, progression, and/or metastasis of cancers, in particular those listed above or in the paragraph that follows.

Additional diseases or conditions associated with increased cell survival, that may be treated, prevented, diagnosed and/or prognosed with the AIM II polynucleotides, polypeptides and/or agonists or antagonists of the invention include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

Diseases associated with increased apoptosis, that may be treated, prevented, diagnosed and/or prognosed with the AIM II polynucleotides, polypeptides and/or agonists or antagonists of the invention include, but are not limited to, AIDS; neurodegenerative disorders (such as Alzheimer's disease, Parkinson's disease, amyotrophic lateral sclerosis, retinitis pigmentosa, cerebellar degeneration and brain tumor or prior associated disease); autoimmune disorders (such as, multiple sclerosis, Sjogren's syndrome, Grave's disease Hashimoto's thyroiditis, autoimmune diabetes, biliary cirrhosis, Behcet's disease, Crohn's disease, polymyositis, systemic lupus erythematosus, immune-related glomerulonephritis, autoimmune gastritis, thrombocytopenic purpura, and rheumatoid arthritis) myelodysplastic syndromes (such as aplastic anemia), graft vs. host disease (acute and/or chronic), ischemic injury (such as that caused by myocardial infarction, stroke and reperfusion injury), liver injury or disease (e.g., hepatitis related liver injury, cirrhosis, ischemia/reperfusion injury, cholestosis (bile duct injury) and liver cancer); toxin-induced liver disease (such as that caused by alcohol), septic shock, ulcerative colitis, cachexia and anorexia. In preferred embodiments, AIM II polynucleotides, polypeptides, agonists, and/or antagonists are used to treat the diseases and disorders listed above.

Many of the pathologies associated with HIV are mediated by apoptosis, including HIV-induced nephropathy and HIV encephalitis. Thus, in additional preferred embodiments, AIM II polynucleotides, polypeptides, agonists or antagonists of the invention are used to treat AIDS and pathologies associated with AIDS.

Another embodiment of the present invention is directed to the use of AIM II polynucleotides, polypeptides, or antagonists to reduce AIM II-mediated death of T cells in HIV-infected patients. The role of T cell apoptosis in the development of AIDS has been the subject of a number of studies (see, for example, Meyaard et al., *Science* 257:217–219 (1992); Groux et al., *J. Exp. Med.*, 175:331 (1992); and Oyaizu et al., in *Cell Activation and Apoptosis in HIV Infection*, Andrieu and Lu, Eds., Plenum Press, New York, pp. 101–114 (1995)). Fas-mediated apoptosis has been implicated in the loss of T cells in HIV individuals (Katsikis et al., *J. Exp. Med.* 181:2029–2036 (1995). It is also likely that T cell apoptosis occurs through multiple mechanisms. For example, at least some of the T cell death seen in IUV patients is likely to be mediated by AIM II.

Activated human T cells are induced to undergo programmed cell death (apoptosis) upon triggering through the CD3/T cell receptor complex, a process termed activated-induced cell death (AICD). AICD of CD4 T cells isolated from HIV-infected asymptomatic individuals has been reported (Groux et al., supra). Thus, AICD may play a role in the depletion of CD4+ T cells and the progression to AIDS in HIV-infected individuals. Thus, the present invention provides a method of inhibiting AIM II-mediated T cell death in HIV patients, comprising administering AIM II polynucleotides, polypeptides, or antagonists of the invention to the patients. In one embodiment, the patient is asymptomatic when treatment with AIM II polynucleotides, polypeptides, or antagonists commences. If desired, prior to treatment, peripheral blood T cells may be extracted from an HIV patient, and tested for susceptibility to AIM II-mediated cell death by procedures known in the art. In one embodiment, a patient's blood or plasma is contacted with AIM II antagonists (e g., anti-AIM II antibodies) of the invention ex vivo. The AIM II antagonists may be bound to a suitable chromatography matrix by procedures known in the art. The patient's blood or plasma flows through a chromatography column containing AIM II antagonist bound to the matrix, before being returned to the patient. The immobilized AIM II antagonist binds AIM II, thus removing AIM II protein from the patient's blood.

In additional embodiments an AIM II polynucleotide, polypeptide, or antagonist of the invention is administered in combination with other inhibitors of T cell apoptosis. For example, as discussed above, Fas-mediated apoptosis also has been implicated in loss of T cells in HIV individuals (Katsikis et al., *J. Exp. Med.* 181:2029–2036 (1995)). Thus, a patient susceptible to both Fas ligand mediated and AIM II-mediated T cell death may be treated with both an agent that blocks AIM II/AIM II receptor interactions and an agent that blocks Fas-ligand/Fas interactions. Suitable agents for blocking binding of Fas-ligand to Fas include, but are not limited to, soluble Fas polypeptides; multimeric forms of soluble Fas polypeptides (e.g., dimers of sFas/Fc); anti-Fas antibodies that bind Fas without transducing the biological signal that results in apoptosis; anti-Fas-ligand antibodies that block binding of Fas-ligand to Fas; and muteins of Fas-ligand that bind Fas but do not transduce the biological signal that results in apoptosis. Preferably, the antibodies employed according to this method are monoclonal antibodies. Examples of suitable agents for blocking Fas-ligand/Fas interactions, including blocking anti-Fas monoclonal antibodies, are described in WO 95/10540, hereby incorporated by reference.

In another example, agents which block binding of TRAIL to a TRAIL receptor are administered with the AIM II polynucleotides, polypeptides, or antagonists of the invention. Such agents include, but are not limited to, soluble TRAIL receptor polypeptides (e.g., a soluble form of OPG, DR4 (WO 98/32856); TR5 (WO 98/30693); DR5 (WO 98/41629); and TR10 (WO 98/54202)); multimeric forms of soluble TRAIL receptor polypeptides; and TRAIL receptor antibodies that bind the TRAIL receptor without transducing the biological signal that results in apoptosis, anti-TRAIL antibodies that block binding of TRAIL to one or more TRAIL receptors, and muteins of TRAIL that bind TRAIL receptors but do not transduce the biological signal that results in apoptosis. Preferably, the antibodies employed according to this method are monoclonal antibodies.

AIM II polypeptides of the invention may also be employed to regulate hematopoiesis and, in particular, erythropoiesis. Hematopoiesis is a multi-step cell proliferation and differentiation process which begins with a pool of multipotent stem cells. These cells can proliferate and differentiate into hematopoietic progenitors in reply to different stimuli. The AIM II polypeptides of the invention, as well as agonists and antagonists thereof, may be used to either stimulate or inhibit development of hematopoietic cells and, in particular, erythropoietic precursor cells.

The AIM II polypeptides used to regulate development of hematopoietic cells may be contacted with hematopoietic target cells in a number of forms, e.g., as full-length or mature polypeptides, AIM II polypeptide fragments, or as hybrid fusion proteins composed of AIM II and a non-AIM II polypeptide (e.g., colony stimulating factors, erythropoietin, interferons, interleukins, etc.). Methods for producing such fusion proteins are described, for example, in Mele et al., U.S. Pat. No. 5,916,773.

As used herein, the phrase "hematopoietic cells" refers cells of hematopoietic origin such as erythrocytes, thrombocytes, lymphocytes, eosinophils, basophils, macrophages, and monocytes. Further, the phrase "erythropoietic precursor cells" refers cells of erythropoietic origin, such as erythrocytes.

As discussed below in Examples 6, 9 and 22, AIM II polypeptides (e.g., a polypeptide comprising, or alternatively consisting of amino acid residues 69 to 240 or 83 to 240 of SEQ ID NO:2), as well as agonists thereof (e.g., anti-AIM II antibodies, soluble forms of AIM II having amino acids sequences contained in the extracellular domain of AIM II) can be used to stimulate the production of cytokines (e.g., GM-CSF, G-CSF, IL-2, IL-3, IL-5, IL-6, IL-7, IL-12, IL-13, IL-15, anti-CD40, CD40L, IFN-γ, TNF-α, vascular endothelial growth factor (VEGF)) by various cell types (e.g., T cells).

AIM II polypeptides, as well as agonists thereof, can be used to modulate T cell immune responses (e.g., to inhibit antigen induced T cell proliferation).

AIM II polypeptides, as well as agonists thereof, can also be used to modulate cell mediated immune responses (e.g., activate cytolytic T cells).

AIM II polypeptides, as well as agonists thereof, can be used to modulate apoptosis.

Further, AIM II polypeptides, as well as agonists thereof, can be used to induce cytolytic T cell responses and facilitate the formation of antigen-specific memory.

AIM II polynucleotides or polypeptides of the invention, or agonists or antagonists thereof, may also find application as the following:

A vaccine adjuvant that enhances immune responsiveness to specific antigen.

An adjuvant to enhance tumor-specific immune responses.

An adjuvant to enhance anti-viral immune responses. Anti-viral immune responses that may be enhanced using the compositions of the invention as an adjuvant, include virus and virus associated diseases or symptoms described herein or otherwise known in the art. In specific embodiments, the compositions of the invention are used as an adjuvant to enhance an immune response to a virus, disease, or symptom selected from the group consisting of: AIDS, meningitis, Dengue, EBV, and hepatitis (e.g., Hepatitis B). In another specific embodiment, the compositions of the invention are used as an adjuvant to enhance an immune response to a virus, disease, or symptom selected from the group consisting of HIV/AIDS, Respiratory syncytial virus, Dengue, Rotavirus, Japanese B encephalitis, Influenza A and B, Parainfluenza, Measles, Cytomegalovirus, Rabies, Junin, Chikungunya, Rift Valley fever, Herpes simplex, and yellow fever.

An adjuvant to enhance anti-bacterial or anti-fungal immune responses. Anti-bacterial or anti-fungal immune responses that may be enhanced using the compositions of the invention as an adjuvant, include bacteria or fungus and bacteria or fungus associated diseases or symptoms described herein or otherwise known in the art. In specific embodiments, the compositions of the invention are used as an adjuvant to enhance an immune response to a bacteria or fungus, disease, or symptom selected from the group consisting of: tetanus, Diphtheria, botulism, and meningitis type B. In another specific embodiment, the compositions of the invention are used as an adjuvant to enhance an immune response to a bacteria or fungus, disease, or symptom selected from the group consisting of *Vibrio cholerae, Mycobacterium leprae, Salmonella typhi, Salmonella paratyphi, Meisseria meningitidis, Streptococcus pneumoniae*, Group B streptococcus, Shigella spp., Enterotoxigenic *Escherichia coli*, Enterohemorrhagic *E. coli, Borrelia burgdorferi*, and Plasmodium (malaria).

An adjuvant to enhance anti-parasitic immune responses. Anti-parasitic immune responses that may be enhanced using the compositions of the invention as an adjuvant, include parasite and parasite associated diseases or symptoms described herein or otherwise known in the art. In specific embodiments, the compositions of the invention are used as an adjuvant to enhance an immune response to a parasite. In another specific embodiment, the compositions of the invention are used as an adjuvant to enhance an immune response to Plasmodium (malaria).

As an agent to boost immunoresponsiveness among B cell and/or T cell immunodeficient individuals, such as, for example, an individual who has undergone a partial or complete splenectomy. B cell immunodeficiencies that may be ameliorated or treated by administering the AIM II polypeptides or polynucleotides of the invention, or agonists thereof, include, but are not limited to, severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency. T cell immunodeficiencies that may be ameliorated or treated by administering the AIM II polypeptides or polynucleotides of the invention, or agonists thereof, include, but are not limited to, DiGeorge anomaly, thymic hypoplasia, chronic mucocutaneous candidiasis, natural killer cell deficiency, idiopathic CD4+ T-lymphocytopenia, and immunodeficiency with predominant T-cell defect.

As an agent to boost immunoresponsiveness among individuals having an acquired loss of B cell function. Conditions resulting in an acquired loss of B or T cell function that may be ameliorated or treated by administering the AIM II polypeptides or polynucleotides of the invention, or agonists thereof, include, but are not limited to, HIV Infection, AIDS, bone marrow transplant, and B cell chronic lymphocytic leukemia (CLL).

As an agent to boost immunoresponsiveness among individuals having a temporary immune deficiency. Conditions resulting in a temporary immune deficiency that may be ameliorated or treated by administering the AIM II polypeptides or polynucleotides of the invention, or agonists thereof, include, but are not limited to, recovery from viral infections (e.g., influenza), conditions associated with malnutrition, recovery from infectious mononucleosis, or conditions associated with stress, recovery from measles, recovery from blood transfusion, recovery from surgery.

AIM II polynucleotides or polypeptides of the invention, or agonists or antagonists thereof, may be used to diagnose, prognose, treat or prevent one or more of the following diseases or disorders, or conditions associated therewith: primary immuodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, AIM II polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19, patients with stable multiple myeloma who are at high risk for infection (e.g., recurrent infection), autoimmune hemolytic anemia (e.g., warm-type autoimmune hemolytic anemia), thrombocytopenia (e.g., neonatal thrombocytopenia), and immune-mediated neutropenia), transplantation (e.g., cytomegalovirus (CMV)-negative recipients of CMV-positive organs), hypogammaglobulinemia (e.g., hypogammaglobulinemic neonates with risk factor for infection or morbidity), epilepsy (e.g., intractable epilepsy), systemic vasculitic syndromes, myasthenia gravis (e.g., decompensation in myasthenia gravis), dermatomyositis, and polymyositis.

Autoimmune disorders and conditions associated with these disorders that may be treated, prevented, and/or diagnosed with the AIM II polynucleotides, polypeptides, and/or antagonist of the invention (e.g., anti-AIM II antibodies), include, but are not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitus, and autoimmune inflammatory eye disease.

Additional autoimmune disorders (that are highly probable) that may be treated, prevented, and/or diagnosed with the compositions of the invention include, but are not limited to, autoimmune thyroiditis, hypothyroidism (i.e., Hashimoto's thyroiditis) (often characterized, e.g., by cell-mediated and humoral thyroid cytotoxicity), systemic lupus erhythematosus (often characterized, e.g., by circulating and locally generated immune complexes), Goodpasture's syndrome (often characterized, e.g., by anti-basement membrane antibodies), Pemphigus (often characterized, e.g., by epidermal acantholytic antibodies), receptor autoimmunities such as, for example, (a) Graves' Disease (often characterized, e.g., by TSH receptor antibodies), (b) Myasthenia Gravis (often characterized, e.g., by acetylcholine receptor antibodies), and (c) insulin resistance (often characterized, e.g., by insulin receptor antibodies), autoimmune hemolytic anemia (often characterized, e.g., by phagocytosis of antibody-sensitized RBCs), autoimmune thrombocytopenic purpura (often characterized, e.g., by phagocytosis of antibody-sensitized platelets.

Additional autoimmune disorders (that are probable) that may be treated, prevented, and/or diagnosed with the compositions of the invention include, but are not limited to, rheumatoid arthritis (often characterized, e.g., by immune complexes in joints), schleroderma with anti-collagen antibodies (often characterized, e.g., by nucleolar and other nuclear antibodies), mixed connective tissue disease (often characterized, e.g., by antibodies to extractable nuclear antigens (e.g., ribonucleoprotein)), polymyositis/dermatomyositis (often characterized, e.g., by nonhistone ANA), pernicious anemia (often characterized, e.g., by antiparietal cell, microsomes, and intrinsic factor antibodies), idiopathic Addison's disease (often characterized, e.g., by humoral and cell-mediated adrenal cytotoxicity, infertility (often characterized, e.g., by anti-spermatozoal antibodies), glomerulonephritis (often characterized, e;g., by glomerular basement membrane antibodies or immune complexes) such as primary glomerulonephritis and IgA nephropathy, bullous pemphigoid (often characterized, e.g., by IgG and complement in basement membrane), Sjogren's syndrome (often characterized, e.g., by multiple tissue antibodies, and/or a specific nonhistone ANA (SS-B)), diabetes millitus (often characterized, e.g., by cell-mediated and humoral islet cell antibodies), and adrenergic drug resistance (including adrenergic drug resistance with asthma or cystic fibrosis) (often characterized, e.g., by beta-adrenergic receptor antibodies).

Additional autoimmune disorders (that are possible) that may be treated, prevented, and/or diagnosed with the compositions of the invention include, but are not limited to, chronic active hepatitis (often characterized, e.g. by smooth muscle antibodies), primary biliary cirrhosis (often characterized, e.g., by mitchondrial antibodies), other endocrine gland failure (often characterized, e.g., by specific tissue antibodies in some cases), vitiligo (often characterized, e.g., by melanocyte antibodies), vasculitis (often characterized, e.g., by Ig and complement in vessel walls and/or low serum complement), post-MI (often characterized, e.g., by myocardial antibodies), cardiotomy syndrome (often characterized, e.g., by myocardial antibodies), urticaria (often characterized, e.g., by IgG and IgM antibodies to IgE), atopic dermatitis (often characterized, e.g., by IgG and IgM antibodies to IgE), asthma (often characterized, e.g., by IgG and IgM antibodies to IgE), inflammatory myopathies, and many other inflammatory, granulamatous, degenerative, and atrophic disorders.

In a preferred embodiment, the autoimmune diseases and disorders and/or conditions associated with the diseases and disorders recited above are treated, prevented, and/or diagnosed using anti-AIM II antibodies.

In a specific preferred embodiment, rheumatoid arthritis is treated, prevented, and/or diagnosed using anti-AIM II antibodies and/or other antagonist of the invention.

In a specific preferred embodiment, lupus is treated, prevented, and/or diagnosed using anti-AIM II antibodies and/or other antagonist of the invention.

In a specific preferred embodiment, nephritis associated with lupus is treated, prevented, and/or diagnosed using anti-AIM II antibodies and/or other antagonist of the invention.

In a specific embodiment, AIM II polynucleotides or polypeptides, or antagonists thereof (e.g., anti-AIM II antibodies) are used to treat or prevent systemic lupus erythematosus and/or diseases, disorders or conditions associated therewith. Lupus-associated diseases, disorders, or conditions that may be treated or prevented with AIM II polynucleotides or polypeptides, or antagonists of the invention, include, but are not limited to, hematologic disorders (e.g., hemolytic anemia, leukopenia, lymphopenia, and thrombocytopenia), immunologic disorders (e.g., anti-DNA antibodies, and anti-Sm antibodies), rashes, photosensitivity, oral ulcers, arthritis, fever, fatigue, weight loss, serositis (e.g., pleuritus (pleuricy)), renal disorders (e.g., nephritis), neurological disorders (e.g., seizures, peripheral neuropathy, CNS related disorders), gastroinstestinal disorders, Raynaud phenomenon, and pericarditis. In a preferred embodiment, the AIM II polynucleotides or polypeptides, or antagonists thereof (e.g., anti-AIM II antibodies) are used to treat or prevent renal disorders associated with systemic lupus erythematosus. In a most preferred embodiment, AIM II polynucleotides or polypeptides, or antagonists thereof (e.g., anti-AIM II antibodies) are used to treat or prevent nephritis associated with systemic lupus erythematosus.

In certain embodiments, soluble AIM II polypeptides of the invention (e.g., a polypeptide comprising, or alternatively consisting of, amino acids 69 to 240 or 83 to 240 of SEQ ID NO:2), or agonists thereof, are administered, to treat, prevent, prognose and/or diagnose an immunodeficiency (e.g., severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency, DiGeorge anomaly, thymic hypoplasia, chronic mucocutaneous candidiasis, natural killer cell deficiency, idiopathic CD4+T-lymphocytopenia, and immunodeficiency with predominant T-cell defect) or conditions associated with an immunodeficiency.

A number of soluble forms of the polypeptides of the present invention can be used to treat, prevent, prognose and/or diagnose disease states. These soluble forms will generally lack the AIM II transmembrane domain. Examples of soluble AIM II polypeptides include those where the extracellular and intracellular domains are present, but the transmembrane domain has been deleted. Further examples comprising, or alternatively consisting of, amino acids 60 to 240, 69 to 240, or 83 to 240 of SEQ ID NO:2.

In a specific embodiment, AIM II polypeptides or polynucleotides of the invention, or agonists thereof, is administered to treat, prevent, prognose and/or diagnose common variable immunodeficiency.

In a specific embodiment, AIM II polypeptides or polynucleotides of the invention, or agonists thereof, is administered to treat, prevent, prognose and/or diagnose X-linked agammaglobulinemia.

In another specific embodiment, AIM II polypeptides or polynucleotides of the invention, or agonists thereof, is administered to treat, prevent, prognose and/or diagnose severe combined immunodeficiency (SCID).

In another specific embodiment, AIM II polypeptides or polynucleotides of the invention, or agonists thereof, is administered to treat, prevent, prognose and/or diagnose Wiskott-Aldrich syndrome.

In another specific embodiment, AIM II polypeptides or polynucleotides of the invention, or agonists thereof, is administered to treat, prevent, prognose and/or diagnose X-linked Ig deficiency with hyper IgM.

In another specific embodiment, AIM II polypeptides or polynucleotides of the invention, or agonists thereof, is administered to treat, prevent, prognose and/or diagnose DiGeorge anomaly.

AIM II antagonists also may be employed in a composition with a pharmaceutically acceptable carrier, e.g., as hereinafter described.

The antagonists may further be employed for instance to treat cachexia which is a lipid clearing defect resulting from a systemic deficiency of lipoprotein lipase, which is believed to be suppressed by AIM II. The AIM II antagonists may also be employed to treat cerebral malaria in which AIM II may play a pathogenic role.

The AIM II antagonists may also be employed to prevent graft-host rejection (e.g., by preventing the stimulation of the immune system in the presence of a graft).

The AIM II antagonists may also be employed to prevent graft-host disease. In a preferred embodiment, anti-AIM II antibody is employed to prevent graft-host disease.

The AIM II antagonists may also be employed to inhibit bone resorption and, therefore, to treat and/or prevent osteoporosis.

The antagonists may also be employed as anti-inflammatory agents, and to treat endotoxic shock. This critical condition results from an exaggerated response to bacterial and other types of infection.

AIM II antagonists may also find application as the following:

As inhibitors of the production of one or more cytokines.

As inhibitors of cytolytic T cell responses and the formation of antigen-specific memory.

As modulators of T cell immune responses (e.g., inhibitors of antigen induced T cell proliferation).

As modulators of cell mediated immune responses (e.g., inhibitors of cytolytic T cell activation).

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11 (5): 155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody nucleic acids (Koller and Smithies, 1989, Proc. Natl. Acad. Sci. USA 86:8932–8935; Zijlstra et al., 1989, Nature 342:435–438). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429–4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g. PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435–438).

In a specific embodiment, viral vectors that contains nucleic acid sequences encoding an antibody of the invention are used. For example, a retroviral vector can be used (see Miller et al., 1993, Meth. Enzymol. 217:581–599). These retroviral vectors have been to delete retroviral sequences that are not necessary for packaging of the viral genome and integration into host cell DNA. The nucleic acid sequences encoding the antibody to be used in gene therapy are cloned into one or more vectors, which facilitates delivery of the gene into a patient. More detail about retroviral vectors can be found in Boesen et al., 1994, Biotherapy 6:291–302, which describes the use of a retroviral vector to deliver the mdrl gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499–503 present a review of adenovirus-based gene therapy. Bout et al., 1994, Human Gene Therapy 5:3–10 demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; Mastrangeli et al., 1993, J. Clin. Invest. 91:225–234; PCT Publication WO94/12649; and Wang et al., 1995, Gene Therapy 2:775–783. In a preferred embodiment, adenovirus vectors are used.

Adeno-associated virus (AAV) has also been proposed for use in gene therapy (Walsh et al., 1993, Proc. Soc. Exp. Biol. Med. 204:289–300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts; muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., PCT Publication WO 94/08598, dated Apr. 28, 1994; Stemple and Anderson, 1992, Cell 71:973–985; Rheinwald, 1980, Meth. Cell Bio. 21A:229; and Pittelkow and Scott, 1986, Mayo Clinic Proc. 61:771).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

As noted above, antagonists and agonists of the invention include AIM II polypeptides. These polypeptides can modulate their effect by, for example, binding to cellular proteins such as receptors. Methods for identifying peptides which interact with a specific protein are known in the art. For example, Phizicky and Fields, "Protein-protein interactions: methods for detection and analysis" *Microbiol. Rev.* 59:94–123 (1995), describe methods for screening peptides to identify those having binding affinity for a second polypeptide. Phizicky and Fields discuss methods such as protein affinity chromatography, affinity blotting, communoprecipitation, and cross-linking. Additional molecular biological methods suitable for use with the present invention include protein probing of expression libraries, the two-hybrid system, cell panning, and phage display.

Another method for identifying AIM II polypeptides of the invention which bind to a cell surface receptor involves transfecting eukaryotic cells with DNA encoding the receptor, such that the cells expresses the receptor on their surfaces, followed by contacting the cells with a labeled (e.g., radioactive label, biotin, etc.) AIM II polypeptide. The amount of labeled AIM II polypeptide bound to the cells is measured and compared to that bound to control cells. The control cells will generally be cells which do not express the surface receptor. The detection of an increased amount of label bound to the cells which express the receptor as compared to the control cells indicates that the cells which expresses the receptor bind the AIM II polypeptide.

Further, as one skilled in the art would recognize, cells which express and retain AIM II polypeptides can be used to identify AIM II ligands. In one such an embodiment, cells which express AIM II would be contacted with potential ligands which have been detectably labeled. Further, such ligands may be polypeptides which are expressed as part of a library of sequences on the surface of a phage (e.g., a phage display library).

Once an AIM II polypeptide has been identified which binds to the cell surface receptor of interest, assays can be performed to determine whether the AIM II polypeptide induces or inhibits a receptor-mediated cellular response normally elicited by the particular receptor. Whether an AIM II polypeptide activates a receptor-mediated cellular response may be determined by measuring a cellular response known to be elicited by the receptor in the presence of the AIM II polypeptide or another ligand. Further, whether an AIM II polypeptide inhibits a receptor-mediated cellular response may be determined by measuring a cellular response known to be elicited by the receptor in the presence of both a molecule which is known to induce the cellular response and the AIM II polypeptide.

Soluble forms of the polypeptides of the present invention (e.g., an AIM polypeptide comprising, or alternatively consisting of, amino acid 69 to 240 or 83–240 of SEQ ID NO:2), for example, may be utilized in the ligand binding and receptor activation/inhibition assay described above.

AIM II has also been shown to inhibit the differentiation and survival of photoreceptor cells. Further, AIM II has been shown to inhibit the production of rhodopsin by retinal cells. Thus, AIM II polypeptides and AIM II agonists are useful for inhibiting the differentiation and survival of photoreceptor cells (e.g., rods and cones) and inhibiting rhodopsin production by retinal cells (e.g., rods).

AIM II polypeptides, agonists or antagonists of the invention may be used to treat cardiovascular disorders, including peripheral artery disease, such as limb ischemia.

Cardiovascular disorders include cardiovascular abnormalities, such as arterio-arterial fistula, arteriovenous fistula, cerebral arteriovenous malformations, congenital heart defects, pulmonary atresia and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, and ventricular heart septal defects.

Cardiovascular disorders also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular *tuberculosis*.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, heart murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular disorders, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular disorders include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subarachnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

In one embodiment, an AIM II polynucleotide, polypeptide, agonist, or antagonist of the invention is used to treat thrombotic microangiopathies. One such disorder is thrombotic thrombocytopenic purpura (TTP) (Kwaan, H. C., *Semin. Hematol.* 24:71 (1987); Thompson et al., *Blood* 80:1890 (1992)). Increasing TTP-associated mortality rates have been reported by the U.S. Centers for Disease Control (Torok et al., *Am. J. Hematol.* 50:84 (1995)). Plasma from patients afflicted with TTP (including HIV+ and HIV− patients) induces apoptosis of human endothelial cells of dermal microvascular origin, but not large vessel origin (Laurence et al., *Blood* 87:3245 (1996)). Plasma of TTP patients thus is thought to contain one or more factors that directly or indirectly induce apoptosis. Another thrombotic microangiopathy is hemolytic-uremic syndrome (HUS) (Moake, J. L., *Lancet* 343:393 (1994); Melnyk et al., *Arch. Intern. Med.* 155:2077 (1995); Thompson et al., supra). Thus, in one embodiment, the invention is directed to use of AIM II to treat the condition that is often referred to as "adult HUS" (even though it can strike children as well). A disorder known as childhood/diarrhea-associated HUS differs in etiology from adult HUS. In another embodiment, conditions characterized by clotting of small blood vessels may be treated using AIM II. Such conditions include, but are not limited to, those described herein. For example, cardiac problems seen in about 5–10% of pediatric AIDS patients are believed to involve clotting of small blood vessels. Breakdown of the microvasculature in the heart has been reported in multiple sclerosis patients. As a further example, treatment of systemic lupus erythematosus (SLE) is contemplated. In one embodiment, a patient's blood or plasma is contacted with AIM II polypeptides of the invention ex vivo. The AIM II polypeptides of the invention may be bound to a suitable chromatography matrix by procedures known in the art. According to this embodiment, the patient's blood or plasma flows through a chromatography column containing AIM II polynucleotides and/or polypeptides of the invention bound to the matrix, before being returned to the patient. The immobilized AIM II binds AIM II, thus removing AIM II protein from the patient's blood. Alternatively, AIM II polynucleotides, polypeptides, agonists or antagonists of the invention may be administered in vivo to a patient afflicted with a thrombotic microangiopathy. In one embodiment, a soluble form of AIM II polypeptide of the invention is administered to the patient. Thus. the present invention provides a method for treating a thrombotic microangiopathy, involving use of an effective amount of AIM II polynucleotide, polypeptide, agonist or antagonist. An AIM II polypeptide may be employed in in vivo or ex vivo procedures, to inhibit AIM II-mediated damage to (e.g., apoptosis of) microvascular endothelial cells.

AIM II polynucleotides, polypeptides, agonists or antagonists of the invention may be employed in combination with other agents useful in treating a particular disorder. For example, in an in vitro study reported by Laurence et al., Blood 87:3245 (1996), some reduction of TTP plasma-mediated apoptosis of microvascular endothelial cells was achieved by using an anti-Fas blocking antibody, aurintricarboxylic acid, or normal plasma depleted of cryoprecipitate. Thus, a patient may be treated with a polynucleotide and/or polypeptide of the invention in combination with an agent that inhibits Fas-ligand-mediated apoptosis of endothelial cells, such as, for example, an agent described above. In one embodiment, an AIM II polynucleotide, polypeptide, agonist or antagonist, and an anti-FAS blocking antibody are both administered to a patient afflicted with a disorder characterized by thrombotic microangiopathy, such as TTP or HUS. Examples of blocking monoclonal antibodies directed against Fas antigen (CD95) are described in WO 95/10540, hereby incorporated by reference.

The naturally occurring balance between endogenous stimulators and inhibitors of angiogenesis is one in which inhibitory influences predominate. Rastinejad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., Biotech. 9:630–634 (1991); Folkman et al., N. Engl. J. Med. 333:1757–1763 (1995); Auerbach et al., J. Microvasc. Res. 29:401–411 (1985); Folkman, Advances in Cancer Research, Klein and Weinhouse, eds., Academic Press, New York, pp. 175–203 (1985); Patz, Am. J. Opthalmol. 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442–447 (1987).

The present invention provides for treatment of diseases or disorders associated with neovascularization by administration of the AIM II polynucleotides and/or polypeptides of the invention (including AIM II agonists and/or antagonists). Malignant and metastatic conditions which can be treated with the polynucleotides and polypeptides of the invention include, but are not limited to those malignancies, solid tumors, and cancers described herein and otherwise known in the art (for a review of such disorders, see Fishman et al., Medicine, 2d Ed., J. B. Lippincott Co., Philadelphia (1985)).

Additionally, ocular disorders associated with neovascularization which can be treated with the AIM II polynucleotides and polypeptides of the present invention (including AIM II agonists and AIM II antagonists) include, but are not limited to: neovascular glaucoma, diabetic retinopathy, retinoblastoma, retrolental fibroplasia, uveitis, retinopathy of prematurity, macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704–710 (1978) and Gartner et al., Surv. Ophthal. 22:291–312 (1978).

Additionally, disorders which can be treated with the AIM II polynucleotides and polypeptides of the present invention (including AIM II agonists and AIM II antagonists) include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Polynucleotides and/or polypeptides of the invention, and/or agonists and/or antagonists thereof, are useful in the diagnosis and treatment or prevention of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), Helicobacter pylori infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/or agonists and/or antagonists thereof are useful in promoting angiogenesis, wound healing (e.g., wounds, burns, and bone fractures).

Polynucleotides and/or polypeptides of the invention and/or agonists and/or antagonists thereof are also useful as an adjuvant to enhance immune responsiveness to specific antigen and/or anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment or prevention of autoimmune disorders. In specific embodiments, polynucleotides and/or polypeptides of the invention are used to treat or prevent chronic inflammatory, allergic or autoimmune conditions, such as those described herein or are otherwise known in the art.

The uses of the AIM II polypeptides, particularly human AIM II polypeptides, include but are not limited to, the treatment or prevention of viral hepatitis, Herpes viral infections, allergic reactions, adult respiratory distress syndrome, neoplasia, anaphylaxis, allergic asthma, allergen rhinitis, drug allergies (e.g., to penicillin, cephalosporins), primary central nervous system lymphoma (PCNSL), glioblastoma, chroniclymphocyticleukemia (CLL), lymphadenopathy, autoimmune disease, graft versus host disease, rheumatoid arthritis, osteoarthritis, Graves' disease, acute lymphoblastic leukemia (ALL), lymphomas (Hodgkin's disease and non-Hodgkin's lymphoma (NHL)), ophthalmopathy, uveoretinitis, the autoimmune phase of Type 1 diabetes, myasthenia gravis, glomerulonephritis, autoimmune hepatological disorder, autoimmune inflammatory bowel disease, and Crohn's disease. In addition, the AIM II polypeptide of the present invention may be employed to inhibit neoplasia, such as tumor cell growth. The combination of AIM II protein with immunotherapeutic agent such as IL-2 or IL-12 may result in synergistic or additive effects that would be useful for the treatment of established cancers. The AIM II polypeptide may also be useful for tumor therapy. AIM II may further be employed to treat diseases which require growth promotion activity, for example, restenosis, since AIM II has proliferative effects on cells of endothelial origin. AIM II may, therefore, also be employed to regulate hematopoiesis in endothelial cell development.

The AIM II polypeptides of the invention may also be employed to inhibit the differentiation and proliferation of T cells and B cells. AIM II induced inhibition of T and B cell activation, differentiation and/or proliferation may be employed to treat a number of immunological based diseases, several of which are referred to above. Further, depending on the particular AIM II polypeptide employed, the AIM II polypeptides of the invention may also be employed to stimulate activation, differentiation and/or proliferation of T cells and B cells.

AIM II may act as a cytokine adjuvant or costimulatory molecule. The following experiments are performed to assess the in vivo AIM II protein on the host immune system.

Tumor or non-tumor bearing mice are treated with AIM II protein at three different doses (0.1 mg/kg, 1 mg/kg and 10 mg/kg, i.p., QD, 10–14 days, N=5 per group) before or after immunization with tumor antigen or superantigen, the mice are sacrificed weekly post treatment after blood collection. The spleens or the lymph nodes are used for the following in vitro analyses well known to those skilled in the art:
FACS analyses: Expression of surface markers for T cells, B cells, NK cells, Monocytes, Dendritic cells, costimulatory and adhesion molecules.
Cytokine production assays
T cell proliferation or cytotoxicity assay AIM II protein and tumor antigen may result in the induction of protective immunity, which could lead to protecting mice from subsequent tumor challenge. In order to examine this possibility the following experiment can be performed using syngeneic C57BL/6 mice to test the effect of AIM II on induction of tumor or Ag-specific protective immunity.

MC-38 tumor-free mice treated with AIM II protein will be challenged with MC-38 or irrelevant murine sarcoma MCA-102 using techniques well known to those skilled in the art. Three possible results could be observed:

|  | Result #1 | Result #2 | Result #3 |
|---|---|---|---|
| MC-38.WT: | tumor (−) | tumor (−) | tumor (+) |
| MCA-102: | tumor (+) | tumor (−) | tumor (+) |

Indication from #1: Evidence of tumor-specific protective immunity
Indication from #2: Evidence of non-tumor specific immunity
Indication from #3: Lack of protective immunity If generation of tumor-specific protective immunity upon AIM II treatment is demonstrated, the following depletion experiments are performed to identify which leukocyte sub-population is responsible for the tumor rejection. The mice will be treated with various mAb which recognize either CD4+ or CD8+ T cells, NK cells, granulocyte (Gr1+), or specific cytokine such as IFNγ using techniques well known to those skilled in the art. Tumor growth in these antibody-treated mice is measured.

AIM II may also be used to treat rheumatoid arthritis (RA) by inhibiting the increase in angiogenesis or the increase in endothelial cell proliferation required to sustain an invading pannus in bone and cartilage as is often observed in RA. Endothelial cell proliferation is increased in the synovia of RA patients as compared to patients with osteoarthritis (OA) or unaffected individuals. Neovascularization is needed to sustain the increased mass of the invading pannus into bone and cartilage. Inhibition of angiogenesis is associated with a significant decrease in the severity of both early and chronic arthritis in animal models.

The AIM II polypeptide is believed to possess binding activities for a number of proteins, including several human cellular receptors. These receptors include the lymphotoxin- β-receptor (LT-β-R), TR2 (also referred to as the Herpes virus entry mediator (HVEM) and ATAR), CD27, TR6 (also referred to as DcR3), TR9 (DR6) and TRANK (also referred to as receptor activator of nuclear factor-kappa B (RANK)).

Each of the receptors listed immediately above is involved in various physiological processes which may be modulated by the AIM II polypeptides of the invention. More specifically, the polypeptides of the invention can be used to stimulate or block the action of ligands which bind cellular receptors having AIM II binding activity (e.g., LT-β-R, TR2, CD27, TR6, TR9 and TRANK).

LT-β, which binds to the LT-β-R, has been implicated in the development of secondary lymphoid tissues and the maintenance of organized lymphoid tissues in adults. LT-β-R may, in some instances, function in conjunction with TR2 to mediate cellular responses and has been shown to be expressed in a number of tissues in the lung including a subpopulation of T-lymphocytes. LT-β-R has also been implicated in the formation of germinal centers and thus appears to be involved in humoral immune responses. Rennert et al., *Int. Immunol.* 9:1627–1639(1997).

The AIM II polypeptides of the invention may be employed to inhibit the formation of germinal centers and LT-β-R mediated humoral responses by blocking access of cellular ligands to LT-β-R. Further, polypeptides of the invention may stimulate the formation of germinal centers and LT-β-R mediated humoral responses by activating LT-β-R.

One skilled in the art would recognize that different portions of the AIM II polypeptide may have different effects on LT-β-R. One skilled in the art would also recognize that the effect that the AIM II polypeptides of the invention would have on LT-β-R would vary with the individual peptide and the effect it has when bound to LT-β-R. Methods for screening molecules having agonistic and antagonistic activities of cellular receptor are described above.

The core protein of Hepatitis C virus (HCV) has also been shown to associate with LT-β-R and enhance signaling mediated by this receptor. Chen et al., *J. Virol.* 71:9417–9426 (1997). Further, the interaction of this protein with LT-β-R may contribute to the chronically activated, persistent state of HCV-infected cells. The AIM II polypeptides of the invention may be employed to block HVC stimulation of LT-β-R and the pathology associated with this virus.

TR2 is a member of the tumor necrosis factor (TNF) receptor family which is expressed in a number of human tissues and cell lines. This protein is expressed constitutively and in relatively high levels in peripheral blood T cells, B cells, and monocytes. Kwon et al., *J. Biol. Chem.* 272:14272–14276(1997). TR2 serves a number of functions in vivo, including the mediation of Herpes viral entry into cells during infection. Further, a TR2-Fc fusion protein has been demonstrated to inhibit mixed lymphocyte reaction-mediated proliferation. These data suggest that the TR2 and its ligand play a role in T cell stimulation. It has been shown along these lines that overexpression of TR2 activates NF-κB and AP-I. This activation appears to occur through a TNF receptor-associated factor (TRAF)-mediated mechanism.

The AIM II polypeptides of the invention may be employed to inhibit T cell activation, and thus T cell mediated immune responses, by blocking access to TR2 by cellular ligands which activate this receptor. Similarly, polypeptides of the invention may stimulate T cell activation by activating TR2. As noted above for LT-β-R, one skilled in the art would recognize that different portions of the AIM II polypeptide may either inhibit or stimulate TR2 mediated cellular responses.

The AIM II polypeptides of the invention may also be employed to prevent or treat Herpes viral infections.

Expression of CD27, as well as its ligand CD70, is predominantly confined to lymphocytes. Further, CD27 has been shown to interact with CD70 and to be involved in the induction of IgE synthesis in B cells. Nagumo et al., *J. Immunol.* 161:6496–6502 (1998). In addition, activation of CD27 may enhance IgE synthesis. Inhibition of the interaction between CD27 and CD70 thus may inhibit IgE production and allergic responses.

The AIM II polypeptides of the invention may be used for modulating immune responses. For example, AIM II polypeptides may be used to regulate the function of B cells by inhibiting the interaction between CD27 and CD70. AIM II polypeptides may thus bind to CD27 and inhibit B cell differentiation and proliferation, as well as the secretion of proteins (e.g., IgE) by these cells. Therefore, AIM II polypeptides may be employed to suppress IgE antibody formation in the treatment of IgE-induced immediate hypersensitivity reactions, such as allergic rhinitis (also know as hay fever), bronchial asthma, allergic asthma, anaphylaxis, atopic dermatitis and gastrointestinal food allergy.

CD27 is also believed to be the receptor for a pro-apoptotic protein commonly known as Siva. Pandanilam et al., *Kidney Int.* 54:1967–1975 (1998). AIM II polypeptides of the invention may be employed to inhibit the interaction between Siva and CD27 and thus prevent Siva/CD27 mediated induction of apoptosis. Diseases associated with decreased cell survival, or increased apoptosis, include AIDS; neurodegenerative disorders (such as Alzheimer's disease, Parkinson's disease, amyotrophic lateral sclerosis, retinitis pigmentosa, cerebellar degeneration); myelodysplastic syndromes (such as aplastic anemia), ischemic injury (such as that caused by myocardial infarction, stroke and reperfusion injury), toxin-induced liver disease (such as that caused by alcohol), septic shock, cachexia and anorexia.

AIM II polypeptides of the invention may also be employed to enhance activation of the Siva/CD27 apoptotic pathway and thus facilitate the induction of apoptosis. Diseases associated with increased cell survival, or the inhibition of apoptosis, include cancers (such as follicular lymphomas, carcinomas with p53 mutations, and hormone-dependent tumors), autoimmune disorders (such as systemic lupus erythematosus, immune-related glomerulonephritis, and rheumatoid arthritis) and viral infections (such as herpes viruses, pox viruses and adenoviruses), information graft v. host disease, acute graft rejection, and chronic graft rejection.

While CD27 may be membrane-bound, a soluble form of CD27 is produced in the course of the immune response. Soluble CD27 (sCD27) is found in a number of body fluids and may be measured to monitor local and systemic immune activation. Further, CD27 is expressed on human malignant B cells and high levels of sCD27 are present in the sera of patients with various B-cell malignancies. Kersten et al., *Blood* 87:1985–1989 (1996). These elevated levels of sCD27 have been shown to strongly correlate with tumor load.

sCD27 has also been shown to be elevated in patients with a variety lymphoid malignancies and solid tumors of the central nervous system. These afflictions include primary central nervous system lymphoma (PCNSL) and lymphoid malignancies located in the meninges (e.g., acute lymphoblastic leukemia (ALL) and non-Hodgkin's lymphoma (NHL)).

Soluble CD27 has also been found to be elevated in patients with a number of non-hyperproliferative diseases. For example, sCD27 has been shown to be elevated in patients with untreated Graves' hyperthyroidism. Kallio et al., *J. Lab. Clin Med.* 132:478–482 (1998). Further, increases in sCD27 serum levels have been found in patients with systemic lupus erythematosus (SLE) and this increase has been shown to be associated with the activity of the disease. Font et al., *Clin. Immunol. Inmunopathol.* 81:239–243 (1996); Swaak et al., *Clin. Rheumatol.* 14:293–300 (1995). Also, B cells from most patients with chronic lymphocytic leukemia (CLL) have been shown to co-express both membrane-bound and soluble CD27, as well as CD70. Ranheim et al., *Blood* 85:3556–3565(1995).

It has been postulated that sCD27 may prevent leukemic B cells from stimulating T cells via CD70, and thus may impair the ability of B cells to function as antigen-presenting cells. Ranheim et al., *Blood* 85:3556–3565 (1995). Polypeptides of the invention may be employed to inhibit interactions between sCD27 and CD70, and, thus, to enhance the ability of B cells to act as antigen-presenting cells.

AIM II polypeptides of the invention may also be employed to treat diseases and afflictions associated with increased levels of sCD27. While not wishing to be bound to a mechanistic theory, AIM II polypeptides may be useful in treatment regimens for these conditions since AIM II binds sCD27 and prevents it from interacting with cellular ligands.

AIM II polypeptides bind to TR6. (See, Example 13). TR6 (DcR3) is a novel soluble member of the TNFR superfamily, which is constitutively expressed in lung tissue, tumor cells and in endothelial cells. TR6 binds specifically to AIM II and FasL and inhibits their activities. Like DcR1, DcR2 and another soluble member of TNFR superfamily, OPG, TR6 may act as an inhibitor of signaling through TNF family members, FasL and AIM II. TR6 appears to have important roles in the inhibition of apoptosis and tumor modulation. TR6 may act as an inhibitor of AIM II interaction and may also act in distinct roles, depending on cell types. TR6 (DcR3) may act as a decoy receptor and contribute to immune evasion both in slow and rapid tumor cell death, that are mediated by AIM II or FasL mediated apoptosis pathway respectively. Indeed, TR6 (DcR3) has been shown to bind to FasL and might contribute to immune evasion by certain tumors (Pitti, R. M., et al., *Nature* 396:699–703 (1998)). AIM II and FasL are known to be expressed in activated T cells. Therefore, it is believed that TR6 and its ligands are important for interactions between activated T lymphocytes and endothelium. TR6 may be involved in activated T cell trafficking as well as endothelial cell survival. Another possibility is that TR6 may act as a cytokine to trigger membrane-bound FasL or AIM II and directly transduce signals through FasL or AIM II. Recently, the Desbarats and Suzuki groups reported that FasL could itself transduce signals, leading to cell-cycle arrest and cell death in CD4$^+$ T cells but cell proliferation in CD8$^+$ T cells (Desbarats, J., et al., *Nature Medicine* 4:1377–1382 (1998); Suzuki, I., and Fink, P. J., *J. Exp. Med.* 187:123–128 (1998)). Therefore, TR6 may act as a cytokine for signaling through FasL and AIM II.

Because TR6 appears to have important roles in the inhibition of apoptosis and tumor modulation, AIM II polypeptides of the invention may also be employed to treat diseases and afflictions associated with increased levels of TR6, or conditions where increased apoptosis would be desirable. While not wishing to be bound to a mechanistic theory, AIM II polypeptides may be useful in treatment regimens for these conditions since AIM II binds TR6 and prevents TR6 from interacting with cellular ligands to block apoptosis.

AIM II polypeptides are also believed to bind to RANK. (See Anderson et al., *Nature* 390:175–179 (1997).) RANK is a protein which has been implicated in osteoclast differentiation and regulation of interactions between T cells and dendritic cells. RANK apparently mediates its cellular effects via interaction with RANKL (also referred to as osteoprotegerin ligand (OPGL), TRANCE and ODF).

Mice having a disrupted RANKL gene show severe osteoporosis, exhibit defective tooth eruption, and lack osteoclasts. These mice also exhibit defects in T and B lymphocyte differentiation. Additionally, RANKL-deficient mice lack lymph nodes but exhibit normal splenic structure and Peyer's patches. These data indicate that RANKL mediated pathways regulate lymph node organogenesis, lymphocyte development, and osteoclast differentiation and proliferation.

There are two main classes of bone cells: cells which make bone, osteoblasts, and cells which resorb bone, osteoclasts. These cells each have very precise functions and the balance between their activities is critical to the maintenance of the skeletal system. For example, in human adults, between 10 to 15% of trabecular bone surfaces are covered with osteoid (new unmineralized bone made by osteoblasts) while about 4% have active resorptive surfaces. The dynamic nature of the continuing flux of bone cell activity is illustrated by the fact that approximately 18% of total skeletal calcium is often removed and deposited over a period of one year.

The AIM II polypeptides of the invention may be employed to regulate osteoclast differentiation and proliferation (bone formation), as well as bone development and degradation. Polypeptides of the invention may, for example, be employed to inhibit osteoclast differentiation and proliferation and, thus, may be employed to decease the rate of bone degradation. Inhibition of osteoclast differentiation and proliferation and bone degradation may be useful in the treatment of conditions such as osteoporosis, skeletal and dental abnormalities, bone cancers, osteoarthritis, osteogenesis imperfecta, and Hurler and Marfan syndromes. Polypeptides of the invention may also be employed in processes for reshaping bone and teeth and in periodontal reconstructions where lost bone replacement or bone augmentation is required, such as in a jaw bone and supplementing alveolar bone loss resulting from periodontal disease to delay or prevent tooth loss (see, e.g., Sigurdsson et al., *J. Periodontol.* 66: 511–21(1995)).

The AIM II polypeptides of the invention may further be used to regulate T and B lymphocyte differentiation and proliferation. AIM II polypeptides may thus bind to RANK and inhibit the differentiation and proliferation of T and B lymphocyte, as well as the secretion of proteins (e.g., immunoglobins) from these cells. AIM II polypeptides may therefore be employed to suppress lymphocyte-mediated immune responses, for example, to prevent graft rejection. AIM II polypeptides may also be used to inhibit osteoclast differentiation and proliferation. AIM II polypeptides may thus be employed to treat diseases such as bone cancers.

The present invention also provides AIM II polypeptides which mimic one or more of the natural ligands of RANK and stimulate RANK-mediated cellular responses. These cellular responses include the activation of T and B lymphocyte differentiation and proliferation and induction of osteoclast differentiation. AIM II polypeptides may thus be employed to treat diseases such as infections (e.g., bacterial, viral, and protozoal infections). AIM II polypeptides may also be employed to enhance immune responses (e.g., in the treatment of AIDS and AIDS related complexes) and to increase bone degradation rates.

AIM II polypeptide also binds TR9. TR9 (also referred to as DR6) is a novel member of the tumor necrosis factor family of receptors which possesses a cytoplasmic death domain. (See, WO 98/56892). TR9 induces apoptosis in mammalian cells and is capable of engaging the NF-κB and JNK pathways. TR9 is believed to play a role in inflammatory responses and immune regulation.

The AIM II polypeptides may be used to modulate inflammatory responses and immune regulation via TR9. AIM II polypeptides may also be used to induce apoptosis via TR9 via the NF-κB and JNK pathways. AIM 11 polypeptides may thus be employed to treat diseases such as infections. AIM II polypeptides may also be employed to enhance immune responses.

The AIM II polypeptide may be cleaved in vivo to form a soluble form of the molecule. As noted in Example 10, a cleavage site appears to be located between amino acid residues 82 and 83 of the sequence shown in SEQ ID NO:2. Cleavage of the AIM II polypeptide at this location is believed to result in the production of a soluble form of the molecule which comprises, or alternatively consisting of, amino acids 83–240 in SEQ ID NO:2. Soluble forms of AIM II are especially useful for the treatment of diseases where systemic administration of these peptides is preferred. Further, soluble forms of AIM II are also useful for topical administration. The complete and mature AIM II polypeptides of the invention, as well as subfragments of these polypeptides, may be employed to treat afflictions associated with receptors and other ligands to which these molecules bind.

In one embodiment, the invention provides a method of delivering compositions containing the polypeptides of the invention (e.g., compositions containing AIM II polypeptides or anti-AIM II antibodies associated with heterologous polypeptides, heterologous nucleic acids, toxins, or prodrugs) to targeted cells, expressing the membrane-bound form of AIM II on their surface, or alternatively, an AIM II receptor (e.g., TR2, LTbeta receptor, and CD27) on their surface. AIM II polypeptides or anti-AIM II antibodies of the invention may be associated with heterologous polypeptides, heterologous nucleic acids, toxins, or prodrugs via hydrophobic, hydrophilic, ionic and/or covalent interactions.

In one embodiment, the invention provides a method for the specific delivery of compositions of the invention to cells by administering polypeptides of the invention (e.g., AIM II or anti-AIM II antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., AIM II polypeptides or anti-AIM II antibodies) in association with toxins or cytotoxic prodrugs.

In a specific embodiment, the invention provides a method for the specific destruction of cells expressing TR2, LTbeta receptor, and/or CD27 on their surface (e.g., activated T cells, and/or T cell and/or B cell related leukemias or lymphomas) by administering AIM II polypeptides in association with toxins or cytotoxic prodrugs.

In another specific embodiment, the invention provides a method for the specific destruction of cells expressing the membrane-bound form of AIM II on their surface (e.g., spleen, bone marrow, kidney and PBLs) by administering anti-AIM II antibodies in association with toxins or cytotoxic prodrugs.

By "toxin" is meant compounds that bind and activate endogenous cytotoxic effector systems, radioisotopes, holotoxins, modified toxins, catalytic subunits of toxins, cytotoxins (cytotoxic agents), or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. "Toxin" also includes a cytostatic or cytocidal agent, a therapeutic agent or a radioactive metal ion, e.g., alpha-emitters such as, for example, $^{213}$Bi, or other radioisotopes such as, for example, $^{103}$Pd, $^{133}$Xe, $^{131}$I, $^{68}$Ge, $^{57}$Co, $^{65}$Zn, $^{85}$Sr, $^{32}$P, $^{35}$S, $^{90}$Y, $^{153}$Sm, $^{153}$Gd, $^{169}$Yb, $^{51}$Cr, $^{54}$Mn, $^{75}$Se, $^{113}$Sn, $^{90}$Yttrium, $^{117}$Tin, $^{186}$Rhenium, $^{166}$Holmium, and $^{188}$Rhenium; luminescent labels, such as luminol; and fluorescent labels, such as fluorescein and rhodamine, and biotin.

Techniques known in the art may be applied to label proetins (including antibodies) of the invention. Such techniques include, but are not limited to, the use of bifunctional conjugating agents (see, e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety). A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum(II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Diagnosis and Imaging

The invention further relates to the use of the AIM II polynucleotides to detect complementary polynucleotides such as, for example, as a diagnostic reagent. Detection of a mutated form of an AIM II associated with a dysfunction will provide a diagnostic tool that can add or define a diagnosis of a disease or susceptibility to disease which results from under-expression, over-expression or altered expression of AIM II, such as, for example, autoimmune diseases, malignancies and/or immundeficiencies. The polynucleotide encoding the AIM II may also be employed as a diagnostic marker for expression of the polypeptide of the present invention.

The present inventors have discovered that AIM II is expressed in spleen, thymus and bone marrow tissue. For a number of disorders, such as septic shock, inflammation, cerebral malaria, activation of the HIV virus, graft-host rejection, bone resorption, rheumatoid arthritis and cachexia, it is believed that significantly higher or lower levels of AIM II gene expression can be detected in certain tissues (e.g., spleen, thymus and bone marrow tissue) or bodily fluids (e.g., serum, plasma, urine, synovial fluid or spinal fluid) taken from an individual having such a disorder, relative to a "standard" AIM II gene expression level, i.e., the AIM II expression level in tissue or bodily fluids from an individual not having the disorder. Thus, the invention provides a diagnostic method useful during diagnosis of a disorder, which involves: (a) assaying AIM II gene expression level in cells or body fluid of an individual; (b) comparing the AIM II gene expression level with a standard AIM II gene expression level, whereby an increase or decrease in the assayed AIM II gene expression level compared to the standard expression level is indicative of a disorder.

It is also believed that certain tissues in mammals with cancer express significantly reduced levels of the AIM II protein and mRNA encoding the AIM II protein when compared to a corresponding "standard" mammal, i.e., a mammal of the same species not having the cancer. Further, it is believed that reduced levels of the AIM II protein can be detected in certain body fluids (e.g., sera, plasma, urine, and spinal fluid) from mammals with cancer when compared to sera from mammals of the same species not having the cancer. Thus, the invention provides a diagnostic method useful during tumor diagnosis, which involves assaying the expression level of the gene encoding the AIM II protein in mammalian cells or body fluid and comparing the gene expression level with a standard AIM II gene expression level, whereby an decrease in the gene expression level over the standard is indicative of certain tumors.

Where a tumor diagnosis has already been made according to conventional methods, the present invention is useful as a prognostic indicator, whereby patients exhibiting enhanced AIM II gene expression may experience a better clinical outcome relative to patients expressing the gene at a lower level.

By "assaying the expression level of the gene encoding the AIM II protein" is intended qualitatively or quantitatively measuring or estimating the level of the AIM II protein or the level of the mRNA encoding the AIM II protein in a first biological sample either directly (e.g., by determining or estimating absolute protein level or mRNA level) or relatively (e.g., by comparing to the AIM II protein level or mRNA level in a second biological sample).

Preferably, the AIM II protein level or mRNA level in the first biological sample is measured or estimated and compared to a standard AIM II protein level or mRNA level, the standard being taken from a second biological sample obtained from an individual not having the cancer. As will be appreciated in the art, once a standard AIM II protein level or mRNA level is known, it can be used repeatedly as a standard for comparison.

By "biological sample" is intended any biological sample obtained from an individual, cell line, tissue culture, or other source which contains AIM II protein or mRNA. Biological samples include mammalian body fluids (such as sera, plasma, urine, synovial fluid and spinal fluid) which contain secreted mature AIM II protein, and ovarian, prostate, heart, placenta, pancreas liver, spleen, lung, breast and umbilical tissue.

The present invention is useful for detecting cancer in mammals. In particular the invention is useful during diagnosis of the following types of cancers in mammals: breast, ovarian, prostate, bone, liver, lung, pancreatic and spleenic. Preferred mammals include monkeys, apes, cats, dogs, cows, pigs, horses, rabbits and humans. Particularly preferred are humans.

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

The diagnostic assays of the invention can be used for the diagnosis and prognosis of any disease related to the altered expression or production of AIM II. These assays are believed to be particularly useful for the diagnosis and prognosis of graft versus host disease, autoimmune disease and immunodeficiencies.

Antibodies of the invention can be used to assay protein levels in a biological sample using classical immunohistological methods known to those of skill in the art (e.g., see Jalkanen, M. et al., J. Cell. Biol. 101:976–985 (1985); Jalkanen, M. et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^3$H), indium ($^{112}$In), and technetium ($^{99}$Tc); luminescent labels, such as luminol; and fluorescent labels, such as fluorescein and rhodamine, and biotin.

One aspect of the invention is the detection and diagnosis of a disease or disorder associated with aberrant expression of a polypeptide of the interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Total cellular RNA can be isolated from a biological sample using the single-step guanidinium-thiocyanate-phenol-chloroform method described in Chomczynski and Sacchi, Anal. Biochem. 162:156–159 (1987). Levels of mRNA encoding the AIM II protein are then assayed using any appropriate method. These include Northern blot analysis (Harada et al., Cell 63:303–312 (1990)), S I nuclease mapping (Fujita et al., Cell 49:357–367 (1987)), the polymerase chain reaction (PCR), reverse transcription in combination with the polymerase chain reaction (RT-PCR) (Makino et al., Technique 2:295–301 (1990)), and reverse transcription in combination with the ligase chain reaction (RT-LCR).

Assaying AIM II protein levels in a biological sample can occur using antibody-based techniques. For example, AIM II protein expression in tissues can be studied with classical immunohistological methods (Jalkanen, M., et al., J. Cell. Biol. 101:976–985 (1985); Jalkanen, M., et al., J. Cell. Biol. 105:3087–3096 (1987)).

Other antibody-based methods useful for detecting AIM II protein expression include immunoassays, such as the enzyme linked immunosorbent assay (ELISA) and the radio-immunoassay (RIA).

Suitable labels are known in the art and include enzyme labels, such as, Glucose oxidase, and radioisotopes, such as iodine ($^{125}$I, $^{121}$I), carbon ($^{14}$C), sulfur ($^{35}$S), tritium ($^3$H), indium ($^{112}$In), and technetium ($^{99m}$Tc), and fluorescent labels, such as fluorescein and rhodamine, and biotin.

AIM II "Knock-outs" and Homologous Recombination

Endogenous gene expression can also be reduced by inactivating or "knocking out" the gene and/or its promoter using targeted homologous recombination. (e.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate an animal offspring with an inactive targeted gene (see, e.g., Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, e.g., Anderson et al. U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic Non-human Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., *Appl. Microbiol. Biotechnol.* 40:691–698 (1994); Carver et al., *Biotechnology (NY)* 11: 1263–1270 (1993); Wright et al., *Biotechnology (NY)* 9:830–834 (1991); and Hoppe et al., U.S. Pat. No. 4,873,191 (1989)); retrovirus mediated gene transfer into germ lines (Van der Putten et al., *Proc. Natl. Acad. Sci., USA* 82:6148–6152 (1985)), blastocysts or embryos; gene targeting in embryonic stem cells (Thompson et al., *Cell* 56:313–321 (1989)); electroporation of cells or embryos (Lo, *Mol. Cell. Biol.* 3:1803–1814 (1983)); introduction of the polynucleotides of the invention using a gene gun (see, e.g., Ulmer et al., *Science* 259:1745 (1993); introducing nucleic acid constructs into embryonic pleuripotent stem cells and transferring the stem cells back into the blastocyst; and sperm-mediated gene transfer (Lavitrano et al., *Cell* 57:717–723 (1989); etc. For a review of such techniques, see Gordon, "Transgenic Animals," *Intl. Rev. Cytol.* 115:171–229 (1989), which is incorporated by reference herein in its entirety. Further, the contents of each of the documents recited in this paragraph is herein incorporated by reference in its entirety. See also, U.S. Pat. No. 5,464,764 (Capecchi et al., Positive-Negative Selection Methods and Vectors); U.S. Pat. No. 5,631,153 (Capecchi et al., Cells and Non-Human Organisms Containing Predetermined Genomic Modifications and Positive-Negative Selection Methods and Vectors for Making Same); U.S. Pat. No. 4,736,866 (Leder et al., Transgenic Non-Human Animals); and U.S. Pat. No. 4,873,191 (Wagner et al., Genetic Transformation of Zygotes); each of which is hereby incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., *Nature* 380:64–66 (1996); Wilmut et al., *Nature* 385:810–813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., *Proc. Natl. Acad. Sci. USA* 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., *Science* 265:103–106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of AIM II polypeptides, studying conditions and/or disorders associated with aberrant AIM II expression, and in screening for compounds effective in ameliorating such conditions and/or disorders.

Other Uses

The present invention also relates to methods for separating cells into subpopulations based on whether these cells bind either the AIM II polypeptides of the invention or antibodies having specificity for these polypeptides. These separation methods will generally be based on the principle that cells which either express a surface receptor which binds AIM II polypeptides or have an AIM II polypeptide on their surface can be identified using labeled AIM II polypeptides or AIM II specific antibodies. Such cells can then be separated from other cells in a population which do not bind these polypeptides or antibodies. Methods for separating cells, commonly known as "cell sorting", are known in the art and are discussed in Crane, U.S. Pat. No. 5,489,506.

Thus, in one aspect, the invention provides methods for separating cells which bind either AIM II polypeptides or antibodies having specificity for AIM II polypeptides comprising contacting a population of cells with either an AIM II polypeptide or an antibody having specificity for the AIM II polypeptide, wherein the AIM II polypeptide or antibody is labeled with a detectable label and separating cells which bind either the AIM II polypeptide or anti-AIM II polypeptide antibody from cells which do not bind these molecules. Cells which bind AIM II polypeptides are believed to include those which express the lymphotoxin-β-receptor (LT-β-R), TR2, CD27, and TRANK.

In another embodiment, the polypeptides of the present invention are used as a research tool for studying the biological effects that result from inhibiting LTβ receptor/AIM II, TR6/AIM II, and/or TRANK/AIM II interactions on different cell types. AIM II polypeptides also may be employed in in vitro assays for detecting LTβ receptor, TR6, and/or TRANK or AIM II or the interactions thereof.

This invention also provides a method for identification of molecules, such as receptor molecules, that bind AIM II. Genes encoding proteins that bind AIM II, such as receptor proteins, can be identified by numerous methods known to those of skill in the art, for example, ligand panning and FACS sorting. Such methods are described in many laboratory manuals such as, for instance, Coligan et al., *Current Protocols in Immunology*, 1(2):Chapter 5 (1991).

For instance, expression cloning may be employed for this purpose. To this end polyadenylated RNA is prepared from a cell responsive to AIM II, a cDNA library is created from this RNA, the library is divided into pools and the pools are transfected individually into cells that are not responsive to AIM II. The transfected cells then are exposed to labeled AIM II. (AIM II can be labeled by a variety of well-known techniques including standard methods of radio-iodination or inclusion of a recognition site for a site-specific protein kinase.) Following exposure, the cells are fixed and binding of AIM II is determined. These procedures conveniently are carried out on glass slides.

Pools are identified of cDNA that produced AIM II-binding cells. Sub-pools are prepared from these positives, transfected into host cells and screened as described above. Using an iterative sub-pooling and re-screening process, one or more single clones that encode the putative binding molecule, such as a receptor molecule, can be isolated.

Alternatively, a labeled ligand can be photo affinity linked to a cell extract, such as a membrane or a membrane extract, and prepared from cells that express a molecule that it binds, such as a receptor molecule. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention also can be used to assess AIM II binding capacity of AIM II binding molecules, such as receptor molecules, in cells or in cell-free preparations.

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, one of the cDNAs herein disclosed is used to clone genomic DNA of an AIM II protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Therapeutic/prophylactic Administration and Compositions

It will be appreciated that conditions, such as those discussed above, can be treated by administration of AIM II protein. As a result, the invention further provides a method of treating an individual in need of an increased level of AIM II activity comprising administering to such an individual a pharmaceutical composition comprising, or alternatively consisting of, an effective amount of an isolated AIM II polypeptide of the invention, effective to increase the AIM II activity level in such an individual. Thus, the invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429–4432), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the AIM II of the invention may be administered orally, rectally, parenterally, intracistemally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, 1990, Science 249:1527–1533; Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (1990, Science 249:1527–1533).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864–1868), etc. Alternatively, a nucleic acid can be introduced intracellularly and incorporated within host cell DNA for expression, by homologous recombination.

In the treatment of rheumatoid arthritis, particularly preferred modes of administration of AIM II polypeptides of the present invention include, intradermal, subcutaneous and intra-articular injection and infusion. Preferably, AIM II polypeptide administered intra-articularly or intra-dermally per dose will be in the range of about 0.1 to about 1.0 mg/kg of patient body weight.

The compositions of the invention may be administered alone or in combination with other therapeutic agents (e.g., a costimulatory molecule). Therapeutic agents that may be administered in combination with the compositions of the invention, include but are not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second. Thus, in effect, the therapeutic agents may be administered to individuals either at the same time or at different times. In most instances when the therapeutic agents are administered to individuals at different times, they will generally be administered in a manner such that the therapeutic effects of these agents overlap for a period of time.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), APRIL (J. Exp. Med. 188(6):1185–1190), endokine-α (International Publication No. WO 98/07880), TR6 (International Publication No. WO 98/30694), OPG, and neutrokine-α (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), TR12, and soluble forms of CD154, CD70 and CD153.

In a preferred embodiment, the compositions of the invention are administered in combination with CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In a preferred embodiment, the compositions of the invention are administered in combination with one, two, three, four, five, or more of the following compositions: tacrolimus (Fujisawa), thalidomide (e.g., Celgene), anti-Tac(Fv)-PE40 (e.g., Protein Design Labs), inolimomab (Biotest), MAK-195F (Knoll), ASM-981 (Novartis), interleukin-1 receptor (e.g., Immunex), interleukin-4 receptor (e.g., Immunex), ICM3 (ICOS), BMS-188667 (Bristol-Myers Squibb), anti-TNF Ab (e.g., Therapeutic antibodies), CG-1088 (Celgene), anti-B7 Mab (e.g., Innogetics), MEDI-507 (BioTransplant), ABX-CBL (Abgenix).

In certain embodiments, compositions of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir); INVIRASE™ (saquinavir), and VIRACEPT™ (nelfinavir). In a specific embodiment, antiretroviral agents, nucleo side reverse transcriptase inhibitors, non-nucleoside reverse transcriptase inhibitors, and/or protease inhibitors may be used in any combination with compositions of the invention to treat, prevent, and/or diagnose AIDS and/or to treat, prevent, and/or diagnose HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat, prevent, and/or diagnose an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL ™ to prophylactically treat, prevent, and/or diagnose an opportunistic *Mycobacterium avium* complex infection. In another specific embodiment, compositions of the invention are used in any combination with RIFABUTIN™, CLARITHROMYCIM™, and/or AZITHROMYCIN™ to prophylactically treat, prevent, and/or diagnose an opportunistic *Mycobacterium tuberculosis* infection. In another specific embodiment, compositions of the invention are used in any combination with GANCICLOVIR™, FOSCARNET™, and/or CIDOFOVIR™ to prophylactically treat, prevent, and/or diagnose an opportunistic cytomegalovirus infection. In another specific embodiment, compositions of the invention are used in any combination with FLUCONAZOLE™, ITRACONAZOLE™, and/or KETOCONAZOLE™ to prophylactically treat, prevent, and/or diagnose an opportunistic fungal infection. In another specific embodiment, compositions of the invention are used in any combination with ACYCLOVIR™ and/or FAMCICOLVIR™ to prophylactically treat, prevent, and/or diagnose an opportunistic herpes simplex virus type I and/or type II infection. In another specific embodiment, compositions of the invention are used in any combination with PYRIMETHAMINE™ and/or LEUCOVORIN™ to prophylactically treat, prevent, and/or diagnose an opportunistic *Toxoplasma gondii* infection. In another specific embodiment, compositions of the invention are used in any combination with LEUCOVORIN™ and/or NEUPOGEN™ to prophylactically treat, prevent, and/or diagnose an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs cyclophosphamide, cyclophosphamide IV, methylprednisolone, prednisolone, azathioprine, FK-506, 15-deoxyspergualin, and other immunosuppressive agents that act by suppressing the function of responding T cells.

In specific embodiments, compositions of the invention are administered in combination with immunosuppressants. Immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine. In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-IRa gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone. In a more preferred embodiment, the compositions of the invention are administered in combination with an antimalarial, methotrexate, anti-TNF antibody, ENBREL™ and/or suflasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with suflasalazine. In another specific embodiment, the compositions of the invention are administered in combination with methotrexate, anti-TNF antibody, and suflasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and suflasalazine. In another embodiment, the compositions of the invention are administered in combination with ENBREL™, methotrexate and suflasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and suflasalazine. In another specific embodiment, the compositions of the invention are administered in combination with an antimalarial (e.g., hydroxychloroquine), sulfasalazine, anti-TNF antibody, and methotrexate.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that may be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL-2, IL-3, IL-4, IL-5, IL-6, IL-7, IL-10, IL-12, IL-13, IL-15, anti-CD40, CD40L, IFN-γ and TNF-α.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in WO 92/06194; Placental Growth Factor-2 (PlGF-2), as disclosed in Hauser et al., *Growth Factors* 4:259–268 (1993); Vascular Endothelial Growth Factor (VEGF), as disclosed in WO 90/13649; Vascular Endothelial Growth Factor-A (VEGF-A), as disclosed in European Patent Number EP-506477; Vascular Endothelial Growth Factor-2 (VEGF-2), as disclosed in WO 96/39515; Vascular Endothelial Growth Factor B-186 (VEGF-B186), as disclosed in WO 96/26736; Vascular Endothelial Growth Factor-D (VEGF-D), as disclosed in WO 98/02543; Vascular Endothelial Growth Factor-D (VEGF-D), as disclosed in WO 98/07832; and Vascular Endothelial Growth Factor-E (VEGF-E), as disclosed in German Patent Number DE19639601. The above mentioned references are incorporated by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14 and FGF-15.

In additional embodiments, the compositions of the invention are administered in combination with other therapeutic or prophylactic regimens, such as, for example, radiation therapy.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In addition to soluble AIM II polypeptides (i.e., AIM II polypeptides missing all or part of the transmembrane domain), AIM II polypeptides containing the transmembrane region can also be used when appropriately solubilized by including detergents, such as triton X-100, with buffer.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

As a general proposition, the total pharmaceutically effective amount of AIM II polypeptide administered parenterally per dose will be in the range of about 1 μg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the AIM II polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Having generally described the invention, the same will be more readily understood by reference to the following examples, which are provided by way of illustration and are not intended as limiting.

EXAMPLES

Example 1

Expression and Purification of AIM II in *E. coli*

A. Expression of AIM II With an N-terminal 6-His Tag

The DNA sequence encoding the AIM II protein in the cDNA assigned ATCC Accession No. 97689 is amplified using PCR oligonucleotide primers specific to the amino terminal sequences of the AIM II protein and to vector sequences 3' to the gene. Additional nucleotides containing restriction sites to facilitate cloning are added to the 5' and 3' sequences respectively.

A 22 kDa AIM II protein fragment (lacking the N-terminus and transmembrane region) is expressed using the following primers:

The 5' oligonucleotide primer has the sequence 5' GCGGGATCCGGAGAGATGGTCACC 3' (SEQ ID NO:7) containing the underlined BamHI restriction site, which includes nucleotides 244–258 of the AIM II protein coding sequence in FIG. 1A (SEQ ID NO:1).

The 3' primer has the sequence: 5' CGC AAGCTTCCTTCACACCATGAAAGC 3' (SEQ ID NO:8) containing the underlined HindIII restriction site followed by nucleotides complementary to nucleotides 757–774 as shown in FIG. 1B (SEQ ID NO:1).

The entire AIM II protein can be expressed using the following primers:

The 5' oligonucleotide primer has the sequence: 5' GACC GGATCC ATG GAG GAG AGT GTC GTA CGG C 3' (SEQ ID NO:9) containing the underlined BamHI restriction site, which includes nucleotides 49–70 of the AIM II protein coding sequence in FIG. 1A (SEQ ID NO:1).

The 3' primer has the sequence: 5' CGC AAGCTT CCT TCA CAC CAT GAA AGC 3' (SEQ ID NO:10) containing the underlined HindIII restriction site followed by nucleotides complementary to nucleotides 756–783 as shown in FIG. 1B (SEQ ID NO:1).

The restriction sites are convenient to restriction enzyme sites in the bacterial expression vector pQE9, which are used for bacterial expression in these examples. (Qiagen, Inc. 9259 Eton Avenue, Chatsworth, Calif., 91311). pQE9 encodes ampicillin antibiotic resistance ("Amp"") and contains a bacterial origin of replication ("ori"), an IPTG inducible promoter, a ribosome binding site ("RBS"), a 6-His tag and restriction enzyme sites.

The amplified AIM II DNA and the vector pQE9 both are digested with BamHI and HindIII and the digested DNAs are then ligated together. Insertion of the AIM II protein DNA into the restricted pQE9 vector places the AIM II protein coding region downstream of and operably linked to the vector's IPTG-inducible promoter and in-frame with an initiating AUG appropriately positioned for translation of AIM II protein.

B. Expression of AIM II With a C-terminal 6-His Tag

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that an inserted DNA fragment encoding a polypeptide expresses that polypeptide with the six His residues (i.e., a "6×His tag") covalently linked to the carboxyl terminus of that polypeptide.

The DNA sequence encoding the desired portion of the AIM II protein is amplified from the deposited cDNA using PCR oligonucleotide primers which anneal to the amino terminal sequences of the desired portion of the AIM II protein and to sequences in the deposited construct 3' to the cDNA coding sequence. Additional nucleotides containing restriction sites to facilitate cloning in the pQE60 vector are added to the 5' and 3' sequences, respectively.

For cloning the protein, the 5' primer has the sequence: 5' GACGC CCATGG AG GAG GAG AGT GTC GTA CGG C 3' (SEQ ID NO:17) containing the underlined NcoI restriction site followed by nucleotides complementary to the amino terminal coding sequence of the AIM II sequence in FIG. 1A. One of ordinary skill in the art would appreciate, of course, that the point in the protein coding sequence where the 5' primer begins may be varied to amplify a DNA segment encoding any desired portion of the complete protein (shorter or longer). The 3' primer has the sequence: 5' GACC GGATCC CAC CAT GAA AGC CCC GAA GTA AG 3' (SEQ ID NO:18) containing the underlined BamHI restriction site followed by nucleotides complementary to the 3' end of the coding sequence immediately before the stop codon in the AIM II DNA sequence in FIG. 1B, with the coding sequence aligned with the restriction site so as to maintain its reading frame with that of the six His codons in the pQE60 vector.

The amplified AIM II DNA fragment and the vector pQE60 are digested with BamHI and NcoI and the digested DNAs are then ligated together. Insertion of the AIM II DNA into the restricted pQE60 vector places the AIM II protein coding region downstream from the IPTG-inducible promoter and in-frame with an initiating AUG and the six histidine codons.

C. Expression of AIM II Deletion Mutant With an N-terminal 6-His Tag

The DNA sequence encoding the AIM II protein in the deposited cDNA was amplified using PCR oligonucleotide primers specific to sequences of the AIM II protein and to vector sequences 3' to the gene. Additional nucleotides containing restriction sites to facilitate cloning were added to the 5' and 3' sequences respectively.

In particular, an N-terminal deletion AIM II mutant (Met (68) to Val(240) in SEQ ID NO:2) was constructed using the following primers:

The 5' oligonucleotide primer has the sequence: 5'-GGG GGA TCC ATG GTC ACC CGC CTG CC-3' (SEQ ID NO:21) containing the underlined BamHI restriction site, and includes 17 nucleotides of the AIM II protein coding sequence in FIG. 1A (SEQ ID NO:1).

The 3' primer has the sequence: 5'-GGG AAG CTT CAC CAT GAA AGC CCC G-3' (SEQ ID NO:22) containing the underlined HindIII restriction site followed by nucleotides complementary to nucleotides 753–768 as shown in FIG. 1B (SEQ ID NO:1).

These restriction sites are convenient to restriction enzyme sites in the bacterial expression vector pQE9, which are used for bacterial expression in this example. (Qiagen, Inc. 9259 Eton Avenue, Chatsworth, Calif., 91311). pQE9 encodes ampicillin antibiotic resistance ("Amp$^r$") and contains a bacterial origin of replication ("ori"), an IPTG inducible promoter, a ribosome binding site ("RBS"), a 6-His tag and restriction enzyme sites.

The amplified AIM II (aa 68-240) DNA and the vector pQE9 both were digested with BamHI and HindIII and the digested DNAs were then ligated together. Insertion of the AIM II (aa 68-240) protein DNA into the restricted pQE9 vector places the AIM II protein coding region downstream of and operably linked to the vector's IPTG-inducible promoter and in-frame with an initiating AUG appropriately positioned for translation of AIM II deletion protein.

Transformation of the Bacteria:

The ligation mixture from the 6-His tagged expression constructs made in A, B or C, above, is transformed into competent E. coli cells using standard procedures. Such procedures are described in Sambrook et al., Molecular Cloning: a Laboratory Manual, 2nd Ed.; Cold Spring Harbor Laboratory Press, Cold Spring Harbor, N.Y. (1989). E. coli strain M15/rep4, containing multiple copies of the plasmid pREP4, which expresses lac repressor and confers kanamycin resistance ("Kan$^r$"), is used in carrying out the illustrative example described herein. This strain, which is only one of many that are suitable for expressing AIM II protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 µg/ml) and kanamycin (25 µg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2×phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS at a concentration of 95 µg/ml.

D. Expression and Purification of Full Length AIM II Without a 6-His Tag

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6×His tag") covalently linked to the carboxyl terminus of that polypeptide. However, in this example, the polypeptide coding sequence is inserted such that translation of the six His codons is prevented and, therefore, the polypeptide is produced with no 6×His tag.

The DNA sequence encoding the desired portion of the AIM II protein is amplified from the deposited cDNA using PCR oligonucleotide primers which anneal to the amino terminal sequences of the desired portion of the AIM II protein and to sequences in the deposited construct 3' to the cDNA coding sequence. Additional nucleotides containing restriction sites to facilitate cloning in the pQE60 vector are added to the 5' and 3' sequences, respectively.

For cloning the protein, the 5' primer has the sequence 5' GACGC CCATGG AG GAG GAG AGT GTC GTA CGG C 3' (SEQ ID NO:17) containing the underlined NcoI restriction site including nucleotides of the amino terminal coding region of the AIM II sequence in FIG. 1A. One of ordinary skill in the art would appreciate, of course, that the point in the protein coding sequence where the 5' primer begins may be varied to amplify a desired portion of the complete protein (i.e., shorter or longer). The 3' primer has the sequence 5' CGC AAGCTT CCTT CAC ACC ATG AAA GC 3' (SEQ ID NO:19) containing the underlined HindIII restriction site followed by nucleotides complementary to the 3' end of the non-coding sequence in the AIM II DNA sequence in FIG. 1B (SEQ ID NO:1).

The amplified AIM II DNA fragments and the vector pQE60 are digested with NcoI and HindIII and the digested DNAs are then ligated together. Insertion of the AIM II DNA into the restricted pQE60 vector places the AIM II protein coding region including its associated stop codon downstream from the IPTG-inducible promoter and in-frame with an initiating AUG. The associated stop codon prevents translation of the six histidine codons downstream of the insertion point.

E. Construction of an N-terminal AIM II Deletion Mutant

For cloning an AIM II deletion mutant (Met(68) to Val(240) in SEQ ID NO:2), the 5' primer has the sequence 5'-GGG CCA TGG ATG GTC ACC CGC CTG CC-3' (SEQ ID NO:23) containing the underlined NcoI restriction site, and includes followed by 17 nucleotides of the AIM II protein coding sequence in FIG. 1A. The 3' primer has the sequence 5'-GGG AAG CTT CAC CAT GAA AGC CCC G-3' (SEQ ID NO:22) containing the underlined HindIII restriction site followed by nucleotides complementary to nucleotides 753 to 768 in FIG. 1B (SEQ ID NO:1).

The amplified AIM II (aa 68-240) DNA fragments and the vector pQE60 were digested with NcoI and HindIII and the digested DNAs were then ligated together. Insertion of the AIM II (aa 68-240) DNA into the restricted pQE60 vector places the AIM II (aa 68-240) protein coding region downstream from the IPTG-inducible promoter and in-frame with an initiating AUG. The HindIII digestion removes the six histidine codons downstream of the insertion point.

F. Construction of an N-terminal AIM II Deletion Mutant

For cloning an AIM II deletion mutant (Ala(101) to Val(240) in SEQ ID NO:2), the 5' primer has the sequence 5'-GGG CCA TGG GCC AAC TCC AGC TTG ACC-3' (SEQ ID NO:24) containing the underlined NcoI restriction site including nucleotides 349–366 in the AIM II protein coding sequence in FIG. 1A. One of ordinary skill in the art would appreciate, of course, that the point in the protein coding sequence where the 5' primer begins may be varied to amplify a desired portion of the complete protein (i.e., shorter or longer). The 3' primer has the sequence 5'-GGG AAG CTT CAC CAT GAA AGC CCC G-3' (SEQ ID NO:22) containing the underlined HindIII restriction site followed by nucleotides complementary nucleotides 755–768 of the AIM II DNA sequence in FIG. 1B.

The amplified AIM II (aa 101-240) DNA fragments and the vector pQE60 were digested with NcoI and HindIII and the digested DNAs are then ligated together. Insertion of the AIM II (aa 101-240) DNA into the restricted pQE60 vector places the AIM II (aa 101-240) protein coding region downstream from the IPTG-inducible promoter and in-frame with an initiating AUG. The HindIII digestion removes the six histidine codons downstream of the insertion point.

G. Purification of AIM II From E. coli

A polynucleotide sequence encoding a soluble fragment of AIM II (corresponding to amino acid residues L83-V240 of SEQ ID NO:2) was cloned into the HGS E. coli expression vector pHE4. The resulted plasmid DNA (pHE4:AIMII.L83-V240) was used to transform SG13009 E. coli host cells. The bacterial transformants were grown in LB medium containing kanamycin. Upon IPTG induction, recombinant AIM II was expressed in E. coli as an insoluble protein deposited in inclusion bodies.

The E. coli cell paste was resuspended in a buffer containing 0.1M Tris-HCl pH7.4, 2 mM $CaCl_2$ and was lysed by passing twice through a microfluidizer (Microfluidics, Newton, Mass.) at 6000–8000 psi. The lysed sample was mixed with NaCl to a final concentration of 0.5M and then centrifuged at 7000×g for 20 minutes. The resulting pellet was washed again with the same buffer plus 0.5M NaCl and then centrifuged at 7000×g again for 20 minutes.

The partially purified inclusion bodies were then resuspended for 2–4 hours at 20–25 $\mu$C in 2.0 M guanidine hydrochloride containing 100 mM Tris pH 7.4, 2 mM CaCl2, 5 mM Cysteine and centrifuged. The resulting pellet was then resuspended for 48–72 hours at 4 $\mu$C in 3.0–3.5 M guanidine hydrochloride containing 100 mM Tris pH 7.4, 2nM CaCl2, with or without 5 mM Cysteine. At this time, a portion of AIM II was solublized and remained in the soluble phase after 7,000×g centrifugation.

The 3M guanidine hydrochloride extract was quickly diluted with 20–30 volumes of a buffer containing 50 mM Tris-HCl pH8, 150 mM sodium chloride. Detergents such as Tween-20, CHAPS can be added to increase the refold efficacy. Afterwards the mixture was placed at 4 $\mu$C without mixing for 2 to 7 days prior to the chromatographic purification steps described below.

H. Liquid Chromatographic Purification of AIM II

The diluted AIM II sample was clarified using a 0.45 $\mu$m sterile filter. The AIM II protein was then adjusted to pH6–6.8 with 0.5M MES and chromatographed over a strong cation exchange (POROS HS-50) column. The HS column was washed first with 6–10 column volume of a buffer containing 50 mM MES-NaOH pH 6.6 and 150 mM sodium chloride. The bound protein was eluted using 3 to 5 column volume of a stepwise gradient of 300 mM, 700 mM, 1500 mM sodium chloride in 50 mM MES at pH 6.6.

The HS fraction eluted with 0.7 M sodium chloride was diluted 3-fold with water.

Transformation of the Bacteria:

The ligation mixture from expression constructs made in D, E or F, above were transformed into competent E. coli cells using standard procedures such as those described in Sambrook et al., *Molecular Cloning: a Laboratory Manual*, 2nd Ed.; Cold Spring Harbor Laboratory Press, Cold Spring Harbor, N.Y. (1989). E. coli strain M15/rep4, containing multiple copies of the plasmid pREP4, which expresses the lac repressor and confers kanamycin resistance ("Kan"), was used in carrying out the illustrative example described herein. This strain, which was only one of many that are suitable for expressing AIM II protein, was available commercially from QIAGEN, Inc., supra. Transformants were identified by their ability to grow on LB plates in the presence of ampicillin and kanamycin. Plasmid DNA was isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 μg/ml) and kanamycin (25 μg/ml). The O/N culture was used to inoculate a large culture, at a dilution of approximately 1:25 to 1:250. The cells were grown to an optical density at 600 nm ("OD600") of between 0.4 and 0.6. Isopropyl-b-D-thiogalactopyranoside ("IPTG") was then added to a final concentration of 1 mM to induce transcription from the lac repressor sensitive promoter, by inactivating the lacI repressor. Cells subsequently were incubated further for 3 to 4 hours. Cells then were harvested by centrifugation.

The cells were then stirred for 3–4 hours at 4° C. in 6M guanidine-HCl, pH8. The cell debris was removed by centrifugation, and the supernatant containing the AIM II was dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure AIM II protein. The purified protein is stored at 4° C. or frozen at −80° C.

Example 2

Cloning and Expression of AIM II Protein in a Baculovirus Expression System

A. Cloning and Expression of a Full Length AIM II Protein:

The cDNA sequence encoding the full length AIM II protein in the deposited clone assigned ATCC Accession No. 97689 is amplified using PCR oligonucleotide primers corresponding to the 5' and 3' sequences of the gene:

The 5' primer has the sequence 5' GCT CCA GGA TCC GCC ATC ATG GAG GAG AGT GTC GTA CGG C 3' (SEQ ID NO:11) containing the underlined BamHI restriction enzyme site followed by 22 bases (i.e., nucleotides 49–70) of the coding region for the AIM II protein in FIG. 1A. Inserted into an expression vector, as described below, the 5' end of the amplified fragment encoding AIM II provides an efficient signal peptide. An efficient signal for initiation of translation in eukaryotic cells, as described by Kozak, M., *J. Mol. Biol.* 196:947–950 (1987) is appropriately located in the vector portion of the construct.

The 3' primer has the sequence 5' GA CGC GGT ACC GTC CAA TGC ACC ACG CTC CTT CCT TC 3' (SEQ ID NO:12) containing the underlined Asp718 restriction site followed by nucleotides complementary to 770–795 nucleotides of the AIM II set out in FIG. 1A.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein F2.

The vector pA2-GP is used to express the AIM II protein in the baculovirus expression system, using standard methods, as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the *Autographa californica* nuclear polyhedrosis virus (AcPV) followed by convenient restriction sites. The signal peptide of AcMNPV gp67, including the N-terminal methionine, is located just upstream of a BamHI site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill readily will appreciate, that construction provides appropriately located signals for transcription, translation, trafficking and the like, such as an in-frame AUG and a signal peptide, as required. Such vectors are described in Luckow et al., *Virology* 170: 31–39, among others.

The plasmid is digested with the restriction enzyme BamHI and Asp718 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human AIM II gene by digesting DNA from individual colonies using XbaI and then analyzing the digestion product by gel electrophoresis. The sequence of the cloned fragment is confirmed by DNA sequencing. This plasmid is designated herein pBacAIM II.

B. Cloning and Expression of an Alternate Form of the AIM II Protein:

The cDNA sequence encoding the human AIM II protein in the deposited clone identified as ATCC Accession No. 97483 is amplified using PCR oligonucleotide primers corresponding to the 5' and 3' sequences of the gene.

The 5' primer has the sequence 5' CGC GGA TCC CGG AGA GAT GGT CAC C 3' (SEQ ID NO:67) containing the underlined BamHI restriction enzyme site followed by 15 bases of the sequence of AIM II of SEQ ID NO:38. Inserted into an expression vector, as described below, the 5' end of the amplified fragment encoding human AIM II provides an efficient signal peptide. An efficient signal for initiation of translation in eukaryotic cells, as described by Kozak, M., *J. Mol. Biol.*, 196: 947–950 (1987) is appropriately located in the vector portion of the construct.

The 3' primer has the sequence 5' CGC TCT AGA CCT TCA CAC CAT GAA AGC 3' (SEQ ID NO:68) containing the underlined XbaI restriction followed by nucleotides complementary to the last 18 nucleotides of the AIM II coding sequence set out in SEQ ID NO:38, including the stop codon.

The amplified fragment is isolated from a 1% agarose gel using a commercially available kit ("Geneclean," BIO 101 Inc., La Jolla, Calif.), digested with BamHI and Asp718 and again is purified on a 1% agarose gel. The vector is then constructed essentially as described above in section A of this example, but using a pA vector.

C. Construction of N-terminal AIM II Deletion Mutants:

In this illustrative example, the plasmid shuttle vector pA2 GP was used to insert the cloned DNA encoding the an N-terminal deletion of the AIM II protein into a baculovirus to express an AIM II mutant (Gln(60) to Val(240)) and AIM II mutant (Ser(79) to Val(240)) in SEQ ID NO:2, using a baculovirus leader and standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, XbaI and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39.

The cDNA sequence encoding the AIM II (Gln(60) to Val(240), FIG. 1A (SEQ ID NO:2), was amplified using PCR oligonucleotide primers corresponding to the 5' and 3' sequences of the gene.

The 5' primer has the sequence: 5'-GGG GGA TCC CGCA GCT GCA CTG GCG TCT AGG-3' (SEQ ID NO:25) containing the underlined BamHI restriction enzyme site followed by 20 nucleotides (i.e., nucleotides 225–245) encoding the AIM II protein shown in FIGS. 1A and 1B, beginning with amino acid 60 of the protein. The 3' primer has the sequence 5'-GGG TCT AGA CAC CAT GAA AGC CCC G-3' (SEQ ID NO:26) containing the underlined XbaI restriction site followed by nucleotides complementary to nucleotides 753–768 in FIG. 1B (SEQ ID NO:1).

The amplified fragment was isolated from a 1% agarose gel using a commercially available kit ("Geneclean," BIO 101 Inc., La Jolla, Calif.). The fragment then was digested with BamHI and XbaI and again was purified on a 1% agarose gel. This fragment was designated herein "F1".

The plasmid was digested with the restriction enzymes BamHI and XbaI and optionally, can be dephosphorylated using calf intestinal phosphatase, using routine procedures known in the art. The DNA was then isolated from a 1% agarose gel using a commercially available kit ("Geneclean" BIO 101 Inc., La Jolla, Calif.). This vector DNA was designated herein "V1".

Fragment F1 and the dephosphorylated plasmid V1 were ligated together with T4 DNA ligase. *E. coli* HB101 or other suitable *E. coli* hosts such as XL-1 Blue (Stratagene Cloning Systems, La Jolla, Calif.) cells were transformed with the ligation mixture and spread on culture plates. Bacteria were identified that contain the plasmid with the human AIM II gene using the PCR method, in which one of the primers that was used to amplify the gene and the second primer was from well within the vector so that only those bacterial colonies containing the AIM II gene fragment will show amplification of the DNA. The sequence of the cloned fragment was confirmed by DNA sequencing. This plasmid was designated herein pBacAIM II (aa 60-240).

The cDNA sequence encoding the AIM II (Ser(79) to Val(240), FIG. 1A (SEQ ID NO:2), was amplified using PCR oligonucleotide primers corresponding to the 5' and 3' sequences of the gene.

The 5' primer has the sequence: 5' cgc GGATCC C TCCTGGGAGCAGCTGATAC 3' (SEQ ID NO:27) containing the underlined BamHI restriction enzyme site followed by nucleotides 283–301 encoding the AIM II protein shown in FIGS. 1A and 1B, beginning with amino acid 79 of the protein. The 3' primer has the sequence: 5'-cgc GGATCC TCA CACCATGAAAGC 3' (SEQ ID NO:29) containing the underlined BamHI restriction site followed by nucleotides complementary to nucleotides 757–771 in FIG. 1B (SEQ ID NO:1).

The amplified fragment was isolated from a 1% agarose gel using a commercially available kit ("Geneclean," BIO 101 Inc., La Jolla, Calif.). The fragment then was digested with BamHI and again was purified on a 1% agarose gel. This fragment was designated herein "F1".

The plasmid was digested with the restriction enzymes BamHI and optionally, can be dephosphorylated using calf intestinal phosphatase, using routine procedures known in the art. The DNA was then isolated from a 1% agarose gel using a commercially available kit ("Geneclean" BIO 101 Inc., La Jolla, Calif.). This vector DNA was designated herein "V1".

Fragment F1 and the dephosphorylated plasmid V1 were ligated together with T4 DNA ligase. *E. coli* HB101 or other suitable *E. coli* hosts such as XL-1 Blue (Stratagene Cloning Systems, La Jolla, Calif.) cells were transformed with the ligation mixture and spread on culture plates. Bacteria were identified that contain the plasmid with the mutant AIM II gene using the PCR method, in which one of the primers that was used to amplify the gene and the second primer was from well within the vector so that only those bacterial colonies containing the AIM II gene fragment will show amplification of the DNA. The sequence of the cloned fragment was confirmed by DNA sequencing. This plasmid was designated herein pBacAIM II (aa 79-240).

D. Transfection of the Baculovirus Vectors Containing AIM II Sequences:

5 μg of the plasmid either pBacAIM II or pBacAIM II (aa 60-240) was co-transfected with 1.0 μg of a commercially available linearized baculovirus DNA ("BaculoGold™ baculovirus DNA", Pharmingen, San Diego, Calif.), using the lipofection method described by Feigner et al., *Proc. Natl. Acad. Sci. U.S.A.* 84:7413–7417 (1987). 1 μg of BaculoGold™ virus DNA and 5 μg of the plasmid pBac AIM II or pBacAIM II (aa 60-240) was mixed in a sterile well of a microtiter plate containing 50 μl of serum-free Grace's medium (Life Technologies Inc., Gaithersburg, Md.). Afterwards 10 μl Lipofectin plus 90 μl Grace's medium were added, mixed and incubated for 15 minutes at room temperature. Then the transfection mixture was added drop-wise to Sf9 insect cells (ATCC CRL 1711) seeded in a 35 mm tissue culture plate with 1 ml Grace's medium without serum. The plate was rocked back and forth to mix the newly added solution. The plate was then incubated for 5 hours at 27° C. After 5 hours the transfection solution was removed from the plate and 1 ml of Grace's insect medium supplemented with 10% fetal calf serum is added. The plate was put back into an incubator and cultivation was continued at 27° C. for four days.

After four days the supernatant was collected and a plaque assay was performed, as described by Summers and Smith, cited above. An agarose gel with "Blue Gal" (Life Technologies Inc., Gaithersburg) was used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus was added to the cells. After appropriate incubation, blue stained plaques are picked with the tip of an Eppendorf pipette. The agar containing the recombinant viruses was then resuspended in an Eppendorf tube containing 200 µl of Grace's medium. The agar was removed by a brief centrifugation and the supernatant containing the recombinant baculovirus is used to infect Sf9 cells seeded in 35 mm dishes. Four days later the supernatants of these culture dishes were harvested and then they were stored at 4° C. A clone containing properly inserted hESSB I, II and III was identified by DNA analysis including restriction mapping and sequencing. This was designated herein as V-AIM II or V-AIM II (aa 60-240).

Sf9 cells were grown in Grace's medium supplemented with 10% heat-inactivated FBS. The cells were infected with the recombinant baculovirus V-AIM II or V-AIM II (aa 60-240) at a multiplicity of infection ("MOI") of about 2 (about 1 to about 3). Six hours later the medium was removed and was replaced with SF900 II medium minus methionine and cysteine (available from Life Technologies Inc., Gaithersburg). 42 hours later, 5 µCi of $^{35}$S-methionine and 5 µCi $^{35}$S-cysteine (available from Amersham) were added. The cells were further incubated for 16 hours and then they were harvested by centrifugation, lysed and the labeled proteins were visualized by SDS-PAGE and autoradiography.

Example 3

Cloning and Expression in Mammalian Cells

Most of the vectors used for the transient expression of the AIM II protein gene sequence in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human HeLa, 283, H9 and Jurkart cells, mouse NIH3T3 and C127 cells, Cos 1, Cos 7 and CV1, African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10: 169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the *Rous Sarcoma* Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pAIM II HA, is made by cloning a cDNA encoding AIM II into the expression vector pcDNAI/Amp (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polyline.

A DNA fragment encoding the AIM II protein and an HA tag fused in frame to its 3' end is cloned into the polyline region of the vector so that recombinant protein expression is directed by the CMV promoter. The HA tag corresponds to an epitope derived from the influenza hemagglutinin protein described by Wilson et al., *Cell* 37: 767 (1984). The fusion of the HA tag to the target protein allows easy detection of the recombinant protein with an antibody that recognizes the HA epitope.

The plasmid construction strategy for full length AIM II is as follows. The AIM II cDNA of the deposited clone is amplified using primers that contain convenient restriction sites, much as described above regarding the construction of expression vectors for expression of AIM II in *E coli*. To facilitate detection, purification and characterization of the expressed AIM II, one of the primers contains a hemagglutinin tag ("HA tag") as described above.

Suitable primers include the following, which are used in this example. The 5' primer, containing the underlined BamHI site, and an AUG start codon has the following sequence: 5' GAG CTC GGA TCC GCC ATC ATG GAG GAG AGT GTC GTA CGGC 3' (SEQ ID NO:13).

The 3' primer, containing the underlined XbaI site, a stop codon, 9 codons thereafter forming the hemagglutinin HA tag, and 33 bp of 3' coding sequence (at the 3' end) has the following sequence: 5' GAT GTT CTA GAA AGC GTA GTC TGG GAC GTC GTA TGG GTA CAC CAT GAA AGC CCC GAA GTA AGA CCG GGT AC 3' (SEQ ID NO:14).

The PCR amplified DNA fragment and the vector, pcDNAI/Amp, are digested with HindIII and XhoI and then ligated.

The plasmid construction strategy for an alternate form of AIM II is as follows. The AIM II cDNA of the deposited clone identified as ATCC Accession No. 97483 is amplified using primers that contained convenient restriction sites, much as described above regarding the construction of expression vectors for expression of AIM II in E. coli and S. frurgiperda. To facilitate detection, purification and characterization of the expressed AIM II, one of the primers contains a hemagglutinin tag ("HA tag") as described above.

Suitable primers include the following, which are used in this example. The 5' primer, containing the underlined BamHI site, an AUG start codon and 5 codons thereafter which has the following sequence. 5' CGC GGA TCC ATG GGT CTG GGT CTC TTG 3' (SEQ ID NO:69). The 3' primer, containing the underlined XbaI site and has the following sequence. 5' CGC TCT AGA TCA AGC GTA GTC TGG GAC GTC GTA TGG CAC CAT GAA AGC CCC 3' (SEQ ID NO:70).

The PCR amplified DNA fragment and the vector, pcDNAI/Amp, are digested with appropriate restriction enzymes and then ligated.

In each of the above instances, the ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis and gel sizing for the presence of the AIM II-encoding fragment.

For expression of recombinant AIM II, COS cells are transfected with an expression vector, as described above, using DEAE-DEXTRAN, as described, for instance, in Sambrook et al., Molecular Cloning: a Laboratory Manual, Cold Spring Laboratory Press, Cold Spring Harbor, N.Y. (1989). Cells are incubated under conditions for expression of AIM II by the vector.

Expression of the AIM II HA fusion protein is detected by radiolabelling and immunoprecipitation, using methods described in, for example Harlow et al., Antibodies: A Laboratory Manual, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 1% NP-40, 0.1% SDS, 1% NP-40, 0.5% DOC, 50 mM TRI S, pH 7.5, as described by Wilson et al. cited above. Proteins are precipitated from the cell lysate and from the culture media using an HA-specific monoclonal antibody. The precipitated proteins then are analyzed by SDS-PAGE gels and autoradiography. An expression product of the expected size is seen in the cell lysate, which is not seen in negative controls.

Example 3(b)

Cloning and Expression in CHO Cells

The vector pC4 is used for the expression of AIM II protein. Plasmid pC1 is a derivative of the plasmid pSV2-dhfr (ATCC Accession No. 37146). Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and over-expressed. It is state of the art to develop cell lines carrying more than 1,000 copies of the genes. Subsequently, when the methotrexate is withdrawn, cell lines contain the amplified gene integrated into the chromosome(s).

Plasmid pC4 contains for expressing the gene of interest the strong promoter of the long terminal repeat (LTR) of the Rous Sarcoma Virus (Cullen, et al., Molecular and Cellular Biology, March 1985:438–447) plus a fragment isolated from the enhancer of the immediate early gene of human cytomegalovirus (CMV) (Boshart et al., Cell 41:521–530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the AIM II in a regulated way in mammalian cells (Gossen, M., & Bujard, H. 1992, Proc. Natl. Acad. Sci. U.S.A. 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calfintestinal phosphatase by procedures known in the art. The vector is then isolated from a 1% agarose gel.

The DNA sequence encoding the complete AIM II protein is amplified using PCR oligonucleotide primers corresponding to the 5' and 3' sequences of the gene. The 5' primer has the sequence: 5' GCT CCA GGA TCC GCC ATC ATG GAG GAG AGT GTC GTA CGG C3' (SEQ ID NO:15) containing the underlined BamHI restriction enzyme site followed by an efficient signal for initiation of translation in eukaryotes, as described by Kozak, M., J. Mol. Biol. 196:947–950 (1987), and 22 bases (i.e., nucleotides 49–70) of the coding region of the AIM II protein shown in FIG. 1A (SEQ ID NO:1). The 3' primer has the sequence: 5' GA CGC GGT ACC GTC CAA TGC ACC ACG CTC CTT CCT TC 3' (SEQ ID NO:16) containing the underlined Asp718 restriction site followed by nucleotides complementary to nucleotides 770–795 of the AIM II gene shown in FIG. 1B (SEQ ID NO:1).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Example 3(c)

Cloning and Expression of an AIM II N-terminal Deletion in CHO Cells

The vector pC4 was used for the expression of AIM II mutant (Met(68)-Val(240) in SEQ ID NO:2) protein. The plasmid pC4 was digested with the restriction enzymes BamHI and then dephosphorylated using calf intestinal phosphatase by procedures known in the art. The vector was then isolated from a 1% agarose gel.

The DNA sequence encoding the AIM II (aa 68-240) protein was amplified using PCR oligonucleotide primers corresponding to the 5' and 3' sequences of the gene. The following 5' primer was used: 5' GAC AGT GGA TCC GCC ACC ATG GTC ACC CGC CTG CCT GAC GGA C 3' (SEQ ID NO:40) containing the underlined BamHI restriction enzyme site followed by an efficient signal for initiation of translation in eukaryotes, as described by Kozak, M., *J. Mol. Biol.* 196:947–950 (1987), and nucleotides 202–226 in the coding region for the AIM II polypeptide shown in FIG. 1A (SEQ ID NO:1). The following 3' primer was used: (BamHI+stop codon (italics)) 5'-GGG GGA TCC *TGA* CAC CAT GAA AGC CCC G-3' (SEQ ID NO:28) containing the underlined BamHI restriction site followed by nucleotides complementary nt 753–768 shown in FIG. 1B (SEQ ID NO:1).

The amplified fragment was digested with the endonucleases BamHI and then purified again on a 1% agarose gel. The isolated fragment and the dephosphorylated vector were then ligated with T4 DNA ligase. *E. coli* HB 101 or XL-1 Blue cells were then transformed and bacteria were identified that contain the fragment inserted into plasmid pC4 using, for instance, restriction enzyme analysis.

The vector pC4/Ckβ8 (a pC4 construct wherein the Ckβ8 signal peptide was first cloned into the pC4 vector with a BamHI site at the 3' end of Ckβ8 signal sequence) was used for the expression of AIM II mutant (Trp(80)-Val(240) in SEQ ID NO:2) protein. The plasmid pC4/Ckβ8 was digested with the restriction enzymes BamHI and then dephosphorylated using calf intestinal phosphatase by procedures known in the art. The vector was then isolated from a 1% agarose gel.

The DNA sequence encoding the AIM II (aa 80-240) protein was amplified using PCR oligonucleotide primers corresponding to the 5' and 3' sequences of the gene. The following 5' primer was used: 5' cgc GGATCC TGGGAGCAGCTGATAC 3' (SEQ ID NO:41) containing the underlined BamHI restriction enzyme site followed by nucleotides 286–301 in the coding region for the AIM II polypeptide shown in FIG. 1A (SEQ ID NO:1). The following 3' primer was used: 5' cgc GGATCC TCA CACCATGAAAGC 3' (SEQ ID NO:29) containing the underlined BamHI restriction site followed by nucleotides complementary nt 757–771 shown in FIG. 1B (SEQ ID NO:1).

The amplified fragment was digested with the endonucleases BamHI and then purified again on a 1% agarose gel. The isolated fragment and the dephosphorylated vector were then ligated with T4 DNA ligase. *E. coli* HB101 or XL-1 Blue cells were then transformed and bacteria were identified that contain the fragment inserted into plasmid pC4/Ckβ8 using, for instance, restriction enzyme analysis.

CHO Cell Transfection:

Chinese hamster ovary cells lacking an active DHFR gene are used for transfection. 5 µg of the expression pC4 vectors described above are cotransfected with 0.5 µg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 µM, 20 µM). The same procedure is repeated until clones are obtained which grow at a concentration of 100–200 µM. Expression of the desired gene product is analyzed, for instance, by SDS-PAGE and Western blot or by reverse phase HPLC analysis.

Example 3(d)

Cloning and Expression of an AIM II N-terminal Deletion in CHO Cells

The vector pC4 was used for the expression of AIM II mutant (Met(68)-Val(240) in SEQ ID NO:2) protein that includes a C-terminal Fc immunoglobulin region. In this construct, the Ckβ8 signal peptide was first cloned into pC4 with a BamHI site at the 3' end of Ckβ8. The Fc fragment flanked by BamHI and XbaI sites was cloned into the vector resulting in pC4/Ckβ8/Fc. The AIM II fragment was then cloned between the CK-β8 leader and the Fc fragment in the BamHI site.

The plasmid pC4 was digested with the restriction enzymes BamHI and then dephosphorylated using calf intestinal phosphatase by procedures known in the art. The vector was then isolated from a 1% agarose gel.

The DNA sequence encoding the complete AIM II (aa 68-240) protein was amplified using PCR oligonucleotide primers corresponding to the 5' and 3' sequences of the gene. The following 5' primer was used: 5' GAC AGT GGA TCC GCC ACC ATG GTC ACC CGC CTG CCT GAC GGA C 3' (SEQ ID NO:40) containing the underlined BamHI restriction enzyme site followed by an efficient signal for initiation of translation in eukaryotes, as described by Kozak, M., *J. Mol. Biol.* 196:947–950 (1987), and nucleotides 202–226 in the coding region for the AIM II polypeptide shown in FIG. 1A (SEQ ID NO:1). The following 3' primer was used: (BamHI) 5'-GGG GGA TCC CAC CAT GAA AGC CCC G-3' (SEQ ID NO:30) containing the underlined BamHI restriction site followed by nucleotides complementary to nt 753–768 shown in FIGS. 1A and 1B (SEQ ID NO:1) followed by the Fc immunoglobulin fragment having the following sequence: 5'-G GGATCCGGAGCCCAAATCTTCTGACAAAACTCAC ACATGCCCACCGTGCCCAGCACCTGAAT- TCGAGGGTGCACCGTCAGTCTTCCTCT- TCCCCCCAAAACCCAAGGACACCCTCAT- GATCTCCCGGACTCCTGAGGTCACATGCGTGGTG GTGGACGTAAGCCACGAAGACCCTGAG- GTCAAGTTCAACTGGTACGTGGACG- GCGTGGAGGTGCATAATGCCAAGA- CAAAGCCGCGGGAGGAGCAGTACAACAGCACGT ACCGTGTGGTCAGCGTCCTCACCGTCCT- GCACCAGGACTGGCTGAATGGCAAGGAG- TACAAGTGCAAGGTCTCCAACAAAGC- CCTCCCAACCCCCATCGAGAAAACCATCTCCAAA GCCAAAGGGCAGCCCCGAGAACCACAG- GTGTACACCCTGCCCCCATCCCGGGAT- GAGCTGACCAAGAACCAGGTCAGCCT- GACCTGCCTGGTCAAAGGCTTCTATCCAAGCGAC ATCGCCGTGGAGTGGGAGAG- CAATGGGCAGCCGGAGAACAACTACAA- GACCACGCCTCCCGTGCTGGACTC- CGACGGCTCCTTCTTCCTCTACAGCAAGCTCACC GTGGACAAGAGCAGGTGGCAGCAGGG- GAACGTCTTCTCATGCTCCGTGATGCAT- GAGGCTCTGCACAACCACTACACGCA- GAAGAGCCTCTCCCTGTCTCCGGGTAAATGAGTG CGACGGCCGCGAC<u>TCTAGA</u>GGAT-3' (SEQ ID NO:31).

The amplified fragment was digested with the endonucleases BamHI and then purified again on a 1% agarose gel. The isolated fragment and the dephosphorylated vector were then ligated with T4 DNA ligase. *E. coli* HB101 or XL-1 Blue cells were then transformed and bacteria are identified that contain the fragment inserted into plasmid pC4 using, for instance, restriction enzyme analysis.

CHO Cell Transfection:

Chinese hamster ovary (CHO/dhfr⁻-DG44) cells were transfected with the expression vector (pC4/spCKβ8/Fc/AIM II) using lipofectin. Recombinant clones were isolated by growing the cells in MEM alpha selective medium with 5% dialyzed fetal bovine serum (DiFBS), 1% penicillin/streptomycin (PS), 1 mg/mL geneticin (G418) and 10 nM methotrexate (MTX). High expressing clones, which were confirmed by screening recombinant clones using a BIAcore method (see, below for more details), were then individually amplified by increasing stepwise the concentration of MTX to a final concentration of 100 μM. The high expressing clones were used for the production of AIM II-IgG1 fusion protein in a microcarrier CHO perfusion bioreactor.

CHO.AIM II-IgG1 cells were grown on Cytodex 1 microcarriers (Pharmacia Biotech, Upsala, Sweden) in HGS-CHO-3 medium containing 1% ultra-low IgG FBS. The cells grown in multiple microcarrier spinners were scaled up to a 10 L microcarrier perfusion bioreactor. The perfusion bioreactor was operated continuously for 27 days and during that period of time, 90 liters of microcarrier-free supernatants containing AIM II-IgG1 fusion protein were harvested. The supernatants were clarified through a filtration process using 0.2 μm sterile filters and stabilized by adding 5 mM EDTA. The clarified supernatants were loaded onto an affinity column to capture AIM II-IgG1 fusion protein.

Purification of AIM II-IgG1 Fusion Protein

The AIM I-IgG1 fusion protein was purified from 15 L of CHO conditioned media. The conditioned media was loaded onto a Protein A HyperD (54 ml bed volume, BioSepra) affinity column at a flow rate of 30 ml/min at 10° C. on a BioCad 60 (PerSeptives Biosystems). The column was pre-equilibrated with 25 mM sodium acetate, pH8 and 0.1M NaCl. After loading, the column was washed with 3 column volumes each of 0.1M sodium citrate, pH5 and 0.1M NaCl and 0.1M sodium citrate, pH 2.8 and 0.1M NaCl. The peak fractions containing AIM II-IgG fusion protein were determined by SDS-PAGE analysis and pooled. The identity of the purified protein was confirmed by N-terminal sequence analysis. The final protein yield was about 9 mg/L condition media.

Example 4

AIM II Expression Constructs

Full-length Constructs:

(a) pCMVsport: The eukaryotic expression vector pCMVsport contains nucleotides encoding the AIM II ORF from Met(1) to Val(240). The plasmid construction strategy is as follows. The AIM II cDNA of the deposited clone is amplified using primers that contain convenient restriction sites. Suitable primers include the following which are used in this example. The 5' primer, containing the underlined SalI site, an AUG start codon, nucleotides 51–69 in the coding region of the AIM II polypeptide (SEQ ID NO:1) and has the following sequence: 5'-GGG <u>GTC GAC</u> *GCC ATC* ATG GAG GAG AGT GTC GTA CGG-3' (SEQ ID NO:32).

The 3' primer, containing the underlined NotI site, nucleotides complementary to nucleotides 753–767 in SEQ ID NO:1 and a stop codon and has the following sequence: 5'-GGG <u>GCG GCC</u> GCG CCT TCA CAC CAT GAA AGC CCCG-3' (SEQ ID NO:33).

The PCR amplified DNA fragment is digested with SalI and NotI and then gel purified. The isolated fragment was then ligated into the SalI and NotI digested vector pCMVsport. The ligation mixture is transformed into *E. coli* and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

(b) pG1SamEN: The retroviral expression vector pG1SamEN encodes the AIM II ORF from Met(1) to Val(240). The pG1 vector is described in Morgan, R. A., et al., *Nucl. Acids Res.* 20(6):1293–1299 (1992) and is similar to the LN vector (Miller, A. D. and Rosman, G. J., *Biotechniques* 7:980–990 (1989)), but has additional cloning sites. The plasmid construction strategy is as follows. The AIM II cDNA of the deposited clone is amplified using primers that contain convenient restriction sites. Suitable primers include the following which are used in this example. The 5' primer, containing the underlined NotI site, and an AUG start codon, nucleotides 51–69 in the coding region for the AIM II polypeptide (SEQ ID NO:1) has the following sequence: 5'-GGG <u>GCG GCC GC</u>*G CCA TCA* TGG AGG AGA GTG TCG TAC GG-3' (SEQ ID NO:34).

The 3' primer, containing the underlined SalI site, nucleotides complementary to nucleotides 753–768 in SEQ ID NO:1 and a stop codon has the following sequence: 5'-GGG <u>GTC GAC</u> *GCC TTCA* CAC CAT GAA AGC CCC G-3' (SEQ ID NO:35).

The PCR amplified DNA fragment is digested with SalI and NotI and then gel purified. The isolated fragment was then ligated into the SalI and NotI digested vector. The ligation mixture is transformed into E. coli and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

2. N-terminal Deletion Constructs:

(a) pG1/ckβ8: The eukaryotic expression vector encodes the AIM II mutant (Gln(60) to Val(240) in SEQ ID NO:2) (AIM II (aa 60-240)) and was secreted under the direction of the human Ck-β8 signal peptide. The pG1 vector is described in Morgan, R. A., et al., Nucl. Acids Res. 20(6):1293–1299 (1992) and is similar to the LN vector (Miller, A. D. and Rosman, G. J. Biotechniques 7:980–990 (1989)), but has additional cloning sites. The plasmid construction strategy is as follows. The AIM II cDNA of the deposited clone is amplified using primers that contain convenient restriction sites. Suitable primers include the following which are used in this example. The 5' primer, containing the underlined NotI site, nucleotides in the coding region for the AIM II polypeptide (SEQ ID NO:1) and an AUG start codon has the following sequence:

5'-GGG GCG GCC GCG CCA TCA TGA AGG TCT CCG TGG CTG CCC TCT
CCT GCC TCA TGC TTG TTA CTG CCC TTG GAT CGC AGG CAG CTG
CAC TGG CGT-3' (NotI + Kozak + CK-β8 leader (double underline))(SEQ ID NO:36).

The 3' primer, containing the underlined SalI site, nucleotides complementary to nucleotides 753–768 in SEQ ID NO:1 and a stop codon has the following sequence: 5'-GGG GTC GAC TCA CAC CAT GAA AGC CCC G-3' (SEQ ID NO:37).

The PCR amplified DNA fragment is digested with SalI and NotI and then gel purified. The isolated fragment was then ligated into the SalI and NotI digested vector pG1. The ligation mixture is transformed into E. coli and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II, eukaryotic cells such as COS or CHO are transfected with the expression vector, as described above, using DEAE-DEXTRAN as described above in Example 3. Expression of the AIM II recombinant protein is detected by the methods described above in Example 3.

(b) pHE4: Plasmid pHE4 is a bacterial expression vector containing a strong synthetic promoter with two lac operators. Expression from this promoter is regulated by the presence of a lac repressor, and is induced using IPTG or lactose. The plasmid also contains an efficient ribosomal binding site and a synthetic transcriptional terminator downstream of the AIM II mutant gene. The vector also contains the replication region of pUC plasmids and the kanamycin resistance gene.

The AIM II N-terminal deletion mutants were constructed according to the following scheme. The AIM II cDNA of the deposited clone is amplified using primers that contain convenient restriction sites. Suitable primers include the following which are used in this example.

For the AIM II (Thr(70) to Val(240)) polypeptide in SEQ ID NO:2, the 5' primer, containing the underlined NdeI site, and an AUG start codon, nucleotides 256–271 in the coding region for the AIM II polypeptide (SEQ ID NO:1) has the following sequence: 5'-cgc CATATG A CCCGCCTGCCTGACG-3' (SEQ ID NO:42).

For the AIM II (Ser(79) to Val(240)) polypeptide in SEQ ID NO:2, the 5' primer, containing the underlined NdeI site, and an AUG start codon, nucleotides 283–310 in the coding region for the AIM II polypeptide (SEQ ID NO: 1) has the following sequence: 5'-cgc CATATG A GC TGGGAGCAGCTGATAC-3' (SEQ ID NO:43).

For the AIM II (Ser(103) to Val(240)) polypeptide in SEQ ID NO:2, the 5' primer, containing the underlined NdeI site, and an AUG start codon, nucleotides 355–373 in the coding region for the AIM II polypeptide (SEQ ID NO:1) has the following sequence: 5'-cgc CATATG A GC AGCTTGACCGGCAGCG-3' (SEQ ID NO:44).

The following 3' primers can be used to construct the aforementioned N-terminal deletions:

The 3' primer, containing the underlined Asp718 site, nucleotides complementary to nucleotides 753–768 in SEQ ID NO:1 and a stop codon has the following sequence: 5'-cgc GGTACC TTA CACCATGAAAGCCCCG-3' (SEQ ID NO:45).

The PCR amplified DNA fragment is digested with NdeI and Asp718 and then gel purified. The isolated fragment was then ligated into the appropriately digested pHE4 vector. The ligation mixture is transformed into E. coli and the transformed culture is plated on antibiotic media plates which are then incubated to allow growth of the antibiotic resistant colonies. Plasmid DNA is isolated from resistant colonies and examined by restriction analysis and gel sizing for the presence of the AIM II encoding fragment.

For expression of the recombinant AIM II N-terminal deletion, bacterial cells are transfected with the expression vector, as described above in Example 1. Expression of the AIM II recombinant protein is detected by the methods described above in Example 1.

Example 5

Biological Characterization of the AIM II Polypeptide

The following set of experiments provides the biological characterization of the AIM II protein and demonstrates that AIM II has potent anti-tumor activity in vivo and in vitro.

A. AIM II is Highly Expressed in Activated Lymphocytes but not in Cancer Cells

Northern blot analyses demonstrated that the AIM II mRNA is approximately 1.9 kb in length and is expressed predominantly in spleen, brain and peripheral blood cells. AIM II is also detectable to some extent in prostate, testis, ovary, small intestine, placenta, liver, skeletal muscle and lung. AIM II message was not detected in fetal tissues, many endocrine glands and tumor lines of non-hematopoietic and myeloid origin.

RT-PCR assays were performed to investigate expression of AIM II in activated vs. resting PBMC. Fresh PBMC including mixture of T cells, B lymphocytes, NK cells, monocytes and granulocytes express the AIM II mRNA which is consistent with Northern blot analysis. No expression was found in resting PBLs as mixture of T, B and NK cells, Jurkat cells (resting or activated) or K562 cells. Increased expression of AIM II was found in activated PBLs, CD3+, CD4+ T-cells, CD8+ Tumor infiltrating lymphocytes (TIL), granulocytes, and monocytes. Additional RT-PCR analyses demonstrated the presence of AIM II mRNA in LPS-activated neutrophils and PMA-stimulated U937 cells. Interestingly, expression of AIM II was not detectable in various cancer cell lines derived from breast, prostate or ovary, except in one human breast epithelial-derived, non-tumorigenic cell line MCA-10A cells. In addition, no expression of AIM II was found from three breast cancer samples examined.

B. Constitutive Expression of AIM II Resulted in Growth Inhibition Under Serum Starvation or Treatment With IFNγ

To investigate the biological function of AIM II, the AIM II gene was stably transduced into human breast carcinoma cell line MDA-MB-231 using a retroviral vector. Expression of the AIM II gene in these cells was confirmed by Northern blot analyses. In addition, MDA-MB-231 cells expressing the drug resistance gene Neo were used as control in this study. No difference in the growth rate in vitro was observed within AIM II transfectants (MDA-MB-231/AIM II) compared with that of the parental cells or vector control transfected cells (MDA-MB-231/Neo), when these cells were cultured in medium containing 10% FBS. However, when the serum concentration was reduced to 1%, there was 80% growth inhibition (FIG. 4A) for the MDA-MB-231/AIM II cells, but not for the parental or vector control MDA-MB-231 cells. A dose-dependent growth inhibition with a different amount of serum has also been observed.

Figure 3A:
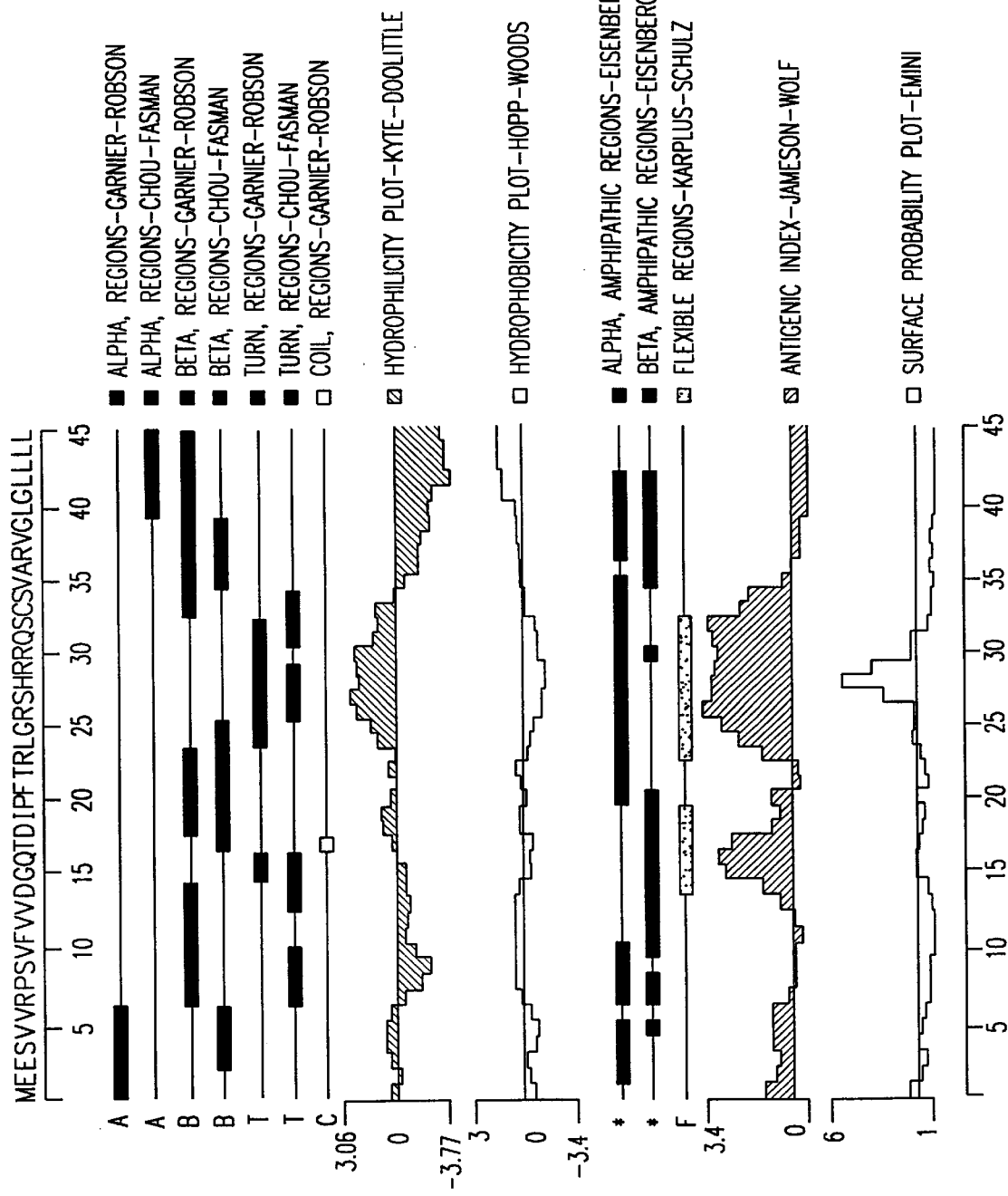
FIGS. 3A–3F show an analysis of the AIM II amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, about amino acid residues 13–20, 23–36, 69–79, 85–94, 167–178, 184–196, 221–233 in FIGS. 1A and 1B (SEQ ID NO:2) correspond to the shown highly antigenic regions of the AIM II protein.
Figure 3B:
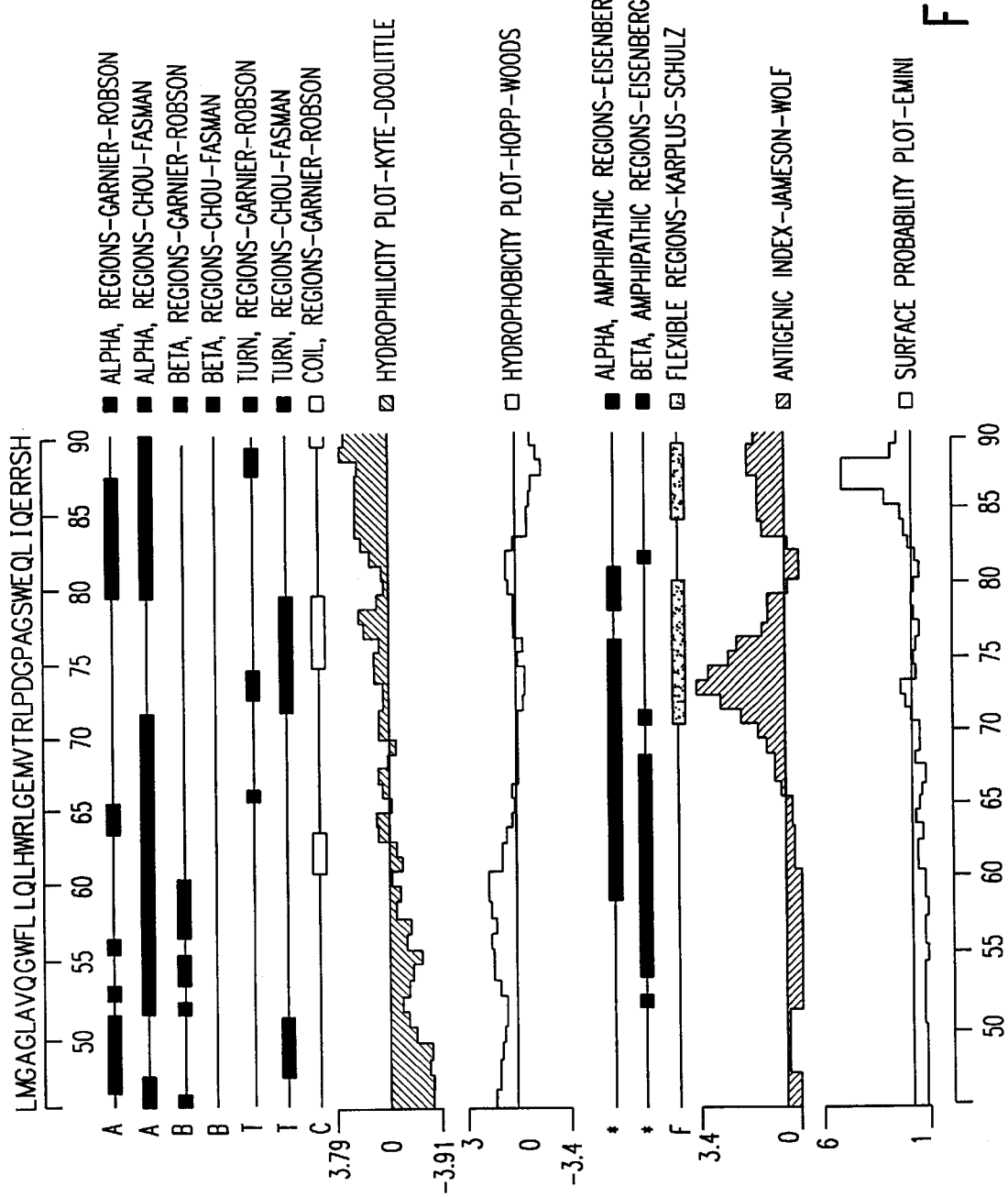
Figure 3C:
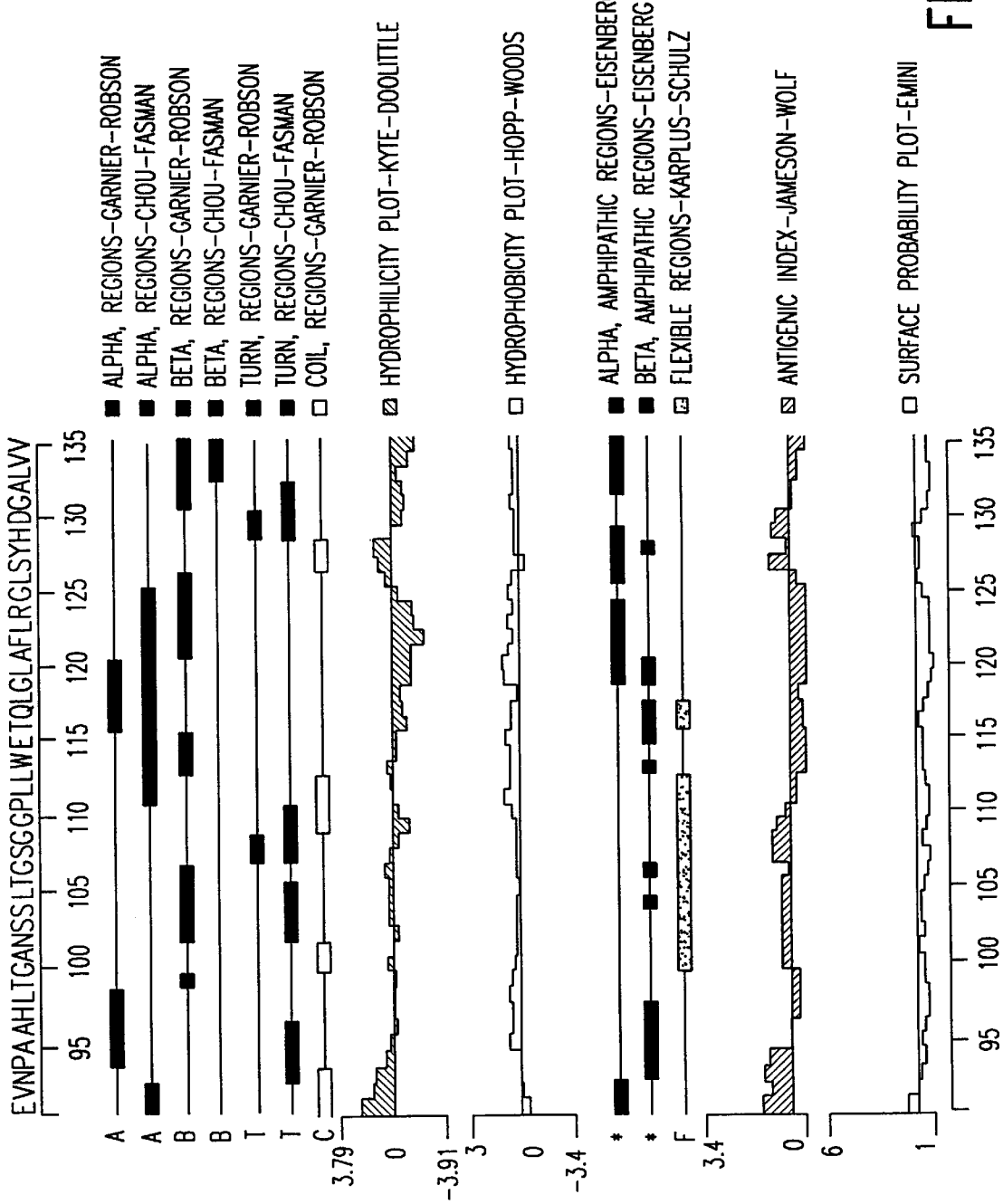
Figure 3D:
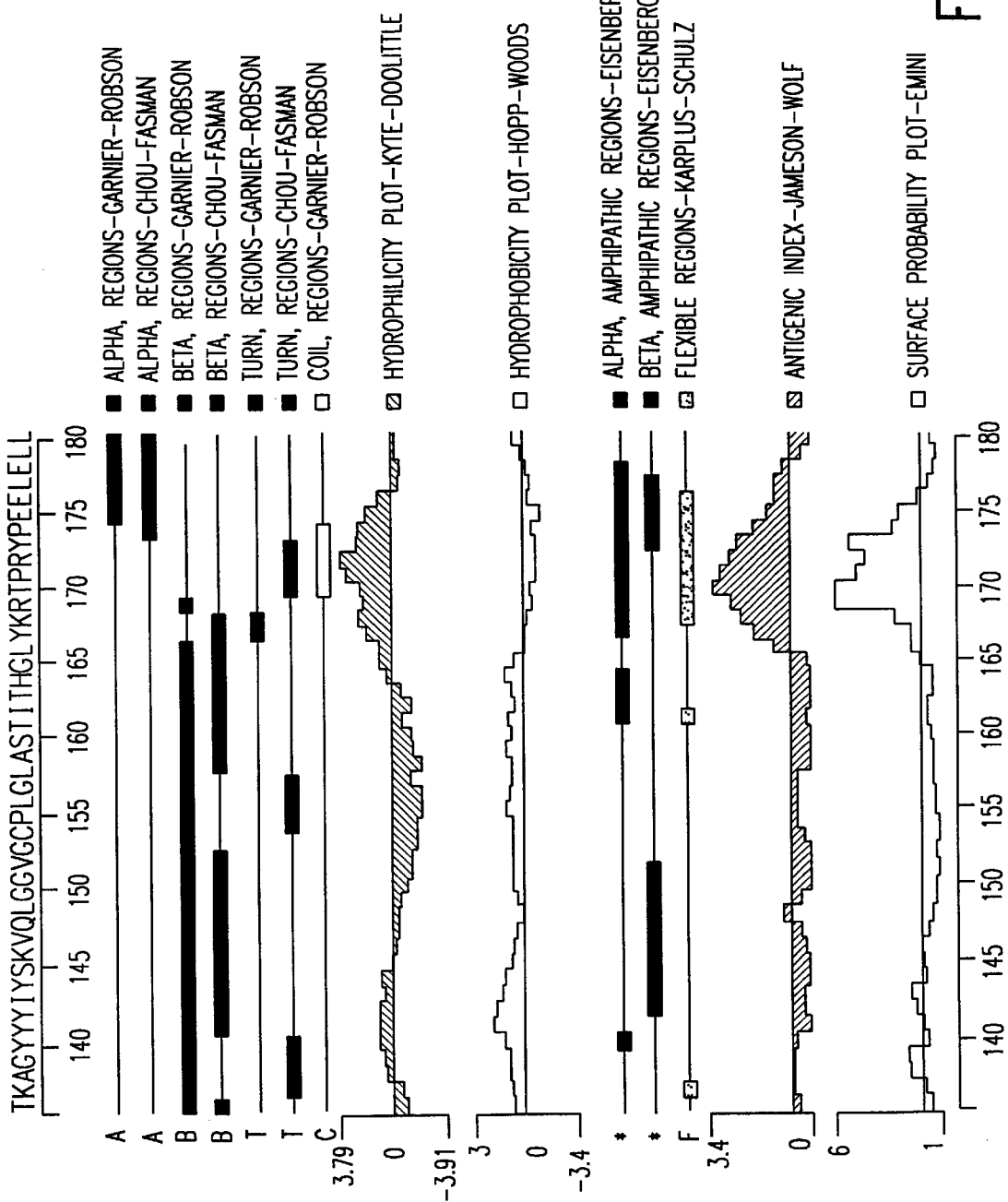
Figure 3E:
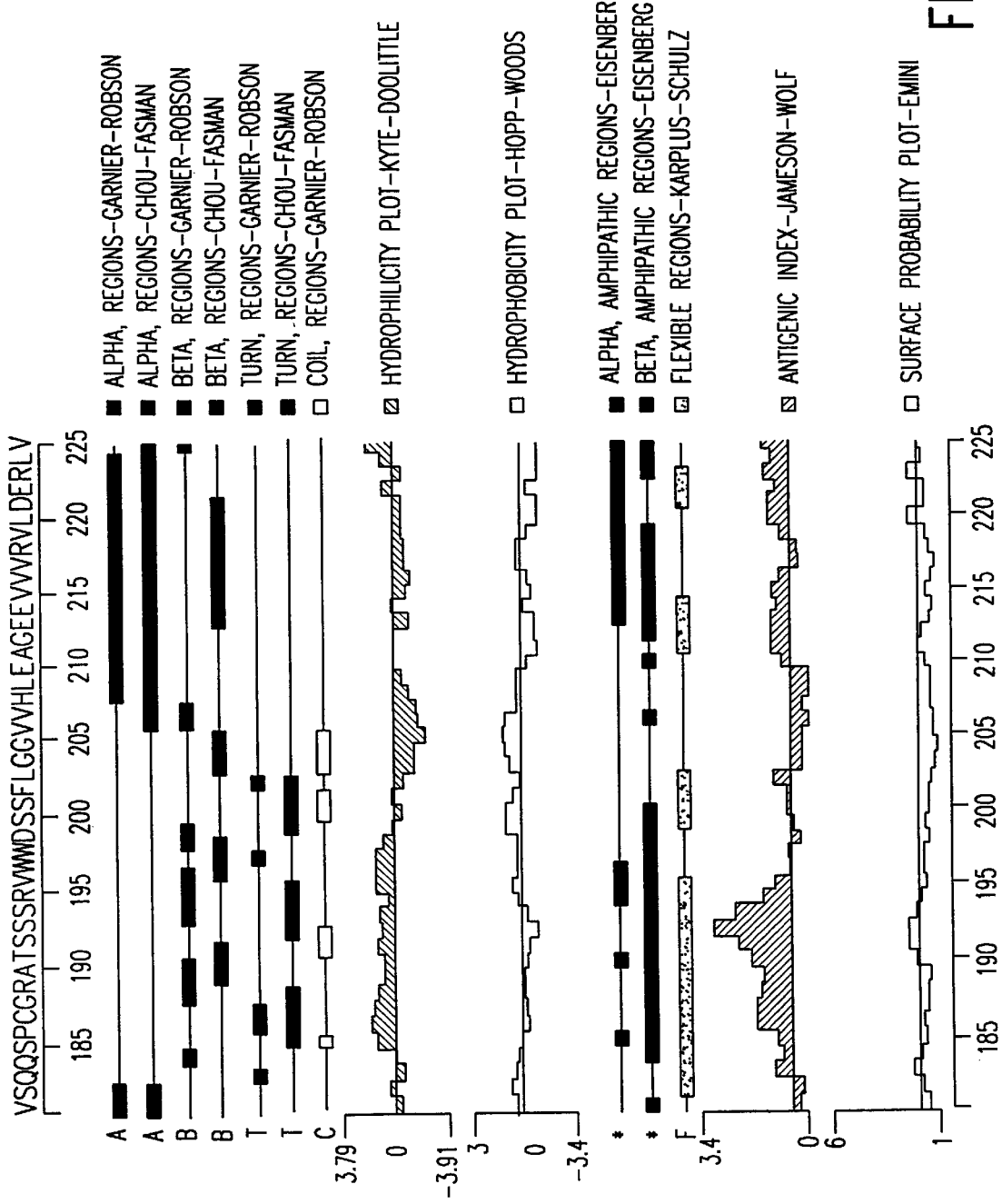
Figure 3F:
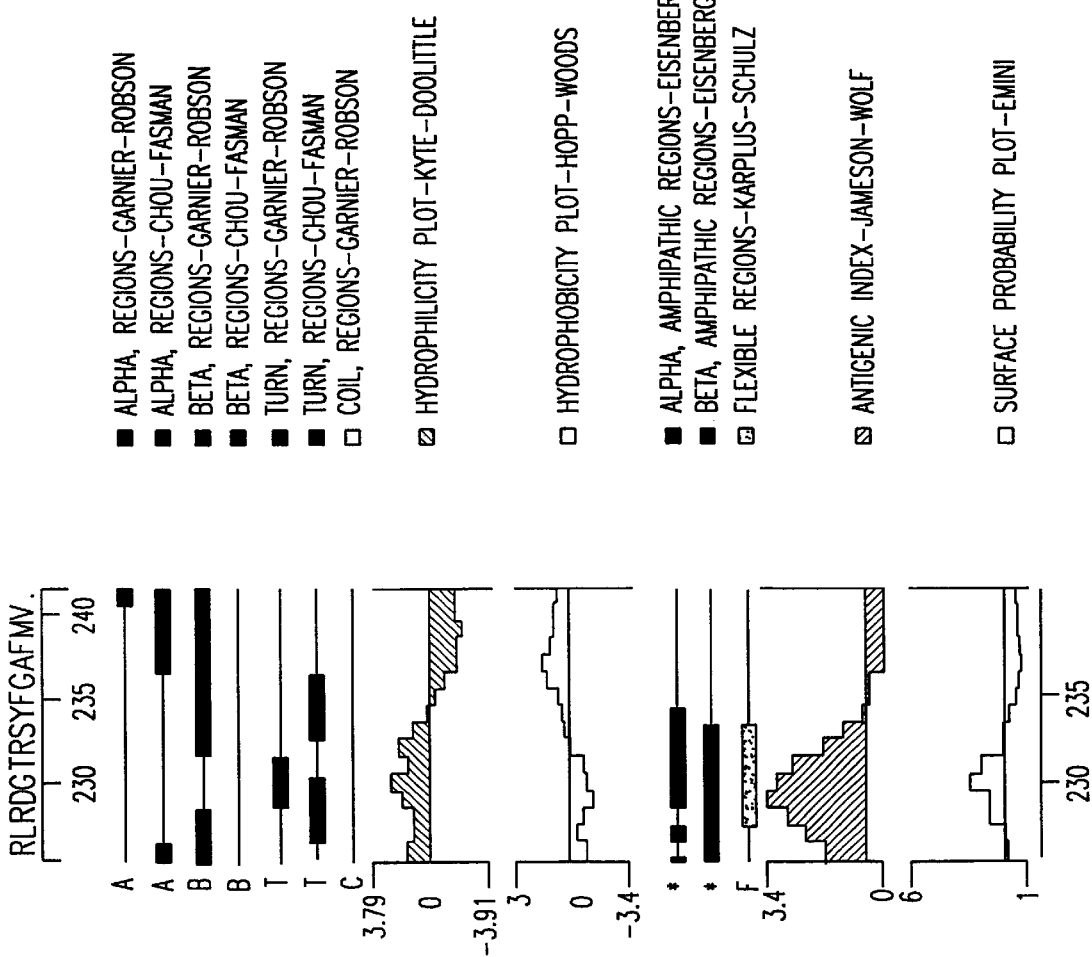
Figure 4A:
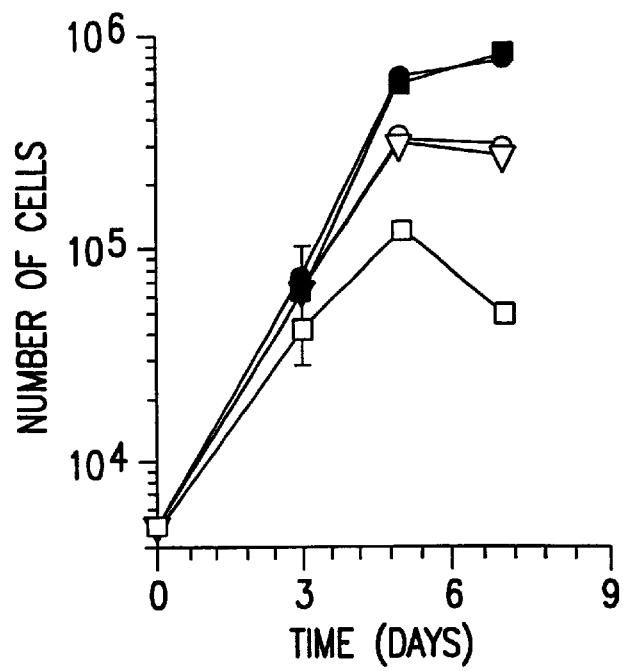
FIGS. 4A and 4B show the effect of AIM II on the in vitro proliferation of MDA-MB-231 human breast cancer cells. 5,000 MDA-MB-231/WT (circle), MDA-MB-231/Neo (triangle) or MDA-MB-231/AIM II (square) cells were plated in triplicate in 24-well plates with IMEM in the presence of either 10% FBS (filled circle, square or triangle) or 1% FBS (open circle, square or triangle). The number of live cells were determined by trypan blue exclusion method at day 3, day 5 or day 7. Cells were fed with fresh medium every two days during this time course.
Figure 4B:
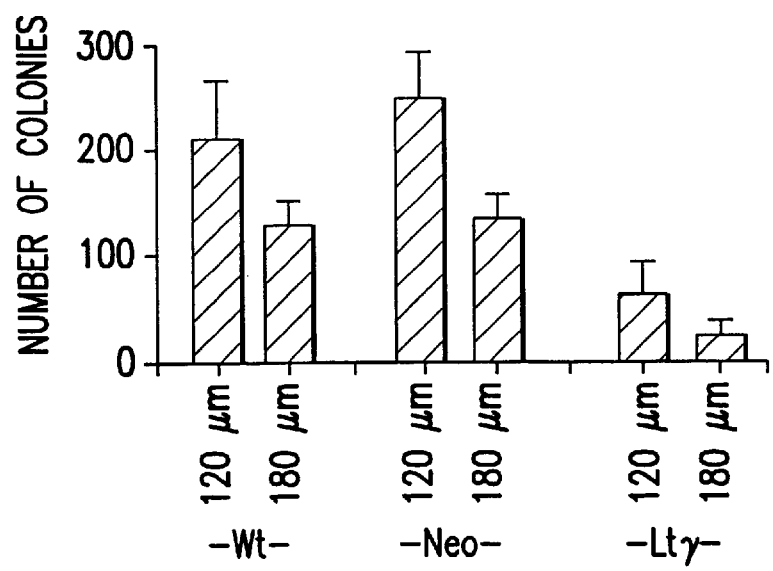

Wild type MDA-MB-231 cells grew to a very high density with typical pile-up features in either 10% or 1% serum (FIG. 4A). Morphological changes were noticed in the MDA-MB-231/AIM II cells, with most cells floating into the medium and keeping a single layer growth pattern throughout the culture. No changes of morphology were found in the vector control MDA-MB-231 cells. Growth inhibition of AIM II expressing MDA-MB-231 cells was further examined with in soft agar colony assay. As shown in FIG. 4B, 80% reduction of colony formation was found in the MDA-MB-231/AIM II cells as compared with that of the parental or vector control cells. Treatment with 25 u/ml of IFNγ can also cause 80% growth inhibition of AIM II expressing MDA-MB-231 cells, whereas in the parental or vector control cells, there is only 20–30% inhibition. Thus, AIM II expressing cells demonstrated enhanced sensitivity towards cytotoxicity mediated by cytokine IFNγ.

C. Enhanced Apoptosis in AIM II Expressing Cells.

Figure 5A:
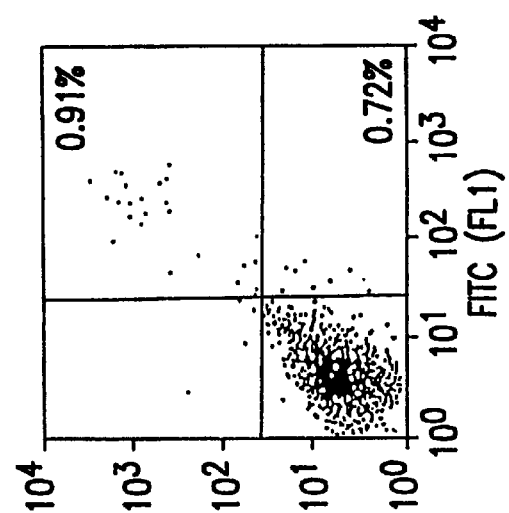
FIGS. 5A–5C show increased apoptotic cells in MDA-MB-231/AIM II (FIG. 5C) in 0.5% serum compared with that of the MDA-MB-231/WT (FIG. 5A) or MDA-MB-231/Neo (FIG. 5B) cells with Annexin-V FACS analysis as described in Example 5 Material and Methods.
Figure 5B:
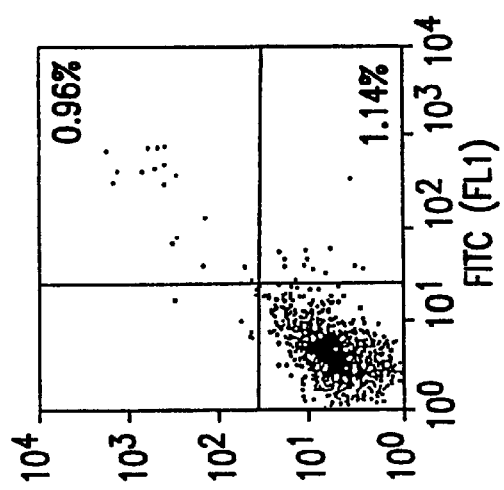
Figure 5C:
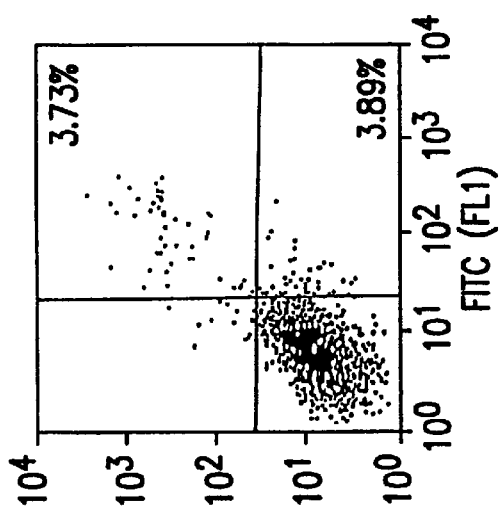

Annexin-V FACS analyses were performed to investigate underlying mechanisms of growth inhibition of AIM II expressing cells. In the presence of 10% serum, there are less than 2% apoptotic cells in all three cell lines. After 48 hours incubation in reduced serum (0.5% FBS), the apoptotic population of the MDA-MB-231 cells showed a three-fold increase, up to 8%. There is little or no increase of apoptosis in the parental or vector control MDA-MB-231 cells (FIGS. 5A–5C). Induction of apoptosis was further confirmed by DNA fragmentation. Fragmented DNA was only seen in the AIM II expressing MDA-MB-231 cells, especially in 1% serum. When AIM II expressing cells were treated with Paclitaxel (taxol), there was much more fragmented DNA observed than seen in parental or vector control cells. Thus, the data suggest that AIM II expression can trigger apoptosis of MDA-MB-231 cells under serum starvation or with the addition of IFNγ or taxol.

D. Potent In Vivo Anti-tumor Activities of AIM II.

Figure 6A:
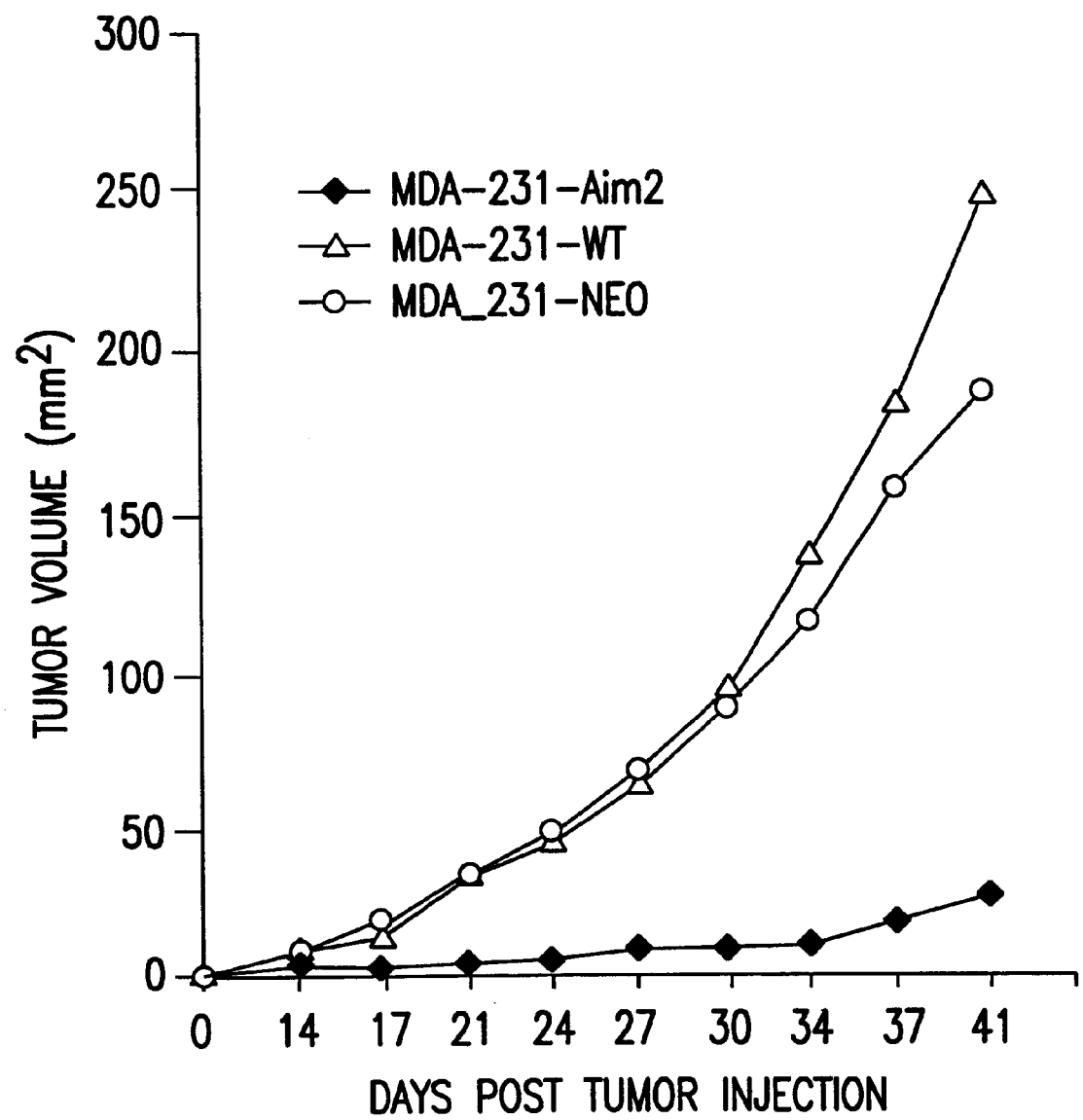
FIG. 6A shows an evaluation of the effects of AIM II on growth of xenograft human breast carcinoma MDA-231 in nude mice. Female athymic nude mice were injected s.c. with $10^6$ cells of parental MDA-231 (MDA-231-WT), or MDA-231 stably transfected with AIM II, or vector control neo (n=10). Mice were then ear tagged and randomized. Tumor growth was assessed twice weekly with a caliper in the blinded fashion. This panel represents three experiments each with ten mice per group.

We have evaluated the effects of AIM II transduction on the tumor growth in vivo. When MDA-MB-231 cells were inoculated into the mammary fat pads, AIM II expression significantly inhibited tumor formation of MDA-MB-231 in nude mice, whereas the vector control MDA-MB-231/Neo cells showed no change in tumor growth as compared with that of the parental MDA-MB-231 cells (FIG. 6A). Similar tumor suppression in the MDA-MB-231/AIM II cells was also demonstrated in SCID mice. A histological examination of the tumors from AIM II expressing MDA-MB-231 cells or those from parental or vector control cells was performed. Parental or vector control MDA-MB-231 cells formed a large solid tumor mass filled with predominantly tumor cells with little or no cellular infiltrates. In contrast, there was extensive necrosis observed even in small residual tumors formed by the MDA-MB-231/AIM II cells in nude mice. Furthermore, in AIM II expressing tumors, there is an significant increase in number of infiltrating neutrophil cells. The average number of neutrophils (mean±S.D.) per mm2 tumor size in wild type, Neo control, and AIM II transduced MDA-MB-231 tumors were 101±26, 77±16 and 226±38, respectively, based on the immunohistological staining using Gr-1 mAb (PharMingen, San Diego, Calif.).

Figure 6B:
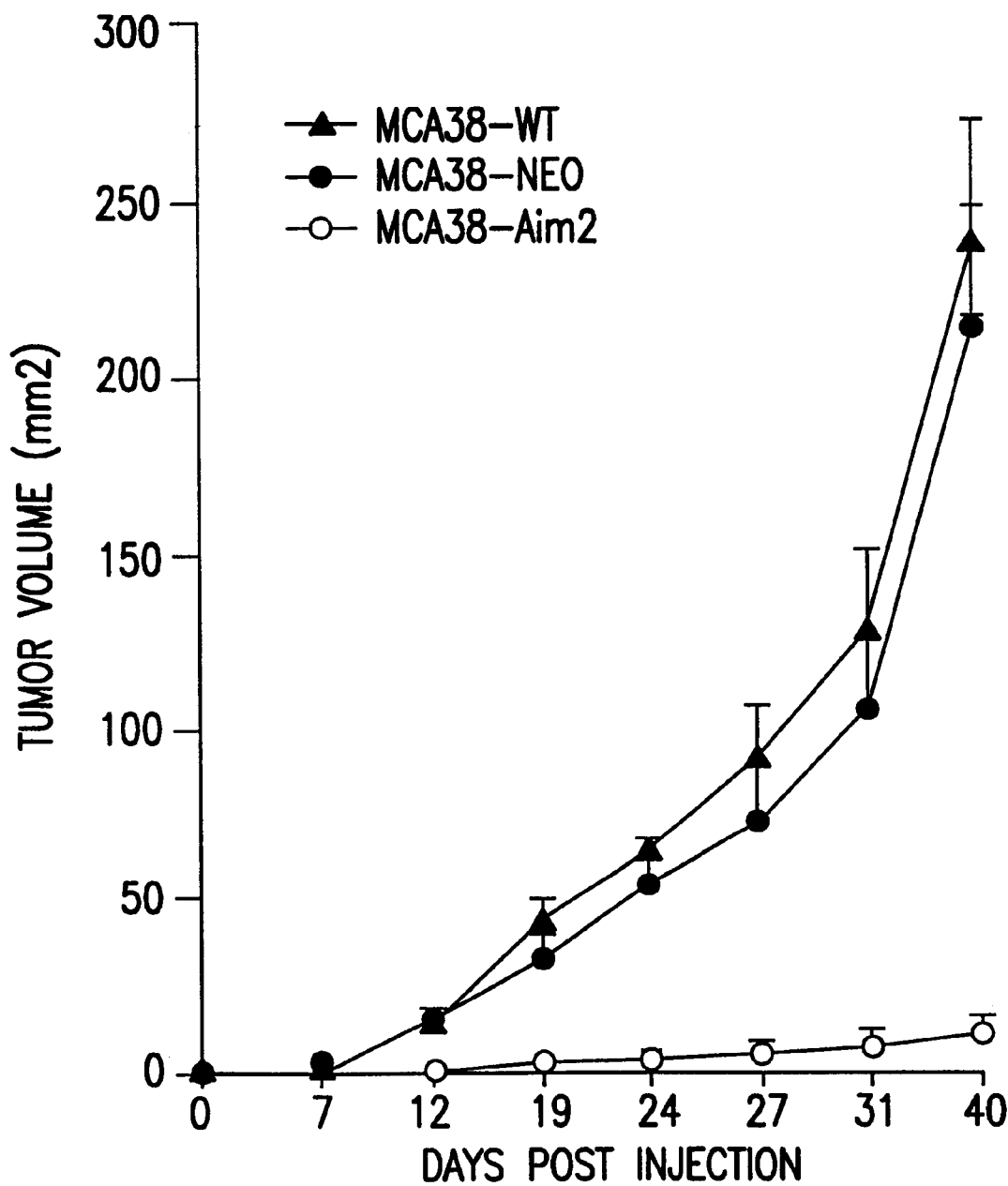
FIG. 6B shows the effect of AIM II transduction on inhibition of growth of MC-38 murine colon cancer in syngeneic C57BL/6 mice. Female C57BL/6 mice were injected s.c. with $10^6$ cells of parental MC-38 (MC-38-WT), or MC-38 stably transfected with AIM II, or vector control neo (n=10). Mice were then ear tagged and randomized. Tumor growth was assessed twice weekly with a caliper in a coded, blinded fashion. This panel represents four experiments each with ten mice per group.

The inhibitory effect of AIM II on tumor suppression was further validated in the syngeneic murine tumor model. Local expression of AIM II in MC-38 murine colon cancer cells resulted in complete suppression of tumor formation in 8 out of 10 C57BL/6 mice (FIG. 6B). Local production of AIM II was also dramatically prolonged the survival of mice bearing MC-38 tumors. All animal experiments were repeated three times and similar results were obtained.

Injection of AIM II-expressing tumor cells did not cause gross abnormalities in the nude mice, SCID mice or C57BL/6 mice, such as weight loss or hepatic injury, during the experimental period. This indicates that locally produced AIM II exerts a potent anti-tumor effect without inducing systemic toxicity.

E. Expression and Cytotoxicity of a Soluble AIM II Protein

Figure 7A:
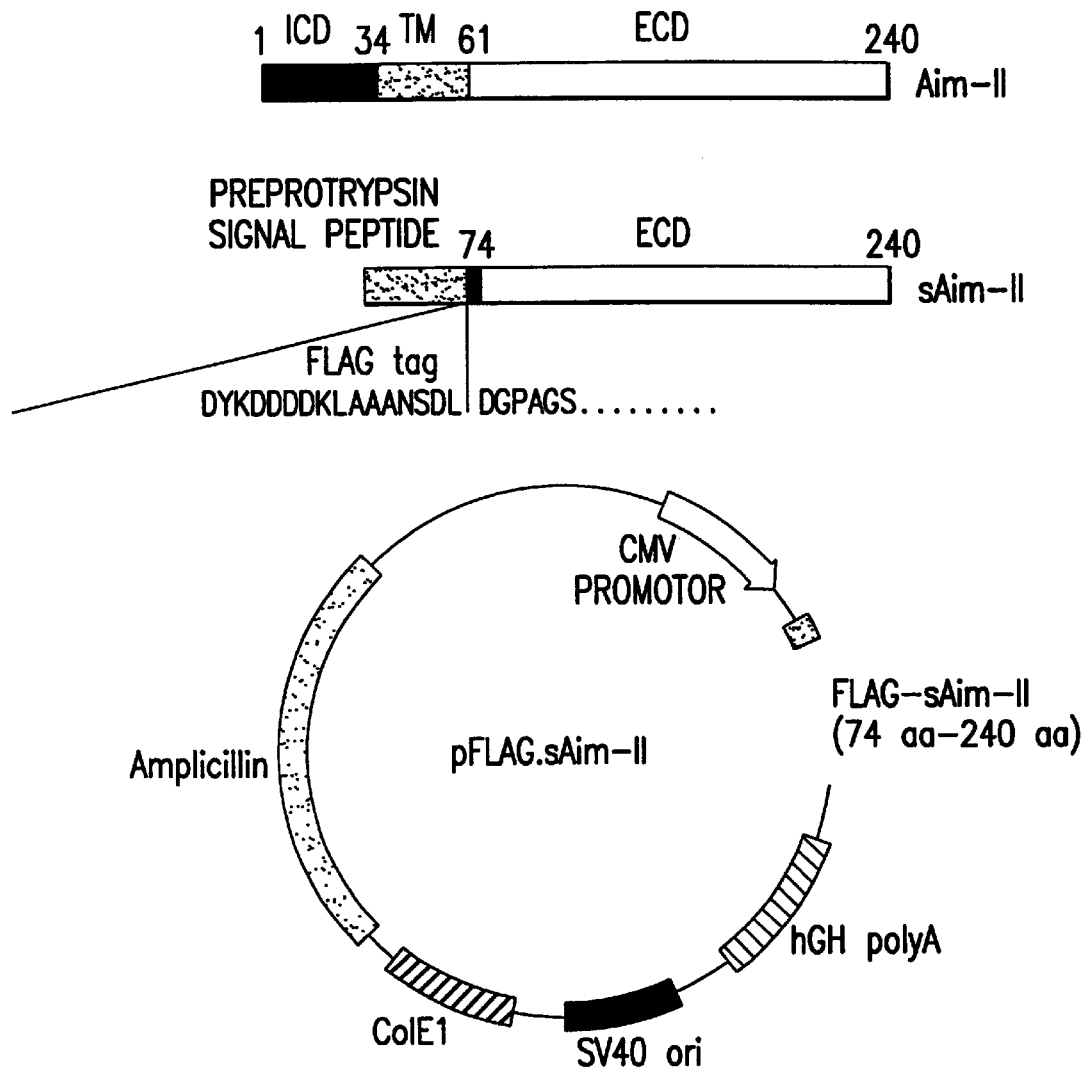
FIG. 7 shows the pFlag-AIM II plasmid construct (FIG. 7A) and cytotoxicity of a recombinant soluble form of AIM II (sAIM II) in MDA-MB-231 cells in the presence or absence of IFNγ (FIG. 7B) or with IFNγ alone (FIG. 7C). Experiments were carried out as described in Example 5 Materials and Methods.
Figure 7B:
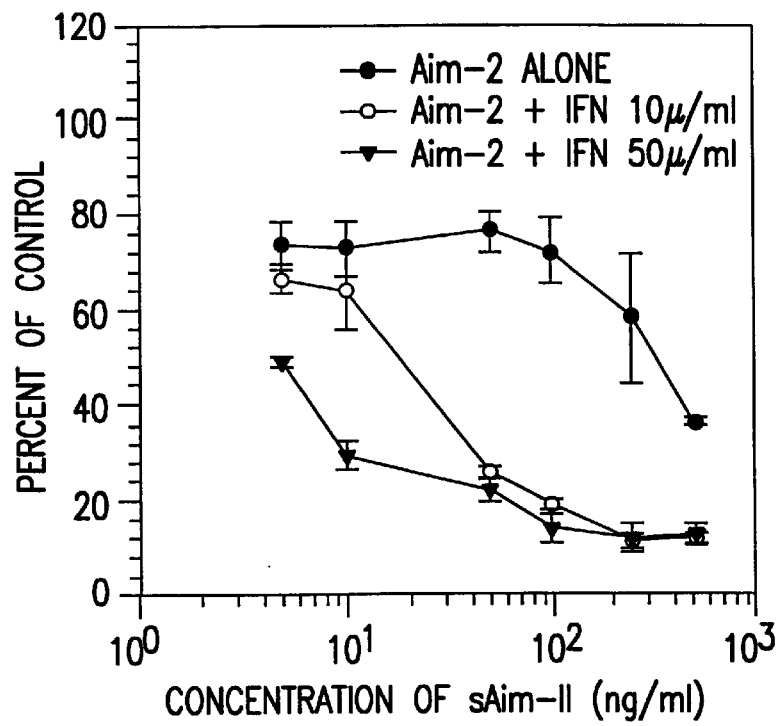
Figure 7C:
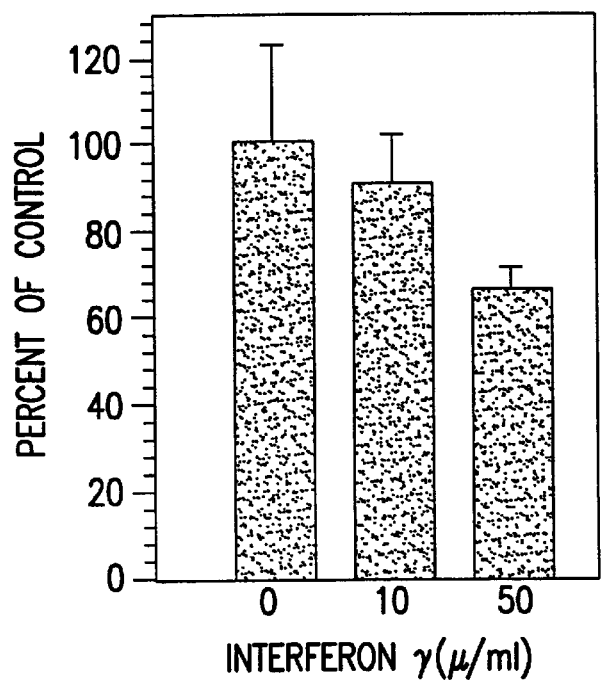

In order to study the activities of the AIM II protein, a recombinant soluble form of AIM II protein (sAIM II) was produced by transient transfecting 293T cells with a construct pFlag-AIM II. This construct encodes the extracellular domain of AIM II, but lacks the transmembrane portion of AIM II (FIG. 7A). A single 20 kDa polypeptide (sAIM II) can be purified from the conditioned medium of pFlag-AIM II transduced 293T cells with anti-Flag monoclonal antibody. The proliferation of breast cancer MDA-MB-231 cells were inhibited in response to the treatment with this soluble AIM II protein, in a dose dependent manner (FIGS. 7B–7C). Addition of IFNγ, at 10 u/ml or 50 u/ml, dramatically enhanced cytotoxicity of the soluble AIM II protein. IFNγ alone showed little activity on the MDA-MB-231 cells (FIGS. 7B–7C). This is consistent with previous report that MDA-MB-231 cells is resistant to single cytokines such as TNF or IFNγ treatment.

A series of normal and cancer cell lines were tested for their sensitivity to the cytotoxic effects of soluble AIM II protein at sub-optimal concentration (50 ng/ml) in the presence of 10 u/ml of INFγ. As shown in FIG. 8L, cells from MDA-130, MCF-7, HT-29 are sensitive to the cytotoxic effects of AIM II, whereas cells from U93T, MC3-1, SW480, MCF-10A are resistant to AIM II-mediated cell killing.

Among all the cell lines tested, colon adenocarcinoma cell line HT-29 is the most sensitive, with $IC_{50}$ less than 1 ng/ml. It has been shown that HT-29 is very sensitive to TNF, Fas or lymphotoxin β receptor mediated killing in the presence of IFNγ.

F. Both LTβR and TR2 are Required for AIM II Induced Growth Inhibition of Cancer Cells.

AIM II was originally identified from an activated T-cell cDNA library but does not induce apoptosis in lymphocyte cell lines. Using the RT-PCR analyses, all lymphopoietic cells examined showed no expression of LTβR, but TR2 expression was found in all these cells, especially in activated Jurkat cells or PBLs. This is consistent with the previous reports that peripheral lymphocytes do not express the LTβR, while TR2 expression is associated with T-cell activation.

Figure 8A:
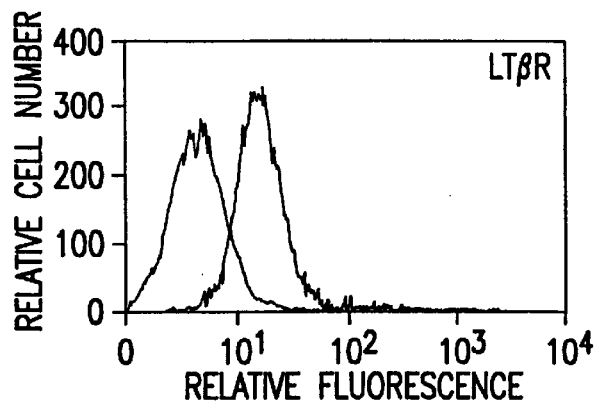
Figure 8B:
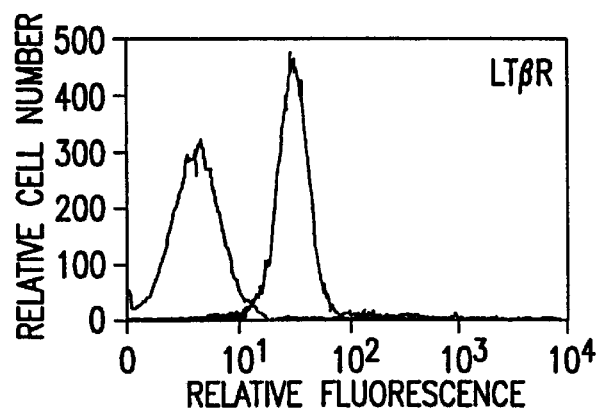
Figure 8C:
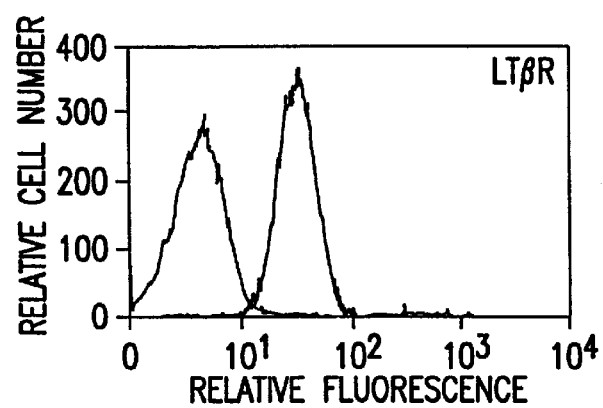
Figure 8D:
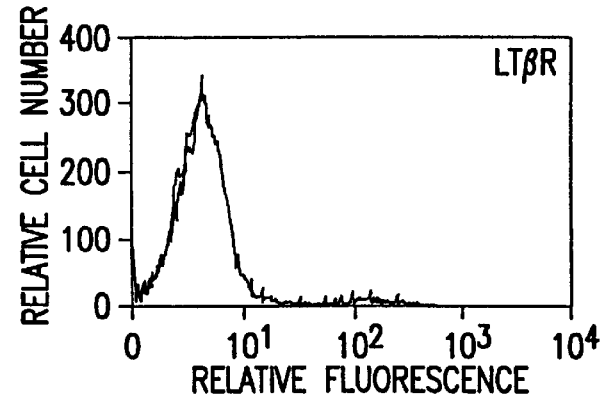
Figure 8E:
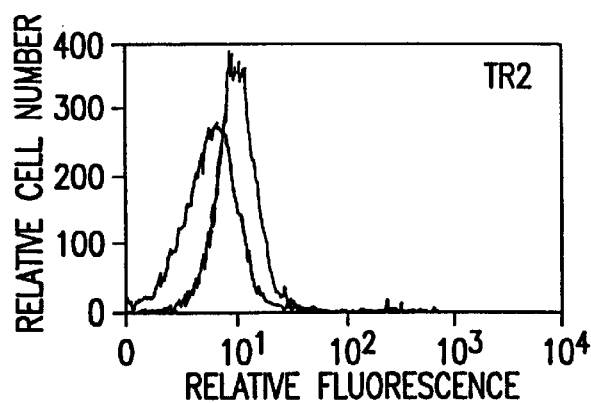
Figure 8F:
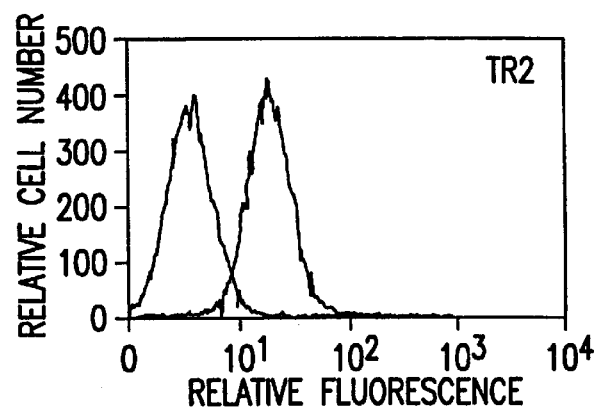
Figure 8G:
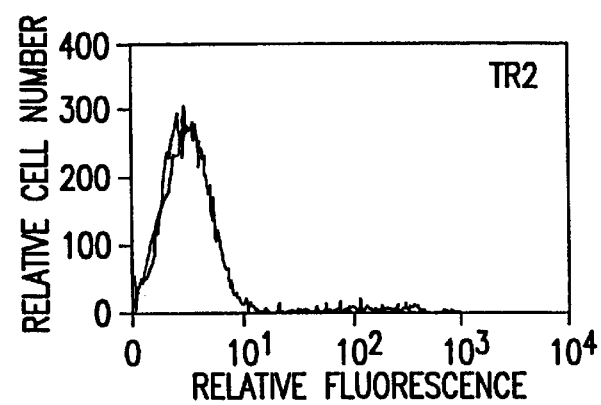
Figure 8H:
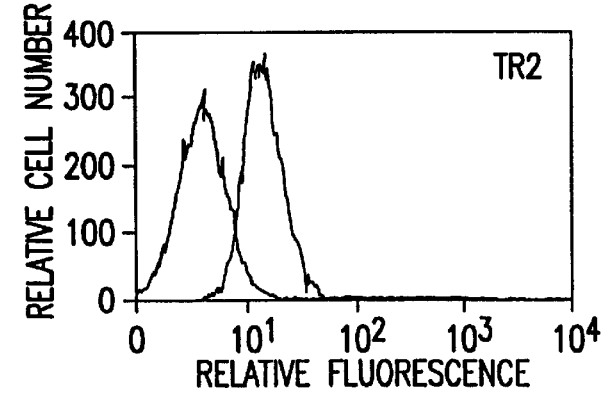

Cell surface expression of the LTβR and TR2 in a series of human cancer cells was examined using monoclonal antibodies against the LTβR or TR2 by FACS analysis. As shown in FIGS. 8A–8H, high levels of both receptors were found on the MDA-MB-231, and HT-29 cells, whereas MC3-1 cells do not express TR2 and Jurkat cells do not express LTβR. FIG. 8L summarizes surface expression of both receptors in all the cell lines examined. Cell lines that express only one of the receptors, such as Jurkat or MC3-1 are resistant to the cytotoxicity of AIM II. Taken together, these data suggest that AIM II-mediated growth inhibition in tumor cells may require both LTβR and TR2 receptors, while cells expressing only one of the receptors is not sufficient to mediate cell killing.

Figure 8I:
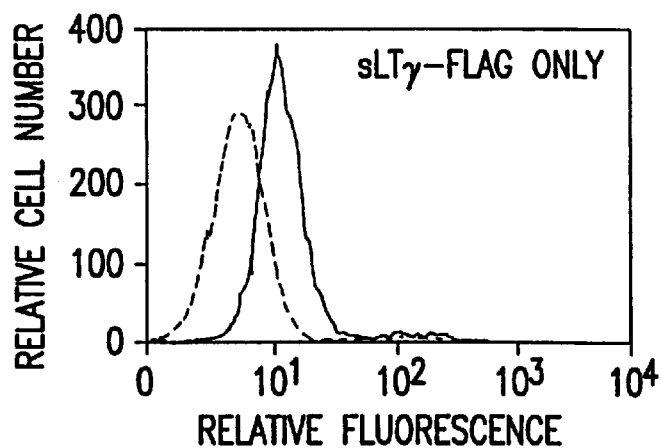
Figure 8J:
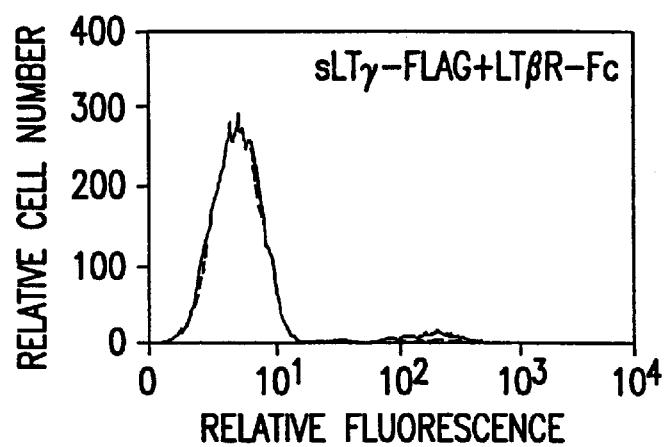
Figure 8K:
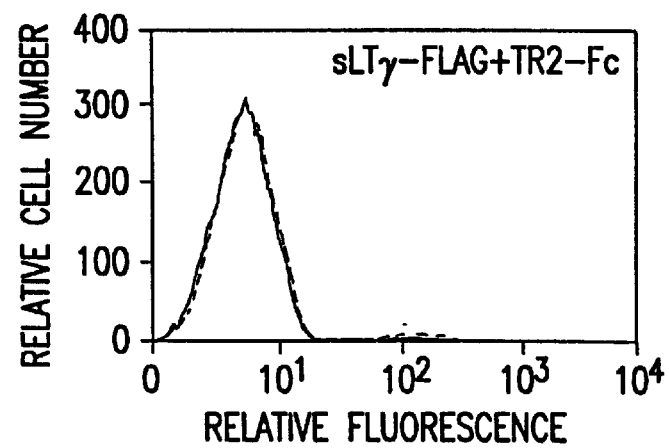

To further demonstrate that the AIM II is a relevant ligand for both LTβR and TR2 receptors and the importance of both receptors in AIM II mediated tumor cell growth inhibition, the Flag-tagged AIM II protein was incubated with MDA-MB-231 or HT-29 cells, then FACS analyses were carried out using anti-Flag mAb. As shown in FIGS. 8I–8K, there is a positive shift in binding of MDA-MB-231 or HT-29 cells with Flag-tagged soluble AIM II protein. The specificity of binding was further confirmed by pre-incubation of LTβR-Fc or TR2-Fc fusion protein with a soluble AIM II-flag protein in the same cells, which effectively blocked binding of both receptors (FIGS. 8I–8K).

Figure 8M:
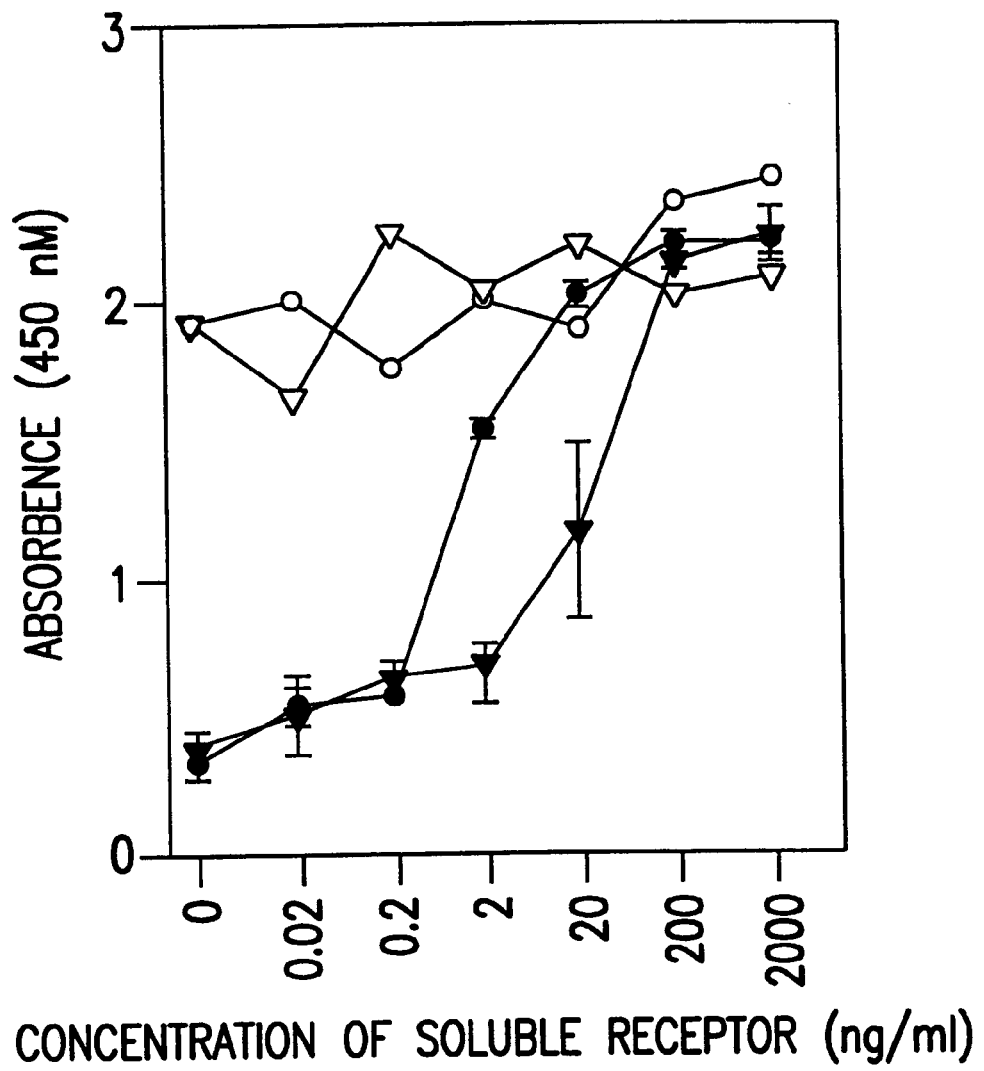

The importance of the involvement of both LTβR and TR2 in the AIM II-mediated cytotoxicity toward tumor cells was further supported by the data obtained from the in vitro growth assays: sAIM II-mediated cytotoxicity of HT-29 was abolished by the addition of LTβR-Fc or TR2-Fc fusion protein in a dose-depended manner whereas the LTβR-Fc or TR2-Fc fusion protein itself showed no effect on cell growth (FIG. 8M). In addition, in a similar assay, sAIM II was unable to bind to other members of TNFR, such as TNFRI, Fas, DR3 or DR14.

In addition, co-culture of MDA-MB-231/Wt or HT-29 cells with MDA-MB-231/AIM II cells resulted in killing of the MDA-MB-231/Wt or wild type HT-29 cells. However, conditioned media collected from the co-cultured MDA-MB-231/AIM II or MC-38/AIM II cells showed no inhibitory effect on the in vitro proliferation of HT-29 cells. The results indicated that the natural AIM II protein may not be cleaved and secreted into the medium. Thus, the membrane-bound AIM II is functional in cells which express appropriate surface receptors such as MDA-MB-231 or HT-29. Taken together, this data suggests that the AIM II-mediated growth inhibition of tumor cells may require both LTβR and TR2 receptors, while cells expressing only one of the receptors is not sufficient to mediate cell killing.

G. Effects of AIM II on the Lymphocytes

AIM II was originally identified from an activated T-cell cDNA library but does not induce apoptosis in lymphocyte cell lines. Using RT-PCR analyses, all lymphopoietic cells examined showed no expression of LTβR, but TR2 was positive in all these cells, especially in activated Jurkat cells or PBLs. This is consistent with previous reports that peripheral lymphocytes do not express the LTβR, while TR2 expression was associated with T-cell activation.

To investigate whether the membrane-bound AIM II exerts different activities on the lymphocytes, co-culture experiments of TIL1200 cells with MDA-MB-231/AIM II cells was carried out. TL1200 is a $CD8^+$ (995) tumor infiltrating lymphocyte line expressing a high level of Fas. The membrane-bound AIM II did not induce apoptosis of TIL1200, whereas the addition of Fas antibody triggered 90% of TIL1200 undergone apoptosis. Similar results were obtained with fresh TIL cells or Jurkat cells.

Figure 9:
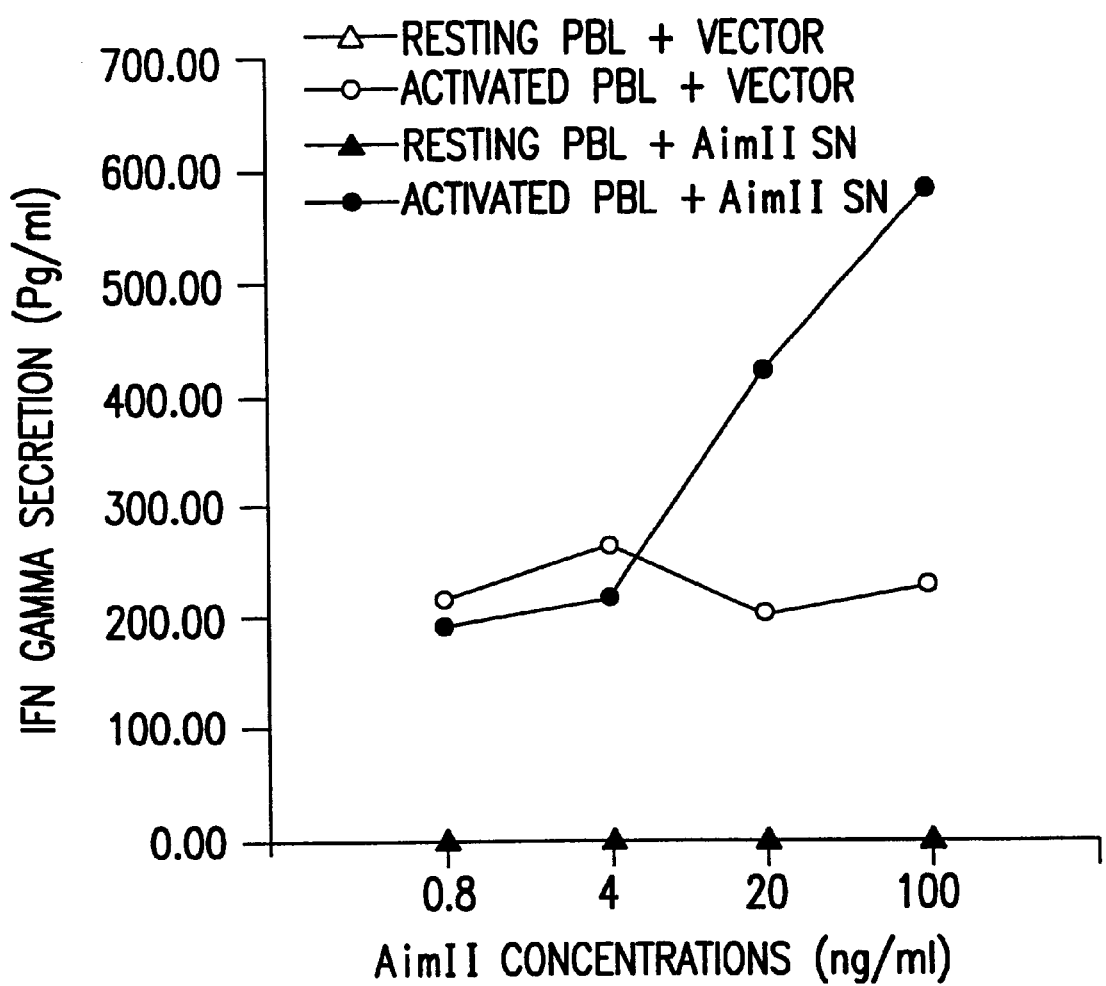
FIG. 9 shows secretion of IFN-γ by sAIM II treated human PBL cells. Human PBLs ($5\times10^5$ cells per well in the 96 well plate) were treated with or without anti-CD3 mAb and IL-2 (20 U/ml) in the presence or absence of sAIM II for 5 days. The supernatants were then collected from the following groups of cells: PBLs in the presence (filled circle) or absence (open circle) of sAIM II, or the resting PBLs with (filled triangle) or without (open triangle) sAIM II. Human IFNγ concentrations were determined by ELISA.

Furthermore, several lymphoid cell lines and PBLs were screened for their responsiveness to the soluble AIM II protein. No cytotoxicity of AIM II was shown in Jurkat cells (either resting or CD3 mAb activated), K562 cells, or TIL1200 (tumor infiltrating lymphocytes), PBMC (fresh or IL-2/CD3 mAb activated) (FIG. 8L). In contrast, treatment of PBLs with sAIM II, resulted in activation of TR2 expressing T cells as demonstrated by release of IFNγ (FIG. 9).

Discussion

In the foregoing experiments, the biological functions of AIM II and its possible mechanisms of action as a novel ligands of LTβR and TR2 have been characterized. The results demonstrate that the AIM II protein exhibits potent cytotoxicity primarily in transformed tumor cells both in vitro and in vivo, while at the same time, activating lymphocytes. The biological activities of AIM II in vitro and in vivo clearly distinguish AIM II from other known members of the TNF/FasL family in several ways including binding to two distinct signaling pathways: LTβR and TR2. Since the ability of AIM II expression to inhibit tumor growth was demonstrated in both xenographic (immunodeficient) and syngeneic (immunocompetent) models, the results suggest that the T-cell mediated tumor specific response may not be an essential factor for the primary tumor rejection in this study.

Activation of the TNF receptors family can directly induce cell proliferation, or differentiation or death. The foregoing experiments show that AIM II expression resulted in growth inhibition and apoptosis in the human breast carcinoma cell line MDA-MB-231 in conjunction with serum starvation, or addition of IFNγ. Induction of apoptosis appears to be the primary cause for the growth inhibition in vitro as shown in Annexin-V FACS analysis and DNA fragmentation. The morphology and growth pattern of MDA-MB-231/LT-γ cells suggest involvement of some loss of cells adhesion. Browning et al. have shown that Fas activation led to rapid cell death (12–24 h), TNF effects requires 24 h and LTcx102 heterotrimers were slowest (2–3 days) in induction of apoptosis for HT-29 cells. Lysis of the LTγR and TR2 expressing MDA-MB-231 and HT-29 cells in response to the treatment with the soluble AIM II protein showed similar slow effect, i.e. at least 3–5 days. Substantial cell lysis does not occur even after 3–4 days for some cell lines. The dynamics of action of AIM II are more similar to LTα1β2 heterotrimers.

AIM II was originally identified from a human activated T cell library by screening of sequence homology with cysteine-rich motif of the TNF/Fas ligand and receptor superfamily. Like other TNF-related ligands, AIM II is a type-II transmembrane protein with C-terminus on the exterior cell surface, a single transmembrane domain, and a short cytoplasmic tail. As predicted, transduction of a full-length cDNA of AIM II gene resulted in cell surface expression of a protein which binds to two receptors as demonstrated in FACS analyses. A soluble AIM II protein is sufficient to bind to both receptors and trigger cytotoxic effects on the target cells. However in the transwell co-culture experiment, where two type of cells shared the culture medium but are physically separated, cytotoxicity from the AIM II expressing MDA-MB-231 cells towards the wild type MDA-MB-231 or HT-29 cells was not observed. In the direct co-culture assay, membrane-bound AIM II effectively mediated killing from close contact. Thus, it seems that natural AIM II protein may not be a secreted protein. Fluorescence in situ hybridization (FISH) localized AIM II gene to human chromosome 16, band p11.2. The AIM II position is in close proximity with Core binding protein, sulfotransferase, syntaxin IB, retinoblastoma-binding protein 6, zinc finger protein 44, cell adhesion regulator and Wilms tumor-3 gene. Genes encoding other known TNF ligands such as TNF, LTα, and LTβ are tightly linked on human chromosome 6 within the major histocompatibility complex (MHC) sandwiched between the class lil and HLA-B locus.

Both LTβR and TR2 lack the death domain. Thus, the demonstration of AIM II binding to both LTβR and TR2 is intriguing. Although LTβR and TR2 could activate common signaling pathways via association with TNFR-associated factors (TRAFs), AIM II-LTβR and AIM II-TR2 interactions may trigger the distinct biological events. As shown in this Example, expression of AIM II leads to the death of cells expressing both LTβR and TR2 while activate lymphocytes which expressing only the TR2 receptor. Signaling through the LTβR activates a TRAF3-dependent pathway. In contrast, AIM II-TR2 interaction probably elicits stimulatory responses of host immune system through TRAFs (TRAF1, TRAF2, TRAF3 and TRAF5). This AIM II dual signaling hypothesis is further supported by the distinct tissue and cell expression patterns of LTβR and TR2. LTβR is prominent in tumor and other epithelial cells, but is absent on the T and B cells. In contrast, TR2 is abundantly expressed in comparable levels in resting and activated T cells, B cells and monocytes and granulocyte. Hence, AIM II probably plays critical roles such as induction of apoptosis and immune activation and, therefore, may have an therapeutic application for cancer.

The LTβR was originally described as a transcribed sequence encoded on human chromosome 12p, a member of the TNFR superfamily. The LTβR is implicated as a critical element in controlling lymph node development and cellular immune reactions. It has been showed that LTβR is expressed in a variety of tissues and cell lines including tumor lines. Unlike other members of the TNFR family, LTβR is not expressed by T nor B lymphocytes. Activation of LTβR by using recombinant LTα1β2 heterotrimers or by cross-linking with immobilized antibodies, induces the death of adenocarcinoma cell lines and production of chemokine IL-8 and RANTES, even though LTβR does not contain the death domain in its cytoplasmic region.

TR2 is expressed in multiple human tissues and shows a constitutive and relatively high expression in hemopoietic lineage cells including resting and activated CD4+ and CD8+ T cells, B cells, monocytes and neutrophils. The TR2 cytoplasmic tail does not contain the death domain seen in the Fas and TNFR-I intracellular domains, and appears to be more related to those of CD40 and 4-1BB. Signals through 4-1BB and CD40 have been shown to be co-stimulatory to T cells and B cells, respectively. A TR2-Fc fusion protein inhibited a mixed lymphocyte reaction-mediated proliferation, in contrast to FasL and TNF, which trigger apoptosis. All the hemopoietic derived cells tested expresses the TR2 receptor but are resistant to AIM II mediated killing observed in the tumor cells. This indicates that TR2 alone does not mediate death signal. However, since all cancer cells examined expressed both LTβR and TR2, it remains to be elucidated whether both AIM II-LTβR and AIM II-TR2 signaling contributes equally for the AIM II mediated cytotoxicity in tumor cells. We also can not exclude the possibility that AIM II interacts with other known or unknown death receptors such as DR3, DR4 and DR5, although soluble AIM II does not bind to DR3, DR4 and DR5 in an in vitro binding assay.

The dose-limiting toxicity of TNF and cytotoxicity of FasL for T-cells limits their clinical application. Treatment with AIM II could be alternatively attractive approach since AIM II trigger the stimulatory signal rather than the death signal to the host immune cells which expressing the TR2 but lacking the LTβR. AIM II has the ability to selectively induce death of tumor cells probably through LTβR and TR2 and at the same time can trigger secretion of IFNγ from lymphocytes apparently through the TR2 signaling pathway. This model thus demonstrates that AIM II is not only an attractive candidate for the future development an anti-cancer agent, but more importantly, it provides an novel system, distinct from the previously defined TNF or Fas system, for the further understanding of the signaling pathway of members of TNF ligand-receptor interactions.

Methods

Molecular Cloning of AIM II Full Length Gene.

A database containing more than one million ESTs (expression sequence tags) obtained from over 500 different cDNA libraries has been generated through the combined efforts of Human Genome Science Inc. and The Institute for Genomic Research using high throughput automated DNA sequence analysis of randomly selected human cDNA clones. Sequence homology comparisons of each EST were performed against the GenBank database using the blastn and blastn algorithms, ESTs having homology to previously identified sequences (probability equal or less than 0.01) were given a tentative name based on the name of the sequence to which it was homologous. A specific homology and motif search using the conserved amino acid sequence, GLYLIYSQVLF (SEQ ID NO:46), of the TNF/Fas ligand family against this human EST database revealed several EST having >50% homology. One clone containing GYYY-IYSKVQL (SEQ ID NO:47) from human activated T cell library was selected. This EST was sequenced on both strands to the 3' end. Its homology was confirmed. The initial clone lacks the 5' portion of the gene in comparison to other members of TNF family. To obtain the full length sequence, a nested PCR reaction was carried out using two gene specific oligonucleotides and two vector-specific primers. An additional 72 nucleotides at the 5' end was obtained. The full length sequence was then cloned into the vector pCM-Vsport 2.0 (Life Technologies Inc., Rockville, Md.).

Northern Blot Analysis.

Human multiple tissue Northern blots (Clontech, MTN blots, #7759-1 and #7760-1) were probed with a $^{32}$P-labelled AIM II full length cDNA according to the vendor's instructions. The blots were hybridized overnight in Hybrisol solution (Oncor), preheated to 42° C. before use, followed by two subsequent washes in 2×SSC/0.1% SDS and 0.2×SSC/0.1% SDS at 42° C. and visualized using a Phospholmager™ (Molecular Dynamics Co.).

In situ Hybridization and FISH Detection.

To determine the precise chromosomal location of the AIM II gene, single-copy gene fluorescence in situ hybridization (FISH) to normal human metaphase chromosome spreads was attempted (Lawrence et al., 1988). A 2 Kb cDNA was nick-translated using Digoxigenin-11-dUTP (Boehringer Mannheim) and FISH was carried out as detailed in Johnson et al., 1991b. Individual chromosomes were counterstained with DAPI and color digital images, containing both DAPI and gene signal detected with Rhodamine, were recorded using a triple-band pass filter set (Chroma Technology, Inc., Brattleburo, Vt.) in combination with a cooled charge coupled-device camera (Photometrics, Inc., Tucson, Ariz.) and variable excitation wave length filters (Johnson et al., 1991a). Images were analyzed using the ISEE software package (Inovision Corp., Durham, N.C.).

Cells and Reagents

The human breast carcinoma MDA-MB-231, subclone 2LMP, obtained from in vivo passage of MDA-MB-231 cells in athymic nude mice, was used in all the experiments. MC-38 is a 1,2-dimethylhydrazine induced murine colon adenocarcinoma which is of H-2b origin. Human T lymphoma line Jurkat and CHO lines were obtained from the American Type Culture Collection (ATCC, Rockville, Md.). A human melanoma antigen gp100 reactive CD8+ T-cell line TIL1200 was kindly provided by Dr. Yutaka Kawakami (National Cancer Institute, Bethesda, Md.). All tumor cell lines were grown and maintained in RPMI 1640 medium containing 10% FCS, except MDA-MB-231, which used Dulbecco's modified Eagle's medium as basal medium. HLA-A2 restricted TIL1200 was grown in Aim-V medium containing 10% human serum and 1000 U of IL-2. The apoptosis inducing anti-Fas Mab CH-11 was obtained from Upstate Biotechnology. Interferon was obtained from Biosource International (CA).

Production of Soluble AIM II.

The sequence encoding amino acids 74–240 of AIM II, i.e., the putative extracellular domain, was subcloned into the vector pFLAG. CMV-1 in frame with sequences encoding the preprotrypsin signal peptide and the FLAG peptide tag. The resulting construct, pFLAG-sAIM II, was transfected into 293T cells to generate recombinant sAIM II. Culture media from cells transfected pFLAG.CMV-1 or pFLAG-sAIM II were passed through anti-FLAG mAb (Eastman Kodak Co.) affinity columns. The column eluents were fractionated by SDS-PAGE and sAIM II was detected by western blot analysis, using the anti-FLAG mAb and ECL detection reagents (Amersham International).

Generation of Recombinant Receptor-Fc Fusion Proteins

A cDNA encoding extracellular domain of human LTβR was amplified from a HepG2 cells by RT-PCR technique. The sequences of oligonucleotide primers are as following: Forward 5' CGGGATCCATGCTCCTGCCTTGGGCCAC 3' (SEQ ID NO:48); and Reverse: 5' GCGGATC-CTGGGGGCAGTGGCTCTAATGG 3' (SEQ ID NO:49) and contained BamHI restriction sites on each end to facilitate the cloning of PCR product into the pSK+ vector (Stratagene). The amplified sequence was subjected to BamHI digestion and ligated to BamHI cut pSK+ vector for sequencing. The fidelity of amplified cDNA fragment was confirmed by dideoxy DNA sequencing. To obtain human LTβR-Fc fusion protein, extracellular domain of LTR was excised from pSK+ vector with BamHI restriction endonuclease and ligated to BglII cut pUC19-IgG1-Fc vector to allow in frame ligation. To generate recombinant baculovirus, fusion gene was firstly excised with HpaI/ HindIII from pUC19-IgG-Fc vector, followed by ligation with SmaI cut pBacPAK9 vector (Clontech Co.) after fill-in, then co-transfected with linearized BacPAK6 DNA (Clontech Co.) into Sf9 cells. To obtain recombinant soluble LTβR fusion protein, five days culture supernatants from recombinant virus infected insect Sf21 cells was filtered and trapped onto protein A Sepharose beads, the bound sLTβR protein was then eluted with glycine buffer (pH 3.0) and followed by dialysis in PBS. Production of TR2-Fc fusion protein has been described.

Generation of LβTR and TR2 Antibodies

Balb/cJ mice (The Jackson Laboratory, Bar Harbor, Me.) were immunized with LTβR-Fc fusion proteins in Freund's adjuvant. Mice were boosted three times then the spleen cells were fused with the murine myeloma NS-1 cells in the presence of 50% polyethylene glycol in HEPES (PEG 1500, Boehringer Mannheim), followed by culture in RPMI1640/HAT and RPMI1640/HT selective media (Boehringer Co.). Supernatant from positive wells were tested for the ability to bind LTβR-Fc fusion protein, but not human IgG1 by ELISA. Hybridomas producing antibodies against LTβR-Fc fusion protein were cloned by limiting dilution three times. To produce large amount of mAbs, $10^7$ hybridoma cells were injected into pristane treated peritoneal cavity of Balb/c mice, and mAbs was subsequently purified from ascites by affinity chromatography. Similarly, using TR2-GST fusion protein, monoclonal antibodies against TR2 were produced and screened by ELISA assay.

In Vitro Growth Assays

Cells (5,000 cells per well) were plated in triplicate in 24-multiwell tissue culture plates with IMEM in the presence of either 10% FBS or 1% FBS. The number of live cells were determined by trypan blue exclusion method at day 3, day 5 or day 7. Cells were refed with fresh medium every two days during this time course.

A soluble tetrazolium/formazan (XTT) assay for cell growth in a 96-well plate was performed. Cells (2,000–4,000 cells/well) were grown in IMEM medium with 10% FBS or 1% FBS. After four to five days culture, XTT (1.0 mg/ml plus PMS at 1.53 mg/ml) was added to each well and incubated for four hours at 37° C. Absorbance at 450 nm was measured with the Dynatech Model MR700.

FACS Analysis

Cells were collected by trypsinization or aspiration, and centrifuged at 1500–2000 rpm for 5 min. The cell pellets were resuspended and washed in 5 ml ice-cold PBS twice. And then, the cells were incubated with Flag-tagged AIM II protein or Abs at 10 μg/ml in the binding buffer (HBSS containing 10% BSA, 20 mM HEPES, pH 7.2, 0.02% NaN₃, and 25 μg/ml normal rat Ig) for 30 min at 4° C. Cells were then washed and stained with phycoerythrin (PE) conjugated to goat anti-mouse IgG at 20 μg/ml as described. To compete for cell surface binding, soluble LTβR-Fc fusion protein, TR2-Fc at 10 μg/ml was preincubated with AIM II for 30 min before adding to cells. Fluorescence was analyzed by a FACscan flow cytometer (Becton Dickinson, Mountain View, Calif.).

For apoptosis assay, cell pellets were resuspended in 1×binding buffer (10 mM HEPES pH 7.4, 0.15 M NaCl, 5 mM KCl, 1 mM MgCl₂, 1.8 mM CaCl₂) containing 1:100 dilution of Annexin V-FITC (Trevigen, Gaithersburg, Md.) and 50 μg/ml of propidium iodide and incubated at 4° C. for 15 min. The fluorescence of Annexin V-FITC and propidium iodide of individual cells were analyzed by flow cytometry (Coulter).

Retroviral Transduction of Tumor Cells

A retroviral vector was used to stably transduce tumor cells with AIM II gene. To construct a plasmid encoding the AIM II, a 1.9 kb NotI/SalI fragment containing the AIM II cDNA was inserted into a parental plasmid pG1SamEN. This retroviral backbone was derived from the Moloney murine leukemiavirus and the AIM II gene was under the transcription control of the long-terminal repeat from the Moline murine leukemia virus. Generation of the retroviral packaging line was described previously (Markowitz et al.). Briefly, 30 µg of pG1SamEN-AIM II DNA were used to transfect a mixture of $2\times10^5$ PA317 amphotropic packaging line and $3\times10^5$ GP+E86 ecotropic packaging line. After 2 week of selection, high-titer G418-resistant PA317 clones were then selected to recreate the packaging line PA-AIM II and used for gene transfer into tumor cells. A control retrovirus producing line PA-neo was also used. These packaging lines were grown for 20 h and the retroviral supernatants were harvested, added to a 75% confluent flask of wild type MDA-MB-231 or MC-38 respectively. Following transduction with a recombinant retrovirus encoding the human AIM II, AIM II expressing MDA-MB-231 or MC-38 cells were selected with the neomycin analogue G418 and designated MDA-MB-231/AIM II or MC-38/AIM II respectively. AIM II expression in these tumor cells was confirmed by Northern blot analyses. All stable transfectants including MDA-MB-231/AIM II, vector control line MDA-MB-231/neo, MC-38/AIM II and the vector control line MC-38/neo were grown and maintained in the presence of G418 at 1.5 mg/ml and 0.375 mg/ml, respectively.

Coculture Assays of Jurkat Cells The MDA-MB-231 cells were plated in 6-well tissue culture plates and allowed to grow to confluence. Following removal of media and washing of the monolayers with 1×PBS, $1\times10^6$ Jurkat cells (nonadherant) were plated in 1 ml of RPMI medium over a monolayer or an empty wells. Wells with MDA-MB-231 cells alone (without overlaying Jurkat cells) were maintained as additional control. After 24 or 48 hours of culture, the nonadherant phase of the mixed culture was collected from the 6-well plated after gentle rocking of the plate and assayed for viability using trypan blue exclusion. For detection of apoptosis, 20,000 cells were measured per sample using Annexin V-FITC FACScan flow cytometer.

Lymphokine Release Assay

The lymphokine release assays were performed to detect human PBL reactivity with AIM II as previously described. (Zhai et al.) Briefly, human PBL cells were incubated for 5 days in the presence of anti-CD3 mAb (0.1 µg/ml) and rIL-220 U/ml plus AIM II protein at various concentrations, the supernatants were collected and the secretion of IFNγ were determined using ELISA kits purchased from R&D Systems (Minneapolis, Minn.).

Tumorigenicity Studies

Female athymic Ncr-nu nude mice, 6 week old, were obtained from the Frederick Cancer Research and Development Center, National Institute of Health (Frederick, Md.) and Charles River Laboratories (Raleigh, N.C.). Female C57BL/6 mice, 6–7 wk old, were purchased from Harlan Sprague Dawley (Indianapolis, Ind.). MDA-MB-231 cells ($1\times10^6$) were injected on day 0 into the mammary fat pad of the female athymic nude mice and similarly, MC-38 cells were injected s.c. into the flank region of C58BL/6 mice. Mice were then ear tagged and randomized. Tumor size was assessed by measuring perpendicular diameters with a caliper twice weekly in a blinded fashion. Each treatment group consisted often animals and experiments were repeated three times. Tumor histological examination was carried out with H/E staining.

Example 6

Detection of AIM II Expression by BIAcore Analysis

CHO cells were transfected with either an AIM II-Flag tag expression vector or an BAP-Flag (negative control). Three days after transfection, AIM II expression was determined using the BIAcore instrument (BIAcore, Inc.) which permits real-time measurements of protein binding events to immobilized AIM II receptor, lymphotoxin-β receptor (BIAcore sensorgram detects binding by changes in refractive index at the surface of the flow cell). A lymphotoxin-β receptor-Fc fusion protein was covalently immobilized to the BIAcore flow cell via amine groups using N-ethyl-N'-(dimethylaminopropyl)carbodiimide/N-hydroxysuccinimide chemistry. Various dilutions of AIM II-Flag and the negative control (BAP-Flag) conditioned serum-free media were applied to the lymphotoxin-β-receptor-derivatized flow cell at 5 µl/min for a total volume of 50 µl. The amount of bound protein was determined after washing the flow cell with HBS buffer (10 mM HEPES, pH 7.4, 150 mM NaCl, 3.4 mM EDTA, 0.005% Surfactant P20). The flow cell surface was regenerated by displacing bound protein by washing with 20 µl of 10 mM HCl.

The specific binding to the lymphotoxin-β-receptor was detected at up to 10-fold dilution of the conditioned media from AIM II-Flag cultures, whereas, no significant binding was observed for the negative control (BAP-Flag) conditioned media. This demonstrates that AIM II-Flag binding is specific to lymphotoxin-β-receptor and not to the Fc portion of the fusion protein. Moreover, specific receptor binding by AIM II-Flag protein indicates that it exhibits a native structure as secreted by the cells. Thus, this BIAcore-based assay can be used to detect expression of AIM II from conditioned media and other biological fluids. Further, by using known amounts of pure AIM II protein this assay can be developed into a quantitative assay for determining AIM II concentrations.

Example 7

Activation-induced Apoptosis Assay

Activation-induced apoptosis is assayed using SupT-13 T leukemia cells and is measured by cell cycle analysis. The assay is performed as follows. SupT-13 cells are maintained in RPMI containing 10% FCS in logarithmic growth (about $1\times10^6$). Sup-T13 cells are seeded in wells of a 24 well plate at $0.5\times10^6$/ml, 1 ml/well. AIM II protein (0.01, 0.1, 1, 10, 100, 1000 ng/ml) or buffer control is added to the wells and the cells are incubated at 37° C. for 24 hours. The wells of another 24 well plate were prepared with or without anti-CD3 antibody by incubating purified BC3 mAb at a concentration of 10 µg/ml in sterile-filtered 0.05M bicarbonate buffer, pH 9.5 or buffer alone in wells at 0.5 ml/well. The plate is incubated at 4° C. overnight. The wells of antibody coated plates are washed 3 times with sterile PBS, at 4° C. The AIM II treated Sup-T13 cells are transferred to the antibody coated wells and incubated for 18 hr., at 37° C. Apoptosis is measured by cell cycle analysis using propidium iodide and flow cytometry. Proliferation of treated cells is measured by taking a total of 300 µl of each treatment well and delivering in to triplicate wells (100 µl/well) of 96 well plates. To each well add 20 µl/well $^3$H thymidine (0.5 µCi/20 µl, 2 Ci/mM) and incubate 18 hours, at 37° C. Harvest and count $^3$H-thymidine uptake by the cells. This measurement is used to confirm an effect on apoptosis if observed by other methods. The positive control for the assay is Anti-CD3 crosslinking alone. In addition, profound and reproducible apoptosis in this line using anti-fas monoclonal antibody (500 ng/ml in soluble form-IgM mAb) has been demonstrated. The negative control for the assay is medium or buffer alone. Also, crosslinking with another anti-CD3 mAB (OKT3) has been shown to have no effect.

If an effect is observed by cell cycle analysis the cells will be further stained for the TUNEL assay for flow cytometry or with Annexin V, techniques well known to those skilled in the art.

Example 8

CD3-induced Proliferation Assay

A CD3-induced proliferation assay is performed on PBMCs and is measured by the uptake of $^3$H-thymidine. The assay is performed as follows. Ninety-six well plates are coated with 100 μl/well of mAb to CD3 (HIT3a, Pharmingen) or isotype-matched control mAb (B33.1) overnight at 4° C. (1 μg/ml in 0.05M bicarbonate buffer, pH 9.5), then washed three times with PBS. PBMC are isolated by F/H gradient centrifugation from human peripheral blood and added to quadruplicate wells (5×10$^4$/well) of mAb coated plates in RPMI containing 10% FCS and P/S in the presence of varying concentrations of AIM II protein (total volume 200 μl). Relevant protein buffer and medium alone are controls. After 48 hr. culture at 37° C., plates are spun for 2 min. at 1000 rpm and 100 μl of supernatant is removed and stored −20° C. for measurement of IL-2 (or other cytokines) if effect on proliferation is observed. Wells are supplemented with 100 μl of medium containing 0.5 μCi of $^3$H-thymidine and cultured at 37° C. for 18–24 hr. Wells are harvested and incorporation of $^3$H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative control for CD3-induced proliferation and medium or buffer are used as negative controls for the effects of AIM II proteins.

Example 9

Effect of AIM II on the Expression of MHC Class II, Costimulatory and Adhesion Molecules and Cell Differentiation of Monocyte Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FcγRII, upregulation of CD83). These changes correlate with increased antigen-presenting capacity and with functional maturation of the dendritic cells.

FACS analysis of surface antigens is performed as follows. Cells are treated 1–3 days with various concentrations of AIM II (0.1, 1, 10, 100, 1000 ng/ml) or LPS as positive control, washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA will be used to measure the IL-12 release as follows. Dendritic cells (10$^6$/ml) are treated with AIM II (0.1, 1, 10, 100, 1000 ng/ml) for 24 hours. LPS (100 ng/ml) is added to the cell culture as positive control. Supernatants from the cell cultures are then collected and analyzed for IL-12 content using commercial ELISA kit. The standard protocols provided with the kits are used.

Effect on the Expression of MHC Class II, Costimulatory and Adhesion Molecules

Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis will be used to examine the surface antigens as follows. Monocytes are treated 1–5 days with various concentrations of AIM II (0.1, 1, 10, 100, 1000 ng/ml) or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on Monocyte Survival

Human peripheral blood monocytes progressively lose viability when cultured in absence of serum or other stimuli. Their death results from internally regulated processes (apoptosis). Addition to the culture of activating factors, such as TNF-α, dramatically improves cell survival and prevents DNA fragmentation.

Propidium iodide staining will be used to measure apoptosis as follows. Monocytes (10$^7$/ml) are cultured in suspension in polypropylene tubes in DMEM for two days in presence or absence of TNF-α (100 ng/ml, positive control) or AIM II (0.1, 1, 10, 100, 1000 ng/ml). Cell viability is assessed by propidium iodide (PI) staining. Cells are suspended at a concentration of 2×10$^6$/ml in PBS containing PI at a final concentration of 5 μg/ml, and then incubated at room temperature for 5 minutes before FACScan analysis. PI uptake has been demonstrated to correlate with DNA fragmentation in this experimental paradigm.

Effect on Cytokine Release

An important function of monocytes/macrophages is their regulatory activity on other cellular populations of the immune system through the release of cytokines after stimulation. An ELISA to measure the IL-1β release is performed as follows. Human monocytes are added at 10$^6$/ml in 48-well plates and various concentrations of AIM II are added (0.1, 1, 10, 100, 1000 ng/ml) in presence or absence of 100 ng/ml LPS. After 24 hour incubation, the supernatants are collected and assayed for the presence of cytokines by ELISA kits. The standard protocols provided with the kits are used.

Example 10

Affinity Purification of Soluble AIM II for N-terminal Sequence Analysis

Previous data indicated that a BIAcore chip derivatized with the lymphotoxin beta receptor (LTβR)-Fc fusion protein was able to specifically bind AIM II (a.a. 74-240)-Flag fusion protein (See Example 5, section E and FIG. 7A). The LTβR BIAcore chip was then used to detect expression of soluble AIM II protein from conditioned media of non-Flag tagged AIM II stable transfectants in order to determine which cell line(s) should be used for further purification for N-terminal sequence analysis.

CHO cells were transfected with an expression construct (pC4 vector) consisting of the extracellular region of AIM II (amino acids 60-240) fused to the ck-beta 8 signal peptide. Clones were selected for high expression by growth in media containing methotrexate. The clones with the highest amount of binding to LTβR BIAcore chip were further amplified. Conditioned media (20 ml) from CHO11, a high level AIM II producing clone, was obtained. A second AIM II construct encoding the complete full length cDNA was transfected into murine MCA-38 carcinoma cells and subject to selection with G418. Conditioned media was obtained from these transfected MCA-38 cells.

Conditioned media from the stable transfectants, CHO11 or MCA-38 cells, were filtered, centrifuged at 10,000×g and then passed over an MCIF-Fc affinity column (control column) followed by the LTβR-Fc affinity column (0.2 mL bed volume). The columns were washed with several bed column volumes HEPES buffered saline containing 0.005% Surfactant P-20. Bound protein was eluted with 10 mM HCl (3×0.5 ml fractions) and immediately neutralized with TRIS buffer. The fractions eluted from the LTβR column retained binding to LTβR BIAcore chip, whereas, fractions eluted from the control MCIF-Fc column were negative for binding. The eluted fractions were dried in Spedvac then resuspended in 20 μl water. An aliquot of the eluted protein was analyzed by reducing SDS-PAGE gels and detected by silver staining. A band of approximately ~25 kDa and ~21 kDa was detected specifically bound to the LTβR column from CHO-11 and MCA-38 cell lines. The remaining eluted material was subject to SDS-PAGE and blotted onto PVDF membrane for N-terminal sequence analysis.

The N-terminus of the AIM II molecule purified from MCA-38 cells started at residue 83 within the predicted extracellular region of the molecule (Table 3). The results of the AIM II from CHO-11 also confirmed that this protein correspond to AIM II protein; the N-terminus contained two sequences starting three residues apart which start within the ck-β8 signal peptide followed by the extracellular region of AIM II starting at residue 60 (Table 3). Thus, the natural processed form of AIM II should correspond to residues 83–240 and have a molecular mass of 17,284 daltons. The apparent electrophoretic mobility of ~21 kDa is consistent with glycosylation as evident by presence of several electrophoretic species. Similarly, the ~25kDa apparent molecular mass of the CHO-11 expressed ck-β8/AIM II fusion protein was larger than that predicted from its sequence (20,361). Again this might also be due to glycosylation of the protein (there is one N-glycosylation site at residue 104 of full length AIM II).

TABLE 3

N-terminus of AIM2 purified from MCA-38 or CHO-11 clone conditioned media.

| N-terminus MCA-38[1] | _____LIQER .... |
| --- | --- |
| N-terminus CHO11[1] (40%) | SQAGS................................ |
| N-terminus CHO-11[1] (40%) | ____GSQLH............................ |
| ck-beta-8-AIM2 sequence | SQAGSQLHWRLGEMVTRLPDGPAGSWEQLIQERN |

[1] = Affinity purified AIM II from MCA-38 or CHO-11 conditioned media.
2 = Amino acid sequence at junction of ck-beta-8 and extracellular region of AIM II.
Double underlined sequence corresponds to ck beta 8 signal sequence (SQA), and in the case of the GS residues sequence introduced during cloning. AIM II sequence starts at the 6th residue, Q.
Values in parenthesis represent percentage of each sequence found in AIM II sample.

Figure 12:
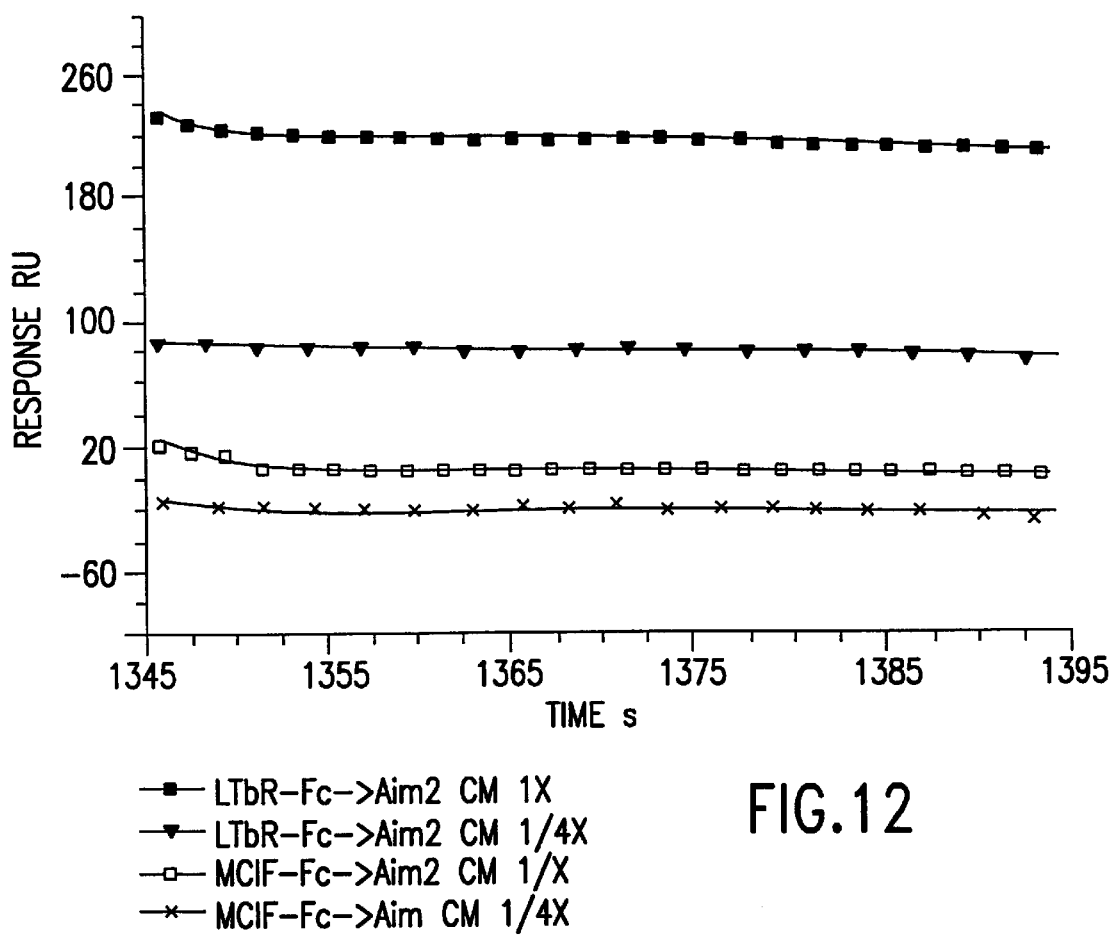
FIG. 12 shows a sensorgram of specificity of binding of MCA-38 AIM II conditioned media to LTβR-Fc versus MCIF-Fc immobilized on BIAcore chip. Conditioned media was analyzed on a BIAcore instrument flowcell derivatized with lymphotoxin beta receptor Fc fusion protein. The conditioned media (100 μl) was flown over the chip at 5 μl/min and washed with HBS buffer also at 5 μl/min. The shown data represents the net bound (off-rate) region of the plot after binding of AIM II to immobilized receptor and is measured in relative mass units (RU) versus time. The binding conditions were performed at high receptor chip densities under diffusion-limited conditions. Legend: LTβR-Fc and MCIF-Fc refer to binding data from LTβR-Fc or MCIF-Fc immobilized BIAcore chip surfaces, respectively.

The Sensorgram of specificity of binding of MCA-38 AIM II conditioned media to LTβR-Fc versus MCIF-Fc immobilized on BIAcore chip is shown in FIG. 12. The conditioned media was analyzed on a BIAcore instrument flowcell derivatized with lymphotoxin beta receptor Fc fusion protein. The conditioned media (100 μl) was flown over the chip at 5 μl/min and washed with HBS buffer also at 5 μl/min. The shown data represents the net bound (off-rate) region of the plot after binding of AIM II to immobilized receptor and is measured in relative mass units (RU) versus time. The binding conditions were performed at high receptor chip densities under diffusion-limited conditions. Legend: LTβR-Fc and MCIF-Fc refer to binding data from LTβR-Fc or MCIF-Fc immobilized BIAcore chip surfaces, respectively.

Figure 13:
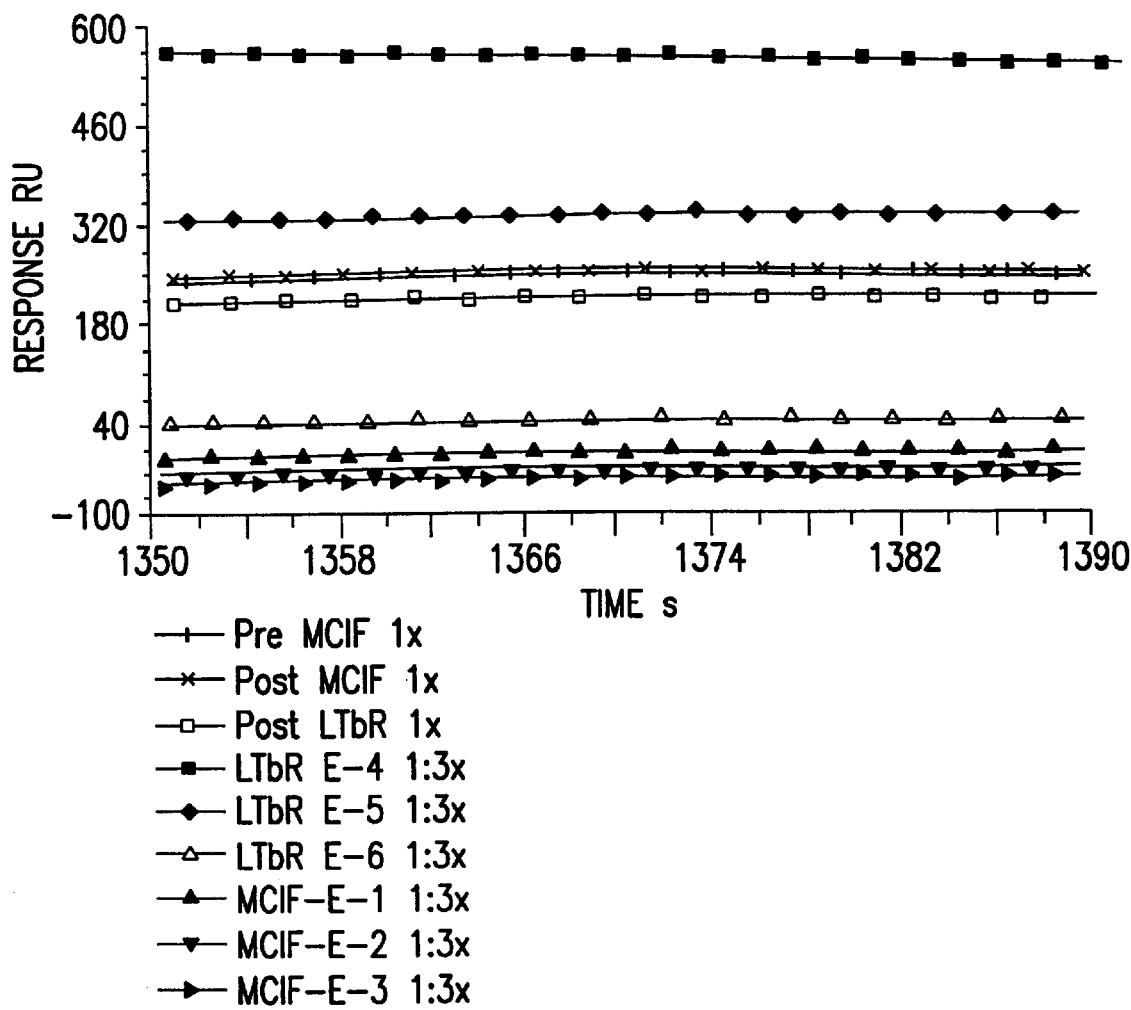
FIG. 13 shows the determination of the LTβR binding by AIM II eluted from LTβR-Fc column. Binding conditions were as described in FIG. 11. Legend: LTβR and MCIF refer to binding data from LTβR-Fc or MCIF-Fc immobilized BIAcore chip surfaces, respectively. Undiluted conditioned media from MCA38 cells was analyzed before (pre) and after passage through MCIF-Fc (post-MCIF) and LTβR-Fc (post-LTβR) affinity columns. Fractions (1 ml) eluted from the LTβR (E4-6) and MCIF-Fc (E1-3) affinity columns were diluted 3-fold and tested for binding to LTβR BIAcore chip.

Determination of the LTβR binding by AIM II eluted from LTβR-Fc column is shown in FIG. 13. LTβR and MCIF refer to binding data from LTβR-Fc or MCIF-Fc immobilized BIAcore chip surfaces, respectively. Undiluted Conditioned media from MCA38 cells was analyzed before (pre) and after passage through MCIF-Fc (post-MCIF) and LTβR-Fc (post-LTβR) affinity columns. Fractions (1 ml) eluted from the LTβR (E4-6) and MCIF-Fc (E1-3) affinity columns were diluted 3-fold and tested for binding to LTβR BIAcore chip.

Example 11

Effect of AIM II in Treating Adjuvant-induced Arthritis in Rats

An analysis of the use of AIM II to treat rheumatoid arthritis (RA) is performed through the use of an adjuvant-induced arthritis (AIA) model in rats. AIA is a well-characterized and reproducible animal model of rheumatoid arthritis which is well-known to one of ordinary skill in the art (Pearson, *Ann. Rheum. Dis.* 15: 379 (1956); Pearson et al., *Arthritis Rheum.* 2: 440 (1959)). AIM II is expected to inhibit the increase in angiogenesis or the increase in endothelial cell proliferation required to sustain the invading pannus in bone and cartilage observed in this animal model of RA. Lewis and BB rats (available from Charles River Lab, Raleigh, N.C. and the University of Massachusetts Medical Center, Worcester, Mass.) are used as the common and responsive strains for adjuvant-induced arthritis in these experiments.

Initiation of the arthritic condition is induced by the intradermal injection of 0.1 ml adjuvant (5 mg/ml) into the base of the tail. Groups of 5 to 6 rats receive either 0.1 to 1.0 mg/kg AIM II or vehicle intra-articularly 20 days after the injection of adjuvant. At this time point acute inflammation reaches a maximal level and chronic pannus formation will have just begun. The effect of AIM II on pannus formation is analyzed radiologically once each week after day 15 following adjuvant challenge essentially as described by Taurog and colleagues (*J. Exp. Med.* 162: 962 (1985)). Briefly, rats are anesthetized with ether or chloral hydrate and positioned so that both hind limbs are X-rayed together. The X-ray films are examined blindly using a scoring system of 0–3 for periosteal reaction, bony erosions, joint space narrowing and destruction. When there is a significant amount of joint damage in vehicle-treated rats, the animals are sacrificed. At this point, the paws are evaluated histologically for the relative degree of tissue damage and for the therapeutic effect AIM II has elicited on these joints.

Finally, AIM II- and vehicle-treated animals undergo a clinical evaluation twice per week to assess hind paw volume using a plethysmometer system and body weight.

Example 12

Effect of AIM II in Treating Collagen-induced Arthritis in Mice

An analysis of the use of AIM II to treat rheumatoid arthritis (RA) may be performed through the use of a collagen-induced autoimmune arthritis (CIA) model in mice. CIA is another well-characterized and reproducible animal model of rheumatoid arthritis which is well-known to one of ordinary skill in the art (Courtenay et al., *Nature* 283: 666 (1980); Wooley et al., *J. Exp. Med.* 154: 688 (1981); Holmdahl et al., *Immunol. Reviews* 118: 193 (1990)). AIM II is expected to induce apoptosis and inhibit the synovial cell proliferation required to form the invading pannus in bone and cartilage observed in both rheumatoid arthritis and this autoimmune animal model of RA.

DBA/1 Lac J mice, available from Jackson Lab (Bar Harbor, Me.) are used as the most universally susceptible strain for collagen-induced arthritis in these experiments.

Initiation of the arthritic condition is induced by the intradermal injection of 0.1 ml of 1 mg/ml of bovine type II collagen in Complete Freund's Adjuvant into the base of the tail. Three weeks later, the animal are injected with 40 µg of LPS to accelerate the development of arthritis. Groups of 10 mice will receive either 0.1–1 mg/kg AIM II or vehicle intradermally or intra-articularly 7–15 days after the injection of LPS. At this time point, acute inflammation is expected to reached a maximal level and chronic pannus formation will have just begun. The effect of AIM II on arthritis is monitored and analyzed clinically using the following score: 0=normal, 0.5=swollen digits, 1=entire paw swollen, 2=deformity and 3=ankylosis. When it is determined that a significant amount of ankylosis has occurred in the paws of vehicle-treated rats, the animals will be sacrificed and the paws are evaluated histologically for the relative degree of pannus formation, cartilage and bone destruction and for what effect AIM II has elicited on these joints.

Example 13

TR6 Suppresses AIM II (LIGHT, HVEM-L)-Mediated Apoptosis

TR6 (DcR3) is a new member of the tumor necrosis factor receptor (TNFR) family. The following study shows that AIM II is a ligand for TR6.
Background The members of the tumor necrosis factor (TNF) family are involved in regulating diverse biological activities such as regulation of cell proliferation, differentiation, cell survival, cell death, cytokine production, lymphocyte co-stimulation, immunoglobulin secretion, and isotype switching (Armitage, R., *Curr. Opin. Immunol.* 6:407–413 (1994); Tewari, M. and Dixit, V. M., *Curr. Opin. Genet. Dev.* 6:39–44 (1996)). Receptors in this family share a common structural motif in their extracellular domains consisting of multiple cysteine-rich repeats of approximately 30 to 40 amino acids (Gruss, H.-J. and Dower, S. K., *Blood* 85:3378–3404(1995)). While TNFR1, CD95/Fas/APO-1, DR3/TRAMP/APO-3, DR4/TRAIL-R1/APO-2, DR5/TRAIL-R2, and DR6 receptors contain a conserved intracellular motif of 30–40 amino acids called death domain, associated with the activation of apoptotic signaling pathways, other members which contain a low sequence identity in the intracellular domains, stimulate the transcription factors NF-κB and AP-1 (Armitage, R., *Curr. Opin. Immunol.* 6:407–413 (1994); Tewari, M. and Dixit, V. M., *Curr. Opin. Genet. Dev.* 6:39–44 (1996); Gruss, H.-J. and Dower, S. K., *Blood* 85:3378–3404 (1995)).

Most TNF receptors contain functional cytoplasmic domain and they include TNFR1 (Loetscher, H., et al., *Cell* 61:351–356 (1990); Schall, T.J., et al., *Cell* 61:361–370 (1990)), TNFR2 (Smith, C. A., et al., *Science* 248:1019–1023 (1990)), lymphotoxin β receptor (LTβR) (Baens, M., et al., *Genomics* 16:214–218 (1993)), 4-1BB (Kwon, B. S. and Weissman, S. M., *Proc. Natl. Acad. Sci. U.S.A.* 86:1963–1967 (1989)), HVEM/TR2/ATAR (Kwon, B. S., et al., *J. Biol. Chem.* 272:14272–14276 (1997); Montgomery, R. I., et al., *Cell* 87:427–436 (1996); Hsu, H., et al., *J. Biol. Chem.* 272:13471–13474 (1997)), NGFR (Johnson, D., et al., *Cell* 47:545–554 (1986)), CD27 (Van Lier, R. A., et al., *J. Immunol.* 139:1589–1596 (1987)), CD30 (Durkorp, H., et al., *Cell* 68:421–427 (1992)), CD40 (Banchereau, J., et al., *Cell* 68:421–427 (1994)), OX40 (Mallett, S., et al., *EMBO. J.* 9:1063–1068 (1990)), Fas (Itoh, N., et al., *Cell* 66:233–243 (1991)), DR3/TRAMP (Chinnaiyan, A. M., et al., *Science* 274:990–992 (1996)), DR4/TRAIL-R1 (Chinnaiyan, A. M., et al., *Science* 274:990–992 (1996)), DR5/TRAIL-R2 (Pan, G., et al., *Science* 277:815–818 (1997)), and RANK (Anderson, D. M., et al., *Nature* 390:175–179 (1997)). Some members of the TNFR superfamily do not have cytoplasmic domains and are secreted, such as osteoprotegerin (OPG) (Simmonet, W. S., et al., *Cell* 89:309–319 (1997)), or linked to the membrane through a glycophospholipid tail, such as TRID/DcR1/TRAIL-R3 (Degli-Esposti, M. A., et al., *J. Exp. Med.* 186:1165–1170 (1997); Sheridan, J. P., e al., *Science* 277:818–821 (1997)). Viral open reading frames encoding soluble TNFRs have also been identified, such as SFV-T2 (Smith, C. A., et al., *Science* 248:1019–1023 (1990)), Va53 (Howad, S. T., e al., *Virology* 180:633–647 (1991)), G4RG (Hu, F. Q., et al., *Virology* 204:343–356 (1994)), and crmB (Gruss, H.-J. & Dower, S. K., *Blood* 85:3378–3404 (1995)).

By searching an expressed sequence tag (EST) database, a new member of the TNFR superfamily was identified, named TR6, and was characterized as a soluble cognate ligand for AIM II (also referred to as LIGHT) and FasL/CD95L.

AIM II (LIGHT) and FasL mediate the apoptosis, which is the most common physiological form of cell death and occurs during embryonic development, tissue remodeling, immune regulation and tumor regression.

AIM II (LIGHT) is highly induced in activated T lymphocytes and macrophages. AIM II (LIGHT) was characterized as a cellular ligand for HVEM/TR2 and LTβR (Mauri, D. N., et al., *Immunity* 8:21–30 (1998)). HVEM/

TR2 is a receptor for herpes simplex virus type 1 (HSV-1) entry into human T lymphoblasts. Soluble forms of HVEM/TR2-Fc and antibodies to HVEM/TR2 were shown to inhibit a mixed lymphocyte reaction, suggesting a role for this receptor or its ligand in T lymphocyte proliferation (Kwon, B. S., et al., *J. Biol. Chem.* 272:14272–14276 (1997); Mauri, D. N., et al., *Immunity* 8:21–30 (1998); Harrop, J. A., et al., *J. Immunol.* 161:1786–1794 (1998)). The level of LTβR expression is prominent on epithelial cells but is absent in T and B lymphocytes. Signaling via LTβR triggers cell death in some adenocarcinomas (Browning, J. L., et al., *J. Exp. Med.* 183:867–878 (1996)). AIM II (LIGHT) produced by activated lymphocytes could evoke immune modulation from hematopoietic cells expressing only HVEM/TR2, and induce apoptosis of tumor cells, which express both LTβR and HVEM/TR2 receptors (Zhai, Y., et al., *J. Clin. Invest.* 102:1142–1151 (1998); Harrop, J. A., et al., *J. Biol. Chem.* 273:27548–27556 (1998)).

FasL is one of the major effectors of cytotoxic T lymphocytes and natural killer cells. It is also involved in the establishment of peripheral tolerance, in the activation-induced cell death of lymphocytes. Moreover, expression of FasL in nonlymphoid and tumor cells contributes to the maintenance of immune privilege of tissues by preventing the infiltration of Fas-sensitive lymphocytes (Nagata, S., *Cell* 88:355–365 (1997)). FasL is also processed and shed from the surface of human cell (Schneider, P., et al., *J. Exp. Med.* 187:1205–1213 (1998)).

The following experiments demonstrate that TR6 (DcR3), a new member of the TNFR superfamily binds AIM II (LIGHT) and FasL. Therefore, TR6 (DcR3) is expected to act as an inhibitor in AIM II (LIGHT)-induced tumor cell death by blocking AIM II (LIGHT) interaction with its receptors.

Identification and Cloning of New Members of the TNFR Superfamily

An EST cDNA database, obtained from more than 600 different cDNA libraries, was screened for sequence homology with the cysteine-rich motif of the TNFR superfamily, using the BLASTN and TBLASTN algorithms. Three EST clones containing an identical open reading frame whose amino acid sequence showed significant homology to TNFR-II were identified from cDNA libraries of human normal prostate and pancreas tumor. A full-length TR6 cDNA clone encoding an intact N-terminal signal peptide was obtained from a human normal prostate library.

RT-PCR Analysis

For RT-PCR analysis, total RNA was isolated using Trizol (GIBCO) from various human cell lines before and after stimulation with PMA/Ionomycin or LPS. RNA was converted to cDNA by reverse transcription and amplified for 35 cycles by PCR. Primers used for amplification of the TR6 fragment are according to the sequence of TR6. β-actin was used as an internal control for RNA integrity. PCR products were run on 2% agarose gel, stained with ethidium bromide and visualized by UV illumination.

Recombinant Protein Production and Purification

The recombinant TR6 protein was produced with hexa-histidine at the C-terminus. TR6-(His) encoding the entire TR6 protein was amplified by PCR. For correctly oriented cloning, a HindIII site on the 5' end of the forward primer (5'-AGACCCAAGCTTC CTGCTCCA GCAAGGACCATG-3') (SEQ ID NO:60) and a BamHI site on the 5' end of the reverse primer (5'-AGACG GGATCCTTAGTGGTGGTGGTGGTGGTGCACAGGG AGGAAGCGCTC-3') (SEQ ID NO:61) were created. The amplified fragment was cut with HindIII/BamHI and cloned into mammalian expression vector, pCEP4 (Invitrogen). The TR6-(His)/pCEP4 plasmid was stably transfected into HEK 293 EBNA cells to generate recombinant TR6-(His). Serum free culture media from cells transfected TR6-(His)/pCEP4 were passed through Ni-column (Novagen). The column eluents were fractionated by SDS-PAGE and TR6-(His) was detected by western blot analysis using the anti-poly(His)$_6$ antibody (Sigma).

Production of HVEM/TR2-Fc, LTβR-Fc and Flag-tagged soluble AIM II (sAIM II, sLIGHT) fusion proteins were previously described (Zhai, Y., et al., *J. Clin. Invest.* 102:1142–1151 (1998)). Fc fusion protein-containing supernatants were filtered and trapped onto protein-G Sepharose beads. Flag-tagged sAIM II (sLIGHT) proteins were purified with anti-Flag mAb affinity column.

Immunoprecipitation

TR6-(His) was incubated overnight with various Flag-tagged ligands of TNF superfamily and anti-Flag agarose in binding buffer (150 mM NaCl, 0.1% NP-40, 0.25% gelatin, 50 mM HEPES, pH 7.4) at 4° C., and then precipitated. The bound proteins were resolved by 12.5% SDS-PAGE and detected by western blot with HRP-conjugated anti-poly (His)$_6$ or anti-human IgG1 antibodies.

Cell-binding Assay

For cell-binding assays, HEK 293 EBNA cells were stably transfected using calcium phosphate method with pCEP4/full sequence of AIM II (LIGHT) cDNA or pCEP4 vector alone. After selection with Hygromycin B, cells were harvested with 1 mM EDTA in PBS and incubated with TR6-(His), HVEM/TR2-Fc, or LTβR-Fc for 20 minutes on ice. For detecting Fc-fusion protein, cells were stained with FITC-conjugated goat anti-human IgG. To detect TR6 binding, cells were stained with anti-poly(His)$_6$ and FITC conjugated goat anti-mouse IgG consecutively. The cells were analyzed by FACScan (Becton Dickinson).

Cytotoxicity Assay

Cytotoxicity assays using HT29 cells were carried out as described previously (Browning, J. L., et al., *J. Exp. Med.* 183:867–878 (1996)). Briefly, 5000 HT29 cells were seeded in 96-well plates with 1% FBS, DMEM and treated with sAIM II (sLIGHT) (10 ng/ml) and 10 units/ml human recombinant interferon-γ (IFN-γ). Serial dilutions of TR6-(His) were added in quadruplicate to microtiter wells. Cells treated with IFN-γ and sAIM II (sLIGHT) were incubated with various amounts of TR6-(His) for 4 days before the addition of [$^3$H]thymidine for the last 6 h of culture. Cells were harvested, and thymidine incorporation was determined using a liquid scintillation counter.

Results and Discussion

TR6 is a New Member of the TNFR Superfamily

TR6 was identified by searching an EST database. Three clones containing an identical open reading frame were identified from cDNA libraries of human normal prostate and pancreas tumor. A full-length TR6 cDNA encoding an intact N-terminal signal peptide was obtained from a human normal prostate library. The open reading frame of TR6 encodes 300 amino acids. To determine the N-terminal amino acid sequence of mature TR6, hexa-histidine tagged TR6 was expressed in mammalian cell expression system and the N-terminal amino acid sequence were determined by peptide sequencing. The N-terminal sequence of the processed mature TR6-(His) started from amino acid 30, indicating that the first 29 amino acids constituted the signal sequence (FIG. 14A). Therefore, the mature protein of TR6 was composed of 271 amino acids with no transmembrane region. There was one potential N-linked glycosylation site (Asn173) in TR6. Like OPG (Simmonet, W. S., et al., *Cell*

89:309–319 (1997)), the predicted protein was a soluble, secreted protein and the recombinant TR6 expressed in mammalian cells was ~40 kD as estimated on polyacrylamide gel. FIG. 14B shows the potential cysteine-rich motif-aligned among TNFR-I, TNFR-II, 4-1BB, TR2HVEM, LTβR, TR1/OPG and TR6. TR6 contained two perfect and two imperfect cysteine-rich motifs and its amino acid sequence was remarkably similar to TR1/OPG amino acid sequence. TR6 shares ~30% sequence homology with OPG and TNFR-II.

mRNA Expression

Expression of TR6 mRNA in human multiple tissues was analyzed by Northern blot hybridization. Northern blot analyses indicated that TR6 mRNA is ~1.3 kb in length and is expressed predominantly in lung tissue and colorectal adenocarcinoma cell line SW480. RT-PCR analyses were performed to determine the expression patterns of TR6 in various cell lines. TR6 transcript was detected weakly in most hemopoietic cell lines and the expression was induced upon activation signal in stimulated Jurkat T leukemia cells. Interestingly, TR6 mRNA was constitutively expressed in endothelial cell line, HUVEC at high level.

Identification of the Ligand for TR6

To identify the ligand for TR6, several Flag-tagged soluble proteins of TNF ligand family members were screened for binding to recombinant TR6-(His) protein by immuno-precipitation. TR6-(His) selectively bound AIM II (LIGHT)-Flag and FasL-Flag among Flag-tagged soluble TNF ligand members tested (i.e., TRANCE, TL-3, TL-6, TL-7, 4-1BBL, AIM II and FasL). This result indicates that TR6 binds at least two ligands, AIM II (LIGHT) and FasL. AIM II (LIGHT) exhibits significant sequence homology with the C-terminal receptor-binding domain of FasL (31%) but sAIM II (sLIGHT) is unable to bind to Fas (Mauri, D. N., et al., *Immunity* 8:21–30 (1998); Zhai, Y., et al., *J. Clin. Invest.* 102:1142–1151 (1998)). They may have a similar binding epitope for TR6 binding.

Previously, Zhai and Harrop (Zhai, Y., et al., *J. Clin. Invest.* 102:1142–1151 (1998); Harrop, J. A., et al., *J. Biol. Chem.* 273:27548–27556 (1998)) reported the biological functions of AIM II (LIGHT) and its possible mechanisms of action as a ligand for HVEM/TR2 and/or LTβR. AIM II (LIGHT) is expressed in activated T cells. AIM II (LIGHT), in conjunction with serum starvation or addition of IFN-γ, inhibits the cell proliferation in tumor cells, MDA-MB-231 and HT29.

To determine whether TR6 might act as an inhibitor to AIM II (LIGHT) interactions with HVEM/TR2 or LTβR, TR6-(His) was used as a competitive inhibitor in AIM II (LIGHT)-HVEM/TR2 interaction. When AIM II (LIGHT) was immunoprecipitated with HVEM/TR2-Fc in the presence of TR6-(His), HVEM/TR2-Fc binding to AIM II (LIGHT) was decreased competitively by TR6-(His) but TR6-(His) binding to AIM II (LIGHT) was not changed by HVEM/TR2-Fc. Furthermore, the binding of HVEM/TR2-Fc (6 nM) or LTβR (6 nM) was completely inhibited by 20 nM of TR6-(His) protein in immunoprecipitation assays. These results support the notion that TR6 may act as a strong inhibitor of AIM II (LIGHT) function through HVEM/TR2 and LTβR.

Binding of TR6-(His) to AIM II (LIGHT)-transfected cells To determine whether TR6 binds to AIM II (LIGHT) expressed on cell surface membranes, a binding assay was performed using AIM II (LIGHT)-transfected HEK 293 EBNA cells by flow cytometry. AIM II (LIGHT) HEK 293 EBNA cells were stained significantly by TR6-(His) as well as HVEM/TR2-Fc, LTβR-Fc. No binding was detected on pCEP4 vector-transfected HEK 293 EBNA cells with any fusion protein (FIGS. 15A–15C). Furthermore, control isotype did not bind to AIM II (LIGHT)-transfected HEK 293 EBNA cells, and any of above fusion proteins did not bind to vector-transfected cells, confirming the specificity of these bindings. These bindings indicate that TR6 can bind to both soluble and membrane-bound forms of AIM II (LIGHT).

TR6 inhibits AIM II (LIGHT)-induced cytotoxicity to HT29 cells Browning et al. (*J. Exp. Med.* 183:867–878 (1996)) have shown that Fas activation leads to rapid cell death (12–24 h) whereas LTβR takes 2–3 days in induction of apoptosis for colorectal adenocarcinoma cell line, HT29. Zhai, Y., et al., *J. Clin. Invest.* 102:1142–1151 (1998) and Mauri, D. N., et al., *Immunity* 8:21–30 (1998) also reported that AIM II (LIGHT) leads to the death of the cells expressing both LTβR and HVEM/TR2 but not the cells expressing only the LTβR or HVEM/TR2 receptor. Both HVEM/TR2 and LTβR are involved cooperatively in AIM II (LIGHT)-mediated killing of HT29 cells (Zhai, Y., et al., supra).

Figure 16A:
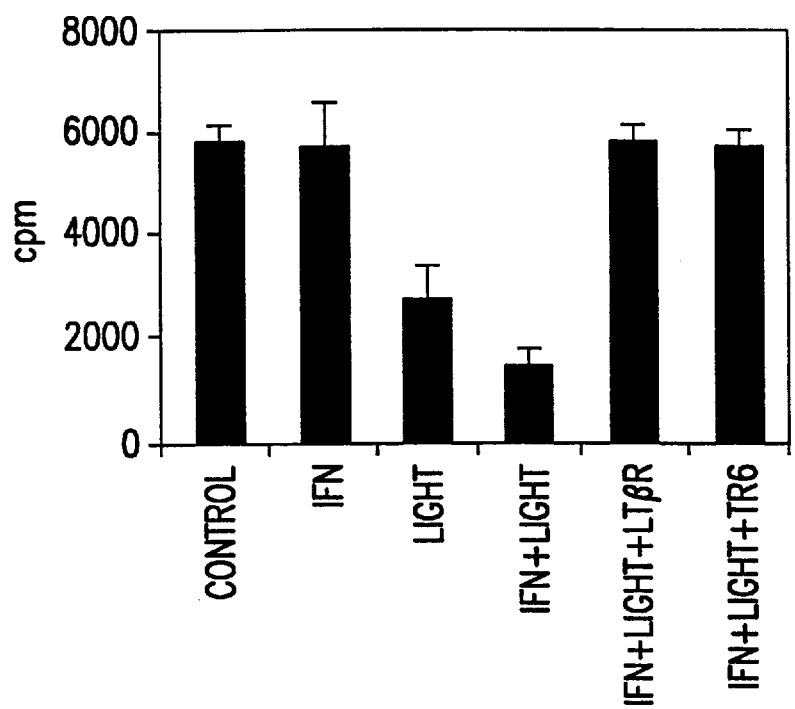
FIGS. 16A and 16B show TR6 inhibits AIM II (LIGHT)-induced cell death in HT29 cells. (A) HT29 cells were incubated in 96-well plates with control medium, 10 U/ml IFN-γ alone, purified sAIM II (sLIGHT) protein (10 ng/ml) in the absence or presence of IFN-γ (10 U/ml), purified sLTβR-Fc (200 ng/ml) or TR6-(His) (200 ng/ml) in the presence of IFN-γ (10 U/ml) and sAIM II (sLIGHT) (10 ng/ml). (B) Cells were incubated with various dose of TR6-(His) and IFN-γ (10 U/ml) with (open circle) or without (filled circle) sAIM II (sLIGHT) (10 ng/ml). In all assays, cells were cultured for 4 days, and proliferation was detected during the last 6 h of culture by the addition of 1 γCi of [$^3$H]thymidine. Cells were harvested, and thymidine incorporation was determined using a liquid scintillation counter.
Figure 16B:
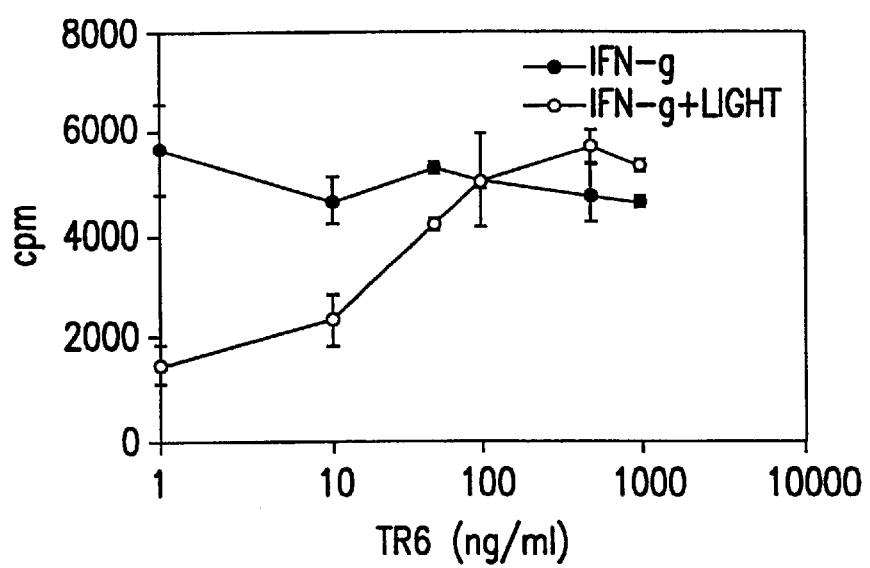

To determine whether binding of TR6 inhibits AIM II (LIGHT)-mediated cytotoxicity, HT29 cells were incubated with 10 ng/ml of sAIM II (sLIGHT) and IFN-γ (10 U/ml) in the presence of 200 ng/ml of LTβR-Fc or TR6-(His). As shown in FIG. 16A, TR6-(His) blocked nearly the entire AIM II (LIGHT)-mediated cell killing. Cells were also incubated with sAIM II (sLIGHT) and/or IFN-γ in the presence of varying concentration of TR6-(His). TR6-(His) blocked sAIM II (sLIGHT)-induced cell death dose-dependently (FIG. 16B). Taken together, TR6 may act as a natural inhibitor of AIM II (LIGHT)-induced tumor cell death and contribute to immune evasion by tumors.

AIM II (LIGHT) interaction with HVEM/TR2 and/or LTβR is expected to trigger the distinct biological events, such as T cell proliferation, blocking of HVEM-dependent HSV1 infection and anti-tumor activity (Mauri, D. N., et al., *Immunity* 8:21–30 (1998); Zhai, Y., et al., *J. Clin. Invest.* 102:1142–1151 (1998); Harrop, J. A., et al., *J. Biol. Chem.* 273:27548–27556 (1998)). TR6 is believed to act as an inhibitor of AIM II (LIGHT) interaction and is believed to also act in distinct roles, depending on cell types. Indeed, TR6 (DcR3) has been shown to bind to FasL and is believed to contribute to immune evasion by certain tumors (Pitti, R. M., et al., *Nature* 396:699–703 (1998)). TR6 (DcR3) is believed to act as a decoy receptor and contribute to immune evasion both in slow and rapid tumor cell death, that are mediated by AIM II (LIGHT) or FasL mediated apoptosis pathway respectively.

Another possibility is that TR6 may act as a cytokine to trigger membrane-bound FasL or AIM II (LIGHT) and directly transduce signals through FasL or AIM II (LIGHT). Recently Desbarats and Suzuki groups reported that FasL could itself transduce signals, leading to cell-cycle arrest and cell death in CD4+T cells but cell proliferation in CD8-T cells (Desbarats, J., et al., *Nature Medicine* 4:1377–1382 (1998); Suzuki, I., and Fink, P. J., *J. Exp. Med.* 187:123–128 (1998)). Therefore, TR6 may act as a cytokine for signaling through FasL and AIM II (LIGHT).

HUVEC cells constitutively expressed TR6 in RT-PCR analysis. AIM II (LIGHT) and FasL have been known to be expressed in activated T cells. Therefore, it is believed that TR6 and its ligands are important for interactions between activated T lymphocytes and endothelium. TR6 may be involved in activated T cell trafficking as well as endothelial cell survival.

Thus, a novel soluble member of the TNFR superfamily, TR6, has been identified. TR6 is constitutively expressed in lung tissue, tumor cells and in endothelial cells. The ligands for TR6 appear to be AIM II (LIGHT) and FasL, which are involved in the cell death pathway. TR6 binds specifically to AIM II (LIGHT) and FasL and inhibits their activities. Like DcR1, DcR2 and another soluble member of TNFR superfamily, OPG, TR6 is believed to act as an inhibitor of signaling through TNF family members, FasL and AIM II (LIGHT). Hence, TR6 is believed to have important roles in the inhibition of apoptosis and tumor modulation.

Example 14

Isolation of Antibody Fragments Directed Against Polypeptides of the Present Invention From a Library of scFvs Naturally occurring V-genes isolated from human PBLs are constructed into a large library of antibody fragments which contain reactivities against polypeptides of the present invention to which the donor may or may not have been exposed (see, e.g., U.S. Pat. No. 5,885,793 incorporated herein in its entirety by reference).

Rescue of the Library

A library of scFvs is constructed from the RNA of human PBLs as described in WO92/01047. To rescue phage displaying antibody fragments, approximately $10^9$ E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, $2\times10^8$ TU of delta gene 3 helper phage (M13 delta gene III, see WO92/01047) are added and the culture incubated at 37° C. for 45 minutes without shaking and then at 37° C. for 45 minutes with shaking. The culture is centrifuged at 4000 r.p.m. for 10 minutes and the pellet resuspended in 2 liters of 2×TY containing 100 µg/ml ampicillin and 50 µg/ml kanamycin and grown overnight. Phage are prepared as described in WO92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are pelleted (IEC-Centra 8, 4000 revs/min for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately $10^{13}$ transducing units/ml (ampicillin-resistant clones).

Panning of the Library

Immunotubes (Nunc) are coated overnight in PBS with 4 ml of either 100 mg/ml or 10 mg/ml of a polypeptide of the present invention. Tubes are blocked with 2% Marvel-PBS for 2 hours at 37° C. and then washed 3 times in PBS. Approximately $10^{13}$ TU of phage are applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders

Eluted phage from the 3rd and 4th rounds of selection are used to infect E. coli HB 2151 and soluble scFv is produced (Marks et al., J. Mol. Biol. 222:581–597(1991)) from single colonies for assay. ELISAs are performed with microtitre plates coated with either 10 µg/ml of the polypeptide of the present invention in 50 mM bicarbonate pH 9.6. Clones positive in ELISA are further characterized by PCR fingerprinting (see, e.g., WO92/01047) and then by sequencing.

Example 15

Method of Determining Alterations in the AIM II Gene

RNA is isolated from entire families or individual patients presenting with a phenotype of interest (such as a disease). cDNA is then generated from these RNA samples using protocols known in the art. (See Sambrook et al.). The cDNA is then used as a template for PCR, employing primers surrounding regions of interest in SEQ ID NO:1. Suggested PCR conditions consist of 35 cycles at 95° C. for 30 seconds; 60–120 seconds at 52–58° C.; and 60–120 seconds at 70° C. using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of AIM II are also determined and genomic PCR products analyzed to confirm the results. PCR products harboring suspected mutations in AIM II are then cloned and sequenced to validate the results of the direct sequencing.

PCR products of AIM II are cloned into T-tailed vectors as described in Holton, T. A. and Graham, M. W., Nucleic Acids Research 19:1156 (1991) and sequenced with T7 polymerase (United States Biochemical). Affected individuals are identified by mutations in AIM II not present in unaffected individuals.

Genomic rearrangements are also observed as a method of determining alterations in the AIM II gene. Genomic clones isolated using techniques known in the art are nick-translated with digoxigenindeoxy-uridine 5'-triphosphate (Boehringer Manheim), and FISH performed as described in Johnson, C. et al., Methods Cell Biol. 35:73–99 (1991). Hybridization with the labeled probe is carried out using a vast excess of human cot-1 DNA for specific hybridization to the AIM II genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl. 8:75 (1991).) Image collection, analysis and chromosomal fractional length measurements are performed using the ISee Graphical Program System. (Inovision Corporation, Durham, N.C.). Chromosome alterations of the genomic region of AIM II (hybridized by the probe) are identified as insertions, deletions, and translocations. These AIM II alterations are used as a diagnostic marker for an associated disease.

Example 16

Method of Detecting Abnormal Levels of AIM II in a Biological Sample

AIM II polypeptides can be detected in a biological sample, and if an increased or decreased level of AIM II is detected, this polypeptide is a marker for a particular phenotype. Methods of detection are numerous, and thus, it is understood that one skilled in the art can modify the following assay to fit their particular needs.

For example, antibody-sandwich ELISAs are used to detect AIM II in a sample, preferably a biological sample. Wells of a microtiter plate are coated with specific antibodies to AIM II, at a final concentration of 0.2 to 10 µg/ml. The antibodies are either monoclonal or polyclonal and are produced using technique known in the art. The wells are blocked so that non-specific binding of AIM II to the well is reduced.

The coated wells are then incubated for >2 hours at RT with a sample containing AIM II. Preferably, serial dilutions of the sample should be used to validate results. The plates are then washed three times with deionized or distilled water to remove unbounded AIM II.

Next, 50 µl of specific antibody-alkaline phosphatase conjugate, at a concentration of 25–400 ng, is added and incubated for 2 hours at room temperature. The plates are again washed three times with deionized or distilled water to remove unbounded conjugate.

75 µl of 4-methylumbelliferyl phosphate (MUP) or p-nitrophenyl phosphate (NPP) substrate solution is then added to each well and incubated 1 hour at room temperature to allow cleavage of the substrate and flourescence. The flourescence is measured by a microtiter plate reader. A standard curve is preparded using the experimental results from serial dilutions of a control sample with the sample concentration plotted on the X-axis (log scale) and fluorescence or absorbance on the Y-axis (linear scale). The AIM II polypeptide concentration in a sample is then interpolated using the standard curve based on the measured flourescence of that sample.

Example 17

Method of Treating Increased Levels of AIM II

The present invention relates to a method for treating an individual in need of a decreased level of AIM II biological activity in the body comprising, administering to such an individual a composition comprising, or alternatively consisting of, a therapeutically effective amount of AIM II antagonist. Preferred antagonists for use in the present invention are AIM II-specific antibodies.

Moreover, it will be appreciated that conditions caused by a decrease in the standard or normal expression level of AIM II in an individual can be treated by administering AIM II, preferably in a soluble and/or secreted form. Thus, the invention also provides a method of treatment of an individual in need of an increased level of AIM II polypeptide comprising administering to such an individual a pharmaceutical composition comprising, or alternatively consisting of, an amount of AIM II to increase the biological activity level of AIM II in such an individual.

For example, a patient with decreased levels of AIM II polypeptide receives a daily dose 0.1–100 µg/kg of the polypeptide for six consecutive days. Preferably, the polypeptide is in a soluble and/or secreted form.

Example 18

Method of Treating Decreased Levels of AIM II

The present invention also relates to a method for treating an individual in need of an increased level of AIM II biological activity in the body comprising administering to such an individual a composition comprising, or alternatively consisting of, a therapeutically effective amount of AIM II or an agonist thereof Antisense technology is used to inhibit production of AIM II. This technology is one example of a method of decreasing levels of AIM II polypeptide, preferably a soluble and/or secreted form, due to a variety of etiologies, such as cancer.

For example, a patient diagnosed with abnormally increased levels of AIM II is administered intravenously antisense polynucleotides at 0.5, 1.0, 1.5, 2.0 and 3.0 mg/kg day for 21 days. This treatment is repeated after a 7-day rest period if the treatment is determined to be well tolerated.

Example 19

Method of Treatment Using Gene Therapy—Ex Vivo

One method of gene therapy transplants fibroblasts, which are capable of expressing soluble and/or mature AIM II polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37° C. for approximately one week.

At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7:219–25 (1988)), flanked by the long terminal repeats of the Moloney murine sarcoma virus, is digested with EcoRI and HindIII and subsequently treated with calfintestinal phosphatase. The linear vector is fractionated on agarose gel and purified, using glass beads.

The cDNA encoding AIM II can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform E. coli HB101, which are then plated onto agar containing kanamycin for the purpose of confirming that the vector contains properly inserted AIM II.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the AIM II gene is then added to the media and the packaging cells transduced with the vector. The packaging cells now produce infectious viral particles containing the AIM II gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a Millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether AIM II protein is produced.

The engineered fibroblasts are then transplanted onto the host, either alone or after having been grown to confluence on cytodex 3 microcarrier beads.

Example 20

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) AIM II sequences into an animal to increase or decrease the expression of the AIM II polypeptide. The AIM II polynucleotide may be operatively linked to a promoter or any other genetic elements necessary for the expression of the AIM II polypeptide by the target tissue. Such gene therapy and delivery techniques and methods are known in the art, see, for example, WO90/11092, WO98/11779; U.S. Pat. Nos. 5693622, 5705151, 5580859; Tabata H. et al., *Cardiovasc. Res.* 35:470–479 (1997); Chao J. et al., *Pharmacol. Res.* 35:517–522 (1997); Wolff J. A. *Neuromuscul. Disord.* 7:314–318 (1997); Schwartz B. et al,. *Gene Ther.* 3:405–411 (1996); Tsurumi Y. et al., *Circulation* 94:3281–3290 (1996) (incorporated herein by reference).

The AIM II polynucleotide constructs may be delivered by any method that delivers injectable materials to the cells of an animal, such as, injection into the interstitial space of tissues (heart, muscle, skin, lung, liver, intestine and the like). The AIM II polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the AIM II polynucleotides may also be delivered in liposome formulations (such as those taught in Felgner P. L. et al. *Ann. NY Acad. Sci.* 772:126–139 (1995), and Abdallah B. et al. *Biol. Cell* 85:1–7 (1995)) which can be prepared by methods well known to those skilled in the art.

The AIM II polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The AIM II polynucleotide construct can be delivered to the interstitial space of tissues within an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked AIM II polynucleotide injection, an effective dosage amount of DNA or RNA will be in the range of from about 0.05 $\mu$g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked AIM II polynucleotide constructs can be delivered to arteries during angioplasty by the catheter used in the procedure.

The dose response effects of injected AIM II polynucleotide in muscle in vivo are determined as follows. Suitable AIM II template DNA for production of mRNA coding for AIM II polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The AIM II template DNA is injected in 0.1 ml of carrier in a I cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 μm cross-section of the individual quadriceps muscles is histochemically stained for AIM II protein expression. A time course for AIM II protein expression may be done in a similar fashion except that quadriceps from different mice are harvested at different times. Persistence of AIM II DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using AIM II naked DNA.

Example 21

Gene Therapy Using Endogenous AIM II Gene

Another method of gene therapy according to the present invention involves operably associating the endogenous AIM II sequence with a promoter via homologous recombination as described, for example, in U.S. Pat. No. 5,641, 670, issued Jun. 24, 1997; WO 96/29411, published Sep. 26, 1996; WO 94/12650, published Aug. 4, 1994; Koller et al., Proc. Natl. Acad. Sci. U.S.A. 86:8932–8935 (1989); and Zijlstra et al., Nature 342:435–438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous AIM II, flanking the promoter. The targeting sequence will be sufficiently near the 5' end of AIM II so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous AIM II sequence. This results in the expression of AIM II in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES, pH 7.3, 13 7 mM NaCl, 5 mM KCl, 0.7 mM $Na_2HPO_4$, 6 mM dextrose). The cells are recentrifuged, the supernatant aspirated, and the cells resuspended in electroporation buffer containing 1 mg/ml acetylated bovine serum albumin. The final cell suspension contains approximately $3 \times 10^6$ cells/ml. Electroporation should be performed immediately following resuspension.

Plasmid DNA is prepared according to standard techniques. For example, to construct a plasmid for targeting to the AIM II locus, plasmid pUC18 (MBI Fermentas, Amherst, N.Y.) is digested with HindIII. The CMV promoter is amplified by PCR with an XbaI site on the 5' end and a BamHI site on the 3' end. Two AIM II non-coding sequences are amplified via PCR: one AIM II non-coding sequence (AIM II fragment 1) is amplified with a HindIII site at the 5' end and an XbaI site at the 3' end; the other AIM II non-coding sequence (AIM II fragment 2) is amplified with a BamHI site at the 5' end and a HindIII site at the 3' end. The CMV promoter and AIM II fragments are digested with the appropriate enzymes (CMV promoter—XbaI and BamHI; AIM II fragment I—XbaI; AIM II fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 μg/ml. 0.5 ml of the cell suspension (containing approximately $1.5 \times 10^6$ cells) is then added to the cuvette, and the cell suspension and DNA solutions are gently mixed. Electroporation is performed with a Gene-Pulser apparatus (Bio-Rad). Capacitance and voltage are set at 960 μF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 22

Modulation of T Cell-mediated Immunity in Tumor and Graft Versus Host Disease Models Through AIM II Costimulatory Pathway Introduction T lymphocytes often require two distinct signals to proliferate and further to differentiate into effector cells that mediate immune responses (Schwartz, R. H., *Cell* 71:1065–1068 (1992)). In addition to antigen signals delivered by the TCR, the interactions between costimulatory receptors on T cells and their ligands or counterreceptors on professional antigen-presenting cells (APC) are essential in optimal activation and survival of T cells. Blockage of B7-CD28 costimulatory pathway by soluble CTLA4-Ig or anti-B7 monoclonal antibodies (mAb) inhibits progress of autoimmune disease, rejection of transplanted organs and graft-versus-host disease (GVHD) (Cross, A. H., et al., *J. Clin. Invest.* 95:2783–2789 (1995); Lenschow, D. J., et al., *Science* 257:789–792 (1992); Blazar, B. R., et al., *Blood* 83:3815–3825 (1994)). On the other hand, stimulation of costimulatory signals by gene transfer of B7 or agonistic mAb against 4-1BB can enhance anti-tumor immune responses (Chen, L., et al., *Cell* 71:1093–1102 (1992); Melero, I., et al., *Nat. Med.* 3:682–685 (1997)). These studies demonstrate that costimulatory interaction plays critical roles during the induction of immune responses. More importantly, costimulatory pathways can be manipulated for therapeutic purposes.

AIM II, also referred to as LIGHT (homologous to lymphotoxins, exhibits, inducible expression, and competes with HSV glycoprotein D for HVEM, a receptor expressed by T lymphocytes), is a member of the TNF cytokine family (Mauri, D. N., et al., *Immunity* 8:21–30 (1998)) and its mRNA can be detected in the majority of peripheral blood mononuclear cells (PBMC) upon activation (Mauri, D. N., et al., *Immunity* 8:21–30 (1998); Zhai, Y., et al., *J. Clin. Invest.* 102:1142–1151 (1998)). Two cellular receptors, HVEM (ATAR, TR2) and LTβR are found to bind AIM II in high affinity (Mauri, D. N., et al., *Immunity* 8:21–30 (1998)). Expression of HVEM can be detected in the majority of hemotopoietic cells including T, B and NK cells and weakly in endothelial cells (Harrop, J. A., et al., *J. Immunol.* 161:1786–1794 (1998); Kwon, B. S., et al., *J. Bio. Chem.* 272:14272–14276 (1997)). In contrast, LTβR is not found in T and B cells, but expressed in high levels in monocytes and stromal cells (Browning, J. L., et al., *J. Immunol.* 159:3288–3298 (1997)). AIM II triggers apoptosis of some tumor lines in vitro and in vivo and the effect appears to require expression of both HVEM and LTβR on tumor cells (Zhai, Y., et al., *J. Clin. Invest.* 102:1142–1151 (1998)) although these receptors lack typical death domain (Montgomery, R. I., et al., *Cell* 87:427–436 (1996); Smith, C. A., et al., *Cell* 76:959–962 (1994)). A recent report indicates that AIM II may also bind TR6, a decoy receptor (DcR3), which is expressed only in soluble form due to lack of a transmembrane sequence (Yu, K. Y., et al., *J. Biol. Chem.* 274:13733–13736 (1999)).

Several recent studies suggest that AIM II may be involved in the regulation of cellular immune responses. AIM II stimulates a 3-way mixed lymphocyte reaction (MLR) of peripheral blood mononuclear cells (PBMC) (Harrop, J. A., et al., *J. Biol. Chem.* 273:27548–27556 (1998)). This stimulation is likely mediated through HVEM ligation since T cells do not express LTβR (Browning, J. L., et al., *J. Immunol.* 159:3288–3298 (1997)). HVEM interacts with several TNF receptor-associated factors (TRAF), and over-expression of HVEM in 293 cells leads to activation of nuclear factor (NF)-κB (Hsu, H., et al., *J. Biol. Chem.* 272:13471–13474 (1997); Marsters, S. A., et al., *J. Biol. Chem.* 272:14029–14032 (1997)). Blockade of HVEM by HVEM-Ig or a specific mAb can inhibit an allogeneic MLR of PBMC (Harrop, J. A., et al., J Immunol. 161:1786–1794 (1998); Kwon, B. S., et al., *J. Bio. Chem.* 272:14272–14276 (1997)). Altogether, these results support that AIM II and HVEM interaction participates in the generation of allogeneic T cell response.

The mouse homologue of human AIM II was cloned and characterized. Further, it was demonstrated that AIM II is a CD28-independent co-stimulatory molecule critical for T cell growth and differentiation. It was also shown that T cell-mediated immune responses in tumor and GVHD can be modulated by in vivo manipulation of AIM II costimulatory pathway.

Molecular Cloning of Mouse AIM II

Figures 1, 21A:
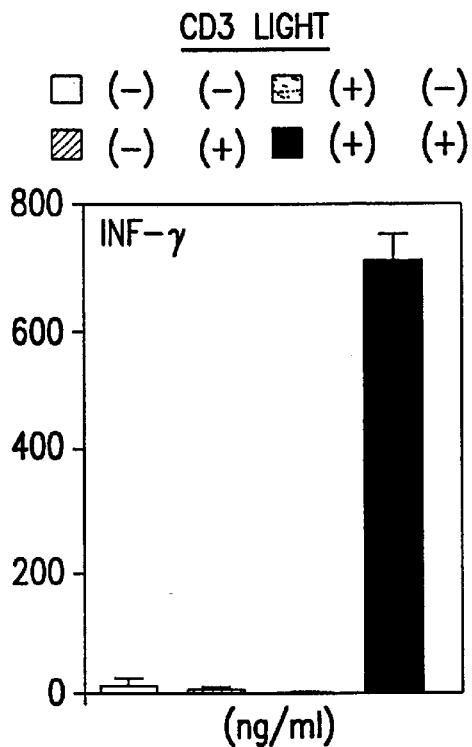
Figures 2, 21A:
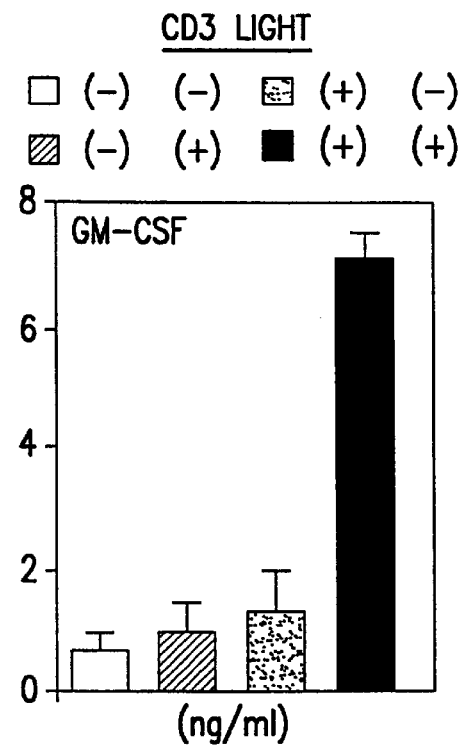
Figures 3, 21A:
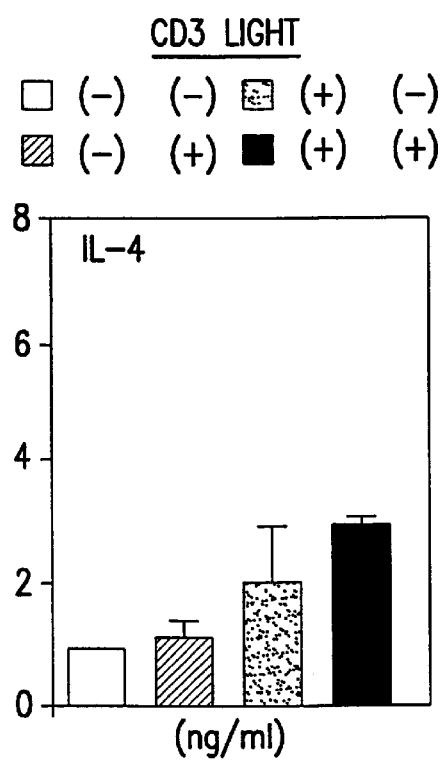
Figures 4, 21A:
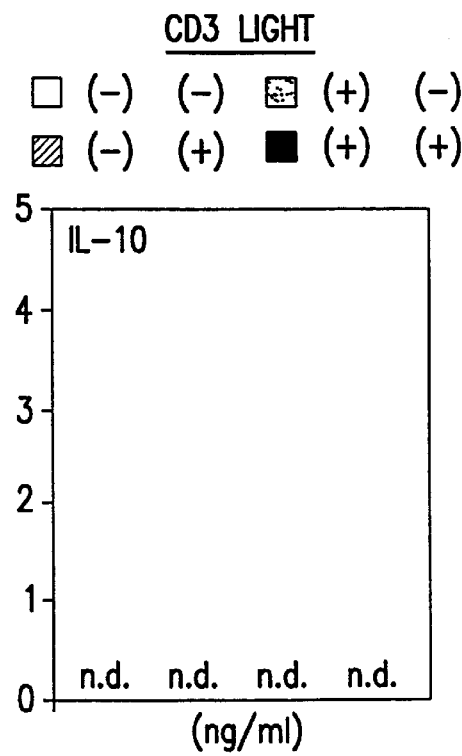

A full-length cDNA of mouse homologue of human AIM II was isolated from Con A-activated mouse T cells by a combination of RACE (rapid amplification of cDNA ends) and RT-PCR and cloned into pcDNA3 mammalian cell expression vector (pmAIM II). Mouse AIM II cDNA encodes a putative 239-amino acid protein, which has the characteristic of a type II transmembrane protein and demonstrates 77% amino acid homology with human AIM II (FIG. 17A). The putative receptor-binding region of mouse AIM II exhibits a significant sequence homology with that of Fas ligand (33%), LTβ (30%), LTα (28%), TNF (27%), RANK ligand (26%) and TRAIL (23%) (data not shown). Upon transfection of pmAIM II into 293 cells, surface expression of AIM II was stained with rabbit anti-AIM II antiserum or LTβR-Ig fusion protein by a flow cytometry analysis (FIGS. 17B-1 to 17B-4).

AIM II Costimulates CD28-independent T Cell Responses

Figure 18A:
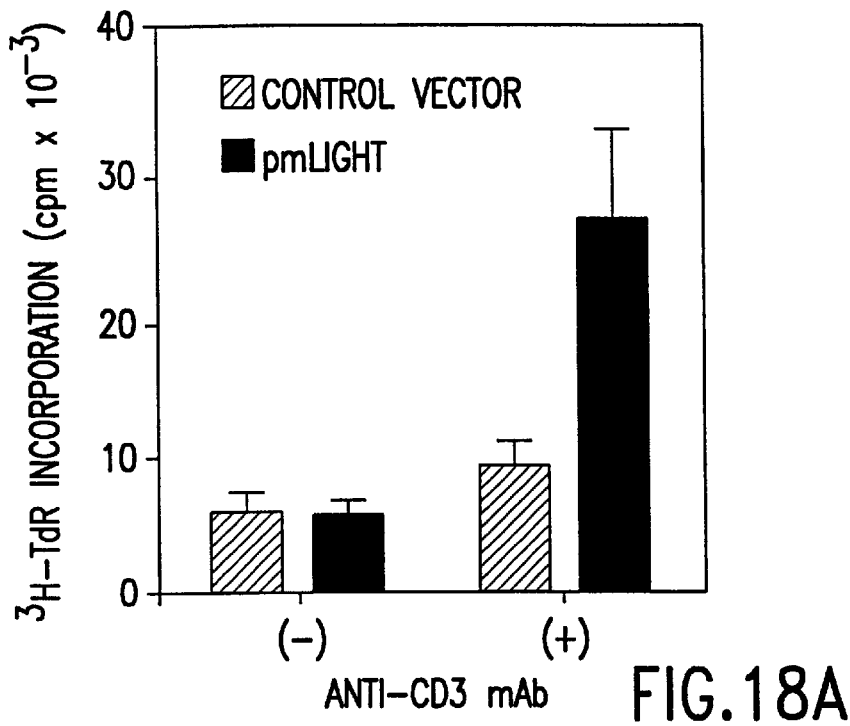
FIG. 18 shows the costimulatory activity of mouse AIM II. Purified T cells (1×10$^6$ cells/ml) were stimulated with either 5×10$^4$ cells/ml of irradiated COS cells, which were transfected with pcDNA3 or pmAIM II plasmid for 72 hours (FIG. 18A), or indicated doses of immobilized AIM II.flag fusion proteins (FIG. 18B) in 96-well flat-bottomed microplates in the presence or absence of immobilized anti-CD3. The concentration of anti-CD3 mAb was 2 μg/ml in FIG. 18A and 0.2 μg/ml in FIG. 18B. Purified T cells (1×10$^6$ cells/ml) of either CD28$^{-/-}$ or CD28$^{+/+}$ splenocytes were stimulated with immobilized AIM II.flag fusion protein (4 μg/ml) or soluble anti-CD28 (1 μg/ml) in the presence of immobilized anti-CD3 (0.2 μg/ml) (FIG. 18C). In all assays, the cells were incubated for 72 hr and the proliferative responses of the T cells were monitored by $^3$H-TdR incorporation during the last 15 hr.
Figure 18B:
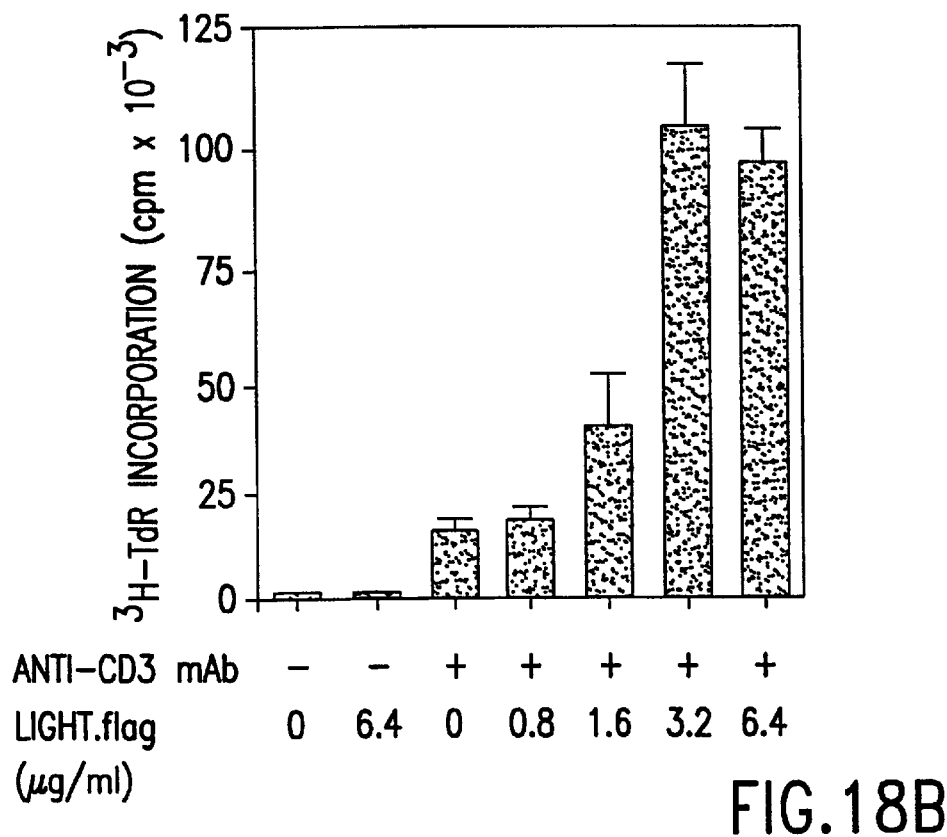

It has been shown that human AIM II protein can enhance proliferative responses of human peripheral blood mononuclear cells to allogeneic antigens in in vitro cultures (Harrop, J. A., et al., *J. Biol. Chem.* 273:27548–27556 (1998)) suggesting that AIM II may be involved in a T cell response. However, the nature of this enhancement is not clear. The possibility that AIM II can function as a costimulatory molecule in the presence of T cell receptor signal was examined. For this purpose, an in vitro costimulation assay using COS cells expressing transfected AIM II to stimulate purified murine T cells in the presence of an immobilized anti-CD3 mAb at a suboptimal dose was employed. COS cells transfected with the pmAIM II induced a significant increase of T cell proliferation in comparison with that of control vector-transfected COS cells (FIG. 18A). In the absence of anti-CD3, pmAIM II-transfected COS cells did not stimulate T cell proliferation (FIG. 18A). This result indicates that AIM II can costimulate T cell growth in the presence of antigenic signal. To provide direct evidence for this conclusion, a fusion protein, AIM II.flag, consisting of extracellular domain of mouse AIM II fused with 8 amino acid flag peptide was prepared. As shown in FIG. 18B, immobilized AIM II.flag strongly stimulated proliferation of purified mouse T cells in the presence of suboptimal anti-CD3 in a dose-dependent manner. Similar to the result in FIG. 18A, AIM II.flag did not stimulate T cells in the absence of anti-CD3 (FIG. 18B). These results demonstrate that AIM II can costimulate T cell growth when engagement of TCR occurs.

Figure 18C:
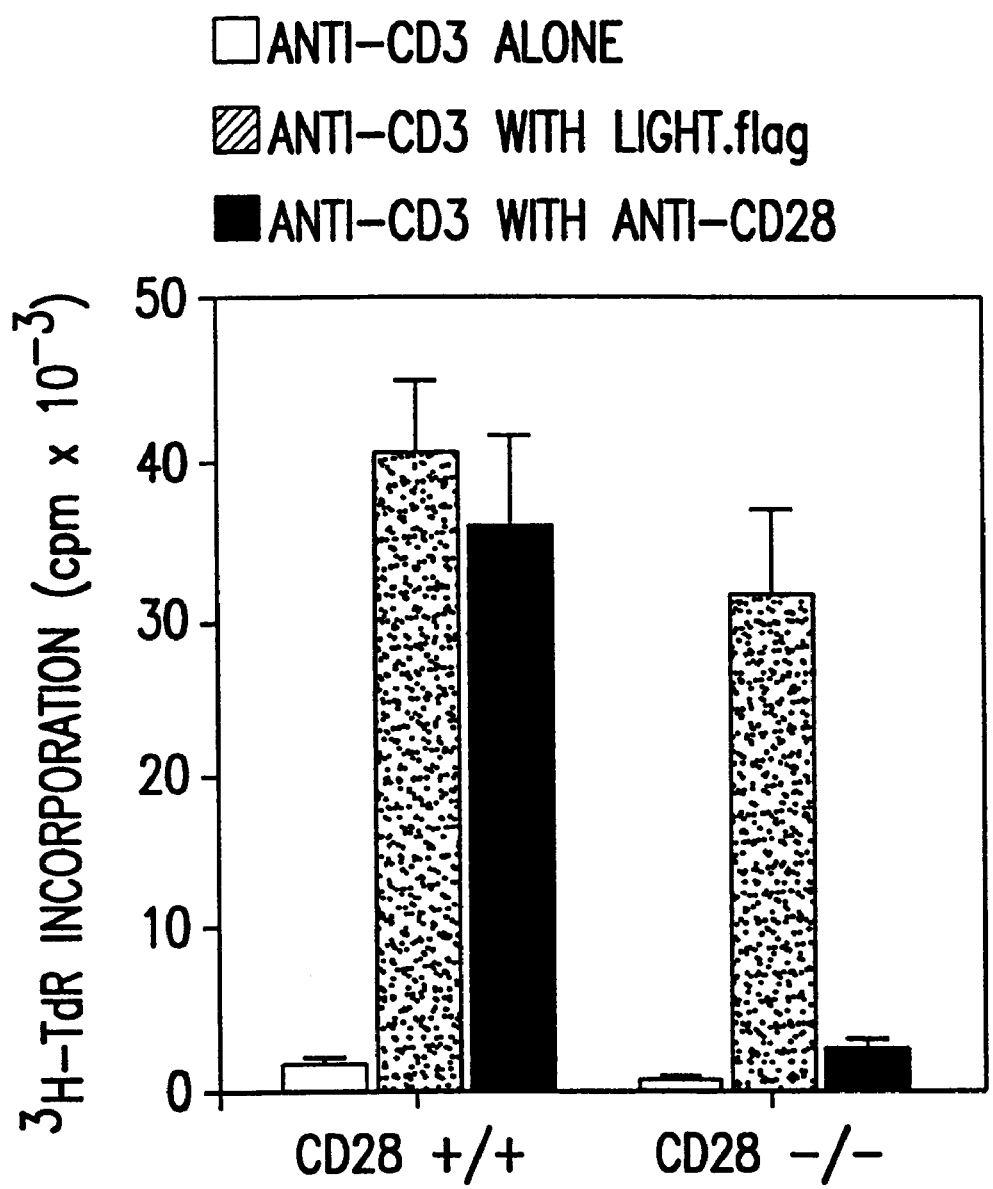

To determine whether AIM II costimulation is linked to B7-CD28 pathway, the most intensively studied costimulatory pathway (Lenschow, D. J., et al., *Annu. Rev. Immunol.* 14:233–258 (1996)), the ability of the AIM II.flag to costimulate proliferation of T cells isolated from CD28-deficient (CD28$^{-/-}$) mice and from normal littermates in the presence of an anti-CD3 mAb was compared. As shown in FIG. 18C, AIM II.flag fusion protein stimulated the proliferation of the CD28$^{-/-}$ T cells in the levels comparable to that of the CD28$^{+/+}$ T cells while the proliferative response to anti-CD28 mAb in CD28$^{-/-}$ mice was vanished. Taken together, these results demonstrate that AIM II can function independent of CD28 costimulatory pathway.

Augmentation of T-cell Mediated Tumor Immunity by AIM II Gene Transfer In Vivo

To test whether augmentation of AIM II costimulation can increase cell-mediated immune response in vivo, the pmAIM II plasmid was directly injected into established tumor nodules induced by P815 tumor cells and the effect of AIM II expression in the induction of cytolytic T cells (CTL) to tumor antigens and in the regression of the tumor nodules were examined. Administration of liposome-carried or naked plasmids encoding immunostimulatory genes such as antigens, B7s and cytokines is able to express molecules in mammalian tissues and has been shown to be effective in stimulating T cell response (Kim, J. J., et al., *Nat. Biotech.* 15:641–646 (1997); Templeton, N. S., et al., *Nat. Biotech.* 15:647–652 (1997); Plautz, G. E., et al., *Proc. Natl. Acad. Sci. USA* 90:4645–4649 (1993); Syrengelas, A. D., et al., *Nat. Med.* 2:1038–1041 (1996); Iwaski, A., et al., *J. Immunol.* 158:4591–4601 (1997)). In addition, it has previously been demonstrated that the mice inoculated with $2 \times 10^5$ P815 cells subcutaneously (s.c.) grow palpable tumors ranging in size from 3 to 5 mm in average diameters in a week (Chen, L., et al., *J. Exp. Med.* 179:523–532 (1994)).

Liposome-carried pmAIM II was injected into tumor nodules repeatedly starting at day 7 upon s.c. inoculation of tumor cells. Expression of transfected AIM II can be detected in tumor nodules by RT-PCR (data not shown). One week after the last plasmid injection, spleen cells were stimulated in a 4-day mixed lymphocyte-tumor culture and assayed for their CTL activity against P815 cells in a standard $^{51}$Cr release assay (Chen, L., et al., *Cell* 71:1093–1102 (1992)). Mice treated with the pmAIM II had clearly increased CTL activity against P815 cells in comparison with those treated with medium or the control vector (FIG. 19A-1). While CTL lysed P815 cells in high level, they did not kill L 1210 cells in the same assay (FIG. 19A-2), suggesting that the CTL are specific for P815 tumor antigens. These results demonstrate that AIM II costimulation in vivo can augment CTL response to P815 tumor antigen.

Repeated injections of the pm-AIM II further led to regression of the tumors in all treated mice within 3 weeks from the beginning of injections (FIG. 19B) while the mice in the control groups treated by medium or control vector developed progressive growing tumors. In some mice, the injections of the control vector resulted in a sAIM II retardation of tumor growth, probably due to nonspecific inflammation. In any cases, all tumors in the control groups grew progressively and eventually killed the mice.

The mice with regressed tumors after the pmAIM II plasmid injections remained tumor-free >40 days without recurrence (FIG. 19B). To examine whether a long-term tumor immunity was developed, the mice were challenged with lethal dose of P815 cells. As shown in FIG. 19C-1, these mice remained tumor free after the challenge while all naive mice developed tumors. The protection was specific for P815 since challenge of the mice with the cells of L1210, an antigenically irrelevant syngeneic lymphoma, led to tumor growth in a speed similar to those in naive mice (FIG. 19C-2).

Amelioration of Allo-reactive T Cell-mediated GVHD by Blockage of AIM II

To determine the role of endogenous AIM II in cell-mediated immune responses, LTβR-Ig, a soluble receptor of AIM II, was administered and the effect of blocking AIM II pathway in a murine acute GVHD model was examined. In this model, infusion of B6 ($H-2^b$)-derived T cells into sub-lethally irradiated or non-irradiated BDF 1 ($H-2^{b \times d}$) recipient mice induces an acute GVHD accompanied with rapid weight loss, expansion of allo-reactive donor T cells, decrease of host splenocytes, shrinkage of thymus and rapid death of mice (Via, C. S. and Shearer, G. M., *Immunol. Today* 9:207–213 (1988)). After intravenous (i.v.) injection with $7 \times 10^7$ splenocytes from B6 mice, recipient mice received LTβR-Ig i.v. every 3 days beginning from 1 day before of splenocyte transfer. All of the mice treated with LTβR-Ig survived up to 30 days (FIG. 20A), increased their body weight with a temporal decrease after GVHD induction (FIG. 20B) and had decreased allo-reactive (against $H-2^d$) CTL activity in spleen assayed at 11 days after B6 splenocyte transfer (FIG. 20C). In contrast, all mice treated with control Ig died within 2 weeks after splenocyte transfer accompanied with severe weight loss (FIG. 20A and 20B). High levels of allo-reactive CTL activity can be detected in the mice underwent GVHD compared with the control BDF I mice to which splenocytes from BDF1 mice were transferred (FIG. 20C-1 and 20C-2). Furthermore, the reduction of host spleen B lymphocytes and double-positive thymocytes, which are typical consequences by GVHD, were significantly inhibited by LTβR-Ig injections (data not shown). These results demonstrate that LTβR-Ig can ameliorate alloreactive T cell-mediated GVHD.

Although these data implicate that blockage of AIM II costimulatory pathway prevents GVHD, it is possible that LTβ may play an additional role since LTβR-Ig can neutralize endogenous LTβ production in GVHD-suffering mice. To exclude this possibility, splenocytes from LTα-deficient B6 mice, in which both of LTα3 complexes and LTα1β2 heterotrimers (LTβ) are deficient (Ware, C. F., et al., *Curr. Top. Microbiol. Immunol.* 198:175–218 (1995)), were transferred into non-irradiated BDF1 mice and the generation of anti-host CTL activity was examined. BDF1 recipient mice transferred with splenocytes from LTα-deficient mice exhibited an allo-reactive CTL response similar to that of LTα$^{+/+}$ littermate control (FIGS. 20D-1 and 20D-2). This result demonstrates that LTβ production from donor cells is not necessary to generate allo-reactive CTL responses in this GVHD model.

Figures 1, 20E:
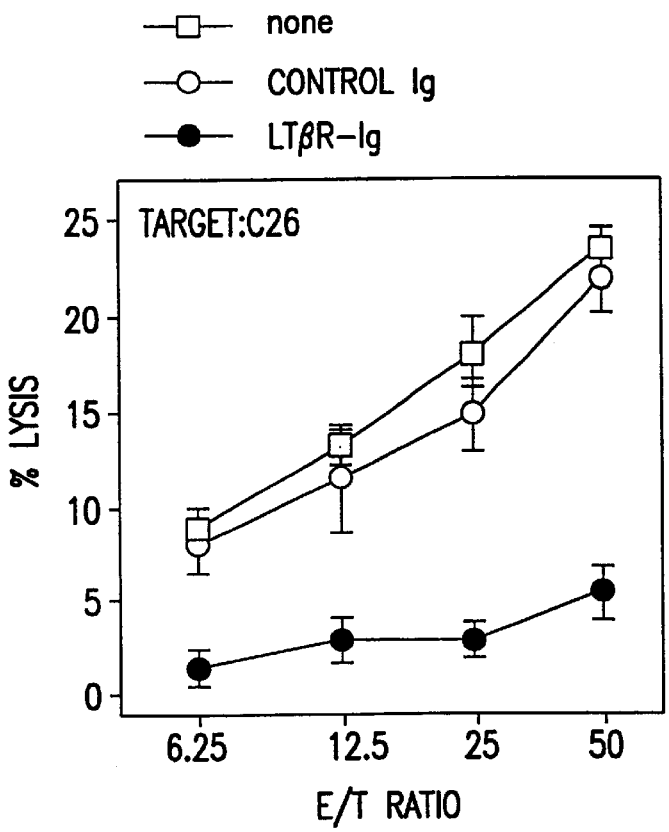
Figures 2, 20E:
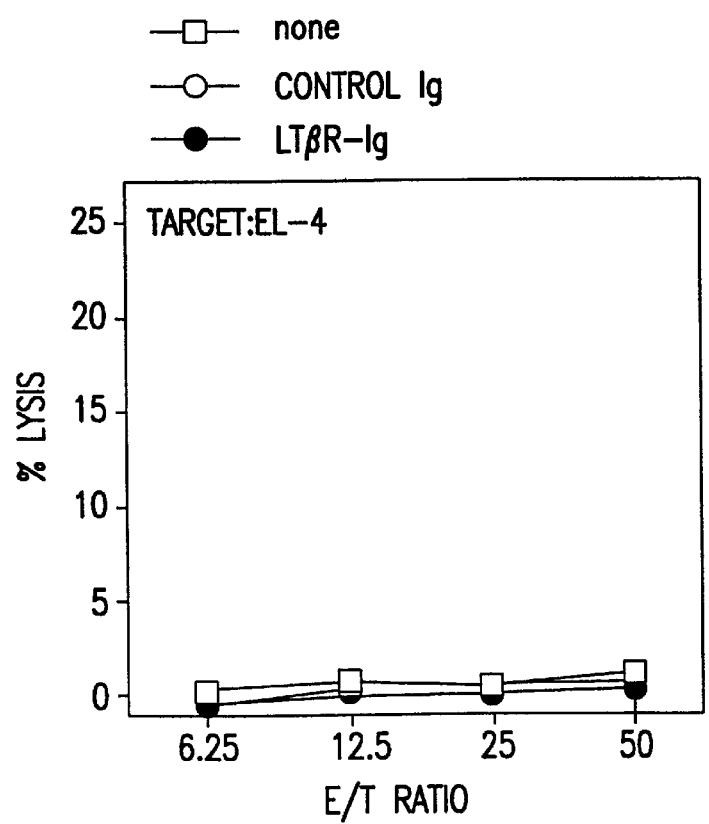

The effect of LTβR-Ig on the generation of CTL to allogeneic antigens in vitro using LTα$^{-/-}$ T cells was also examined. As showed in FIGS. 20E-1 and 20E-2, stimulation of LTα$^{-/-}$ B6 T cells by irradiated BALB/c splenocytes for 5 days induced a significant CTL activity against $H-2^d$ targets. Similar to in vivo experiment shown in FIGS. 20D-1 and 20D-2, therefore, in vitro induction of allo-reactive T cells is independent on LT. Furthermore, inclusion of LTβR-Ig but not control Ig, in the culture significantly inhibited allo-reactive CTL response (FIGS. 20E-1 and 20E-2). Taken together, these results exclude the involvement of LT in the generation of allo-reactive T cells and suggest that blockade of AIM II by LTβR-Ig may be responsible for the inhibition of allo-reactive CTL-mediated GVHD.

Preferential Induction of Th1-like Cytokines by AIM II Costimulation

Figures 1, 21B:
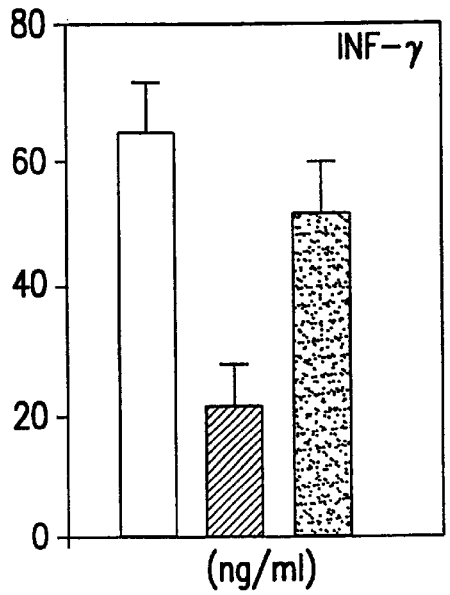
Figures 2, 21B:
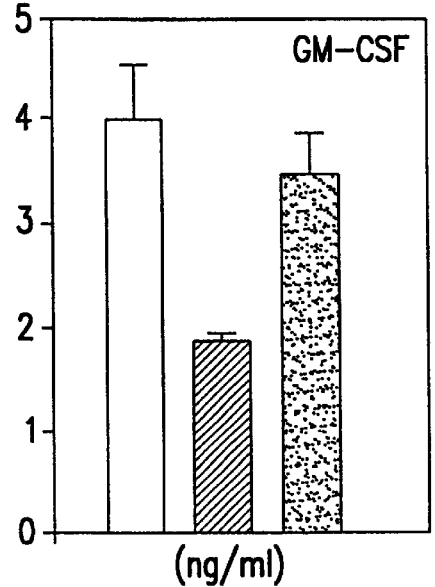
Figures 3, 21B:
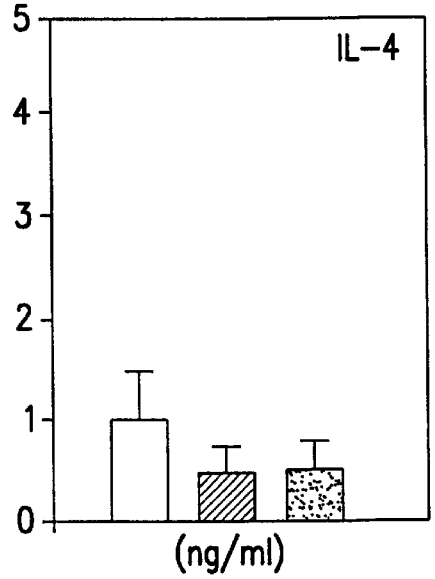
Figures 4, 21B:
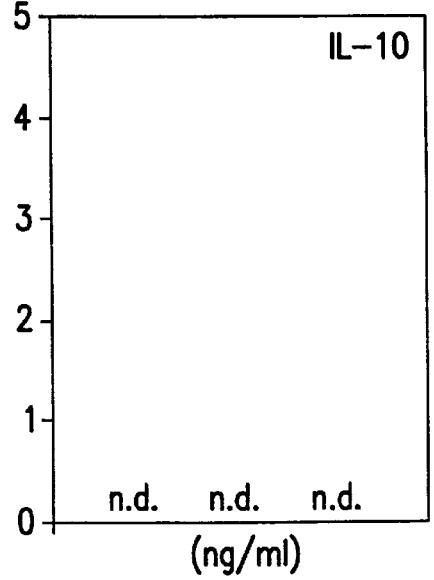

The effect of AIM II costimulation and inhibition in differentiation of T cells is studied. Purified T cells from B6 mice were stimulated with immobilized AIM II.flag fusion protein in the presence of suboptimal dose of anti-CD3 for 2 days, and the culture supernatants were analyzed for Th1- and Th2-type cytokines by sandwich ELISA. As shown in FIG. 21A, AIM II.flag drastically costimulated the production of IFN-γ and GM-CSF (FIGS. 21A-1 and 21A-2) while the secretion of IL-4 and IL-10 was not changed (FIGS. 21A-3 and 21A-4). As shown in FIG. 21B, cytokine production in the culture supernatant of allogeneic MLR was examined. T cells purified from LTα-deficient splenocytes were used to exclude the effect of LT. The culture supernatant of allogeneic MLR contained high levels of IFN-γ and GM-CSF (FIG. 21B-1 and 21B-2) while IL-4 and IL-10 were either marginal or undetectable (FIGS. 21B-3 and 21B-4). The inclusion of LTβR-Ig significantly inhibited IFN-γ and GM-CSF production (FIGS. 21B-1 and 21B-2). These results demonstrate that the AIM II costimulatory pathway preferentially induces Th1-type T cell responses while the blockage of AIM II costimulation decreases Th1-type cytokine production.

Discussion

The mouse homologue of human AIM II was cloned and its immunoregulatory functions were investigated. The data obtained demonstrated that AIM II is an important costimulatory molecule for CD28-independent T cell activation and preferentially induces Th1-type cytokine production. By employing two mouse models, T cell-mediated immune responses to P815 tumor and to allogeneic antigens in acute GVHD were examined. AIM II gene transfer stimulated tumor-specific CTL activity leading to regression of established P815 tumor, and blockage of AIM II by LTβR-Ig can ameliorate GVHD. These studies thus establish the novel costimulatory molecule, AIM II, as a critical component for the induction of cell-mediated immune response.

Although AIM II can potentially bind three receptors, HVEM, LTβR and DcR3/TR6 (Mauri, D. N., et al., *Immunity* 8:21–30 (1998); Yu, K. Y., et al., *J. Biol. Chem.* 274:13733–13736 (1999)) to transmit the signal and to interact with other cells, it is likely that only HVEM is responsible for T cell costimulation as described in this study. This is based on previous findings that LTβR is not found on T cells (Browning, J. L., et al., *J. Immunol.* 159:3288–3298 (1997)) and DcR3/TR6 protein does not have a transmembrane domain (Yu, K. Y., et al., *J. Biol. Chem.* 274:13733–13736 (1999); Pitti, R. M., et al., *Nature* 396:699–703 (1998)). While engagement of HVEM by AIM II clearly delivers a costimulatory signal, other receptors may also be involved in the regulation of AIM II-mediated costimulation. Given the fact that LTβR is expressed by multiple nonlymphoid stromal cells of lymphoid tissues (Browning, J. L., et al., *J. Immunol.* 159:3288–3298 (1997); Force, W. R., et al., *J. Immunol.* 155:5280–5288 (1995)) and binds AIM II in high affinity (Mauri, D. N., et al., *Nat. Med.* 3:682–685 (1997)), one may speculate that access of AIM II to HVEM in lymphoid organs will be interfered by LTβR. Although it is not known what is the consequence upon AIM II and LTβR interaction, cross-linking of LTβR by specific mAb or LTβ induces secretion of chemokine IL-8 and RANTES (Degli-Esposti, M. A., et al., *J. Immunol.* 158:1756–1762 (1997)) and delivers a growth inhibitory signal for some tumor lines in vitro (Degli-Esposti, M. A., et al., *J. Immunol.* 158:1756–1762 (1997); Browning, J. L., et al., *J. Exp. Med.* 183:867–878 (1996)). Therefore, it is possible that, by binding to different receptors, AIM II may be involved in the regulation innate and adaptive immune responses. It is of particular interest that another receptor of AIM II, DcR3/TR6, is found to be over-expressed in many lung and colon cancers and also binds to FasL (Pitti, R. M., et al., *Nature* 396:699–703 (1998)). These results suggest that in addition to prevention of Fas-FasL mediated apoptosis by DcR3/TR6 as indicated by Pitti and colleagues' study (Pitti, R. M., et al., *Nature* 396:699–703 (1998)), some tumors may secrete soluble DcR3/TR6 to neutralize AIM II to evade T cell activation. These studies, however, demonstrate that enhanced AIM II-HVEM interaction by gene transfer of AIM II into tumor nodules can induce regression of established tumors cells (FIGS. 19B, 19C-1 and 19C-2), suggesting that AIM II-HVEM costimulatory pathway can be manipulated leading to enhanced T cell responses against tumor. It is not known at this time whether gene transfer by AIM II can be effective for a broad spectrum of tumors in addition to P815.

AIM II can induce death of tumor cells in the absence of other components of the immune system. It has been shown that AIM II directly triggers apoptosis of some tumor cells in cell cultures, and an AIM II-transfected human breast carcinoma line is regressed in T cell-deficient athymic nude mice (Zhai, Y., et al., *J. Clin. Invest.* 102:1142–1151 (1998)). It is of interest that only the cells expressing both LTβR and HVEM are susceptible to AIM II-mediated apoptosis (Zhai, Y., et al., *J. Clin. Invest.* 102:1142–1151 (1998)). Nevertheless, this apoptosis mechanism can be excluded in these studies because P815 was negative for both LTβR and HVEM by RT-PCR analysis (data not shown). Moreover, the mechanism for the regression of P815 tumor is apparently correlated to an amplified CTL response specific for P815 (FIG. 19A-1). Preliminary studies showed that depletion of CD4$^+$, CD8$^+$ T cells or NK cells abrogated, at least in part, the effect of AIM II-induced tumor regression (data not shown), suggesting that these subset of lymphocytes are involved in AIM II-induced tumor immunity.

Blockade of endogenous costimulatory pathways such as B7-CD28 and CD40L-CD40 can induce remission of GVHD in animal models (Blazar, B. R., et al., *Blood* 83:3815–3825 (1994); Durie, F. H., et al., *J. Clin. Invest.* 94:1333–1338 (1994)). AIM II can be detected in the majority of activated PBMC (Harrop, J. A., et al., *J. Immunol.* 161:1786–1794 (1998)) and the roles of these endogenously expressed AIM II in immune responses are less known. A recent study showed that a mAb to HVEM can significantly inhibit the proliferation of T cells in allogeneic MLR in vitro, (Harrop, J. A., et al., *J. Immunol.* 161:1786–1794 (1998)) suggesting that endogenous AIM II-HVEM interaction is required for the induction of allogeneic T cells. These studies extend this observation and shows that infusion of LTβR-Ig, prevents the onset of GVHD in F1 recipients and inhibits allogeneic CTL activity (FIG. 20) as well as expansion of donor T cells in F1 recipients (data not shown). While these results can be interpreted as the consequence of blockade of endogenous AIM II by LTβR-Ig, several alternative interpretations should be considered. Genetic disruption of LTα, LTβ or LTβR or injection of LTβR-Ig into pregnant mice inhibits the lymph node genesis and prevents the development of normal spleen architecture (Chaplin, D. D. and Fu, Y., *Curr. Opin. Immunol.* 10:289–297 (1998)). In adult mice, infusion of LTβR-Ig decreases follicular dendritic cell (FDC) leading to impaired humoral immune responses (Mackay, F., and Browning, J. L., *Nature* 395:26–27 (1998)). However, it appears that FDC decrease does not affect antigen presentation functions in these mice. For example, GVHD can be induced in TNFRp55-deficient mice (Matsumoto, M., et al., *Science* 271:1289–1291 (1996)) whereas these mice have disrupted FDC networks and impaired spleen architecture similar to those observed in LTα knock-out mice (Speiser, D. E., et al., *J. Immunol.* 158:5185–5190 (1997)). Transfer of LTα$^{-/-}$ donor cells, in which both LTα and membrane-bound LTβ are deficient (Ware, C. F., et al., *Curr. Top. Microbiol. Immunol.* 198:175–218 (1995)), can still generate anti-host CTL response in vivo (FIG. 20), indicating that T cells in LTα-deficient mice are functionally normal and LTα or LTαβ complex of donor cells are not required for the induction phase of GVHD.

In addition, these studies demonstrate that co-culture of purified B6 T cells from LTα-deficient mice with irradiated BALB/c spleen cells induce allogeneic CTL normally, again indicating that LTα or LTαβ complex of donor cells are not required for the induction of allogeneic CTL in this system. Finally, inclusion of LTβR-Ig completely abrogated the allogeneic CTL generation from LTα-deficient T cells in the MLR assay. It is unlikely that LTβ from recipients plays a role in GVHD observed in this study because donor T cells, which are critical responders for GVHD, do not express LTβR. In addition, donor T cells transferred into irradiated BDF1 mice, in which radiosensitive LTβ-producing cells including T, B, NK cells are eliminated, can still be sensitized leading to GVHD (FIGS. 20A, 20B). Taken together, these data exclude the roles of LT in the generation of GVHD and support important contribution of AIM II in these responses. In summary, these studies demonstrated AIM II is a critical component in cell-mediated immune response, and AIM II costimulatory pathway can be manipulated towards therapeutic benefit of diseases such as cancer, transplantation and autoimmune diseases.

Methods

Mice. Female C57BL/6 (B6), BALB/c, DBA/2 and F1 (B6×DBA/2) (BDF1) mice were purchased from the National Cancer Institute-Frederick, Md. $CD28^{-/-}$ mice and $LT\alpha^{-/-}$ mice in B6 background were described previously (Johnson, A. J., et al., *J. Virol.* 73:3702–3708 (1999); DeTogni, P., et al., *Science* 264:703–707 (1994)).

Cell lines. COS, 293 human kidney epithelial cells, P815 mouse mastocytoma, L1210 mouse lymphoma and EL-4 mouse T cell lymphoma were purchased from the American Type Culture Collection (ATCC). C26 mouse colon cancer line was kindly provided by Dr. Robert Evans of the Jackson Laboratory, Bar Harbor, Me. Cell lines were maintained in a complete medium of RPMI-1640 (Gibco BRL, Gaithersburg, Md.) supplemented with 10% FBS (HyClone, Logan, Utah), 25 mM HEPES, 100 U/ml penicillin G and 100 µg/ml streptomycin sulfate.

Isolation of mouse AIM II cDNA. Mouse AIM II cDNA was isolated by PCR using degenerate primers of human AIM II. The sense primer (5'-TTTCGTIGATCGGICA-3' (SEQ ID NO:62) in which I denotes inosine) carries a sequence corresponding to the human AIM II sequence at 31–47. The antisense (5' AGGATGIACIACICCICC-3' (SEQ ID NO:63)) corresponds to human AIM II sequence at 609–626. Poly(A)$^+$ RNA from the spleen of BALB/c mice was reverse-transcribed, and subjected to PCR with the above primers. The sequence of the PCR product was highly homologous to that of human AIM II cDNA, and was used to isolate the missing 5' end and 3' end by the RACE (rapid amplification of cDNA ends) procedure using Marathon™ cDNA Amplification kit (Clontech, Palo Alto, Calif.). The full-length cDNA of the mouse AIM II was cloned into pcDNA3 vector (Invitrogen, Carlsbad, Calif.). The homology between mouse and human AIM II was analyzed by ClustalW program of Macvector 6.5.

Fusion proteins and antibodies. To prepare mouse LTβR-Ig fusion protein, a cDNA encoding mouse LTβR extracellular domain was generated by RT-PCR using the sense primer: (5'-AAAGGCCGCCATGGGCCT-3' (SEQ ID NO:64)) and the anti-sense primer: (5'-TTAAGCTTCAGTAGCATTGCTCCTGGCT-3' (SEQ ID NO:65)) from mouse lung mRNA. After digestion with NcoI/HindIII, the PCR product was used with a IL-3 leader sequence in p30242 vector and then sub-cloned into pX58 vector containing IE-175 promoter and Fc portion of human IgG1. The construct was then transfected into BHKIVP16 cells and the mouse LTβR-Ig fusion protein was purified from the conditioned media by a Sepharose Protein A affinity column. Fractions were then analyzed by SDS-PAGE through 4–20% gradient gels to confirm the presence of the desired protein and further dialyzed against PBS. Following purification, the resultant mouse LTβR-Ig was greater than 95% purity as determined from Coomassie blue staining of a SDS-PAGE gel.

To produce AIM II.flag fusion protein, a cDNA encoding mouse AIM II extracellular domain was fused with the flag peptide sequence, and was expressed in inclusion bodies in *E. coli*. After solubilization in 6M guanidine hydrochloride, the proteins were subsequently diluted and allowed to fold. The folded protein was then purified to near homogeneity by cation exchange chromatography. The final product was greater than 95% purity as determined from Coomassie blue staining of a SDS-PAGE gel. The endotoxin concentration was less than 1 pg/mg of purified protein according to LAL assays (CAPE COD, Woods Hole, Mass.).

Rabbit anti-mouse AIM II peptide antibodies were prepared at the Cocalico Biologicals, Inc. (Reamstown, Pa.) by immunization with a synthetic peptide (CEAGEEVVVRVPGNRLVRPRDGTRS (SEQ ID NO:66)) at 209–232 of mouse AIM II conjugated to KLH. The antibodies were affinity-purified from the serum with the peptide-conjugated column. Purified mAbs to mouse CD3, CD28, fluorescein isothiocynate (FITC)-conjugated CD4 and CD8 were purchased from Pharmingen (San Diego, Calif.). FITC-conjugated goat anti-human and anti-rabbit mAb were purchased from Biosource International (Camarillo, Calif.) and Southern Biotechnology Associates, Inc. (Birmingham, Ala.), respectively. Purified human IgG1 and rabbit IgG were purchased from Sigma (St. Louis, Mo.) and Rockland (Gilbertsville, Pa.), respectively.

Flow cytometric analysis. Human 293 cells ($1\times10^6$ cells) were transfected with either mouse AIM II pcDNA3 vector (10 µg) or mock vector (10 µg) by calcium phosphate methods. After 30 hr of transfection, 293 cells were harvested and stained with 1 µg of mouse LTβR-Ig or the anti-AIM II antibody in 50 µl of PBS supplemented with 5% FBS and 0.02% azide for 30 min at 4° C. The cells were then washed and further incubated with FITC-conjugated anti-human IgG or anti-rabbit IgG for 30 min at 4° C., respectively. Fluorescence was analyzed by a FACSCalibur flow cytometry (Becton Dickinson, Mountain View, Calif.) with Cell Quest software (Becton Dickinson).

Tumor therapy model. DBA/2 mice at groups of 5–10 were inoculated s.c. with $2\times10^5$ P815 cells. One week later, the mice with palpable tumors in 3–5 mm in average diameter were used for therapy. To prepare AIM II DNA for in vivo injection, 10 µg of the pmAIM II and 25 µg of cationic liposome, DMRIE-C (Gibco BRL), were mixed in 50 µl of Opti-MEM I (Gibco BRL) and incubated in polystyrene tube at room temperature for 30 min. The complex was injected intratumorally on day 7, 10, 14 and 17 after the tumor inoculation. For the controls, 50 µl of Opti-MEM I or the mixture of parental pcDNA3 (10 µg) and DMRIE-C (25 µg) in 50 µl of Opti-MEM I were injected as above. Tumor sizes were assessed by measuring perpendicular diameters every 3 or 4 days.

The DBA/2 mice which had regressed P815 tumor after the pmAIM II injections were re-challenged s.c. with $2\times10^5$ P815 cells at the right back and the same number of L1210 cells at the left back 40 days after primary tumor inoculation. Naive DBA/2 mice receiving with $2\times10^5$ cells of P815 and L1210 were used as controls. Afterwards, tumor sizes were assessed by measuring perpendicular diameters as described (Chen, L., et al., *Cell* 71:1093–1102 (1992)).

For CTL assay, splenocytes of DBA/2 mice that were inoculated with $2\times10^5$ P815 cells s.c. on day and treated with either pmAIM II or controls as described above on day 7, 9, 11 were harvested on day 18. Splenocytes ($5\times10^6$ cells/ml) were cultured in the presence of 150 Gy irradiated P815 cells for 4 days, and then assayed for CTL activity in a standard $^{51}$Cr release assay (Chen, L., et al., Cell 71:1093–1102 (1992)). After 4 hr of incubation, 100 µl of the supernatants were harvested and the radioactivity measured in a Micro-Beta TriLux liquid scintillation counter (Wallac, Finland).

GVHD model and in vitro allogeneic MLR. For the induction of acute GVHD, $7\times10^7$ cells of splenocytes from B6 mice were injected i.v. into either sub-lethally irradiated (4 Gy) or non-irradiated BDF1 recipients (B6-F1). The irradiated recipient mice were administered i.v. with 100 µg of LTβR-Ig, or control human IgG1 one day before splenocytes injection, and repeatedly administered every 3 days for additional 6 times. The mice were monitored survival and body weights daily. For the CTL assay, the non-irradiated recipients were administered i.v. with 100 µg of LTβR-Ig, or control Ig one day before splenocyte injection, and repeatedly administered every other day for additional 5 times. At day 11, CTL activity of the recipient splenocytes were assayed by co-culture with labeled P815 (H-$2^d$) or EL-4 (H-$2^b$) in a standard $^{51}$Cr release assay. The splenocytes from BDF1 mice received BDF1 splenocyte transfer (F1-F1) were used as a negative control. Identical experiments were also conducted using splenocytes from B6 LTα$^{-/-}$ mice, and age-matched B6 mice were used as controls in this experiment.

In vitro induction of CTL to alloantigens in MLR was performed as described (DeTongi, P., et al., Science 264:703–707 (1994)). Briefly, T cells were positively selected by FITC-conjugated anti-CD4 and CD8 mAb using anti-FITC microbeads in the magnetic field as instructed by manufacture (Miltenyi Biotec Inc. Auburn, Calif.). The purity of isolated T cells was >95% as assessed by flow cytometry using anti-CD3 mAb. Purified B6 LTα$^{-/-}$ mice T cells were co-cultured at $1\times10^6$ cells/ml with the same numbers of 30 Gy-irradiated BALB/c splenocytes in the presence or absence of LTβR-Ig or control human IgG1. After 5 days, the CTL activity against C26 (H-$2^d$) and EL-4 (H-$2^b$) was examined in a standard $^{51}$Cr release assay.

T cell costimulation assay. Magnetic bead-purified T cells at $1\times10^6$ cells/ml from splenocytes of mice were stimulated with plate-coated anti-CD3 mAb in the presence of 150 Gy-irradiated COS cells ($5\times10^4$ cell/ml), which had been transfected with either pcDNA3 or pmAIM II by DEAE-Dextran method for 48 hrs. Alternatively, anti-CD3-coated plates were further coated with the indicated doses of AIM II.flag fusion protein at 37° C. for 4 hr. After washing, T cells ($1\times10^6$ cells/ml) purified from spleen of either B6, CD28$^{-/-}$ mice or littermates were added into the wells. Anti-CD28 (1 µg/ml) mAb was used as soluble form. The proliferation of T cells was assessed by the addition of 1 µCi/well of $^3$H-TdR during the last 15 h of the 3-day culture. $^3$H-TdR incorporation was counted by a MicroBeta TriLux liquid scintillation counter (Wallac, Finland).

Cytokine assay. Purified B6 T cells at $1\times10^6$ cells/ml were stimulated with plate-coated AIM II. flag (3.2 µg/ml) in the presence of anti-CD3 (0.5 µg/ml) as described above. The culture supernatants were harvested at 48 hrs and assayed by sandwich ELISA for IFN-γ, GM-CSF, IL-4 and IL-10 following the manufacture's instructions (PharMingen). For assaying cytokine production in allogeneic MLR, purified B6 LTα$^{-/-}$ T cells at $1\times10^6$ cells/ml were stimulated with the same numbers of irradiated BALB/c splenocytes in the presence or absence of LTβR-Ig fusion protein and control human IgG. The culture supernatants were harvested at 72 hrs and assayed for IFN-γ, GM-CSF, IL-4 and IL-10 production by ELISA.

Example 23

Production of an Antibody

A. Hybridoma Technology

The antibodies of the present invention can be prepared by a variety of methods. (See, Ausubel et al., eds., 1998, Current Protocols in Molecular Biology, John Wiley & Sons, NY, Chapter 2.) As one example of such methods, cells expressing AIM II are administered to an animal to induce the production of sera containing polyclonal antibodies. In a preferred method, a preparation of AIM II protein is prepared and purified to render it substantially free of natural contaminants. Such a preparation is then introduced into an animal in order to produce polyclonal antisera of greater specific activity.

Monoclonal antibodies specific for protein AIM II are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with AIM II polypeptide or, more preferably, with a secreted AIM II polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981). The hybridoma cells obtained through such a selection are then assayed to identify clones which secrete antibodies capable of binding the AIM II polypeptide.

Alternatively, additional antibodies capable of binding to AIM II polypeptide can be produced in a two-step procedure using anti-idiotypic antibodies. Such a method makes use of the fact that antibodies are themselves antigens, and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the AIM II protein-specific antibody can be blocked by AIM II. Such antibodies comprise anti-idiotypic antibodies to the AIM II protein-specific antibody and are used to immunize an animal to induce formation of further AIM II protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed infra. (See, for review, Morrison, Science 229:1202 (1985); Oi et al., BioTechniques 4:214

(1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

B. Isolation of Antibody Fragments Directed Against AIM II From a Library of scFvs Naturally occurring V-genes isolated from human PBLs are constructed into a library of antibody fragments which contain reactivities against AIM II to which the donor may or may not have been exposed (see, e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately $10^9$ E. coli harboring the phagemid are used to inoculate 50 ml of 2×TY containing 1% glucose and 100 μg/ml of ampicillin (2×TY-AMP-GLU) and grown to an O.D. of 0.8 with shaking. Five ml of this culture is used to innoculate 50 ml of 2×TY-AMP-GLU, $2×10^8$ TU of delta gene 3 helper (M13 delta gene III, see PCT publication WO 92/01047) are added and the culture incubated at 37° C. for 45 minutes without shaking and then at 37° C. for 45 minutes with shaking. The culture is centriftiged at 4000 r.p.m. for 10 min. and the pellet resuspended in 2 liters of 2×TY containing 100 μg/ml ampicillin and 50 μg/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 μg ampicillin/ml and 25 μg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 μm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 μg/ml or 10 μg/ml of a polypeptide of the present invention. Tubes are blocked with 2% Marvel-PBS for 2 hours at 37° C. and then washed 3 times in PBS. Approximately $10^{13}$ TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 μg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks et al., 1991) from single colonies for assay. ELISAs are performed with microtitre plates coated with either 10 μg/ml of the polypeptide of the present invention in 50 mM bicarbonate pH 9.6. Clones positive in ELISA are further characterized by PCR fingerprinting (see, e.g., PCT publication WO 92/01047) and then by sequencing.

Example 24

Tissue Distribution of AIM II Expression

Northern blot analysis is carried out to examine the levels of expression of AIM II in human tissues, using methods described by, among other, Sambrook et al., cited above. Total cellular RNA samples are isolated with RNAzol™ B system (Biotecx Laboratories, Inc., 6023 South Loop East, Houston, Tex.).

About 10 μg of total RNA is isolated from tissue samples. The RNA is size resolved by electrophoresis through a 1% agarose gel under strongly denaturing conditions. RNA is blotted from the gel onto a nylon filter; and the filter then is prepared for hybridization to a detectably labeled polynucleotide probe.

As a probe to detect mRNA that encodes the AIM II, the antisense strand of the coding region of the cDNA insert in the deposited clone identified as ATCC Accession No. 97483 is labeled to a high specific activity. The cDNA is labeled by primer extension, using the Prime-It kit, available from Stratagene. The reaction is carried out using 50 ng of the cDNA, following the standard reaction protocol as recommended by the supplier. The labeled polynucleotide is purified away from other labeled reaction components by column chromatography using a Select-G-50 column, obtained from 5 Prime-3 Prime, Inc. of 5603 Arapahoe Road, Boulder, Colo.

The labeled probe is hybridized to the filter, at a concentration of 1,000,000 cpm/ml, in a small volume of 7% SDS, 0.5 M $NaPO_4$, pH 7.4 at 65° C., overnight.

Thereafter the probe solution is drained and the filter is washed twice at room temperature and twice at 60° C. with 0.5×SSC, 0.1% SDS. The filter is then dried and exposed to film at −70° C. overnight with an intensifying screen.

Autoradiography shows that mRNA for AIM II is abundant in spleen, bone marrow and thymus.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

SEQUENCE LISTING

<160> NUMBER OF SEQ ID NOS: 70

<210> SEQ ID NO 1
<211> LENGTH: 1169
<212> TYPE: DNA
<213> ORGANISM: Homo sapiens
<220> FEATURE:
<221> NAME/KEY: CDS
<222> LOCATION: (49)..(768)

<400> SEQUENCE: 1

| | | | | | |
|---|---|---|---|---|---|
| gaggttgaaag gacccaggcg tgtcagccct gctccagaga ccttgggc atg gag gag | | | | | 57 |
| | | | | Met Glu Glu | |
| | | | | 1 | |
| agt gtc gta cgg ccc tca gtg ttt gtg gtg gat gga cag acc gac atc | | | | | 105 |
| Ser Val Val Arg Pro Ser Val Phe Val Val Asp Gly Gln Thr Asp Ile | | | | | |
| 5 | | 10 | | 15 | |
| cca ttc acg agg ctg gga cga agc cac cgg aga cag tcg tgc agt gtg | | | | | 153 |
| Pro Phe Thr Arg Leu Gly Arg Ser His Arg Arg Gln Ser Cys Ser Val | | | | | |
| 20 | | 25 | 30 | | 35 |
| gcc cgg gtg ggt ctg ggt ctc ttg ctg ttg ctg atg ggg gct ggg ctg | | | | | 201 |
| Ala Arg Val Gly Leu Gly Leu Leu Leu Leu Leu Met Gly Ala Gly Leu | | | | | |
| | 40 | | 45 | | 50 |
| gcc gtc caa ggc tgg ttc ctc ctg cag ctg cac tgg cgt cta gga gag | | | | | 249 |
| Ala Val Gln Gly Trp Phe Leu Leu Gln Leu His Trp Arg Leu Gly Glu | | | | | |
| | 55 | | 60 | | 65 |
| atg gtc acc cgc ctg cct gac gga cct gca ggc tcc tgg gag cag ctg | | | | | 297 |
| Met Val Thr Arg Leu Pro Asp Gly Pro Ala Gly Ser Trp Glu Gln Leu | | | | | |
| | 70 | 75 | | 80 | |
| ata caa gag cga agg tct cac gag gtc aac cca gca gcg cat ctc aca | | | | | 345 |
| Ile Gln Glu Arg Arg Ser His Glu Val Asn Pro Ala Ala His Leu Thr | | | | | |
| 85 | | 90 | | 95 | |
| ggg gcc aac tcc agc ttg acc ggc agc ggg ggg ccg ctg tta tgg gag | | | | | 393 |
| Gly Ala Asn Ser Ser Leu Thr Gly Ser Gly Gly Pro Leu Leu Trp Glu | | | | | |
| 100 | | 105 | | 110 | 115 |
| act cag ctg ggc ctg gcc ttc ctg agg ggc ctc agc tac cac gat ggg | | | | | 441 |
| Thr Gln Leu Gly Leu Ala Phe Leu Arg Gly Leu Ser Tyr His Asp Gly | | | | | |
| | 120 | | 125 | | 130 |
| gcc ctt gtg gtc acc aaa gct ggc tac tac tac atc tac tcc aag gtg | | | | | 489 |
| Ala Leu Val Val Thr Lys Ala Gly Tyr Tyr Tyr Ile Tyr Ser Lys Val | | | | | |
| | 135 | | 140 | | 145 |
| cag ctg ggc ggt gtg ggc tgc ccg ctg ggc ctg gcc agc acc atc acc | | | | | 537 |
| Gln Leu Gly Gly Val Gly Cys Pro Leu Gly Leu Ala Ser Thr Ile Thr | | | | | |
| | 150 | | 155 | | 160 |
| cac ggc ctc tac aag cgc aca ccc cgc tac ccc gag gag ctg gag ctg | | | | | 585 |
| His Gly Leu Tyr Lys Arg Thr Pro Arg Tyr Pro Glu Glu Leu Glu Leu | | | | | |
| 165 | | 170 | | 175 | |
| ttg gtc agc cag cag tca ccc tgc gga cgg gcc acc agc agc tcc cgg | | | | | 633 |
| Leu Val Ser Gln Gln Ser Pro Cys Gly Arg Ala Thr Ser Ser Ser Arg | | | | | |
| 180 | | 185 | | 190 | 195 |
| gtc tgg tgg gac agc agc ttc ctg ggt ggt gta cac ctg gag gct | | | | | 681 |
| Val Trp Trp Asp Ser Ser Phe Leu Gly Gly Val Val His Leu Glu Ala | | | | | |
| | 200 | | 205 | | 210 |
| ggg gag gag gtg gtc gtc cgt gtg ctg gat gaa cgc ctg gtt cga ctg | | | | | 729 |
| Gly Glu Glu Val Val Val Arg Val Leu Asp Glu Arg Leu Val Arg Leu | | | | | |
| | 215 | | 220 | | 225 |
| cgt gat ggt acc cgg tct tac ttc ggg gct ttc atg gtg tgaaggaagg | | | | | 778 |
| Arg Asp Gly Thr Arg Ser Tyr Phe Gly Ala Phe Met Val | | | | | |
| | 230 | | 235 | 240 | |
| agcgtggtgc attggacatg ggtctgacac gtggagaact cagagggtgc ctcagggaa | | | | | 838 |

-continued

```
agaaaactca cgaagcagag gctgggcgtg gtggctctcg cctgtaatcc cagcactttg      898
ggaggccaag gcaggcggat cacctgaggt caggagttcg agaccagcct ggctaacatg      958
gcaaaacccc atctctacta aaaatacaaa aattagccgg acgtggtggt gcctgcctgt     1018 aatcccagcta ctcaggaggc tgaggcagga taattttgct taaacccggg aggcggaggt    1078
tgcagtgagc cgagatcaca ccactgcact ccaacctggg aaacgcagtg agactgtgcc     1138
tcaaaaaaaa aaaaaaaaa aaaaaaaaa a                                       1169
```

<210> SEQ ID NO 2
<211> LENGTH: 240
<212> TYPE: PRT
<213> ORGANISM: Homo sapiens

<400> SEQUENCE: 2

```
Met Glu Glu Ser Val Val Arg Pro Ser Val Phe Val Val Asp Gly Gln
  1               5                  10                  15

Thr Asp Ile Pro Phe Thr Arg Leu Gly Arg Ser His Arg Arg Gln Ser
                 20                  25                  30

Cys Ser Val Ala Arg Val Gly Leu Gly Leu Leu Leu Leu Leu Met Gly
             35                  40                  45

Ala Gly Leu Ala Val Gln Gly Trp Phe Leu Leu Gln Leu His Trp Arg
         50                  55                  60

Leu Gly Glu Met Val Thr Arg Leu Pro Asp Gly Pro Ala Gly Ser Trp
 65                  70                  75                  80

Glu Gln Leu Ile Gln Glu Arg Ser His Glu Val Asn Pro Ala Ala
                 85                  90                  95

His Leu Thr Gly Ala Asn Ser Ser Leu Thr Gly Ser Gly Pro Leu
            100                 105                 110

Leu Trp Glu Thr Gln Leu Gly Leu Ala Phe Leu Arg Gly Leu Ser Tyr
            115                 120                 125

His Asp Gly Ala Leu Val Val Thr Lys Ala Gly Tyr Tyr Tyr Ile Tyr
        130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 3
<211> LENGTH: 455
<212> TYPE: PRT
<213> ORGANISM: Homo sapiens

<400> SEQUENCE: 3

```
Met Gly Leu Ser Thr Val Pro Asp Leu Leu Leu Pro Leu Val Leu Leu
  1               5                  10                  15

Glu Leu Leu Val Gly Ile Tyr Pro Ser Gly Val Ile Gly Leu Val Pro
                 20                  25                  30
```

```
His Leu Gly Asp Arg Glu Lys Arg Asp Ser Val Cys Pro Gln Gly Lys
         35                  40                  45

Tyr Ile His Pro Gln Asn Asn Ser Ile Cys Cys Thr Lys Cys His Lys
     50                  55                  60

Gly Thr Tyr Leu Tyr Asn Asp Cys Pro Gly Pro Gly Gln Asp Thr Asp
 65              70                  75                      80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
             100                 105             110

Glu Ile Ser Ser Cys Thr Val Asp Arg Asp Thr Val Cys Gly Cys Arg
         115                 120             125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145             150                 155                     160

Lys Gln Asn Thr Val Cys Thr Cys His Ala Gly Phe Phe Leu Arg Glu
                 165             170                 175

Asn Glu Cys Val Ser Cys Ser Asn Cys Lys Lys Ser Leu Glu Cys Thr
             180                 185             190

Lys Leu Cys Leu Pro Gln Ile Glu Asn Val Lys Gly Thr Glu Asp Ser
         195                 200             205

Gly Thr Thr Val Leu Leu Pro Leu Val Ile Phe Phe Gly Leu Cys Leu
         210                 215             220

Leu Ser Leu Leu Phe Ile Gly Leu Met Tyr Arg Tyr Gln Arg Trp Lys
225             230                 235                     240

Ser Lys Leu Tyr Ser Ile Val Cys Gly Lys Ser Thr Pro Glu Lys Glu
                 245             250                 255

Gly Glu Leu Glu Gly Thr Thr Thr Lys Pro Leu Ala Pro Asn Pro Ser
             260                 265             270

Phe Ser Pro Thr Pro Gly Phe Thr Pro Thr Leu Gly Phe Ser Pro Val
         275                 280             285

Pro Ser Ser Thr Phe Thr Ser Ser Ser Thr Tyr Thr Pro Gly Asp Cys
         290                 295             300

Pro Asn Phe Ala Ala Pro Arg Arg Glu Val Ala Pro Pro Tyr Gln Gly
305             310                 315                     320

Ala Asp Pro Ile Leu Ala Thr Ala Leu Ala Ser Asp Pro Ile Pro Asn
                 325             330                 335

Pro Leu Gln Lys Trp Glu Asp Ser Ala His Lys Pro Gln Ser Leu Asp
             340                 345             350

Thr Asp Asp Pro Ala Thr Leu Tyr Ala Val Val Glu Asn Val Pro Pro
         355                 360             365

Leu Arg Trp Lys Glu Phe Val Arg Arg Leu Gly Leu Ser Asp His Glu
         370                 375             380

Ile Asp Arg Leu Glu Leu Gln Asn Gly Arg Cys Leu Arg Glu Ala Gln
385             390                 395                     400

Tyr Ser Met Leu Ala Thr Trp Arg Arg Arg Thr Pro Arg Arg Glu Ala
                 405             410                 415

Thr Leu Glu Leu Leu Gly Arg Val Leu Arg Asp Met Asp Leu Leu Gly
             420                 425             430

Cys Leu Glu Asp Ile Glu Glu Ala Leu Cys Gly Pro Ala Ala Leu Pro
         435                 440             445
```

```
Pro Ala Pro Ser Leu Leu Arg
    450             455

<210> SEQ ID NO 4
<211> LENGTH: 205
<212> TYPE: PRT
<213> ORGANISM: Homo sapiens

<400> SEQUENCE: 4

Met Thr Pro Pro Glu Arg Leu Phe Leu Pro Arg Val Cys Gly Thr Thr
 1               5                  10                  15

Leu His Leu Leu Leu Leu Gly Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
        50                  55                  60

Ala His Leu Ile Gly Asp Pro Ser Lys Gln Asn Ser Leu Leu Trp Arg
 65                 70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205

<210> SEQ ID NO 5
<211> LENGTH: 205
<212> TYPE: PRT
<213> ORGANISM: Homo sapiens

<400> SEQUENCE: 5

Met Thr Pro Pro Glu Arg Leu Phe Leu Pro Arg Val Cys Gly Thr Thr
 1               5                  10                  15

Leu His Leu Leu Leu Leu Gly Leu Leu Val Leu Leu Pro Gly Ala
            20                  25                  30

Gln Gly Leu Pro Gly Val Gly Leu Thr Pro Ser Ala Ala Gln Thr Ala
            35                  40                  45

Arg Gln His Pro Lys Met His Leu Ala His Ser Thr Leu Lys Pro Ala
        50                  55                  60

Ala His Leu Ile Gly Asp Pro Ser Lys Gln Asn Ser Leu Leu Trp Arg
 65                 70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110
```

```
Val Val Phe Ser Gly Lys Ala Tyr Ser Pro Lys Ala Thr Ser Ser Pro
            115                 120                 125

Leu Tyr Leu Ala His Glu Val Gln Leu Phe Ser Ser Gln Tyr Pro Phe
        130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                    165                 170                 175

Gln Gly Asp Gln Leu Ser Thr His Thr Asp Gly Ile Pro His Leu Val
                180                 185                 190

Leu Ser Pro Ser Thr Val Phe Phe Gly Ala Phe Ala Leu
            195                 200                 205

<210> SEQ ID NO 6
<211> LENGTH: 281
<212> TYPE: PRT
<213> ORGANISM: Homo sapiens

<400> SEQUENCE: 6

Met Gln Gln Pro Phe Asn Tyr Pro Tyr Pro Gln Ile Tyr Trp Val Asp
  1               5                  10                  15

Ser Ser Ala Ser Ser Pro Trp Ala Pro Pro Gly Thr Val Leu Pro Cys
                 20                  25                  30

Pro Thr Ser Val Pro Arg Arg Pro Gly Gln Arg Arg Pro Pro Pro Pro
             35                  40                  45

Pro Pro Pro Pro Pro Leu Pro Pro Pro Pro Pro Pro Pro Pro Leu Pro
         50                  55                  60

Pro Leu Pro Leu Pro Pro Leu Lys Lys Arg Gly Asn His Ser Thr Gly
 65                  70                  75                  80

Leu Cys Leu Leu Val Met Phe Phe Met Val Leu Val Ala Leu Val Gly
                 85                  90                  95

Leu Gly Leu Gly Met Phe Gln Leu Phe His Leu Gln Lys Glu Leu Ala
                100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
                180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
            275                 280
```

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 7
gcgggatccg gagagatggt cacc                                              24

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 8
cgcaagcttc cttcacacca tgaaagc                                           27

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: DNA Primer

<400> SEQUENCE: 9
gaccggatcc atggaggaga gtgtcgtacg gc                                     32

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 10
cgcaagcttc cttcacacca tgaaagc                                           27

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: DNA Primer

<400> SEQUENCE: 11
gctccaggat ccgccatcat ggaggagagt gtcgtacggc                             40

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: DNA Primer

<400> SEQUENCE: 12
gacgcggtac cgtccaatgc accacgctcc ttccttc                                37

<210> SEQ ID NO 13
<211> LENGTH: 40
<212> TYPE: DNA
<213> ORGANISM: Artificial Sequence
<220> FEATURE:

<223> OTHER INFORMATION: Description of Artificial Sequence: DNA Primer

<400> SEQUENCE: 13
gagctcggat ccgccatcat ggaggagagt gtcgtacggc                               40

<210> SEQ ID NO 14
<211> LENGTH: 71
<212> TYPE: DNA
<213> ORGANISM: Artificial Sequence
<220> FEATURE:
<223> OTHER INFORMATION: Description of Artificial Sequence: DNA Primer

<400> SEQUENCE: 14
gatgttctag aaagcgtagt ctgggacgtc gtatgggtac accatgaaag ccccgaagta        60
agaccgggta c                                                              71

<210> SEQ ID NO 15
<211> LENGTH: 40
<212> TYPE: DNA
<213> ORGANISM: Artificial Sequence
<220> FEATURE:
<223> OTHER INFORMATION: Description of Artificial Sequence: DNA Primer

<400> SEQUENCE: 15
gctccaggat ccgccatcat ggaggagagt gtcgtacggc                               40

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: DNA Primer

<400> SEQUENCE: 16
gacgcggtac cgtccaatgc accacgctcc ttccttc                                  37

<210> SEQ ID NO 17
<211> LENGTH: 32
<212> TYPE: DNA
<213> ORGANISM: Artificial Sequence
<220> FEATURE:
<223> OTHER INFORMATION: Description of Artificial Sequence: DNA Primer

<400> SEQUENCE: 17
gacgcccatg gaggaggaga gtgtcgtacg gc                                       32

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: DNA Primer

<400> SEQUENCE: 18
gaccggatcc caccatgaaa gccccgaagt aag                                      33

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 19
cgcaagcttc cttcacacca tgaaagc                                             27

<210> SEQ ID NO 20
<211> LENGTH: 503
<212> TYPE: DNA
<213> ORGANISM: Homo sapiens

<400> SEQUENCE: 20

```
aattccccgg gaccggntgg gtctgggtct cttgctgttg ctgatggggg ccgggctggn      60
cgtncaaggc tggttcctcc tgcagctgca ctggngtcta ggngagatgg tcacccgcct     120
gcctgaacgg acctgcaggc tcctgggagc agctgataca agagcgangt ctcacgaggt     180
caacccagca gcgcatctca caggggccaa ctccagcttg accggcagcg ggggccgct      240 tttatgggag actcagctgg gnctggncttt cctgagggggt ntcanctacc acgatggggn    300
cccttntggt naccaaagtt gggtactact nacaacttat tncaagnggc agttgggcgg    360
tgttgggttg cccnctgggg ctgggnaaaa aannanaaaa naagggcttt taaaaagggg    420
aaaaccggtt aacncgaggn agntggagtt tttggttnaa ncatgattaa acctgggnag    480
ggncanaaaa aatncnggtg ntt                                           503
```

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: DNA Primer

<400> SEQUENCE: 21

```
gggggatcca tggtcacccg cctgcc                                         26
```

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: DNA Primer

<400> SEQUENCE: 22

```
gggaagcttc accatgaaag ccccg                                          25
```

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: DNA Primer

<400> SEQUENCE: 23

```
gggccatgga tggtcacccg cctgcc                                         26
```

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence: DNA Primer

<400> SEQUENCE: 24

```
gggccatggg ccaactccag cttgacc                                        27
```

<210> SEQ ID NO 25
<211> LENGTH: 31
<212> TYPE: DNA

```
<213> ORGANISM: Artificial Sequence
<220> FEATURE:
<223> OTHER INFORMATION: Description of Artificial Sequence: DNA Primer

<400> SEQUENCE: 25
gggggatccc gcagctgcac tggcgtctag g                              31

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: DNA Primer

<400> SEQUENCE: 26
gggtctagac accatgaaag ccccg                                     25

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: DNA Primer

<400> SEQUENCE: 27
cgcggatccc tcctgggagc agctgatac                                 29

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 28
gggggatcct gacaccatga aagccccg                                  28

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: DNA Primer

<400> SEQUENCE: 29
cgcggatcct cacaccatga aagc                                      24

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: DNA Primer

<400> SEQUENCE: 30
gggggatccc accatgaaag ccccg                                     25

<210> SEQ ID NO 31
<211> LENGTH: 733
<212> TYPE: DNA
<213> ORGANISM: Homo sapiens

<400> SEQUENCE: 31
gggatccgga gcccaaatct tctgacaaaa ctcacacatg cccaccgtgc ccagcacctg     60
aattcgaggg tgcaccgtca gtcttcctct tccccccaaa acccaaggac accctcatga   120
```

```
tctcccggac tcctgaggtc acatgcgtgg tggtggacgt aagccacgaa gaccctgagg      180
tcaagttcaa ctggtacgtg gacggcgtgg aggtgcataa tgccaagaca aagccgcggg      240
aggagcagta caacagcacg taccgtgtgg tcagcgtcct caccgtcctg caccaggact      300
ggctgaatgg caaggagtac aagtgcaagg tctccaacaa agccctccca accccatcg       360 agaaaaccat ctccaaagcc aagggcagc cccgagaacc acaggtgtac accctgcccc       420
catcccggga tgagctgacc aagaaccagg tcagcctgac ctgcctggtc aaaggcttct      480
atccaagcga catcgccgtg gagtgggaga gcaatgggca gccggagaac aactacaaga      540
ccacgcctcc cgtgctggac tccgacggct ccttcttcct ctacagcaag ctcaccgtgg      600
acaagagcag gtggcagcag gggaacgtct tctcatgctc cgtgatgcat gaggctctgc      660
acaaccacta cacgcagaag agcctctccc tgtctccggg taaatgagtg cgacggccgc      720
gactctagag gat                                                         733
```

```
<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: DNA Primer

<400> SEQUENCE: 32
ggggtcgacg ccatcatgga ggagagtgtc gtacgg                                 36

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: DNA Primer

<400> SEQUENCE: 33
ggggcggccg cgccttcaca ccatgaaagc cccg                                   34

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: DNA Primer

<400> SEQUENCE: 34
ggggcggccg cgccatcatg gaggagagtg tcgtacgg                               38

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: DNA Primer

<400> SEQUENCE: 35
ggggtcgacg ccttcacacc atgaaagccc cg                                     32

<210> SEQ ID NO 36
<211> LENGTH: 93
<212> TYPE: DNA
<213> ORGANISM: Artificial Sequence
<220> FEATURE:
<223> OTHER INFORMATION: Description of Artificial Sequence: DNA Primer

<400> SEQUENCE: 36
```
ggggcggccg cgccatcatg aaggtctccg tggctgccct ctcctgcctc atgcttgtta   60
ctgcccttgg atcgcaggca gctgcactgg cgt                                93

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 37
ggggtcgact cacaccatga aagcccccg                                     28

<210> SEQ ID NO 38
<211> LENGTH: 1017
<212> TYPE: DNA
<213> ORGANISM: Homo sapiens
<220> FEATURE:
<221> NAME/KEY: CDS
<222> LOCATION: (1)..(624)

<400> SEQUENCE: 38

| att ccc cgg gcc cgg gtg ggt ctg ggt ctc ttg ctg ttg ctg atg ggg | 48 |
|---|---|
| Ile Pro Arg Ala Arg Val Gly Leu Gly Leu Leu Leu Leu Leu Met Gly | |
| 1               5                   10                  15 | |

| gcc ggg ctg gcc gtc caa ggc tgg ttc ctc ctg cag ctg cac tgg cgt | 96 |
|---|---|
| Ala Gly Leu Ala Val Gln Gly Trp Phe Leu Leu Gln Leu His Trp Arg | |
|         20                  25                  30 | |

| cta gga gag atg gtc acc cgc ctg cct gac gga cct gca ggc tcc tgg | 144 |
|---|---|
| Leu Gly Glu Met Val Thr Arg Leu Pro Asp Gly Pro Ala Gly Ser Trp | |
|     35                  40                  45 | |

| gag cag ctg ata caa gag cga agg tct cac gag gtc aac cca gca gcg | 192 |
|---|---|
| Glu Gln Leu Ile Gln Glu Arg Arg Ser His Glu Val Asn Pro Ala Ala | |
| 50                  55                  60 | |

| cat ctc aca ggg gcc aac tcc agc ttg acc ggc agc ggg ggg ccg ctg | 240 |
|---|---|
| His Leu Thr Gly Ala Asn Ser Ser Leu Thr Gly Ser Gly Gly Pro Leu | |
| 65                  70                  75                  80 | |

| tta tgg gag act cag ctg ggc ctg gcc ttc ctg agg ggc ctc agc tac | 288 |
|---|---|
| Leu Trp Glu Thr Gln Leu Gly Leu Ala Phe Leu Arg Gly Leu Ser Tyr | |
|         85                  90                  95 | |

| cac gat ggg gcc ctt gtg gtc acc aaa gct ggc tac tac tac atc tac | 336 |
|---|---|
| His Asp Gly Ala Leu Val Val Thr Lys Ala Gly Tyr Tyr Tyr Ile Tyr | |
|         100                 105                 110 | |

| tcc aag gtg cag ctg ggc ggt gtg ggc tgc ccg ctg ggc ctg gcc agc | 384 |
|---|---|
| Ser Lys Val Gln Leu Gly Gly Val Gly Cys Pro Leu Gly Leu Ala Ser | |
|     115                 120                 125 | |

| acc atc acc cac ggc ctc tac aag cgc aca ccc cgc tac ccc gag gag | 432 |
|---|---|
| Thr Ile Thr His Gly Leu Tyr Lys Arg Thr Pro Arg Tyr Pro Glu Glu | |
| 130                 135                 140 | |

| ctg gag ctg ttg gtc agc cag cag tca ccc tgc gga cgg gcc acc agc | 480 |
|---|---|
| Leu Glu Leu Leu Val Ser Gln Gln Ser Pro Cys Gly Arg Ala Thr Ser | |
| 145                 150                 155                 160 | |

| agc tcc cgg gtc tgg tgg gac agc agc ttc ctg ggt ggt gtg gta cac | 528 |
|---|---|
| Ser Ser Arg Val Trp Trp Asp Ser Ser Phe Leu Gly Gly Val Val His | |
|         165                 170                 175 | |

| ctg gag gct ggg gag gag gtg gtc gtc cgt gtg ctg gat gaa cgc ctg | 576 |
|---|---|
| Leu Glu Ala Gly Glu Glu Val Val Val Arg Val Leu Asp Glu Arg Leu | |
|         180                 185                 190 | |

| gtt cga ctg cgt gat ggt acc cgg tct tac ttc ggg gct ttc atg gtg | 624 |
|---|---|
| Val Arg Leu Arg Asp Gly Thr Arg Ser Tyr Phe Gly Ala Phe Met Val | |
|     195                 200                 205 | |

-continued

```
tgaaggaagg agcgtggtgc attggacatg ggtctgacac gtggagaact cagagggtgc    684
ctcaggggaa agaaaactca cgaagcagag gctgggcgtg gtggctctcg cctgtaatcc    744
cagcactttg ggaggccaag gcaggcggat cacctgaggt caggagttcg agaccagcct    804
ggctaacatg gcaaaacccc atctctacta aaaatacaaa aattagccgg acgtggtggt    864
gcctgcctgt aatccagcta ctcaggaggc tgaggcagga taattttgct aaacccggg    924 aggcggaggt tgcagtgagc cgagatcaca ccactgcact ccaacctggg aaacgcagtg    984
agactgtgcc tcaaaaaaaa caaaaaaaaa aaa                                 1017
```

<210> SEQ ID NO 39
<211> LENGTH: 208
<212> TYPE: PRT
<213> ORGANISM: Homo sapiens

<400> SEQUENCE: 39

```
Ile Pro Arg Ala Arg Val Gly Leu Gly Leu Leu Leu Leu Met Gly
 1               5                  10                  15

Ala Gly Leu Ala Val Gln Gly Trp Phe Leu Leu Gln Leu His Trp Arg
            20                  25                  30

Leu Gly Glu Met Val Thr Arg Leu Pro Asp Gly Pro Ala Gly Ser Trp
        35                  40                  45

Glu Gln Leu Ile Gln Glu Arg Arg Ser His Glu Val Asn Pro Ala Ala
    50                  55                  60

His Leu Thr Gly Ala Asn Ser Ser Leu Thr Gly Ser Gly Gly Pro Leu
65                  70                  75                  80

Leu Trp Glu Thr Gln Leu Gly Leu Ala Phe Leu Arg Gly Leu Ser Tyr
                85                  90                  95

His Asp Gly Ala Leu Val Val Thr Lys Ala Gly Tyr Tyr Tyr Ile Tyr
            100                 105                 110

Ser Lys Val Gln Leu Gly Gly Val Gly Cys Pro Leu Gly Leu Ala Ser
        115                 120                 125

Thr Ile Thr His Gly Leu Tyr Lys Arg Thr Pro Arg Tyr Pro Glu Glu
    130                 135                 140

Leu Glu Leu Leu Val Ser Gln Gln Ser Pro Cys Gly Arg Ala Thr Ser
145                 150                 155                 160

Ser Ser Arg Val Trp Trp Asp Ser Ser Phe Leu Gly Gly Val Val His
                165                 170                 175

Leu Glu Ala Gly Glu Glu Val Val Arg Val Leu Asp Glu Arg Leu
            180                 185                 190

Val Arg Leu Arg Asp Gly Thr Arg Ser Tyr Phe Gly Ala Phe Met Val
        195                 200                 205
```

<210> SEQ ID NO 40
<211> LENGTH: 43
<212> TYPE: DNA
<213> ORGANISM: Homo sapiens

<400> SEQUENCE: 40

```
gacagtggat ccgccaccat ggtcacccgc ctgcctgacg gac                       43
```

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: DNA Primer

<400> SEQUENCE: 41
cgcggatcct gggagcagct gatac                                                25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: DNA Primer

<400> SEQUENCE: 42
cgccatatga cccgcctgcc tgacg                                                25

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 43
cgccatatga gctgggagca gctgatac                                             28

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 44
cgccatatga gcagcttgac cggcagcg                                             28

<210> SEQ ID NO 45
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 45
cgcggtacct tacaccatga aagccccg                                             28

<210> SEQ ID NO 46
<211> LENGTH: 11
<212> TYPE: PRT
<213> ORGANISM: Homo sapiens

<400> SEQUENCE: 46

Gly Leu Tyr Leu Ile Tyr Ser Gln Val Leu Phe
 1               5                  10

<210> SEQ ID NO 47
<211> LENGTH: 11
<212> TYPE: PRT
<213> ORGANISM: Homo sapiens

<400> SEQUENCE: 47

Gly Tyr Tyr Tyr Ile Tyr Ser Lys Val Gln Leu
 1               5                  10

<210> SEQ ID NO 48
<211> LENGTH: 28
<212> TYPE: DNA

<213> ORGANISM: Artificial Sequence
<220> FEATURE:
<223> OTHER INFORMATION: Description of Artificial Sequence: DNA Primer

<400> SEQUENCE: 48
cgggatccat gctcctgcct tgggccac                                              28

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: DNA Primer

<400> SEQUENCE: 49
gcggatcctg ggggcagtgg ctctaatgg                                             29

<210> SEQ ID NO 50
<211> LENGTH: 3974
<212> TYPE: DNA
<213> ORGANISM: Artificial Sequence
<220> FEATURE:
<223> OTHER INFORMATION: Description of Artificial Sequence: Vector

<400> SEQUENCE: 50

| | | | | | |
|---|---|---|---|---|---|
| ggtacctaag | tgagtagggc | gtccgatcga | cggacgcctt | tttttttgaat | tcgtaatcat | 60 |
| ggtcatagct | gtttcctgtg | tgaaattgtt | atccgctcac | aattccacac | aacatacgag | 120 |
| ccggaagcat | aaagtgtaaa | gcctggggtg | cctaatgagt | gagctaactc | acattaattg | 180 |
| cgttgcgctc | actgcccgct | ttccagtcgg | gaaacctgtc | gtgccagctg | cattaatgaa | 240 |
| tcggccaacg | cgcggggaga | ggcggtttgc | gtattgggcg | ctcttccgct | tcctcgctca | 300 |
| ctgactcgct | gcgctcggtc | gttcggctgc | ggcgagcggt | atcagctcac | tcaaaggcgg | 360 |
| taatacggtt | atccacagaa | tcaggggata | acgcaggaaa | gaacatgtga | gcaaaaggcc | 420 |
| agcaaaaggc | caggaaccgt | aaaaaggccg | cgttgctggc | gtttttccat | aggctccgcc | 480 |
| cccctgacga | gcatcacaaa | aatcgacgct | caagtcagag | gtggcgaaac | ccgacaggac | 540 |
| tataaagata | ccaggcgttt | ccccctggaa | gctccctcgt | gcgctctcct | gttccgaccc | 600 |
| tgccgcttac | cggatacctg | tccgcctttc | tcccttcggg | aagcgtggcg | ctttctcata | 660 |
| gctcacgctg | taggtatctc | agttcggtgt | aggtcgttcg | ctccaagctg | ggctgtgtgc | 720 |
| acgaaccccc | cgttcagccc | gaccgctgcg | ccttatccgg | taactatcgt | cttgagtcca | 780 |
| acccggtaag | acacgactta | tcgccactgg | cagcagccac | tggtaacagg | attagcagag | 840 |
| cgaggtatgt | aggcggtgct | acagagttct | tgaagtggtg | gcctaactac | ggctacacta | 900 |
| gaagaacagt | atttggtatc | tgcgctctgc | tgaagccagt | taccttcgga | aaaagagttg | 960 |
| gtagctcttg | atccggcaaa | caaaccaccg | ctggtagcgg | tggttttttt | gtttgcaagc | 1020 |
| agcagattac | gcgcagaaaa | aaaggatctc | aagaagatcc | tttgatcttt | tctacggggt | 1080 |
| ctgacgctca | gtggaacgaa | aactcacgtt | aagggatttt | ggtcatgaga | ttatcgtcga | 1140 |
| caattcgcgc | gcgaaggcga | agcggcatgc | atttacgttg | acaccatcga | atggtgcaaa | 1200 |
| acctttcgcg | gtatggcatg | atagcgcccg | gaagagagtc | aattcagggt | ggtgaatgtg | 1260 |
| aaaccagtaa | cgttatacga | tgtcgcagag | tatgccggtg | tctcttatca | gaccgtttcc | 1320 |
| cgcgtggtga | accaggccag | ccacgtttct | gcgaaaacgc | gggaaaaagt | ggaagcggcg | 1380 |
| atggcggagc | tgaattacat | tcccaaccgc | gtggcacaac | aactggcggg | caaacagtcg | 1440 |
| ttgctgattg | gcgttgccac | ctccagtctg | gccctgcacg | cgccgtcgca | aattgtcgcg | 1500 |

-continued

```
gcgattaaat ctcgcgccga tcaactgggt gccagcgtgg tggtgtcgat ggtagaacga    1560
agcggcgtcg aagcctgtaa agcggcggtg cacaatcttc tcgcgcaacg cgtcagtggg    1620
ctgatcatta actatccgct ggatgaccag gatgccattg ctgtggaagc tgcctgcact    1680
aatgttccgg cgttatttct tgatgtctct gaccagacac ccatcaacag tattattttc    1740
tcccatgaag acggtacgcg actgggcgtg gagcatctgt tcgcattggg tcaccagcaa    1800
atcgcgctgt tagcgggccc attaagttct gtctcggcgc gtctgcgtct ggctggctgg    1860
cataaatatc tcactcgcaa tcaaattcag ccgatagcgg aacgggaagg cgactggagt    1920
gccatgtccg gttttcaaca aaccatgcaa atgctgaatg agggcatcgt tcccactgcg    1980
atgctggttg ccaacgatca gatggcgctg gcgcaatgc cgccattac cgagtccggg    2040
ctgcgcgttg gtgcggatat ctcggtagtg ggatacgacg ataccgaaga cagctcatgt    2100
tatatcccgc cgttaaccac catcaaacag gattttcgcc tgctggggca aaccagcgtg    2160
gaccgcttgc tgcaactctc tcagggccag gcggtgaagg gcaatcagct gttgcccgtc    2220
tcactggtga aagaaaaaac cacctggcg cccaatacgc aaaccgcctc tccccgcgcg    2280
ttggccgatt cattaatgca gctggcacga caggtttccc gactggaaag cgggcagtga    2340
gcgcaacgca attaatgtaa gttagcgcga attgtcgacc aaagcggcca tcgtgcctcc    2400
ccactcctgc agttcggggg catggatgcg cggatagccg ctgctggttt cctggatgcc    2460
gacggatttg cactgccggt agaactccgg gaggtcgtcc agcctcaggc agcagctgaa    2520
ccaactcgcg aggggatcga gcccggggtg ggcgaagaac tccagcatga gatccccgcg    2580
ctggaggatc atccagccgg cgtcccggaa aacgattccg aagcccaacc tttcatagaa    2640
ggcggcggtg gaatcgaaat ctcgtgatgg caggttgggc gtcgcttggt cggtcatttc    2700
gaacccagaa gtcccgctca gaagaactcg tcaagaaggc gatagaaggc gatgcgctgc    2760
gaatcgggag cggcgatacc gtaaagcacg aggaagcggt cagcccattc gccgccaagc    2820
tcttcagcaa tatcacgggt agccaacgct atgtcctgat agcggtccgc cacacccagc    2880
cggccacagt cgatgaatcc agaaaagcgg ccattttcca ccatgatatt cggcaagcag    2940
gcatcgccat gggtcacgac gagatcctcg ccgtcgggca tgcgcgcctt gagcctggcg    3000
aacagttcgg ctggcgcgag cccctgatgc tcttcgtcca gatcatcctg atcgacaaga    3060
ccggcttcca tccgagtacg tgctcgctcg atgcgatgtt tcgcttggtg gtcgaatggg    3120
caggtagccg gatcaagcgt atgcagccgc cgcattgcat cagccatgat ggatactttc    3180
tcggcaggag caaggtgaga tgacaggaga tcctgccccg gcacttcgcc caatagcagc    3240
cagtcccttc ccgcttcagt gacaacgtcg agcacagctg cgcaaggaac gcccgtcgtg    3300
gccagccacg atagccgcgc tgcctcgtcc tgcagttcat tcagggcacc ggacaggtcg    3360
gtcttgacaa aaagaaccgg cgccccctgc gctgacagcc ggaacacggc ggcatcagag    3420
cagccgattg tctgttgtgc ccagtcatag ccgaatagcc tctccaccca agcggccgga    3480
gaacctgcgt gcaatccatc ttgttcaatc atgcgaaacg atcctcatcc tgtctcttga    3540
tcagatcttg atcccctgcg ccatcagatc cttggcggca agaaagccat ccagtttact    3600
ttgcagggct tcccaacctt accagagggc gccccagctg gcaattccgg ttcgcttgct    3660
gtccataaaa ccgcccagtc tagctatcgc catgtaagcc cactgcaagc tacctgcttt    3720
ctctttgcgc ttgcgttttc ccttgtccag atagcccagt agctgacatt catccggggt    3780
cagcaccgtt tctgcggact ggctttctac gtgttccgct tcctttagca gcccttgcgc    3840
```

```
cctgagtgct tgcggcagcg tgaagcttaa aaaactgcaa aaatagttt gacttgtgag      3900 cggataacaa ttaagatgta cccaattgtg agcggataac aatttcacac attaaagagg    3960
agaaattaca tatg                                                       3974
```

<210> SEQ ID NO 51
<211> LENGTH: 112
<212> TYPE: DNA
<213> ORGANISM: Artificial Sequence
<220> FEATURE:
<223> OTHER INFORMATION: Description of Artificial Sequence: Promoter
      Region

<400> SEQUENCE: 51

```
aagcttaaaa aactgcaaaa aatagtttga cttgtgagcg ataacaatt aagatgtacc     60 caattgtgag cggataacaa tttcacacat taaagaggag aaattacata tg            112
```

<210> SEQ ID NO 52
<211> LENGTH: 300
<212> TYPE: PRT
<213> ORGANISM: Homo sapiens

<400> SEQUENCE: 52

```
Met Arg Ala Leu Glu Gly Pro Gly Leu Ser Leu Leu Cys Leu Val Leu
  1               5                  10                  15

Ala Leu Pro Ala Leu Leu Pro Val Pro Ala Val Arg Gly Val Ala Glu
                 20                  25                  30

Thr Pro Thr Tyr Pro Trp Arg Asp Ala Glu Thr Gly Glu Arg Leu Val
             35                  40                  45

Cys Ala Gln Cys Pro Pro Gly Thr Phe Val Gln Arg Pro Cys Arg Arg
         50                  55                  60

Asp Ser Pro Thr Thr Cys Gly Pro Cys Pro Arg His Tyr Thr Gln
 65                  70                  75                  80

Phe Trp Asn Tyr Leu Glu Arg Cys Arg Tyr Cys Asn Val Leu Cys Gly
                 85                  90                  95

Glu Arg Glu Glu Glu Ala Arg Ala Cys His Ala Thr His Asn Arg Ala
                100                 105                 110

Cys Arg Cys Arg Thr Gly Phe Phe Ala His Ala Gly Phe Cys Leu Glu
            115                 120                 125

His Ala Ser Cys Pro Pro Gly Ala Gly Val Ile Ala Pro Gly Thr Pro
        130                 135                 140

Ser Gln Asn Thr Gln Cys Gln Pro Cys Pro Pro Gly Thr Phe Ser Ala
145                 150                 155                 160

Ser Ser Ser Ser Ser Glu Gln Cys Gln Pro His Arg Asn Cys Thr Ala
                165                 170                 175

Leu Gly Leu Ala Leu Asn Val Pro Gly Ser Ser Ser His Asp Thr Leu
            180                 185                 190

Cys Thr Ser Cys Thr Gly Phe Pro Leu Ser Thr Arg Val Pro Gly Ala
        195                 200                 205

Glu Glu Cys Glu Arg Ala Val Ile Asp Phe Val Ala Phe Gln Asp Ile
    210                 215                 220

Ser Ile Lys Arg Leu Gln Arg Leu Leu Gln Ala Leu Glu Ala Pro Glu
225                 230                 235                 240

Gly Trp Gly Pro Thr Pro Arg Ala Gly Arg Ala Ala Leu Gln Leu Lys
                245                 250                 255

Leu Arg Arg Arg Leu Thr Glu Leu Leu Gly Ala Gln Asp Gly Ala Leu
            260                 265                 270
```

```
Leu Val Arg Leu Leu Gln Ala Leu Arg Val Ala Arg Met Pro Gly Leu
            275                 280                 285

Glu Arg Ser Val Arg Glu Arg Phe Leu Pro Val His
            290                 295                 300

<210> SEQ ID NO 53
<211> LENGTH: 154
<212> TYPE: PRT
<213> ORGANISM: Homo sapiens

<400> SEQUENCE: 53

Val Cys Pro Gln Gly Lys Tyr Ile His Pro Gln Asn Asn Ser Ile Cys
  1               5                  10                  15

Cys Thr Lys Cys His Lys Gly Thr Tyr Leu Tyr Asn Asp Cys Pro Gly
             20                  25                  30

Pro Gly Gln Asp Thr Asp Cys Arg Glu Cys Glu Ser Gly Ser Phe Thr
         35                  40                  45

Ala Ser Glu Asn His Leu Arg His Cys Leu Ser Cys Ser Lys Cys Arg
     50                  55                  60

Lys Glu Met Gly Gln Val Glu Ile Ser Ser Cys Thr Val Asp Arg Asp
 65                  70                  75                  80

Thr Val Cys Gly Cys Arg Lys Asn Gln Tyr Arg His Tyr Trp Ser Glu
                 85                  90                  95

Asn Leu Phe Gln Cys Phe Asn Cys Ser Leu Cys Leu Asn Gly Thr Val
            100                 105                 110

His Leu Ser Cys Gln Glu Lys Gln Asn Thr Val Cys Thr Cys His Ala
        115                 120                 125

Gly Phe Phe Leu Arg Glu Asn Glu Cys Val Ser Cys Ser Asn Cys Lys
    130                 135                 140

Lys Ser Leu Glu Cys Thr Lys Leu Cys Leu
145                 150

<210> SEQ ID NO 54
<211> LENGTH: 163
<212> TYPE: PRT
<213> ORGANISM: Homo sapiens

<400> SEQUENCE: 54

Thr Cys Arg Leu Arg Glu Tyr Tyr Asp Gln Thr Ala Gln Met Cys Cys
  1               5                  10                  15

Ser Lys Cys Ser Pro Gly Gln His Ala Lys Val Phe Cys Thr Lys Thr
             20                  25                  30

Ser Asp Thr Val Cys Asp Ser Cys Glu Asp Ser Thr Tyr Thr Gln Leu
         35                  40                  45

Trp Asn Trp Val Pro Glu Cys Leu Ser Cys Gly Ser Arg Cys Ser Ser
     50                  55                  60

Asp Gln Val Glu Thr Gln Ala Cys Thr Arg Glu Gln Asn Arg Ile Cys
 65                  70                  75                  80

Thr Cys Arg Pro Gly Trp Tyr Cys Ala Leu Ser Lys Gln Glu Gly Cys
                 85                  90                  95

Arg Leu Cys Ala Pro Leu Arg Lys Cys Arg Pro Gly Phe Gly Val Ala
            100                 105                 110

Arg Pro Gly Thr Glu Thr Ser Asp Val Val Cys Lys Pro Cys Ala Pro
        115                 120                 125

Gly Thr Phe Ser Asn Thr Thr Ser Ser Thr Asp Ile Cys Arg Pro His
    130                 135                 140
```

```
Gln Ile Cys Asn Val Val Ala Ile Pro Gly Asn Ala Ser Met Asp Ala
145                 150                 155                 160

Val Cys Thr

<210> SEQ ID NO 55
<211> LENGTH: 132
<212> TYPE: PRT
<213> ORGANISM: Homo sapiens

<400> SEQUENCE: 55

Cys Ser Asn Cys Pro Ala Gly Thr Phe Cys Asp Trp Asn Arg Asn Gln
  1               5                  10                  15

Ile Cys Ser Pro Cys Pro Pro Asn Ser Phe Ser Ser Ala Gly Gly Gln
             20                  25                  30

Arg Thr Cys Asp Ile Cys Arg Gln Cys Lys Gly Val Phe Arg Thr Arg
         35                  40                  45

Lys Glu Cys Ser Ser Thr Ser Asn Ala Glu Cys Asp Cys Thr Pro Gly
 50                  55                  60

Phe His Cys Leu Gly Ala Gly Cys Ser Met Cys Glu Gln Asp Cys Lys
 65                  70                  75                  80

Gln Gly Gln Glu Leu Thr Lys Lys Gly Cys Lys Asp Cys Cys Phe Gly
             85                  90                  95

Thr Phe Asn Lys Gln Lys Arg Gly Ile Cys Arg Pro Trp Thr Asn Cys
            100                 105                 110

Ser Leu Asp Gly Lys Ser Val Leu Val Asn Gly Thr Lys Glu Arg Asp
            115                 120                 125

Val Val Cys Gly
            130

<210> SEQ ID NO 56
<211> LENGTH: 161
<212> TYPE: PRT
<213> ORGANISM: Homo sapiens

<400> SEQUENCE: 56

Ser Cys Lys Glu Asp Glu Tyr Pro Val Gly Ser Glu Cys Cys Pro Lys
  1               5                  10                  15

Cys Ser Pro Gly Tyr Arg Val Lys Glu Ala Cys Gly Glu Leu Thr Gly
             20                  25                  30

Thr Val Cys Glu Pro Cys Pro Pro Gly Thr Tyr Thr Ala His Leu Asn
         35                  40                  45

Gly Leu Ser Lys Cys Leu Gln Cys Gln Met Cys Asp Pro Ala Met Gly
 50                  55                  60

Leu Arg Ala Ser Arg Asn Cys Ser Arg Thr Glu Asn Ala Val Cys Gly
 65                  70                  75                  80

Cys Ser Pro Gly His Phe Cys Ile Val Gln Asp Gly Asp His Cys Ala
             85                  90                  95

Cys Arg Ala Tyr Ala Thr Ser Ser Pro Gly Gln Arg Val Gln Lys Ser
            100                 105                 110

Gly Thr Glu Ser Gln Asp Thr Leu Cys Gln Asn Cys Pro Pro Gly Thr
            115                 120                 125

Phe Ser Pro Asn Gly Thr Leu Glu Glu Cys Gln His Gln Thr Lys Cys
            130                 135                 140

Ser Trp Leu Val Thr Lys Ala Gly Ala Gly Thr Ser Ser Ser His Trp
145                 150                 155                 160
```

Val

<210> SEQ ID NO 57
<211> LENGTH: 170
<212> TYPE: PRT
<213> ORGANISM: Homo sapiens
<220> FEATURE:
<221> NAME/KEY: UNSURE
<222> LOCATION: (7)
<223> OTHER INFORMATION: May be any amino acid

<400> SEQUENCE: 57

Thr Cys Arg Asp Gln Glu Xaa Glu Tyr Tyr Glu Pro Gln His Arg Ile
1               5                   10                  15

Cys Cys Ser Arg Cys Pro Pro Gly Thr Tyr Val Ser Ala Lys Cys Ser
            20                  25                  30

Arg Ile Arg Asp Thr Val Cys Ala Thr Cys Ala Glu Asn Ser Tyr Asn
        35                  40                  45

Glu His Trp Asn Tyr Leu Thr Ile Cys Gln Leu Cys Arg Pro Cys Asp
    50                  55                  60

Pro Val Met Gly Leu Glu Ile Ala Pro Cys Thr Ser Lys Arg Lys
65                  70                  75                  80

Thr Gln Cys Arg Cys Gln Pro Gly Met Phe Cys Ala Ala Trp Ala Leu
            85                  90                  95

Glu Cys Thr His Cys Glu Leu Leu Ser Asp Cys Pro Pro Gly Thr Glu
        100                 105                 110

Ala Glu Leu Lys Asp Glu Val Gly Lys Gly Asn Asn His Cys Val Pro
    115                 120                 125

Cys Lys Ala Gly His Phe Gln Asn Thr Ser Ser Pro Ser Ala Arg Cys
130                 135                 140

Gln Pro His Thr Arg Cys Glu Asn Gln Gly Leu Val Glu Ala Ala Pro
145                 150                 155                 160

Gly Thr Ala Gln Ser Asp Thr Thr Cys Lys
                165                 170

<210> SEQ ID NO 58
<211> LENGTH: 146
<212> TYPE: PRT
<213> ORGANISM: Homo sapiens

<400> SEQUENCE: 58

Cys Asp Lys Cys Pro Pro Gly Thr Tyr Leu Lys Gln His Cys Thr Ala
1               5                   10                  15

Lys Trp Lys Thr Val Cys Ala Pro Cys Pro Asp His Tyr Tyr Thr Asp
            20                  25                  30

Ser Trp His Thr Ser Asp Glu Cys Leu Tyr Cys Ser Pro Val Cys Lys
        35                  40                  45

Glu Leu Gln Tyr Val Lys Gln Glu Cys Asn Arg Thr His Asn Arg Val
    50                  55                  60

Cys Glu Cys Lys Glu Gly Arg Tyr Leu Glu Ile Glu Phe Cys Leu Lys
65                  70                  75                  80

His Arg Ser Cys Pro Pro Gly Phe Gly Val Val Gln Ala Gly Thr Pro
            85                  90                  95

Glu Arg Asn Thr Val Cys Lys Arg Cys Pro Asp Gly Phe Phe Ser Asn
        100                 105                 110

Glu Thr Ser Ser Lys Ala Pro Cys Arg Lys His Thr Asn Cys Ser Val
    115                 120                 125

```
Phe Gly Leu Leu Leu Thr Gln Lys Gly Asn Ala Thr His Asp Asn Ile
            130                 135                 140

Cys Ser
145

<210> SEQ ID NO 59
<211> LENGTH: 146
<212> TYPE: PRT
<213> ORGANISM: Homo sapiens

<400> SEQUENCE: 59

Cys Ala Gln Cys Pro Pro Gly Thr Phe Val Gln Arg Pro Cys Arg Arg
  1               5                  10                  15

Asp Ser Pro Thr Thr Cys Gly Pro Cys Pro Pro Arg His Tyr Thr Gln
             20                  25                  30

Phe Trp Asn Tyr Leu Glu Arg Cys Arg Tyr Cys Asn Val Leu Cys Gly
         35                  40                  45

Glu Arg Glu Glu Glu Ala Arg Ala Cys His Ala Thr His Asn Arg Ala
 50                  55                  60

Cys Arg Cys Arg Thr Gly Phe Phe Ala His Ala Gly Phe Cys Leu Glu
 65                  70                  75                  80

His Ala Ser Cys Pro Pro Gly Ala Gly Val Ile Ala Pro Gly Thr Pro
                 85                  90                  95

Ser Gln Asn Thr Gln Cys Gln Pro Cys Pro Pro Gly Thr Phe Ser Ala
            100                 105                 110

Ser Ser Ser Ser Ser Glu Gln Cys Gln Pro His Arg Asn Cys Thr Ala
            115                 120                 125

Leu Gly Leu Ala Leu Asn Val Pro Gly Ser Ser Ser His Asp Thr Leu
            130                 135                 140

Cys Thr
145

<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: DNA Primer

<400> SEQUENCE: 60
agacccaagc ttcctgctcc agcaaggacc atg                                    33

<210> SEQ ID NO 61
<211> LENGTH: 50
<212> TYPE: DNA
<213> ORGANISM: Artificial Sequence
<220> FEATURE:
<223> OTHER INFORMATION: Description of Artificial Sequence: DNA Primer

<400> SEQUENCE: 61
agacgggatc cttagtggtg gtggtggtgg tgcacaggga ggaagcgctc                  50

<210> SEQ ID NO 62
<211> LENGTH: 16
<212> TYPE: DNA
<213> ORGANISM: Artificial Sequence
<220> FEATURE:
<223> OTHER INFORMATION: Description of Artificial Sequence: DNA Primer
<220> FEATURE:
<221> NAME/KEY: unsure
<222> LOCATION: (7)
<223> OTHER INFORMATION: Inosine
```

```
<220> FEATURE:
<221> NAME/KEY: unsure
<222> LOCATION: (14)
<223> OTHER INFORMATION: Inosine

<400> SEQUENCE: 62
tttcgtngat cggnca                                                    16

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: DNA Primer
<220> FEATURE:
<221> NAME/KEY: unsure
<222> LOCATION: (7)
<223> OTHER INFORMATION: Inosine
<220> FEATURE:
<221> NAME/KEY: unsure
<222> LOCATION: (10)
<223> OTHER INFORMATION: Inosine
<220> FEATURE:
<221> NAME/KEY: unsure
<222> LOCATION: (13)
<223> OTHER INFORMATION: Inosine
<220> FEATURE:
<221> NAME/KEY: unsure
<222> LOCATION: (16)
<223> OTHER INFORMATION: Inosine

<400> SEQUENCE: 63
aggatgnacn acnccncc                                                  18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: DNA Primer

<400> SEQUENCE: 64
aaaggccgcc atgggcct                                                  18

<210> SEQ ID NO 65
<211> LENGTH: 28
<212> TYPE: DNA
<213> ORGANISM: Artificial Sequence
<220> FEATURE:
<223> OTHER INFORMATION: Description of Artificial Sequence: DNA Primer

<400> SEQUENCE: 65
ttaagcttca gtagcattgc tcctggct                                       28

<210> SEQ ID NO 66
<211> LENGTH: 25
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 66

Cys Glu Ala Gly Glu Glu Val Val Val Arg Val Pro Gly Asn Arg Leu
 1               5                  10                  15

Val Arg Pro Arg Asp Gly Thr Arg Ser
            20                  25
```

-continued

```
<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 67
cgcggatccc ggagagatgg tcacc                                          25

<210> SEQ ID NO 68
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 68
cgctctagac cttcacacca tgaaagc                                        27

<210> SEQ ID NO 69
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 69
cgcggatcca tgggtctggg tctcttg                                        27

<210> SEQ ID NO 70
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 70
cgctctagat caagcgtagt ctgggacgtc gtatggcacc atgaaagccc c             51
```

What is claimed is:

1. An isolated antibody or portion thereof that binds to a protein selected from the group consisting of:
   a) a protein whose sequence consists of an immunogenic fragment of the amino acid residues 68–240 of SEQ ID NO:2;
   b) a protein whose sequence consists of a fragment of amino acids residues 68–240 of SEQ ID NO:2, wherein said fragment comprises at least 30 animo acid residues; and
   c) a protein whose sequence consists of a fragment of amino acid residues 68–240 of SEQ ID NO:2 wherein said fragment comprises at least 50 amino acids.

2. The antibody or portion thereof of claim 1 which is a monoclonal antibody.

3. The antibody or portion thereof of claim 1 which is a polyclonal antibody.

4. The antibody or portion thereof of claim 1 which is a chimeric antibody.

5. The antibody or portion thereof of claim 1 which is a single chain antibody.

6. The antibody or portion thereof of claim 1 which is a Fab fragment.

7. An isolated cell that produces the antibody of claim 1.

8. A hybridoma that produces the antibody of claim 1.

9. A method of detecting in a biological sample a protein that binds the antibody or portion thereof of claim 1 comprising:
   (a) contacting the biological sample with the antibody or portion thereof; and
   (b) detecting the protein in the biological sample.

10. A composition comprising the antibody or portion thereof of claim 1 and a carrier.

11. A hybridoma that produces the antibody of claim 5.

12. The method of claim 9 wherein the antibody is a monoclonal antibody.

13. The method of claim 9 wherein the antibody is a polyclonal antibody.

14. The method of claim 9 wherein the antibody is a chimeric antibody.

15. The composition of claim 10, wherein the antibody or portion thereof is a monoclonal antibody.

16. The composition of claim 10, wherein the antibody or portion thereof is a chimeric antibody.

17. The composition of claim 10, wherein the antibody or portion thereof is a single chain antibody.

18. The composition of claim 10, wherein the antibody or portion thereof is a Fab fragment.

19. An isolated antibody or portion thereof produced by immunizing an animal with a protein selected from the group consisting of:

a) a protein whose sequence consists of an immunogenic fragment of the amino acid residues 68–240 of SEQ ID NO:2;
b) a protein whose sequence consists of a fragment of amino acids residues 68–240 of SEQ ID NO:2, wherein said fragment comprises at least 30 amino acid residues; and
c) a protein whose sequence consists of a fragment of amino acids residues 68–240 of SEQ ID NO:2 wherein said fragment comprises at least 50 amino acids; wherein said antibody or portion thereof binds the protein of a), b), or c).

20. A method of detecting in a biological sample a protein that binds the antibody or portion thereof of claim 19 comprising:
(a) contacting the biological sample with the antibody or portion thereof; and
(b) detecting the protein in the biological sample.

21. A composition comprising the antibody or portion thereof of claim 19 and a carrier.

22. The method of claim 20 wherein the antibody is a monoclonal antibody.

23. The method of claim 20 wherein the antibody is a polyclonal antibody.

24. The method of claim 20 wherein the antibody is a chimeric antibody.

25. The method of claim 20 wherein the antibody is a humanized antibody.

26. The method of claim 20 wherein the antibody is a single chain antibody.

27. The composition of claim 21, wherein the antibody or portion thereof is a monoclonal antibody.

28. The composition of claim 21, wherein the antibody or portion thereof is a chimeric antibody.

29. The composition of claim 21, wherein the antibody or portion thereof is a single chain antibody.

30. The composition of claim 21, wherein the antibody or portion thereof is a Fab fragment.

31. An isolated antibody or portion thereof that binds to a protein whose sequence consists of amino acid residues 68 to 240 of SEQ ID NO:2.

32. The antibody or portion thereof of claim 31 which is a monoclonal antibody.

33. The antibody or portion thereof of claim 31 which is a polyclonal antibody.

34. The antibody or portion thereof of claim 31 which is a chimeric antibody.

35. The antibody or portion thereof of claim 31 which is a single chain antibody.

36. The antibody or portion thereof of claim 31 which is a Fab fragment.

37. An isolated cell that produces the antibody of claim 31.

38. A hybridoma that produces the antibody of claim 31.

39. A hybridoma that produces the antibody of claim 31.

* * * * *